United States Patent
Combier et al.

(10) Patent No.: US 12,024,543 B2
(45) Date of Patent: *Jul. 2, 2024

(54) MICROPEPTIDES AND USE OF SAME FOR MODULATING GENE EXPRESSION

(71) Applicants: UNIVERSITE PAUL SABATIER TOULOUSE III, Toulouse (FR); CENTRE NATIONAL DE LA RECHERCHE SCIENTIFIQUE, Paris (FR)

(72) Inventors: Jean-Philippe Combier, Castanet Tolosan (FR); Dominique Lauressergues, Toulouse (FR); Guillaume Becard, Odars (FR); François Payre, Pompertuzat (FR); Serge Plaza, Ramonville Saint Agne (FR); Jérôme Cavaille, Ramonville Saint Agne (FR)

(73) Assignees: UNIVERSITE PAUL SABATIER TOULOUSE III, Toulouse (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 310 days.

This patent is subject to a terminal disclaimer.

(21) Appl. No.: 16/595,926

(22) Filed: Oct. 8, 2019

(65) Prior Publication Data

US 2020/0131234 A1 Apr. 30, 2020

Related U.S. Application Data

(63) Continuation of application No. 14/320,703, filed on Jul. 1, 2014, now abandoned.

(30) Foreign Application Priority Data

Oct. 31, 2013 (FR) ..................... 1360727
Jun. 3, 2014 (FR) ..................... 1455044

(51) Int. Cl.
| | | |
|---|---|---|
| C07K 14/415 | (2006.01) |
| A01N 37/46 | (2006.01) |
| A01N 57/16 | (2006.01) |
| A01N 65/00 | (2009.01) |
| A01N 65/08 | (2009.01) |
| A01N 65/20 | (2009.01) |
| A01N 65/28 | (2009.01) |
| A01N 65/44 | (2009.01) |
| C07K 5/10 | (2006.01) |
| C07K 5/103 | (2006.01) |
| C07K 7/06 | (2006.01) |
| C07K 7/08 | (2006.01) |
| C12N 15/113 | (2010.01) |
| C12N 15/63 | (2006.01) |
| C12N 15/82 | (2006.01) |
| C12Q 1/68 | (2018.01) |
| C12Q 1/6895 | (2018.01) |
| A61K 38/00 | (2006.01) |
| A61K 48/00 | (2006.01) |

(52) U.S. Cl.
CPC ............ *C07K 14/415* (2013.01); *A01N 37/46* (2013.01); *A01N 57/16* (2013.01); *A01N 65/00* (2013.01); *A01N 65/08* (2013.01); *A01N 65/20* (2013.01); *A01N 65/28* (2013.01); *A01N 65/44* (2013.01); *C07K 5/10* (2013.01); *C07K 5/1013* (2013.01); *C07K 7/06* (2013.01); *C07K 7/08* (2013.01); *C12N 15/113* (2013.01); *C12N 15/63* (2013.01); *C12N 15/8218* (2013.01); *C12N 15/8261* (2013.01); *C12Q 1/68* (2013.01); *C12Q 1/6895* (2013.01); *A61K 38/00* (2013.01); *A61K 48/00* (2013.01); *C12Q 2600/13* (2013.01); *C12Q 2600/158* (2013.01); *C12Q 2600/178* (2013.01); *Y02A 40/146* (2018.01)

(58) Field of Classification Search
None
See application file for complete search history.

(56) References Cited

PUBLICATIONS

Wang et al. (Electrophoresis 27.13 (2006): 2782-2786). (Year: 2006).*
Schwab et al. (EMBO Rep 14(7): 615-21, 2013). (Year: 2013).*
Bielewicz et al. (EMBO Rep 14(7): 622-28, 2013). (Year: 2013).*
"Administer" definition retrieved from dictionary.com website, Dec. 23, 2016.
Ehsan Sabaghian, et al., "An integrated network of Arabidopsis growth regulators and its use for gene prioritization", Scientific Reports, 2015, 5: 17617, DOI: 10.10/1038/srep17617, pp. 1-13.
Calvin D. Lietzow, et al., "QTL mapping of parthenocarpic fruit set in North American processing cucumber", Theor Appl Genet, 2016, 129:2387-2401, DOI: 10.1007/s00122-016-2778-z, 15 pages.
C. D. Town, Genbank Accession AC157488, submitted Feb. 17, 2005, annotated Mar. 24, 2007, 45 pages.
Rebecca Schwab, et al., "Enhanced microRNA accumulation through stemloop-adjacent introns", EMBO Reports, vol. 14, No. 7, 2013, pp. 615-621.
David Bielewicz et al., "Introns of plant primiRNAs enhance miRNA biogenesis", EMBO Reports, vol. 14, No. 7, 2013, pp. 622-628.
Maximo Ibo Galindo, et al., "Peptides Encoded by Short ORFs Control Development and Define a New Eukaryotic Gene Family", PLOS Biology, vol. 5, No. 5, May 2007, pp. 1052-1062, DOI: 10.1371/journal.pbio.0050106.

(Continued)

*Primary Examiner* — Charles Logsdon
(74) *Attorney, Agent, or Firm* — Maier & Maier, PLLC

(57) ABSTRACT

Process for detecting and identifying micropeptides (miPEPs) encoded by a nucleotide sequence contained in the sequence of the primary transcript of a microRNA and use thereof for modulating gene expression.

6 Claims, 21 Drawing Sheets

Specification includes a Sequence Listing.

(56) References Cited

PUBLICATIONS

Yuji Kageyama, et al., "Coding vs non-coding: Translatability of short ORFs found in putative non-coding transcripts", Biochimie 93, 2011, pp. 1981-1986, DOI: 10.1016/j.biochi.2011.06.024.
T. Kondo, et al., "Small Peptides Switch the Transcriptional Activity of Shavenbaby During *Drosophila embryogenesis*", Science, vol. 329, No. 5989, Jul. 16, 2010, pp. 336-339.
Miriam I. Rosenberg, et al., "Hiding in Plain Sight", Science, vol. 329, No. 5989, Jul. 16, 2010, pp. 284-285.
Jin Dai, et al., "Plant Phenolics: Extraction, Analysis and Their Antioxidant and Anticancer Properties", Molecules, vol. 15, No. 10, 2010, pp. 7313-7352, ISSN: 1420-3049, DOI: 10.3390/molecules15107313.

\* cited by examiner

A) Control plant

B) Plant treated with miPEP 164a

A) Control plant

B) Plant treated with miPEP319a

SEQUENCE LISTING

```
<160> NUMBER OF SEQ ID NOS: 423

<210> SEQ ID NO 1
<211> LENGTH: 33
<212> TYPE: PRT
<213> ORGANISM: Arabidopsis thaliana

<400> SEQUENCE: 1

Met Phe Cys Ser Ile Gln Cys Val Ala Arg His Leu Phe Pro Leu His
1               5                   10                  15

Val Arg Glu Ile Lys Lys Ala Thr Arg Ala Ile Lys Lys Gly Lys Thr
            20                  25                  30

Leu
```

-continued

```
<210> SEQ ID NO 2
<211> LENGTH: 24
<212> TYPE: PRT
<213> ORGANISM: Arabidopsis thaliana

<400> SEQUENCE: 2

Met Arg Arg Gln Thr Ser Val Pro Phe Ala Cys Lys Arg Asp Lys Glu
1               5                   10                  15

Ser Asp Lys Ser His Lys Glu Arg
            20

<210> SEQ ID NO 3
<211> LENGTH: 37
<212> TYPE: PRT
<213> ORGANISM: Arabidopsis thaliana

<400> SEQUENCE: 3

Met Val Met Phe Phe Leu Asp Leu Asp Lys Asn Pro Arg Phe Asp Leu
1               5                   10                  15

Leu Lys Gly Leu Lys Trp Asn Leu Phe Ser Ser His Ile Ser Pro Ser
            20                  25                  30

Leu Pro Pro Ser Leu
        35

<210> SEQ ID NO 4
<211> LENGTH: 11
<212> TYPE: PRT
<213> ORGANISM: Arabidopsis thaliana

<400> SEQUENCE: 4

Met Lys Asp Asn Phe Pro Leu Leu Leu Arg Leu
1               5                   10

<210> SEQ ID NO 5
<211> LENGTH: 4
<212> TYPE: PRT
<213> ORGANISM: Arabidopsis thaliana

<400> SEQUENCE: 5

Met Ser Asp Asp
1

<210> SEQ ID NO 6
<211> LENGTH: 16
<212> TYPE: PRT
<213> ORGANISM: Arabidopsis thaliana

<400> SEQUENCE: 6

Met Ile Tyr Ile Asn Lys Tyr Gly Ser Ile Ser Ala Val Glu Asp Asp
1               5                   10                  15

<210> SEQ ID NO 7
<211> LENGTH: 4
<212> TYPE: PRT
<213> ORGANISM: Arabidopsis thaliana

<400> SEQUENCE: 7

Met Ser Gln Arg
1

<210> SEQ ID NO 8
<211> LENGTH: 16
<212> TYPE: PRT
<213> ORGANISM: Arabidopsis lyrata
```

<400> SEQUENCE: 8

Met Thr Cys Pro Leu Leu Ser Leu Ser Phe Leu Leu Ser Lys Tyr Ile
1               5                   10                  15

<210> SEQ ID NO 9
<211> LENGTH: 16
<212> TYPE: PRT
<213> ORGANISM: Arabidopsis thaliana

<400> SEQUENCE: 9

Met Thr Trp Pro Leu Leu Ser Leu Ser Phe Leu Leu Ser Lys Tyr Val
1               5                   10                  15

<210> SEQ ID NO 10
<211> LENGTH: 18
<212> TYPE: PRT
<213> ORGANISM: Capsella rubella

<400> SEQUENCE: 10

Met Thr Cys Thr Leu Ser Ala Leu Ser Leu Ser Leu Asn Met Phe Arg
1               5                   10                  15

Val Asn

<210> SEQ ID NO 11
<211> LENGTH: 5
<212> TYPE: PRT
<213> ORGANISM: Arabidopsis thaliana

<400> SEQUENCE: 11

Met Phe Tyr Leu Ser
1               5

<210> SEQ ID NO 12
<211> LENGTH: 37
<212> TYPE: PRT
<213> ORGANISM: Arabidopsis thaliana

<400> SEQUENCE: 12

Met Val Asn Thr Ser Ser Phe Phe Ile Ser Ser Phe Ile Leu Pro Leu
1               5                   10                  15

Val Leu Ser Glu Ser Asn Cys Leu Leu Phe Arg Thr Ile Tyr Lys Phe
                20                  25                  30

Ser Met Val Leu Tyr
            35

<210> SEQ ID NO 13
<211> LENGTH: 24
<212> TYPE: PRT
<213> ORGANISM: Arabidopsis thaliana

<400> SEQUENCE: 13

Met Phe Cys Leu Leu Ile Pro Ile Phe Ser Phe Val Phe Ser Pro Asn
1               5                   10                  15

Arg His Leu Arg Leu Gln Glu Gln
            20

<210> SEQ ID NO 14
<211> LENGTH: 5
<212> TYPE: PRT
<213> ORGANISM: Arabidopsis thaliana

<400> SEQUENCE: 14

Met Phe Ser Pro Gln
1               5

<210> SEQ ID NO 15
<211> LENGTH: 23
<212> TYPE: PRT
<213> ORGANISM: Arabidopsis thaliana

<400> SEQUENCE: 15

Met Lys Tyr Ile His Ile Leu Ile Leu Phe Lys Ser Arg Ser Thr Tyr
1               5                   10                  15

Lys Leu Ser Thr Asn His Ile
            20

<210> SEQ ID NO 16
<211> LENGTH: 10
<212> TYPE: PRT
<213> ORGANISM: Arabidopsis thaliana

<400> SEQUENCE: 16

Met Lys Ile Pro Leu Phe Leu Pro Lys Leu
1               5                   10

<210> SEQ ID NO 17
<211> LENGTH: 27
<212> TYPE: PRT
<213> ORGANISM: Arabidopsis thaliana

<400> SEQUENCE: 17

Met Val Ser Gly Gln Glu Asp Ser Trp Leu Lys Leu Ser Leu Cys
1               5                   10                  15

Phe Leu Phe Leu Ser Leu Leu Asp Ser Leu Ile
            20                  25

<210> SEQ ID NO 18
<211> LENGTH: 34
<212> TYPE: PRT
<213> ORGANISM: Arabidopsis thaliana

<400> SEQUENCE: 18

Met Phe Leu Leu Ile Phe Leu Arg Leu Ile Met Ile Cys Val Cys Ser
1               5                   10                  15

Ser Thr Asp Phe Leu Arg Ser Val Asn Tyr Phe Cys Leu Phe Ile Tyr
            20                  25                  30

Asp Leu

<210> SEQ ID NO 19
<211> LENGTH: 9
<212> TYPE: PRT
<213> ORGANISM: Arabidopsis thaliana

<400> SEQUENCE: 19

Met Ser Thr Thr Gln Glu His Arg Ser
1               5

<210> SEQ ID NO 20
<211> LENGTH: 25
<212> TYPE: PRT
<213> ORGANISM: Arabidopsis thaliana

<400> SEQUENCE: 20

Met Ile Leu Lys Cys Trp Ser Ser Arg Phe Leu Arg Val Ser Pro Tyr

```
                1               5                  10                 15
Gln Asn Ala His Ser Leu Ser Leu Gly
         20                 25

<210> SEQ ID NO 21
<211> LENGTH: 13
<212> TYPE: PRT
<213> ORGANISM: Arabidopsis lyrata

<400> SEQUENCE: 21

Met Pro Leu Ala Val Ile Arg Gln Gly Ile Val Trp Pro
1               5                   10

<210> SEQ ID NO 22
<211> LENGTH: 24
<212> TYPE: PRT
<213> ORGANISM: Arabidopsis lyrata

<400> SEQUENCE: 22

Met Pro Ser Trp His Asp Met Val Leu Leu Pro Tyr Val Lys His Thr
1               5                   10                  15

His Ala Asn Thr Arg His Ile Thr
         20

<210> SEQ ID NO 23
<211> LENGTH: 8
<212> TYPE: PRT
<213> ORGANISM: Arabidopsis lyrata

<400> SEQUENCE: 23

Met Thr Trp Phe Phe Cys Leu Thr
1               5

<210> SEQ ID NO 24
<211> LENGTH: 37
<212> TYPE: PRT
<213> ORGANISM: Arabidopsis thaliana

<400> SEQUENCE: 24

Met Pro Ser Trp His Gly Met Val Leu Leu Pro Tyr Val Lys His Thr
1               5                   10                  15

His Ala Ser Thr His Thr His Thr His Asn Ile Tyr Gly Cys Ala Cys
         20                  25                  30

Glu Leu Val Phe His
         35

<210> SEQ ID NO 25
<211> LENGTH: 22
<212> TYPE: PRT
<213> ORGANISM: Arabidopsis thaliana

<400> SEQUENCE: 25

Met Ala Trp Tyr Gly Ser Phe Ala Leu Arg Lys Thr His Ser Arg Gln
1               5                   10                  15

His Thr His Thr His Thr
         20

<210> SEQ ID NO 26
<211> LENGTH: 8
<212> TYPE: PRT
<213> ORGANISM: Arabidopsis thaliana

<400> SEQUENCE: 26
```

```
Met Val Trp Phe Phe Cys Leu Thr
1               5
```

<210> SEQ ID NO 27
<211> LENGTH: 7
<212> TYPE: PRT
<213> ORGANISM: Brassica rapa

<400> SEQUENCE: 27

```
Met Met Ile Ile Leu Trp Lys
1               5
```

<210> SEQ ID NO 28
<211> LENGTH: 24
<212> TYPE: PRT
<213> ORGANISM: Brassica rapa

<400> SEQUENCE: 28

```
Met Leu Trp Ala Lys Leu Val Ser Phe Ser Thr Leu His Ser Leu Val
1               5                   10                  15

Phe Leu Leu Ser Pro Ser Phe Ala
            20
```

<210> SEQ ID NO 29
<211> LENGTH: 29
<212> TYPE: PRT
<213> ORGANISM: Brassica rapa

<400> SEQUENCE: 29

```
Met Pro Ser Trp His Gly Ile Val Ile Leu Pro Phe Val Lys His Thr
1               5                   10                  15

His Ala Asn Ile His Tyr Ser Tyr Ser Cys Val Cys Ile
            20                  25
```

<210> SEQ ID NO 30
<211> LENGTH: 34
<212> TYPE: PRT
<213> ORGANISM: Carica papaya

<400> SEQUENCE: 30

```
Met Ile Ala Cys His Pro Tyr Leu Pro Phe Pro Leu Phe Leu Ser Leu
1               5                   10                  15

Thr Phe Tyr Ser Ile Phe Phe Ser Pro Ser Pro Pro Ser Leu
            20                  25                  30

Pro Leu
```

<210> SEQ ID NO 31
<211> LENGTH: 53
<212> TYPE: PRT
<213> ORGANISM: Carica papaya

<400> SEQUENCE: 31

```
Met Pro Ser Leu Leu Ala Phe Ser Pro Phe Pro Phe Ser Asn Ile Leu
1               5                   10                  15

Leu Asn Leu Leu Leu Pro Leu Pro Pro Phe Pro Leu Ser Ala Ile Ile
            20                  25                  30

Thr Ile Ile Lys Pro Leu Ser Leu Ser Leu Pro Leu Ser Leu Ser Leu
        35                  40                  45

Ser Gly Phe Ser Val
    50
```

```
<210> SEQ ID NO 32
<211> LENGTH: 15
<212> TYPE: PRT
<213> ORGANISM: Capsella rubella

<400> SEQUENCE: 32

Met Glu Leu Lys Gly Leu Arg Thr Trp Gln Leu Leu Asp Lys Val
1               5                   10                  15

<210> SEQ ID NO 33
<211> LENGTH: 14
<212> TYPE: PRT
<213> ORGANISM: Capsella rubella

<400> SEQUENCE: 33

Met Pro Ser Trp His Gly Met Ala Cys Phe Tyr Cys Leu Thr
1               5                   10

<210> SEQ ID NO 34
<211> LENGTH: 24
<212> TYPE: PRT
<213> ORGANISM: Capsella rubella

<400> SEQUENCE: 34

Met Ala Trp His Gly Met Phe Leu Leu Pro Tyr Val Lys His Thr His
1               5                   10                  15

Ala Asn Thr Tyr Ser Leu Tyr Met
            20

<210> SEQ ID NO 35
<211> LENGTH: 35
<212> TYPE: PRT
<213> ORGANISM: Gossypium raimondii

<400> SEQUENCE: 35

Met Met Arg Ser Arg Ile Leu Lys Phe Gln Tyr Arg Phe Gly Met Gly
1               5                   10                  15

Ile Gly Gly Arg Lys Gln Leu Lys Asn Gln Leu Cys Gln Ile Gln Gly
            20                  25                  30

Arg Ile Ser
        35

<210> SEQ ID NO 36
<211> LENGTH: 10
<212> TYPE: PRT
<213> ORGANISM: Gossypium raimondii

<400> SEQUENCE: 36

Met Ser Asn Ser Arg Ser Tyr Gln Leu Lys
1               5                   10

<210> SEQ ID NO 37
<211> LENGTH: 17
<212> TYPE: PRT
<213> ORGANISM: Gossypium raimondii

<400> SEQUENCE: 37

Met Asn Glu Asp Leu Glu Ile Ser Thr Arg Lys Arg Thr Pro Gln Leu
1               5                   10                  15

Cys

<210> SEQ ID NO 38
```

```
<211> LENGTH: 12
<212> TYPE: PRT
<213> ORGANISM: Medicago truncatula

<400> SEQUENCE: 38

Met Pro Lys Phe Asp Ile Phe Phe Tyr Ile Phe Val
1               5                   10

<210> SEQ ID NO 39
<211> LENGTH: 83
<212> TYPE: PRT
<213> ORGANISM: Medicago truncatula

<400> SEQUENCE: 39

Met Ser Tyr Ile Ser Leu Ser Pro Lys Leu Leu Pro Ile Asn Thr Lys
1               5                   10                  15

Pro Phe Pro Trp Leu Val Gln Phe Asn Phe Tyr Phe Ser Ser Asn Thr
            20                  25                  30

Lys Cys Asn Lys Leu His Phe Leu Gly Glu Lys Leu Leu Val Gly Glu
        35                  40                  45

Ala Gly His Val Gln Ile Leu Phe Leu Ile His Ser Leu Ile Met His
    50                  55                  60

Ile Asn Ile Phe Cys Thr Cys Ser Pro Ser Pro Thr Arg Leu Pro His
65                  70                  75                  80

Pro Ser Leu

<210> SEQ ID NO 40
<211> LENGTH: 20
<212> TYPE: PRT
<213> ORGANISM: Oryza sativa

<400> SEQUENCE: 40

Met Gln Thr His Ser Asn Thr Pro Gln Ser Thr Tyr Ser Leu Ser Leu
1               5                   10                  15

Ser Leu Ser Glu
            20

<210> SEQ ID NO 41
<211> LENGTH: 15
<212> TYPE: PRT
<213> ORGANISM: Oryza sativa

<400> SEQUENCE: 41

Met Cys Val Cys Asp Ile Asn Met His Ser Met Leu Met Leu Leu
1               5                   10                  15

<210> SEQ ID NO 42
<211> LENGTH: 25
<212> TYPE: PRT
<213> ORGANISM: Arabidopsis lyrata

<400> SEQUENCE: 42

Met Arg Ile Lys Leu Phe Gln Leu Arg Gly Met Leu Ser Gly Ser Arg
1               5                   10                  15

Ile Leu Tyr Ile Tyr Thr Cys Val Cys
            20                  25

<210> SEQ ID NO 43
<211> LENGTH: 18
<212> TYPE: PRT
<213> ORGANISM: Arabidopsis thaliana
```

```
<400> SEQUENCE: 43

Met Arg Val Lys Leu Phe Gln Leu Arg Gly Met Leu Ser Gly Ser Arg
1               5                   10                  15

Ile Leu

<210> SEQ ID NO 44
<211> LENGTH: 36
<212> TYPE: PRT
<213> ORGANISM: Brassica carinata

<400> SEQUENCE: 44

Met Arg Met Lys Leu Phe Gln Leu Arg Gly Met Leu Ser Gly Ser Arg
1               5                   10                  15

Ile Leu Tyr Ile His Lys Tyr Val Tyr Met Leu Ile Gln Val Phe Asp
            20                  25                  30

His Ile Cys Ile
        35

<210> SEQ ID NO 45
<211> LENGTH: 27
<212> TYPE: PRT
<213> ORGANISM: Brassica juncea

<400> SEQUENCE: 45

Met Arg Met Lys Leu Phe Gln Leu Arg Gly Met Leu Ser Gly Ser Arg
1               5                   10                  15

Ile Leu Tyr Ile His Lys Tyr Val Tyr Ile Cys
            20                  25

<210> SEQ ID NO 46
<211> LENGTH: 36
<212> TYPE: PRT
<213> ORGANISM: Brassica napus

<400> SEQUENCE: 46

Met Arg Met Lys Leu Phe Gln Leu Arg Gly Met Leu Ser Gly Ser Arg
1               5                   10                  15

Ile Leu Tyr Ile His Lys Tyr Val Tyr Met Ile Ile Gln Val Phe Asp
            20                  25                  30

His Ile Cys Ile
        35

<210> SEQ ID NO 47
<211> LENGTH: 36
<212> TYPE: PRT
<213> ORGANISM: Brassica oleracea

<400> SEQUENCE: 47

Met Arg Met Lys Leu Phe Gln Leu Arg Gly Met Leu Ser Gly Ser Arg
1               5                   10                  15

Ile Leu Tyr Ile His Lys Tyr Val Tyr Met Leu Ile Gln Val Phe Asp
            20                  25                  30

His Ile Cys Ile
        35

<210> SEQ ID NO 48
<211> LENGTH: 27
<212> TYPE: PRT
<213> ORGANISM: Brassica rapa

<400> SEQUENCE: 48
```

-continued

Met Arg Met Lys Leu Phe Gln Leu Arg Gly Met Leu Ser Gly Ser Arg
1               5                   10                  15

Ile Leu Tyr Ile His Lys Tyr Val Tyr Ile Cys
            20                  25

<210> SEQ ID NO 49
<211> LENGTH: 19
<212> TYPE: PRT
<213> ORGANISM: Arabidopsis thaliana

<400> SEQUENCE: 49

Met Leu Asp Leu Phe Arg Ser Asn Asn Arg Ile Glu Pro Ser Asp Phe
1               5                   10                  15

Arg Phe Asp

<210> SEQ ID NO 50
<211> LENGTH: 4
<212> TYPE: PRT
<213> ORGANISM: Arabidopsis thaliana

<400> SEQUENCE: 50

Met Arg Asp Arg
1

<210> SEQ ID NO 51
<211> LENGTH: 10
<212> TYPE: PRT
<213> ORGANISM: Arabidopsis thaliana

<400> SEQUENCE: 51

Met Asn Arg Lys Ile Ser Leu Ser Leu Ser
1               5                   10

<210> SEQ ID NO 52
<211> LENGTH: 8
<212> TYPE: PRT
<213> ORGANISM: Arabidopsis thaliana

<400> SEQUENCE: 52

Met Met Gly Cys Phe Val Gly Phe
1               5

<210> SEQ ID NO 53
<211> LENGTH: 8
<212> TYPE: PRT
<213> ORGANISM: Arabidopsis thaliana

<400> SEQUENCE: 53

Met Gln Glu Glu Thr Tyr Glu Gly
1               5

<210> SEQ ID NO 54
<211> LENGTH: 59
<212> TYPE: PRT
<213> ORGANISM: Arabidopsis thaliana

<400> SEQUENCE: 54

Met Pro His Thr Asn Leu Lys Asp Leu Phe Ile Phe Ser Pro Asn Val
1               5                   10                  15

Phe Phe Ser Phe Ala Ile Tyr Leu His Asn Ser Trp Asn Lys Asn Tyr
            20                  25                  30

Ile His Lys Arg Glu Asn Phe His Asn Thr Ser Phe Ala Leu Ile Phe

```
               35                  40                  45

Phe Phe Ser Ser Ile Met Ser Ile Asn Tyr Gly
    50                  55

<210> SEQ ID NO 55
<211> LENGTH: 39
<212> TYPE: PRT
<213> ORGANISM: Arabidopsis thaliana

<400> SEQUENCE: 55

Met Phe Phe Phe Arg Leu Leu Phe Ile Ser Thr Ile Leu Gly Thr Lys
1               5                   10                  15

Thr Thr Phe Thr Asn Glu Arg Ile Phe Thr Thr Pro Leu Leu Leu Ser
            20                  25                  30

Phe Phe Phe Phe Arg Pro Leu
        35

<210> SEQ ID NO 56
<211> LENGTH: 6
<212> TYPE: PRT
<213> ORGANISM: Arabidopsis thaliana

<400> SEQUENCE: 56

Met Arg His Lys Glu Ser
1               5

<210> SEQ ID NO 57
<211> LENGTH: 34
<212> TYPE: PRT
<213> ORGANISM: Arabidopsis thaliana

<400> SEQUENCE: 57

Met Asn Leu Leu Lys Lys Glu Arg Gln Arg Arg Gln Arg Ser Ile
1               5                   10                  15

Gly Ser His Cys Ile Ala Ser Leu Val Leu Lys Asp Gly Tyr Met Lys
            20                  25                  30

Lys Ile

<210> SEQ ID NO 58
<211> LENGTH: 9
<212> TYPE: PRT
<213> ORGANISM: Arabidopsis thaliana

<400> SEQUENCE: 58

Met Val Leu Ser Gly Lys Leu Thr Phe
1               5

<210> SEQ ID NO 59
<211> LENGTH: 20
<212> TYPE: PRT
<213> ORGANISM: Medicago truncatula

<400> SEQUENCE: 59

Met Leu Leu His Arg Leu Ser Lys Phe Cys Lys Ile Glu Arg Asp Ile
1               5                   10                  15

Val Tyr Ile Ser
            20

<210> SEQ ID NO 60
<211> LENGTH: 5
<212> TYPE: PRT
<213> ORGANISM: Medicago truncatula
```

<400> SEQUENCE: 60

Met Lys Ile Glu Glu
1               5

<210> SEQ ID NO 61
<211> LENGTH: 34
<212> TYPE: PRT
<213> ORGANISM: Zea mays

<400> SEQUENCE: 61

Met His Leu Pro Ser Thr Pro Ser Arg Pro Pro Gln His Thr Ser
1               5                   10                  15

Leu Ser Phe Leu Gly Lys Glu Met Thr Lys Gly Thr Thr Ala Cys
            20                  25                  30

Phe Gly

<210> SEQ ID NO 62
<211> LENGTH: 10
<212> TYPE: PRT
<213> ORGANISM: Arabidopsis thaliana

<400> SEQUENCE: 62

Met Leu Ser Leu Ser His Phe His Ile Cys
1               5                   10

<210> SEQ ID NO 63
<211> LENGTH: 23
<212> TYPE: PRT
<213> ORGANISM: Medicago truncatula

<400> SEQUENCE: 63

Met Met Val Phe Gly Lys Pro Lys Lys Ala Met Leu Val Arg Phe Asn
1               5                   10                  15

Pro Lys Thr Asp Leu His Val
            20

<210> SEQ ID NO 64
<211> LENGTH: 10
<212> TYPE: PRT
<213> ORGANISM: Medicago truncatula

<400> SEQUENCE: 64

Met Ala Ser Ala Ala Lys Val Tyr Met Ala
1               5                   10

<210> SEQ ID NO 65
<211> LENGTH: 6
<212> TYPE: PRT
<213> ORGANISM: Arabidopsis thaliana

<400> SEQUENCE: 65

Met Ala Ser Lys Ile Trp
1               5

<210> SEQ ID NO 66
<211> LENGTH: 10
<212> TYPE: PRT
<213> ORGANISM: Arabidopsis thaliana

<400> SEQUENCE: 66

Met Val Arg Phe Gln Leu Ser Ile Arg Asp
1               5                   10

<210> SEQ ID NO 67
<211> LENGTH: 12
<212> TYPE: PRT
<213> ORGANISM: Arabidopsis thaliana

<400> SEQUENCE: 67

Met Cys Thr Tyr Tyr Tyr Leu Ile Asn Lys Tyr Phe
1               5                   10

<210> SEQ ID NO 68
<211> LENGTH: 11
<212> TYPE: PRT
<213> ORGANISM: Arabidopsis thaliana

<400> SEQUENCE: 68

Met Phe Pro Ala Lys Trp Cys Arg Leu Glu Ser
1               5                   10

<210> SEQ ID NO 69
<211> LENGTH: 22
<212> TYPE: PRT
<213> ORGANISM: Arabidopsis thaliana

<400> SEQUENCE: 69

Met Gly Ser Leu Ser Leu Phe Lys Ser Gln Leu Glu Ile Leu Met Leu
1               5                   10                  15

Leu Leu Ser Leu Ser Lys
            20

<210> SEQ ID NO 70
<211> LENGTH: 20
<212> TYPE: PRT
<213> ORGANISM: Arabidopsis thaliana

<400> SEQUENCE: 70

Met Ser Val Tyr Ile His Val Pro Ile Ser Leu Asn Cys Phe Ser Pro
1               5                   10                  15

Lys Ser Ser Cys
            20

<210> SEQ ID NO 71
<211> LENGTH: 11
<212> TYPE: PRT
<213> ORGANISM: Arabidopsis thaliana

<400> SEQUENCE: 71

Met Gly Val Pro Asn Phe Arg Pro Arg Asn Arg
1               5                   10

<210> SEQ ID NO 72
<211> LENGTH: 23
<212> TYPE: PRT
<213> ORGANISM: Arabidopsis cebennensis

<400> SEQUENCE: 72

Met Arg Ser Arg Val Ser Phe Phe Phe Lys Ile Met Leu Phe Arg
1               5                   10                  15

Leu Leu Gly Tyr Arg Ser Met
            20

<210> SEQ ID NO 73
<211> LENGTH: 44

```
<212> TYPE: PRT
<213> ORGANISM: Arabidopsis cebennensis

<400> SEQUENCE: 73

Met His Thr Tyr Ile His Thr Ile Ser Asn Ile Ser Ser Ile Phe Phe
1               5                   10                  15

Cys Ser Lys Arg Ser Phe Ser Pro Thr Tyr Ile Arg Ile Ile Val
            20                  25                  30

Val Ile Asp Pro Phe Arg Ile Ala Leu Thr Phe Arg
        35                  40

<210> SEQ ID NO 74
<211> LENGTH: 22
<212> TYPE: PRT
<213> ORGANISM: Arabidopsis halleri

<400> SEQUENCE: 74

Met Arg Ser Arg Val Ser Leu Phe Leu Ser Phe Ser Ser Asn Phe Ala
1               5                   10                  15

Ala Tyr Ser Pro Arg Ser
            20

<210> SEQ ID NO 75
<211> LENGTH: 48
<212> TYPE: PRT
<213> ORGANISM: Arabidospis lyrata

<400> SEQUENCE: 75

Met His Thr Tyr Ile Pro Ser Ser Ser Phe Pro Ile Ser Asn Ile Ser
1               5                   10                  15

Ser Val Phe Phe Cys Tyr Lys Arg Ser Phe Ser Pro Tyr Thr Tyr Ile
            20                  25                  30

Arg Ile Ile Val Val Ile Asp Pro Phe Arg Ile Ala Leu Thr Phe Arg
        35                  40                  45

<210> SEQ ID NO 76
<211> LENGTH: 50
<212> TYPE: PRT
<213> ORGANISM: Arabidopsis thaliana

<400> SEQUENCE: 76

Met Asn Ile His Thr Tyr His His Leu Leu Phe Pro Ser Leu Val Phe
1               5                   10                  15

His Gln Ser Ser Asp Val Pro Asn Ala Leu Ser Leu His Ile His Thr
            20                  25                  30

Tyr Glu Tyr Ile Ile Val Val Ile Asp Pro Phe Arg Ile Thr Leu Ala
        35                  40                  45

Phe Arg
    50

<210> SEQ ID NO 77
<211> LENGTH: 19
<212> TYPE: PRT
<213> ORGANISM: Arabidopsis thaliana

<400> SEQUENCE: 77

Met Phe Gln Thr Leu Tyr Leu Phe Ile Tyr Ile His Thr Asn Ile Leu
1               5                   10                  15

Leu Leu Ser
```

```
<210> SEQ ID NO 78
<211> LENGTH: 45
<212> TYPE: PRT
<213> ORGANISM: Brassica rapa

<400> SEQUENCE: 78

Met Phe Lys Leu Tyr Phe Ser Ala Ile Leu Ser Thr Gln Tyr Met His
1               5                   10                  15

Thr Tyr His His Arg Ile Ala Leu Ile Phe Leu Ser Ile Leu Tyr Pro
            20                  25                  30

Ser Thr Asn Tyr Leu Met Ser Pro Ile Leu Asn Pro Thr
        35                  40                  45

<210> SEQ ID NO 79
<211> LENGTH: 20
<212> TYPE: PRT
<213> ORGANISM: Carica papaya

<400> SEQUENCE: 79

Met Lys Ile Lys Leu Gly Phe Ser Leu Ile Lys Ile Ile Ile Leu Leu
1               5                   10                  15

Asp Lys Asn Ser
            20

<210> SEQ ID NO 80
<211> LENGTH: 21
<212> TYPE: PRT
<213> ORGANISM: Capsella rubella

<400> SEQUENCE: 80

Met His Pro His Thr Tyr Ile His Ile Pro Ser Ser Ser Phe Leu Ile
1               5                   10                  15

Ser Ser Phe Cys Leu
            20

<210> SEQ ID NO 81
<211> LENGTH: 45
<212> TYPE: PRT
<213> ORGANISM: Eucalyptus grandis

<400> SEQUENCE: 81

Met Lys His Ile Gln Arg Trp Arg Tyr Gly Glu Thr Ser Gly Arg Gln
1               5                   10                  15

Gly Asp Trp Lys Arg Leu Glu Ile Lys Val His Ser Asn Pro Ser Leu
            20                  25                  30

Lys Val Lys Lys Asn Thr Asn Asn Phe Ser Ser Ser Leu
        35                  40                  45

<210> SEQ ID NO 82
<211> LENGTH: 28
<212> TYPE: PRT
<213> ORGANISM: Gossypium raimondii

<400> SEQUENCE: 82

Met Ile His Phe Asn Leu Ser Gln Trp Arg Ala Ile Cys Met Ala Asn
1               5                   10                  15

Phe His Leu Thr Tyr Ser Phe Leu Phe Gly Val Leu
            20                  25

<210> SEQ ID NO 83
<211> LENGTH: 21
<212> TYPE: PRT
```

```
<213> ORGANISM: Medicago truncatula

<400> SEQUENCE: 83

Met His Val Tyr Leu Glu Leu Phe Met Val Ile Lys Gly Leu Gly Phe
1               5                   10                  15

Leu Leu Leu Val Lys
            20

<210> SEQ ID NO 84
<211> LENGTH: 23
<212> TYPE: PRT
<213> ORGANISM: Oryza sativa

<400> SEQUENCE: 84

Met Glu Met Ile Gln Arg Pro Cys Leu Ile Leu Lys Phe Phe Phe Lys
1               5                   10                  15

Leu Ser Thr Leu Tyr Ile Pro
            20

<210> SEQ ID NO 85
<211> LENGTH: 38
<212> TYPE: PRT
<213> ORGANISM: Physcomitrella patens

<400> SEQUENCE: 85

Met Phe His Arg Arg Arg Ser Ser Val Leu Leu Pro Pro Phe Gly Gln
1               5                   10                  15

Thr Gln Pro Asn Pro Arg Cys Leu Pro Asp Leu Arg Phe Pro Ser Cys
            20                  25                  30

Phe Thr Pro Cys Thr Ala
        35

<210> SEQ ID NO 86
<211> LENGTH: 42
<212> TYPE: PRT
<213> ORGANISM: Thellungiella halophila

<400> SEQUENCE: 86

Met Thr Ile Cys Lys Val Ser Lys Ala Cys Phe Tyr Ala Gly Lys Ile
1               5                   10                  15

Glu Asn Ser Arg Leu Ile Lys Lys Ile Gly Ile Pro Lys Arg Glu Gly
            20                  25                  30

Ala Pro Phe Ser Pro Ile Arg Glu Asn Gln
        35                  40

<210> SEQ ID NO 87
<211> LENGTH: 37
<212> TYPE: PRT
<213> ORGANISM: Thellungiella halophila

<400> SEQUENCE: 87

Met Glu Ile Gln Ile Lys Lys Lys Asn Leu Tyr Ile Met Asn Thr Gln
1               5                   10                  15

Lys Leu Pro Asn Leu Tyr Ile Tyr Ile Tyr Lys Tyr Val Phe Ile Lys
            20                  25                  30

Leu Met Val Val Glu
        35

<210> SEQ ID NO 88
<211> LENGTH: 43
<212> TYPE: PRT
```

-continued

<213> ORGANISM: Arabidopsis thaliana

<400> SEQUENCE: 88

Met Val Pro Gln Ile Asn Leu Trp Ser Ser Arg Val Ile Leu Lys Ile
1               5                   10                  15

Arg Ile Asp Ser Ser Thr His Arg Glu Glu Asp His Cys Ile Gln Asn
            20                  25                  30

His Lys His Gly Leu Ser Phe Ile Phe Ser Phe
        35                  40

<210> SEQ ID NO 89
<211> LENGTH: 16
<212> TYPE: PRT
<213> ORGANISM: Arabidopsis thaliana

<400> SEQUENCE: 89

Met Ser Leu Gln Phe Tyr Glu Arg Val Ser Phe Lys Asn Thr Val Lys
1               5                   10                  15

<210> SEQ ID NO 90
<211> LENGTH: 12
<212> TYPE: PRT
<213> ORGANISM: Arabidopsis thaliana

<400> SEQUENCE: 90

Met Thr Glu Gln Glu Glu Glu Ser Gln Met Ser Thr
1               5                   10

<210> SEQ ID NO 91
<211> LENGTH: 39
<212> TYPE: PRT
<213> ORGANISM: Arabidopsis thaliana

<400> SEQUENCE: 91

Met Tyr Leu Gln Tyr Ile Asp Asn Val Ile Ser Ile Tyr Ser Asn Asn
1               5                   10                  15

Arg Arg Val Gly Arg Met Phe Ser Arg Val Pro Leu Ser Thr Ser Leu
            20                  25                  30

Glu Ile Gln Phe Phe Ile Lys
        35

<210> SEQ ID NO 92
<211> LENGTH: 12
<212> TYPE: PRT
<213> ORGANISM: Arabidopsis thaliana

<400> SEQUENCE: 92

Met Ser Lys Glu Ile Phe Phe Ser Pro Gly Phe Glu
1               5                   10

<210> SEQ ID NO 93
<211> LENGTH: 44
<212> TYPE: PRT
<213> ORGANISM: Arabidopsis thaliana

<400> SEQUENCE: 93

Met Arg Thr His Glu Gln Ser Thr Ala Ile Thr Thr Leu Arg His Cys
1               5                   10                  15

Tyr Ser Ser Arg Phe Met Cys Ser Gln Val Thr Pro Ala Glu Leu Phe
            20                  25                  30

Leu Tyr Arg Pro Cys Phe Ile Asn Ala Val Ala Arg
        35                  40

```
<210> SEQ ID NO 94
<211> LENGTH: 5
<212> TYPE: PRT
<213> ORGANISM: Arabidopsis thaliana

<400> SEQUENCE: 94

Met Lys Arg Asn Met
1               5

<210> SEQ ID NO 95
<211> LENGTH: 5
<212> TYPE: PRT
<213> ORGANISM: Arabidopsis thaliana

<400> SEQUENCE: 95

Met Gln Cys Glu Ile
1               5

<210> SEQ ID NO 96
<211> LENGTH: 4
<212> TYPE: PRT
<213> ORGANISM: Arabidopsis thaliana

<400> SEQUENCE: 96

Met Phe Cys Ala
1

<210> SEQ ID NO 97
<211> LENGTH: 6
<212> TYPE: PRT
<213> ORGANISM: Arabidopsis thaliana

<400> SEQUENCE: 97

Met Val Met Ala His His
1               5

<210> SEQ ID NO 98
<211> LENGTH: 54
<212> TYPE: PRT
<213> ORGANISM: Arabidopsis thaliana

<400> SEQUENCE: 98

Met Met Lys Pro Arg Trp Asn Cys Ser Leu Tyr Gly Ile Thr Glu Trp
1               5                   10                  15

Thr Asn Asn Gln Asn Gln Lys Ser Lys Arg Lys Gly Arg Arg Lys Thr
            20                  25                  30

Gln Ile Trp Arg Ile Gly Asp Arg Leu Asp Thr Val Glu Cys Ile Thr
        35                  40                  45

Leu Met Leu Ser Ala Tyr
    50

<210> SEQ ID NO 99
<211> LENGTH: 10
<212> TYPE: PRT
<213> ORGANISM: Arabidopsis thaliana

<400> SEQUENCE: 99

Met Leu Leu Ile Ile Val Glu Leu Val Leu
1               5                   10

<210> SEQ ID NO 100
<211> LENGTH: 14
```

-continued

```
<212> TYPE: PRT
<213> ORGANISM: Arabidopsis thaliana

<400> SEQUENCE: 100

Met Leu Cys Phe Asn Phe Arg Cys Val Arg Arg Phe Ala Glu
1               5                   10

<210> SEQ ID NO 101
<211> LENGTH: 36
<212> TYPE: PRT
<213> ORGANISM: Arabidopsis thaliana

<400> SEQUENCE: 101

Met Tyr Thr Tyr Gln Leu Asp Asn Ser Phe Ser Trp Phe Leu Cys Thr
1               5                   10                  15

Arg Phe Cys Leu Tyr Arg Tyr Phe Leu Phe Asn Phe Arg Cys Phe Arg
                20                  25                  30

Arg Phe Ser Glu
        35

<210> SEQ ID NO 102
<211> LENGTH: 88
<212> TYPE: PRT
<213> ORGANISM: Drosophila melanogaster

<400> SEQUENCE: 102

Met Trp Arg Glu Val Cys Ala Gln Lys Ser Gln Thr Lys Arg Arg Asn
1               5                   10                  15

Phe Ile Thr Gly Asn Gln Arg Arg Asn Lys Thr Lys Ala Asn Arg Lys
                20                  25                  30

Ala Glu Thr Lys Gln Gln Lys Val Tyr Glu Phe Phe Val Gln Ala Arg
            35                  40                  45

Glu Arg Cys Lys Thr Arg Lys Lys His Glu Lys Lys Thr Leu Lys Lys
        50                  55                  60

Thr Lys Lys Ile Gln Asn Arg Tyr Arg Ala Val Ser Glu Asn Glu Trp
65                  70                  75                  80

Gly Lys Gly Phe Pro Ser His Ile
                85

<210> SEQ ID NO 103
<211> LENGTH: 36
<212> TYPE: PRT
<213> ORGANISM: Drosophila melanogaster

<400> SEQUENCE: 103

Met Arg Thr Lys Lys Ser Asn Lys Lys Ala Gln Phe Tyr Tyr Gly Gln
1               5                   10                  15

Pro Thr Thr Lys Gln Asn Lys Ser Gln Pro Lys Ser Arg Asn Lys Ala
                20                  25                  30

Ala Lys Ser Leu
        35

<210> SEQ ID NO 104
<211> LENGTH: 71
<212> TYPE: PRT
<213> ORGANISM: Drosophila melanogaster

<400> SEQUENCE: 104

Met Glu Pro Gly Phe Val Phe Val Leu Phe Pro Thr His Leu Ser Thr
1               5                   10                  15
```

```
Gln His Thr Gln Arg Glu Lys Ser Ile Leu Val Met Gly Leu Asn Leu
            20                  25                  30

Gln Ser Ala Lys Gln Ser Asp Lys Gln Asn Ser Lys Glu Arg Lys Lys
        35                  40                  45

Asn Thr Gln Ile Asn Ser Gln Arg Ile Pro Tyr Arg Gln Gly Gly Gln
    50                  55                  60

Cys Ser Lys Val Leu Ser Pro
65                  70

<210> SEQ ID NO 105
<211> LENGTH: 92
<212> TYPE: DNA
<213> ORGANISM: Arabidopsis thaliana

<400> SEQUENCE: 105
atgttctgtt caattcaatg cgtcgccaga catctgttcc ctttgcatgt aagagagata    60
aagaaagcga caagagccat aaagaaaggt aa                                  92

<210> SEQ ID NO 106
<211> LENGTH: 75
<212> TYPE: DNA
<213> ORGANISM: Arabidopsis thaliana

<400> SEQUENCE: 106
atgcgtcgcc agacatctgt tccctttgca tgtaagagag ataaagaaag cgacaagagc    60
cataaagaaa ggtaa                                                     75

<210> SEQ ID NO 107
<211> LENGTH: 114
<212> TYPE: DNA
<213> ORGANISM: Arabidopsis thaliana

<400> SEQUENCE: 107
atggttatgt ttttctcga tttagacaaa aaccctagat tgatcttct aaagggtctc      60 aaatggaatc tcttctcttc tcatatctct ccctctctcc ctccctctct ttga         114

<210> SEQ ID NO 108
<211> LENGTH: 36
<212> TYPE: DNA
<213> ORGANISM: Arabidopsis thaliana

<400> SEQUENCE: 108
atgaaggaca actttcctct tctccttcgg ttataa                              36

<210> SEQ ID NO 109
<211> LENGTH: 15
<212> TYPE: DNA
<213> ORGANISM: Arabidopsis thaliana

<400> SEQUENCE: 109
atgagtgatg actga                                                     15

<210> SEQ ID NO 110
<211> LENGTH: 51
<212> TYPE: DNA
<213> ORGANISM: Arabidopsis thaliana

<400> SEQUENCE: 110
atgatatata taaataaata tgggtcgata tcggctgtgg aggacgacta g              51
```

```
<210> SEQ ID NO 111
<211> LENGTH: 15
<212> TYPE: DNA
<213> ORGANISM: Arabidopsis thaliana

<400> SEQUENCE: 111
atgagccaaa gataa                                                          15

<210> SEQ ID NO 112
<211> LENGTH: 51
<212> TYPE: DNA
<213> ORGANISM: Arabidopsis lyrata

<400> SEQUENCE: 112
atgacgtgtc ctcttctctc tctctctttc cttctctcta agtatattta g                  51

<210> SEQ ID NO 113
<211> LENGTH: 51
<212> TYPE: DNA
<213> ORGANISM: Arabidopsis thaliana

<400> SEQUENCE: 113
atgacgtggc ctcttctctc tctctctttc cttctctcta agtatgttta g                  51

<210> SEQ ID NO 114
<211> LENGTH: 53
<212> TYPE: DNA
<213> ORGANISM: Capsella rubella

<400> SEQUENCE: 114
atgacgtgta ctctctctgc tctatctctc tctctaaata tgtttagggt taa                53

<210> SEQ ID NO 115
<211> LENGTH: 18
<212> TYPE: DNA
<213> ORGANISM: Arabidopsis thaliana

<400> SEQUENCE: 115
atgttttatc tttcataa                                                       18

<210> SEQ ID NO 116
<211> LENGTH: 114
<212> TYPE: DNA
<213> ORGANISM: Arabidopsis thaliana

<400> SEQUENCE: 116
atggttaata ctagtagctt tttcatttca agttttatcc ttccattggt tctttctgag         60
tcaaattgtc tcctgtttcg aaccatatat aagttttcaa tggttttgta ttaa              114

<210> SEQ ID NO 117
<211> LENGTH: 75
<212> TYPE: DNA
<213> ORGANISM: Arabidopsis thaliana

<400> SEQUENCE: 117
atgttttgtt tgttgattcc catcttctct tttgtctttt caccaaatcg tcatttaagg         60
cttcaagaac agtaa                                                          75

<210> SEQ ID NO 118
<211> LENGTH: 18
<212> TYPE: DNA
<213> ORGANISM: Arabidopsis thaliana
```

```
<400> SEQUENCE: 118
atgttttccc ctcaatga                                                   18

<210> SEQ ID NO 119
<211> LENGTH: 72
<212> TYPE: DNA
<213> ORGANISM: Arabidopsis thaliana

<400> SEQUENCE: 119
atgaaataca tacacatttt gattttattt aaatcaagat cgacgtataa gctatccacc     60
aatcatattt aa                                                         72

<210> SEQ ID NO 120
<211> LENGTH: 33
<212> TYPE: DNA
<213> ORGANISM: Arabidopsis thaliana

<400> SEQUENCE: 120
atgaaaattc cattgtttct gccgaagctt tga                                  33

<210> SEQ ID NO 121
<211> LENGTH: 84
<212> TYPE: DNA
<213> ORGANISM: Arabidopsis thaliana

<400> SEQUENCE: 121
atggtatctg gtcaagaaga ttcctggtta aaactttcat ctctctgttt ccttttttctt    60 tctttgttgg attcattaat ttga                                            84

<210> SEQ ID NO 122
<211> LENGTH: 105
<212> TYPE: DNA
<213> ORGANISM: Arabidopsis thaliana

<400> SEQUENCE: 122
atgtttcttt taatcttttt gagattaata atgatttgtg tttgttcatc aaccgatttt     60
ctcagatctg tcaattattt ttgtttattt atttatgatt tatga                     105

<210> SEQ ID NO 123
<211> LENGTH: 30
<212> TYPE: DNA
<213> ORGANISM: Arabidopsis thaliana

<400> SEQUENCE: 123
atgtccacta ctcaagagca taggtcttga                                      30

<210> SEQ ID NO 124
<211> LENGTH: 78
<212> TYPE: DNA
<213> ORGANISM: Arabidopsis thaliana

<400> SEQUENCE: 124
atgatactaa agtgctggag ttcccggttc ctgagagtga gtccatatca aaatgcgcat     60
tcgttatcac ttggttga                                                   78

<210> SEQ ID NO 125
<211> LENGTH: 42
<212> TYPE: DNA
<213> ORGANISM: Arabidopsis lyrata

<400> SEQUENCE: 125
```

```
atgcccttag cagttattag acaagggatt gtttggccct ag                42
```

<210> SEQ ID NO 126
<211> LENGTH: 75
<212> TYPE: DNA
<213> ORGANISM: Arabidopsis lyrata

<400> SEQUENCE: 126

```
atgccatcat ggcatgacat ggttcttttg ccttacgtaa aacacactca cgccaacaca    60
cgccacataa cataa                                                    75
```

<210> SEQ ID NO 127
<211> LENGTH: 27
<212> TYPE: DNA
<213> ORGANISM: Arabidopsis lyrata

<400> SEQUENCE: 127

```
atgacatggt tcttttgcct tacgtaa                                 27
```

<210> SEQ ID NO 128
<211> LENGTH: 114
<212> TYPE: DNA
<213> ORGANISM: Arabidopsis thaliana

<400> SEQUENCE: 128

```
atgccatcat ggcatggtat ggttcttttg ccttacgtaa aacacactca cgccagcaca    60
cacacacaca cacataacat atacggatgt gcgtgtgagc tagtcttcca ttaa         114
```

<210> SEQ ID NO 129
<211> LENGTH: 69
<212> TYPE: DNA
<213> ORGANISM: Arabidopsis thaliana

<400> SEQUENCE: 129

```
atggcatggt atggttcttt tgccttacgt aaaacacact cacgccagca cacacacaca    60
cacacataa                                                           69
```

<210> SEQ ID NO 130
<211> LENGTH: 27
<212> TYPE: DNA
<213> ORGANISM: Arabidopsis thaliana

<400> SEQUENCE: 130

```
atggtatggt tcttttgcct tacgtaa                                 27
```

<210> SEQ ID NO 131
<211> LENGTH: 24
<212> TYPE: DNA
<213> ORGANISM: Brassica rapa

<400> SEQUENCE: 131

```
atgatgataa ttttgtggaa ataa                                    24
```

<210> SEQ ID NO 132
<211> LENGTH: 75
<212> TYPE: DNA
<213> ORGANISM: Brassica rapa

<400> SEQUENCE: 132

```
atgctttggg ccaagctagt ttcttttagc actcttcact cactagtttt tcttctcagc    60
```

```
ccttcttttg cgtga                                                    75

<210> SEQ ID NO 133
<211> LENGTH: 120
<212> TYPE: DNA
<213> ORGANISM: Brassica rapa

<400> SEQUENCE: 133
atgccatcat ggcatggcat tgtcattttg cctttcgtaa aacacactca cgccaacata   60
cattattcat attcatgtgt atgtatatga atgccatcat ggcatatgcc atcatggcat  120

<210> SEQ ID NO 134
<211> LENGTH: 105
<212> TYPE: DNA
<213> ORGANISM: Carica papaya

<400> SEQUENCE: 134
atgattgcat gccatcccta cttgcctttt ccccttttcc tttctctaac attttactca   60
atcttcttct ccccctcccc ccttccccc tctctgccat tataa                   105

<210> SEQ ID NO 135
<211> LENGTH: 162
<212> TYPE: DNA
<213> ORGANISM: Carica papaya

<400> SEQUENCE: 135
atgccatccc tacttgcctt ttcccctttt cctttctcta acattttact caatcttctt   60 ctcccccctcc cccccttccc cctctctgcc attataacca taattaaacc tctctccctc  120
tctctccctc tctctctctc tctctctggg ttctcagtat aa                     162

<210> SEQ ID NO 136
<211> LENGTH: 48
<212> TYPE: DNA
<213> ORGANISM: Capsella rubella

<400> SEQUENCE: 136
atggaattaa aaggtttgag aacttggcag ttattagaca aggtatag                48

<210> SEQ ID NO 137
<211> LENGTH: 45
<212> TYPE: DNA
<213> ORGANISM: Capsella rubella

<400> SEQUENCE: 137
atgccatcat ggcatggcat ggcatgtttc tattgcctta cgtaa                   45

<210> SEQ ID NO 138
<211> LENGTH: 90
<212> TYPE: DNA
<213> ORGANISM: Capsella rubella

<400> SEQUENCE: 138
atggcatggc atgtttctat tgccttacgt aaaacacact cacgccaaca catactcact   60
atacatgtaa ataagtatgt gcgcgtgtga                                    90

<210> SEQ ID NO 139
<211> LENGTH: 108
<212> TYPE: DNA
<213> ORGANISM: Gossypium raimondii

<400> SEQUENCE: 139
```

```
atgatgagat caagaattt aaagtttcaa tatagatttg gcatgggtat tggcggcaga    60
aagcaattaa aaaccagtt atgtcaaatt caaggtcgta tcagttaa              108
```

<210> SEQ ID NO 140
<211> LENGTH: 33
<212> TYPE: DNA
<213> ORGANISM: Gossypium raimondii

<400> SEQUENCE: 140

```
atgtcaaatt caaggtcgta tcagttaaaa tga                                33
```

<210> SEQ ID NO 141
<211> LENGTH: 54
<212> TYPE: DNA
<213> ORGANISM: Gossypium raimondii

<400> SEQUENCE: 141

```
atgaatgaag atttagaaat ttcaacaagg aagaggaccc cacagctttg ttaa         54
```

<210> SEQ ID NO 142
<211> LENGTH: 39
<212> TYPE: DNA
<213> ORGANISM: Medicago truncatula

<400> SEQUENCE: 142

```
atgcccaaat ttgatatttt tttttatata tttgtatag                          39
```

<210> SEQ ID NO 143
<211> LENGTH: 231
<212> TYPE: DNA
<213> ORGANISM: Medicago truncatula

<400> SEQUENCE: 143

```
atgtcatata tctctctctc tcctaagttg ctacctataa atactaagcc tttcccttgg   60
ttggttcaat tcaacttcta cttctcatca aacacaaagt gcaataagct tcatttcctg  120
ggtgagaagc tccttgttgg agaagcaggg cacgtgcaaa tcctctttct gattcattct  180
ctcataatgc atatcaatat cttttgcacg tgctccccct tcccaactag g           231
```

<210> SEQ ID NO 144
<211> LENGTH: 63
<212> TYPE: DNA
<213> ORGANISM: Oryza sativa

<400> SEQUENCE: 144

```
atgcaaaccc actccaacac tccacaatcc acatactctc tctctctctc tctctctgag   60
tag                                                                 63
```

<210> SEQ ID NO 145
<211> LENGTH: 48
<212> TYPE: DNA
<213> ORGANISM: Oryza sativa

<400> SEQUENCE: 145

```
atgtgtgtgt gtgatatcaa tatgcattcg atgttgatgc tactgtag                48
```

<210> SEQ ID NO 146
<211> LENGTH: 78
<212> TYPE: DNA
<213> ORGANISM: Arabidopsis lyrata

```
<400> SEQUENCE: 146
atgagaatta agctatttca gttgaggga atgttgtctg gatcgaggat attatacata        60
tatacatgtg tatgttga                                                      78

<210> SEQ ID NO 147
<211> LENGTH: 57
<212> TYPE: DNA
<213> ORGANISM: Arabidopsis thaliana

<400> SEQUENCE: 147
atgagggtta agctatttca gttgaggga atgttgtctg gatcgaggat attatag            57

<210> SEQ ID NO 148
<211> LENGTH: 111
<212> TYPE: DNA
<213> ORGANISM: Brassica carinata

<400> SEQUENCE: 148
atgagaatga agctatttca gttgaggga atgttgtctg gatcgaggat attatatata        60
cacaaatacg tatatatgtt aatacaagtg tttgatcata tatgtatata g                111

<210> SEQ ID NO 149
<211> LENGTH: 84
<212> TYPE: DNA
<213> ORGANISM: Brassica juncea

<400> SEQUENCE: 149
atgagaatga agctatttca gttgaggga atgttgtctg gatcgaggat attatatata        60
cacaaatatg tatatatatg ttaa                                               84

<210> SEQ ID NO 150
<211> LENGTH: 111
<212> TYPE: DNA
<213> ORGANISM: Brassica napus

<400> SEQUENCE: 150
atgagaatga agctatttca gttgaggga atgttgtctg gatcgaggat attatatata        60
cacaaatacg tatatatgat aatacaagtg tttgatcata tatgtatata g                111

<210> SEQ ID NO 151
<211> LENGTH: 111
<212> TYPE: DNA
<213> ORGANISM: Brassica oleracea

<400> SEQUENCE: 151
atgagaatga agctatttca gttgaggga atgttgtctg gatcgaggat attatatata        60
cacaagtacg tatatatgtt aatacaagtg tttgatcata tatgtatata g                111

<210> SEQ ID NO 152
<211> LENGTH: 84
<212> TYPE: DNA
<213> ORGANISM: Brassica rapa

<400> SEQUENCE: 152
atgagaatga agctatttca gttgaggga atgttgtctg gatcgaggat attatatata        60
cacaaatatg tatatatatg ttaa                                               84

<210> SEQ ID NO 153
<211> LENGTH: 60
```

```
<212> TYPE: DNA
<213> ORGANISM: Arabidopsis thaliana

<400> SEQUENCE: 153
atgttggatc tctttcgatc taacaatcga attgaacctt cagatttcag atttgattag    60

<210> SEQ ID NO 154
<211> LENGTH: 15
<212> TYPE: DNA
<213> ORGANISM: Arabidopsis thaliana

<400> SEQUENCE: 154
atgagagata gataa                                                     15

<210> SEQ ID NO 155
<211> LENGTH: 33
<212> TYPE: DNA
<213> ORGANISM: Arabidopsis thaliana

<400> SEQUENCE: 155
atgaacagaa aaatctctct ttctctttct tga                                 33

<210> SEQ ID NO 156
<211> LENGTH: 27
<212> TYPE: DNA
<213> ORGANISM: Arabidopsis thaliana

<400> SEQUENCE: 156
atgatgggtt gttttgtggg attttaa                                        27

<210> SEQ ID NO 157
<211> LENGTH: 27
<212> TYPE: DNA
<213> ORGANISM: Arabidopsis thaliana

<400> SEQUENCE: 157
atgcaggagg aaacatatga ggggtga                                        27

<210> SEQ ID NO 158
<211> LENGTH: 180
<212> TYPE: DNA
<213> ORGANISM: Arabidopsis thaliana

<400> SEQUENCE: 158
atgccacata caaacttgaa agatctcttc atcttttctc caaatgtttt ttttcgttt     60 gctatttatc tccacaattc ttggaacaaa aactacattc acaaacgaga gaattttcac   120
aacacctctt tgctctcat ttttttttt tcgtccatta tgagtattaa ttatggttag     180

<210> SEQ ID NO 159
<211> LENGTH: 120
<212> TYPE: DNA
<213> ORGANISM: Arabidopsis thaliana

<400> SEQUENCE: 159
atgttttttt ttcgtttgct atttatctcc acaattcttg gaacaaaaac tacattcaca    60
aacgagagaa ttttcacaac acctcttttg ctctcatttt ttttttttcg tccattatga   120

<210> SEQ ID NO 160
<211> LENGTH: 21
<212> TYPE: DNA
<213> ORGANISM: Arabidopsis thaliana
```

```
<400> SEQUENCE: 160
atgagacata aagagagtta a                                              21

<210> SEQ ID NO 161
<211> LENGTH: 105
<212> TYPE: DNA
<213> ORGANISM: Arabidopsis thaliana

<400> SEQUENCE: 161
atgaacctcc tcaagaagga agacagagg aggagacaaa gaagtatagg ttcacattgc     60
atagccagtt tagttttgaa ggatggatat atgaaaaaaa tatga                  105

<210> SEQ ID NO 162
<211> LENGTH: 30
<212> TYPE: DNA
<213> ORGANISM: Arabidopsis thaliana

<400> SEQUENCE: 162
atggttctct ccggtaaatt aacattttag                                     30

<210> SEQ ID NO 163
<211> LENGTH: 63
<212> TYPE: DNA
<213> ORGANISM: Medicago truncatula

<400> SEQUENCE: 163
atgcttcttc ataggctctc caaattttgc aaaattgaaa gagacatagt atatatatct    60
tag                                                                  63

<210> SEQ ID NO 164
<211> LENGTH: 18
<212> TYPE: DNA
<213> ORGANISM: Medicago truncatula

<400> SEQUENCE: 164
atgaagattg aagagtaa                                                  18

<210> SEQ ID NO 165
<211> LENGTH: 105
<212> TYPE: DNA
<213> ORGANISM: Zea mays

<400> SEQUENCE: 165
atgcatctgc ttcaactcc ctctcgcccc ccacccaac acacatctct ctcttttcta      60
gggaaggaaa tgacgaaggg gacgacgacg gcatgcttcg gctag                   105

<210> SEQ ID NO 166
<211> LENGTH: 33
<212> TYPE: DNA
<213> ORGANISM: Arabidopsis thaliana

<400> SEQUENCE: 166
atgttgtctc tttctcattt tcatatctgc taa                                 33

<210> SEQ ID NO 167
<211> LENGTH: 72
<212> TYPE: DNA
<213> ORGANISM: Medicago truncatula

<400> SEQUENCE: 167
atgatggtgt ttgggaagcc gaaaaaagcg atgttggtga ggttcaatcc gaagacggat    60
```
ttacatgtat ag 72

<210> SEQ ID NO 168
<211> LENGTH: 33
<212> TYPE: DNA
<213> ORGANISM: Medicago truncatula

<400> SEQUENCE: 168
atggcttcag ctgcaaaagt atacatggcg tga 33

<210> SEQ ID NO 169
<211> LENGTH: 21
<212> TYPE: DNA
<213> ORGANISM: Arabidopsis thaliana

<400> SEQUENCE: 169
atggcttcca agatctggta a 21

<210> SEQ ID NO 170
<211> LENGTH: 33
<212> TYPE: DNA
<213> ORGANISM: Arabidopsis thaliana

<400> SEQUENCE: 170
atggttaggt tccaactaag tatacgagat taa 33

<210> SEQ ID NO 171
<211> LENGTH: 39
<212> TYPE: DNA
<213> ORGANISM: Arabidopsis thaliana

<400> SEQUENCE: 171
atgtgtacgt actattatct cataaataaa tatttttaa 39

<210> SEQ ID NO 172
<211> LENGTH: 36
<212> TYPE: DNA
<213> ORGANISM: Arabidopsis thaliana

<400> SEQUENCE: 172
atgtttccag caaaatggtg ccgtcttgag tcttga 36

<210> SEQ ID NO 173
<211> LENGTH: 69
<212> TYPE: DNA
<213> ORGANISM: Arabidopsis thaliana

<400> SEQUENCE: 173
atgggatctc tctctttatt taaaagtcaa ttagagatct tgatgctact tctgtccctt 60
tccaagtga 69

<210> SEQ ID NO 174
<211> LENGTH: 63
<212> TYPE: DNA
<213> ORGANISM: Arabidopsis thaliana

<400> SEQUENCE: 174
atgagtgtat atattcatgt acctatctct ctcaattgct tctcaccaaa atcatcttgc 60
tga 63

<210> SEQ ID NO 175

```
<211> LENGTH: 36
<212> TYPE: DNA
<213> ORGANISM: Arabidopsis thaliana

<400> SEQUENCE: 175
atgggagttc caactttag acctcgaaac cgataa                                    36

<210> SEQ ID NO 176
<211> LENGTH: 72
<212> TYPE: DNA
<213> ORGANISM: Arabidopsis cebennensis

<400> SEQUENCE: 176
atgagatcta gggtttcttt cttttcttc aaaatcatgc ttttcgctt gctaggttat          60 agatccatgt aa                                                             72

<210> SEQ ID NO 177
<211> LENGTH: 134
<212> TYPE: DNA
<213> ORGANISM: Arabidopsis cebennensis

<400> SEQUENCE: 177
atgcatacat acatacatac catctctaat atttcatcaa tcttcttttg ttccaaacgc        60
ctttctctcc atttacatac atacgaatca ttgttgtcat agatccgttt agaattgctt       120
taacttttag atga                                                          134

<210> SEQ ID NO 178
<211> LENGTH: 69
<212> TYPE: DNA
<213> ORGANISM: Arabidopsis halleri

<400> SEQUENCE: 178
atgagatcta gggtttcttt gtttctttcg ttttcttcaa attttgctgc atattctcca        60
agatcatga                                                                 69

<210> SEQ ID NO 179
<211> LENGTH: 147
<212> TYPE: DNA
<213> ORGANISM: Arabidospis lyrata

<400> SEQUENCE: 179
atgcatacat acataccatc atcatctttt cccatctcta atatttcatc agtcttcttt        60
tgttacaaac gctctttctc gccatataca tacataagaa tcattgttgt catagatccg       120
tttagaattg ctttaacttt tagatga                                            147

<210> SEQ ID NO 180
<211> LENGTH: 153
<212> TYPE: DNA
<213> ORGANISM: Arabidopsis thaliana

<400> SEQUENCE: 180
atgaatatac atacatacca tcatcttctt ttcccatctc tagttttca tcaatcttct         60 gatgttccaa acgctctatc tcttcatata catacatacg aatatattat tgttgtcata       120
gatccattta gaatcacttt agcttttaga tga                                    153

<210> SEQ ID NO 181
<211> LENGTH: 60
<212> TYPE: DNA
<213> ORGANISM: Arabidopsis thaliana
```

<400> SEQUENCE: 181
atgttccaaa cgctctatct cttcatatac atacatacga atatattatt gttgtcatag    60

<210> SEQ ID NO 182
<211> LENGTH: 138
<212> TYPE: DNA
<213> ORGANISM: Brassica rapa

<400> SEQUENCE: 182
atgtttaagc tctacttctc agcaattctc tccacccaat acatgcatac ataccatcat    60
cgtatcgctc taattttct atcaatcttg tatccttcca caaattatct tatgtctccc    120
attttaaatc ctacatag                                                 138

<210> SEQ ID NO 183
<211> LENGTH: 63
<212> TYPE: DNA
<213> ORGANISM: Carica papaya

<400> SEQUENCE: 183
atgaagatta aattaggttt tagtcttatt aagattatta tattactaga caaaaacagt    60
taa                                                                 63

<210> SEQ ID NO 184
<211> LENGTH: 66
<212> TYPE: DNA
<213> ORGANISM: Capsella rubella

<400> SEQUENCE: 184
atgcatccac atacatacat acatatacca tcatcttctt ttctcatctc tagttttgt     60 ttataa                                                              66

<210> SEQ ID NO 185
<211> LENGTH: 138
<212> TYPE: DNA
<213> ORGANISM: Eucalyptus grandis

<400> SEQUENCE: 185
atgaagcata ttcaaaggtg gagatatggg gagacttccg gaaggcaagg ggattggaaa    60
aggctcgaga tcaaagtgca tagcaacccct tcgctaaagg tgaaaagaa tacgaataac    120 ttcagtagct cactttaa                                                 138

<210> SEQ ID NO 186
<211> LENGTH: 87
<212> TYPE: DNA
<213> ORGANISM: Gossypium raimondii

<400> SEQUENCE: 186
atgatccatt tcaacctgtc acagtggaga gcaatttgta tggctaattt ccatctcacc    60 tattctttc tgtttggggt tctctag                                        87

<210> SEQ ID NO 187
<211> LENGTH: 66
<212> TYPE: DNA
<213> ORGANISM: Medicago truncatula

<400> SEQUENCE: 187
atgcatgtat atcttgaatt gtttatggta ataaaggggt taggatttct ccttttggtg    60
aagtga                                                                        66

<210> SEQ ID NO 188
<211> LENGTH: 72
<212> TYPE: DNA
<213> ORGANISM: Oryza sativa

<400> SEQUENCE: 188
atggaaatga tacaaaggcc gtgtttaatt ttaaaatttt ttttcaaact ttcaacactt    60
tacatcccat aa                                                        72

<210> SEQ ID NO 189
<211> LENGTH: 117
<212> TYPE: DNA
<213> ORGANISM: Physcomitrella patens

<400> SEQUENCE: 189
atgttccacc gtcggagatc ctcggtgctg ctaccccgt tcggccaaac ccaacccaac    60
cctaggtgtc tgccggacct ccgcttcccc tcctgcttca cccctgcac cgcttaa      117

<210> SEQ ID NO 190
<211> LENGTH: 129
<212> TYPE: DNA
<213> ORGANISM: Thellungiella halophila

<400> SEQUENCE: 190
atgacgatat gtaaagtaag caaggcatgt ttttatgcag ggaagattga aaattcaaga    60
ttaatcaaga aaattggaat accaaaaaga gagggagctc ccttcagtcc aatcagagag  120
aatcaatga                                                           129

<210> SEQ ID NO 191
<211> LENGTH: 114
<212> TYPE: DNA
<213> ORGANISM: Thellungiella halophila

<400> SEQUENCE: 191
atggagattc aaattaaaaa gaaaaactta tatataatga atacacaaaa gctacctaat    60
ctgtatatat atatatataa atatgtcttc attaaattaa tggtcgtgga atag         114

<210> SEQ ID NO 192
<211> LENGTH: 132
<212> TYPE: DNA
<213> ORGANISM: Arabidopsis thaliana

<400> SEQUENCE: 192
atggtacctc aaattaatct atggtcatct agggttatct tgaagattag aattgattct    60
agcacgcaca gagaggaaga tcattgcatc cagaatcaca aacatggcct atcttttatc   120
ttttcttttt ga                                                       132

<210> SEQ ID NO 193
<211> LENGTH: 51
<212> TYPE: DNA
<213> ORGANISM: Arabidopsis thaliana

<400> SEQUENCE: 193
atgtctctcc aattttatga gagggtttcc ttcaagaaca cagtaaaata g              51

<210> SEQ ID NO 194
<211> LENGTH: 39

```
<212> TYPE: DNA
<213> ORGANISM: Arabidopsis thaliana

<400> SEQUENCE: 194
atgacagagc aagaagaaga aagtcaaatg tccacatga                              39

<210> SEQ ID NO 195
<211> LENGTH: 120
<212> TYPE: DNA
<213> ORGANISM: Arabidopsis thaliana

<400> SEQUENCE: 195
atgtatctac aatatattga taatgtaata tctatatatt caaacaatcg tcgtgttggt      60
cggatgtttt ctagagttcc tctgagcact tcattggaga tacaattttt tataaaatag    120

<210> SEQ ID NO 196
<211> LENGTH: 39
<212> TYPE: DNA
<213> ORGANISM: Arabidopsis thaliana

<400> SEQUENCE: 196
atgagcaagg agatattttt ttcccctggg tttgaatga                              39

<210> SEQ ID NO 197
<211> LENGTH: 133
<212> TYPE: DNA
<213> ORGANISM: Arabidopsis thaliana

<400> SEQUENCE: 197
atgagaacac acgagcaatc aacggctata acgacgctac gtcattgtta cagctctcgt      60
ttcatgtgtt ctcaggtcac ccctgctgag ctctttctct accgtccatg ttttatcaac    120
gccgtggccc gtg                                                        133

<210> SEQ ID NO 198
<211> LENGTH: 18
<212> TYPE: DNA
<213> ORGANISM: Arabidopsis thaliana

<400> SEQUENCE: 198
atgaagagaa acatgtaa                                                    18

<210> SEQ ID NO 199
<211> LENGTH: 18
<212> TYPE: DNA
<213> ORGANISM: Arabidopsis thaliana

<400> SEQUENCE: 199
atgcaatgtg aaatatga                                                    18

<210> SEQ ID NO 200
<211> LENGTH: 15
<212> TYPE: DNA
<213> ORGANISM: Arabidopsis thaliana

<400> SEQUENCE: 200
atgttttgtg cttga                                                       15

<210> SEQ ID NO 201
<211> LENGTH: 21
<212> TYPE: DNA
<213> ORGANISM: Arabidopsis thaliana
```

```
<400> SEQUENCE: 201
atggtcatgg ctcatcatta g                                               21

<210> SEQ ID NO 202
<211> LENGTH: 165
<212> TYPE: DNA
<213> ORGANISM: Arabidopsis thaliana

<400> SEQUENCE: 202
atgatgaaac ctcgatggaa ctgctctctt tatggaatca cggaatggac aaataatcaa     60
aatcagaaat cgaagcgaaa agggaggaga aaaacgcaga tttggaggat tggggacaga    120
ttagatactg ttgaatgcat cactctaatg ctatcagcct attaa                    165

<210> SEQ ID NO 203
<211> LENGTH: 33
<212> TYPE: DNA
<213> ORGANISM: Arabidopsis thaliana

<400> SEQUENCE: 203
atgctgctta tcatcgtgga gttggttctg taa                                  33

<210> SEQ ID NO 204
<211> LENGTH: 45
<212> TYPE: DNA
<213> ORGANISM: Arabidopsis thaliana

<400> SEQUENCE: 204
atgctttgtt tcaatttcag gtgcgttaga aggtttgcag agtag                     45

<210> SEQ ID NO 205
<211> LENGTH: 108
<212> TYPE: DNA
<213> ORGANISM: Arabidopsis thaliana

<400> SEQUENCE: 205
atgtacacct accagcttga taactctttt tcgtggtttc tgtgtactcg tttctgtttg     60
tacagatact tcttgttcaa tttcagatgc tttagaaggt tttcggag                 108

<210> SEQ ID NO 206
<211> LENGTH: 267
<212> TYPE: DNA
<213> ORGANISM: Drosophila melanogaster

<400> SEQUENCE: 206
atgtggcgcg aagtatgcgc acaaaaaagt caaacaaaaa ggcgcaattt tattacgggc     60
aaccaacgac gaaacaaaac aaaagccaac cgaaaagcag aaacaaagca gcaaaaagtt    120
tatgaatttt ttgtgcaggc gcgtgaaaga tgcaaaacga gaaaaaaaca tgaaaaaaaa    180
acattaaaaa aaacaaaaaa aatccaaaac agataccgag ctgtatccga aaacgagtgg    240
ggaaaggggt ttcccagtca catataa                                        267

<210> SEQ ID NO 207
<211> LENGTH: 111
<212> TYPE: DNA
<213> ORGANISM: Drosophila melanogaster

<400> SEQUENCE: 207
atgcgcacaa aaagtcaaa caaaaaggcg caatttttatt acgggcaacc aacgacgaaa     60
caaaacaaaa gccaaccgaa aagcagaaac aaagcagcaa aaagtttatg a            111
```

<210> SEQ ID NO 208
<211> LENGTH: 216
<212> TYPE: DNA
<213> ORGANISM: Drosophila melanogaster

<400> SEQUENCE: 208

```
atggagcctg gctttgtttt tgttttattt ccaacccact tgagcacaca gcacacacag    60
agagaaaaat caatactcgt tatgggatta aatttacaaa gcgcaaagca aagcgacaaa   120
caaaattcaa agaaagaaa aaaaaacact caaataaact cacaagaat tccttatcgc   180
caaggggggcc aatgttctaa ggttctttcg ccttga                              216
```

<210> SEQ ID NO 209
<211> LENGTH: 614
<212> TYPE: DNA
<213> ORGANISM: Arabidopsis thaliana

<400> SEQUENCE: 209

```
attcattgtt cactctcaaa tctcaagttc attgccattt ttaggtctct ctataaattc    60
aaatgttctg ttcaattcaa tgcgtcgcca gacatctgtt cccttttgcat gtaagagaga   120
taaagaaagc gacaagagcc ataaagaaag gtaagactct tgaaataga gagagataag   180
gttttctctt atcttcttct catcagatct ttgtttcttt accctcttc tttcttttt    240
ttgcttttta tggttatgtt ttttctcgat ttagacaaaa accctagatt tgatcttcta   300
aagggtctca aatggaatct cttctcttct catatctctc cctctctccc tccctctctt   360
tgattctttg tcttctccag ttaaaactca gatctaacac aaagcttaaa agattctcat   420
cgtttcttgt tttctttgtt tcatcttgta gatctctgaa gttggactaa ttgtgaatga   480
aagagttggg acaagagaaa cgcaaagaaa ctgacagaag agagtgagca cacaaaggca   540
atttgcatat cattgcactt gcttctcttg cgtgctcact gctctttctg tcagattccg   600
gtgctgatct cttt                                                      614
```

<210> SEQ ID NO 210
<211> LENGTH: 422
<212> TYPE: DNA
<213> ORGANISM: Arabidopsis thaliana

<400> SEQUENCE: 210

```
ctctgccttt agttctttct tttttggtaa tatatttatt tttcgttacg atttggtcaa    60
aaccctagat ttgttttcca aaagcatatc tgaaaatgaa ggacaacttt cctcttctcc   120
ttcggttata aatattctct ccggttttgc ttgtttaacc taaaagcctc agatctaact   180
ccaacacctt caaagtctgc ctcctttcca atcttctttc ttctgttcga tctctaatct   240
cagaatttgt gtcggtaagg taaaggtgat aatgagtgat gactgatgag ggagttttgg   300
gacaaatttt aagagaaacg catagaaact gacagaagag agtgagcaca caaaggcact   360
ttgcatgttc gatgcatttg cttctcttgc gtgctcactg ctctatctgt cagattccgg   420
ct                                                                   422
```

<210> SEQ ID NO 211
<211> LENGTH: 268
<212> TYPE: DNA
<213> ORGANISM: Arabidopsis thaliana

<400> SEQUENCE: 211

```
tcccacatcc aaagatagaa agatgtaagg tctagagtct tgttcttaat ccctaacag      60 aacaatgata tatataaata aatatgggtc gatatcggct gtggaggacg actagctacg    120
gtttcgagcc tggtcacatg cgtagagtgt gaaaggtaat taggaggtga cagaagagag    180
tgagcacaca tggtggtttc ttgcatgctt ttttgattag ggtttcatgc ttgaagctat    240
gtgtgcttac tctctctctg tcaccct                                       268

<210> SEQ ID NO 212
<211> LENGTH: 328
<212> TYPE: DNA
<213> ORGANISM: Arabidopsis thaliana

<400> SEQUENCE: 212
tcccacagcc aatgagccaa agataaagaa acacctatcc tataataatt tagagcaata     60
tacctccata atggaacatc tatatatata aaggtatccg tatatctcta tatattatat    120
tcattgagtt taaagtggct agggtttata gatgtatgtg atattaagag atatgaaaca    180
tatttgtcga cggtttgagt ggtgaggaat tgatggtgac agaagagagt gagcacacat    240
ggtggctttc ttgcatattt gaaggttcca tgcttgaagc tatgtgtgct cactctctat    300
ccgtcacccc cttctctccc tctccctc                                       328

<210> SEQ ID NO 213
<211> LENGTH: 592
<212> TYPE: DNA
<213> ORGANISM: Arabidopsis lyrata

<400> SEQUENCE: 213
aaaaaatgac gtgtcctctt ctctctctct ctttccttct ctctaagtat atttagggtt     60
aattattagg gttctttatc tctttcttca gtctttgaag tttcttcaat agctttaatt    120
gaagtgattt acctctctgg gtgtttttag tatatatatc atgtacatga tcgaatttct    180
ttctatccaa gttctcatca aaccttctca tgtttttgaag agttaaaggc tttatagttt    240
gcttaggtca gatccataac atactgtatt tgacaagttt ctttgtctca cgatagatct    300
tggtctgacc aaaatgattt tctcgagaaa aaaaaagatg gaagtagagc tccttgaagt    360
tcaaacgaga gttgagcagg gtaaagaaaa gctgctaagc tatggatccc ataagcccta    420
atccttataa agaaaaaaaa ggatttggtt atatggcttg catatctcag gagctttaac    480 ttgccccttta atggcttttta ctcttctttg gattgaaggg agctctacat cttctttcac    540
cttctctatt tttcttttctt tattttctcc tctacagtaa tttatttgga tt            592

<210> SEQ ID NO 214
<211> LENGTH: 599
<212> TYPE: DNA
<213> ORGANISM: Arabidopsis thaliana

<400> SEQUENCE: 214
ttccaaaaca tgacgtggcc tcttctctct ctctctttcc ttctctctaa gtatgtttag     60
ggttaataat tagggttcct cctctctttt gttctgtctt tatatctcct tcatagctct    120
aatgtaagag atttacctct tttggtgttt ttgttaatcc acgttctcat caaaactttc    180
tcattgtttt atgaagagtt aaaggtcttt acagtttgct tatgtcagat ccataatata    240
tttgacaaga tactttgttt ttcgatagat cttgatctga cgatggaagt agagctcctt    300
aaagttcaaa catgagttga gcagggtaaa gaaaagctgc taagctatgg atcccataag    360
ccctaatcct tgtaaagtaa aaaaggattt ggttatatgg attgcatatc tcaggagctt    420
```

```
taacttgccc tttaatggct tttactcttc tttggattga agggagctct acatcttctt    480
tcaccttctc tatttttat ttttctttat ttctactcaa caattattta ttcggattca    540
tctttaattt tccgttataa tttcttttg gtaaggatta ttcgctataa tttgagaat    599
```

<210> SEQ ID NO 215
<211> LENGTH: 623
<212> TYPE: DNA
<213> ORGANISM: Capsella rubella

<400> SEQUENCE: 215

```
ttccaacgaa tgacgtgtac tctctctgct ctatctctct ctctaaatat gtttagggtt     60
aattagggtt cttcatctgt ctctctctct ctctctcttc agagtcttta tagcttcttc    120
caagattttt aattgaaagt aatttacctc ttttggagtt ctgtacatat agaatatcag    180
gagtcgtgtt tcttttttat caaggttctc atctaacctt tatagtattt tcattagttg    240
ataaaggtct tcatagtttg cttagatcag atcttgtctt cgtcttttcg atagatcttg    300
ttctgtccaa tatacagtga ttttatttcg agagcaaaaa agatgagagg tagagctcct    360
tgaagttcaa acgagagttt agcagggtag agaaaagctg ctaagctatg gatcccataa    420
gccctaatcc ttgttaatga taaaggattt ggttatatgg cttgcatatc tcaggagctt    480
taacttgccc tttaattgct tttactcttc tttggattga agggagctct acatcttctt    540
tgacttctct ctctattaag tctttctta tttcttctc tacaatagtt gttttggatc    600
ggaagatctt taagtttccc tta                                          623
```

<210> SEQ ID NO 216
<211> LENGTH: 612
<212> TYPE: DNA
<213> ORGANISM: Arabidopsis thaliana

<400> SEQUENCE: 216

```
tttcactttt gttctcctcc tcccttttt tcttttcagg attcttcttt tctatgtttt     60
atctttcata atagatctga taattttgat ttttcactat atatattatg gttaatacta    120
gtagcttttt catttcaagt tttatccttc cattggttct ttctgagtca aattgtctcc    180
tgtttcgaac catatataag ttttcaatgg ttttgtatta actcaagtat tcaacattat    240
gtctctcttt tcttgcttg gatctctaat gctgttcata ttttaaagca taggtttagg    300
ttagatgcat gtaactgcca attaaagaa ggtcaagagt ttttttgattg tatgaatata    360 tgagttagtc aaagcagatc cacacgatta tatagaaaa caaggaaga agaagaggaa    420 gagctccttg aagttcaatg gagggtttag cagggtgaag taaagctgct aagctatgga    480
tcccataagc cttatcaaat tcaatataat tgatgataag gttttttta tggatgccat    540 atctcaggag ctttcactta cccctttaat ggcttcactc ttctttggat tgaagggagc    600
tcttcatctc tc                                                      612
```

<210> SEQ ID NO 217
<211> LENGTH: 515
<212> TYPE: DNA
<213> ORGANISM: Arabidopsis thaliana

<400> SEQUENCE: 217

```
catcccaccc ttaattgttt tatataaacc atttctcctc ctctctccat caccttcaat     60
ctctctcgat ctctctctgg atccccaatc tcacctccat gttttgtttg ttgattccca    120
```

```
tcttctcttt tgtcttttca ccaaatcgtc atttaaggct tcaagaacag taaccccaat      180
tcctccacaa gagggagaga aaacaaaaga tcttccaatt ccattctcgt acatgcaaat      240
cacaatccat gccatagatt gtttctattc ctccttattt attgcttgta tctgttcatg      300
catggaccag gtggagagag cattacttaa aaatagaatt agctatctgt tttaggcgaa      360
ttagtttcct tacataacca tgtatatgtc atgacgcata tacatatgta gatgtatatg      420
tattatatat gtatgcctgg ctccctgtat gccatatgct gagcccatcg agtatcgatg      480
acctccgtgg atggcgtatg aggagccatg catat                                515

<210> SEQ ID NO 218
<211> LENGTH: 276
<212> TYPE: DNA
<213> ORGANISM: Arabidopsis thaliana

<400> SEQUENCE: 218
actcataact ctccccaaat tcttgaccaa aaatatccgc cactttctct ctggttcatg       60
ttttcccctc aatgaaatac atacacattt tgattttatt taaatcaaga tcgacgtata      120
agctatccac caatcatatt taagggttcc cgtatacata tatactatat atatatatgg      180
aataatagtc gtgcctggct ccctgtatgc cacaagaaaa catcgattta gtttcaaaat      240
cgatcactag tggcgtacag agtagtcaag catgac                               276

<210> SEQ ID NO 219
<211> LENGTH: 243
<212> TYPE: DNA
<213> ORGANISM: Arabidopsis thaliana

<400> SEQUENCE: 219
ctctaactca tccttctctt ctatgaaaat tccattgttt ctgccgaagc tttgatcagt       60
acttctcttt tgcttgatct cggttttga ccagtttatt gcgtcgatca atgcattgaa      120
agtgactaca tcggggttcc gatttttttt gttcttcata tgatgaagcg gaaacagtaa      180
tcaaccctgg tttagtcact ttcactgcat taatcaatgc atttgtaaaa agagggaaaa      240
gca                                                                   243

<210> SEQ ID NO 220
<211> LENGTH: 537
<212> TYPE: DNA
<213> ORGANISM: Arabidopsis thaliana

<400> SEQUENCE: 220
ctagaagaaa aaaccagatc tataaagttt gttattaaaa gatagagaga gaggagggat       60
gtagtaggcc aataggcaaa tcagagaatc acaaatggta tctggtcaag aagattcctg      120
gttaaaactt tcatctctct gtttcctttt tctttctttg ttggattcat taatttgaca      180
tatctctatc atcacactga ttctcttct cccagtttgt ctgcagatgc atgtgtgtaa      240
tctagggtat atgttttttgt ccatttggtt tcataaggca ataaagatcc agctatttac      300
tacttgtggt atagattttg actgttgaat tttcagatct gatgtgtttc gtttgatccg      360
attcggaaaa tttatgtttc gttgacattt tggagtttag ttggaagaag agtgagagtc      420
gctggaggca gcggttcatc gatctcttcc tgtgaacaca ttaaaaatgt aaaagcatga      480
atagatcgat aaacctctgc atccagcgtt tgcctcttgt atctttctta ttgactt        537

<210> SEQ ID NO 221
<211> LENGTH: 261
```

```
<212> TYPE: DNA
<213> ORGANISM: Arabidopsis thaliana

<400> SEQUENCE: 221
ctgcatctat ccacctctct ctgtaaattt atctaaatgt ttcttttaat cttttgaga      60
ttaataatga tttgtgtttg ttcatcaacc gattttctca gatctgtcaa ttattttgt     120
ttatttattt atgatttatg aatgaggaaa gagtgaagtc gctggaggca gcggttcatc    180
gatcaattcc tgtgaatatt tatttttgtt tacaaaagca agaatcgatc gataaacctc    240
tgcatccagc gctgcttgct c                                              261

<210> SEQ ID NO 222
<211> LENGTH: 481
<212> TYPE: DNA
<213> ORGANISM: Arabidopsis thaliana

<400> SEQUENCE: 222
tatcacagtt ctcatcaaat atttgaaagt atcaaacaaa aaaggagag tgagaaaaat      60
aaagagagag atagagagag atcatgtcca ctactcaaga gcataggtct tgattggtgg    120
aagacaagta ccttagataa accgaccaaa acccggtgga taaatcgag ttccaacctc     180
ttcaacgaca acgatttcaa cactctcttc caggaacaac ttcctccagg cagatgatac    240
taaagtgctg gagttccgg ttcctgagag tgagtccata tcaaaatgcg cattcgttat     300
cacttggttg aacccatttg gggatttaaa tttggaggtg aaatggaacg cgtaattgat    360
gactcctacg tggaacctct tcttaggaag agcacggtcg aagaagtaac tgcgcagtgc    420
ttaaatcgta gatgctaaag tcgttgaaga ggacttggaa cttcgatatt atccccgtg    480
t                                                                    481

<210> SEQ ID NO 223
<211> LENGTH: 471
<212> TYPE: DNA
<213> ORGANISM: Arabidopsis lyrata

<400> SEQUENCE: 223
agtagggttg gaaaattttt ttacattttt actctaaaat agaatagagt tggagatgcc      60
cttagcagtt attagacaag ggattgtttg gccctagcga tcctctcttc actctctcac    120
ttttgtagtt caacccttct tttgcgtgag atgccatcat ggcatgacat ggttcttttg    180
ccttacgtaa aacacactca cgccaacaca cgccacataa cataaataaa ttatatatac    240
atatacgtat gtgcgtgtga gtcttccatt aatgcaatct ttgggcctat atatatatac    300
aaaccttcca taaccaaagt tatcatacta caaaagctct ctcgtacttg gaaatgcggg    360
tgagaatctc catgttggag aagcagggca cgtgcaaacc aacaaacacg aaatccgtct    420
catgtgtttt gcacgtactc cccttctcca acatgagctc ctgacccatt g             471

<210> SEQ ID NO 224
<211> LENGTH: 466
<212> TYPE: DNA
<213> ORGANISM: Arabidopsis thaliana

<400> SEQUENCE: 224
agacaagccc ccacactaaa aaaacagtaa tatggaataa aaaaaagctt tcaaaactta      60
gcagttatta gacaaggtat tgtttggccc tagctagcga tcgttagct ctcttcactc     120
tctcactttt ttagttcaac ccttctttg cgtgagatgc catcatggca tggtatggtt    180
```

```
cttttgcctt acgtaaaaca cactcacgcc agcacacaca cacacacaca taacatatac    240
ggatgtgcgt gtgagctagt cttccattaa tgcaatcttt gggcctatat atacaaacct    300
ttccataacc aaagttctca tactacaaac gccccctcatg tgcttggaaa tgcgggtgag   360
```
(line 360 as printed: `ttccataacc aaagttctca tactacaaac gcccctcatg tgcttggaaa tgcgggtgag`)

```
aatctccatg ttggagaagc agggcacgtg caaaccaaca aacacgaaat ccgtctcatt    420
tgcttatttg cacgtactta acttctccaa catgagctct tcaccc                   466
```

<210> SEQ ID NO 225
<211> LENGTH: 450
<212> TYPE: DNA
<213> ORGANISM: Brassica rapa

<400> SEQUENCE: 225

```
agacaaccccc acgttttaaa ataagaaatg atgataattt tgtggaaata aaagctagta    60 tactttttgca ataattagac aaggtattga tgctttgggc caagctagtt tcttttagca  120
ctcttcactc actagttttt cttctcagcc cttcttttgc gtgaaatgcc atcatggcat   180
ggcattgtca ttttgccttt cgtaaaaacac actcacgcca acatcatta ttcatattca    240 tgtgtatgta tatgaatgtt ccattaatgc aatctttggg gcctatatat acgaagctta   300
catcaccaaa gctctcatat tacaaaagct cacatatata cttggaaatg taggtgagaa   360
cctccatgtt ggagaagcag ggcacgtgca aaccaaaaaa catgaaatct gtttcatatg   420
ctttgcacgt gctccccctcc tccaacatga                                    450
```

<210> SEQ ID NO 226
<211> LENGTH: 513
<212> TYPE: DNA
<213> ORGANISM: Carica papaya

<400> SEQUENCE: 226

```
agacaacact cctctttgtt cccttcctca cgtatccact tttgaaattt gtaatttgtg    60
tgcaccacca tgattgcatg ccatccctac ttgcctttc cccttttcct ttctctaaca   120
ttttactcaa tcttcttctc cccctccccc ccttcccccct ctctgccatt ataaccataa   180
ttaaacctct ctccctctct ctccctctct ctctctctct ctctgggttc tcagtataaa   240
tgcagctctg cttatacttc cacacctata tatatatacc tgacccttct tcacctcctt   300
catccacctc ctccttcttc cccaaaaactt tcttaactgt tctctgcata catatatatc   360
cacatacata tatatatata tagagagaga gtgagacaga gaggttaccg aggcaattgg   420
gtgagtagct ccctgttgga gaagcagggc acgtgcaaat tctccatggc tttccctct    480 ttgcacgtgc tccccttctc caacatgggt tcc                                 513
```

<210> SEQ ID NO 227
<211> LENGTH: 464
<212> TYPE: DNA
<213> ORGANISM: Capsella rubella

<400> SEQUENCE: 227

```
cggccacccc cacatttaac aagaaaaaaa ctgatggaat taaaaggttt gagaacttgg    60
cagttattag acaaggtata gtttggcccct agcttctttt aatttagctc tctccactct  120 cacactttc aactttcacc cttctcttgc gtgagtcgcg agatgccatc atggcatggc   180
atggcatgtt tctattgcct tacgtaaaac acactcacgc caacacatac tcactataca   240
tgtaaataag tatgtgcgcg tgtgagtctt ccatccatca atgcaatctt tggggctata   300
tatatacaaa ccttttccat aaccaaagct ctcatataaa ctacaaaagg ctcacttggg   360
```

```
aaatgcgggt gagaatctcc acgttggaga agcagggcac gtgcaaacca acaaacacga    420
aaccctcctc atgtgctttg cacgtactcc ccttctccaa catg                     464
```

<210> SEQ ID NO 228
<211> LENGTH: 571
<212> TYPE: DNA
<213> ORGANISM: Gossypium raimondii

<400> SEQUENCE: 228

```
gaaaacccaa gttcaggcta acaagttatc tgatgatgag atcaagaatt ttaaagtttc     60
aatatagatt tggcatgggt attggcggca gaaagcaatt aaaaaaccag ttatgtcaaa    120
ttcaaggtcg tatcagttaa aatgaatgaa gatttagaaa tttcaacaag gaagaggacc    180
ccacagcttt gttaaattaa gtgtgtggtt tttataatta tcatctcgaa agtttcataa    240
tatcaattag attaaaacat ctctgaattt cataattaca aaccagatag atagatacat    300
gaaaacttag accccagaga tctgtcttta aagaatgccc acttctagac tcaatctcta    360
ttactctctt tttttctctc tctctctctt cggaaaaact tgtatataaa taaatgacac    420
tttctttgct ttctgcactc aactcatgaa cttgaaaagc tttacttgga tgggttggtt    480
gggggtgagt atctcttgtt ggagaagcag ggcacgtgca agttcctatg tttaagtgaa    540
ctttgcacgt gctccccttc tccaccgtga g                                    571
```

<210> SEQ ID NO 229
<211> LENGTH: 592
<212> TYPE: DNA
<213> ORGANISM: Medicago truncatula

<400> SEQUENCE: 229

```
gaagagaaaa aacctagtgt aaaatttgat atactcttta tgtatagtac gaatgttttt     60
ttaaaaatta tgtaaaaaat gataaaataa taactaacta aattaacagt aaaattagaa    120
aagtaaaata ctatgcccaa atttgatatt ttttttata tatttgtata gattattatt     180
atttgatatg taaagtccaa ttaaaaattt gttttaacta agatttgaac taggttttct    240
taaaagactc atcttttact tcaaatttat ttatcatttg aattcaatca ctttctaata    300
ttattattat tatttccacc atactcattg cttctgccac gttactttag ttagatctct    360
tatgtcatat atctctctct ctcctaagtt gctacctata aatactaagc cttccccttg    420
gttggttcaa ttcaacttct acttctcatc aaacacaaag tgcaataagc ttcatttcct    480
gggtgagaag ctccttgttg gagaagcagg gcacgtgcaa atcctctttc tgattcattc    540
tctcataatg catatcaata tcttttgcac gtgctcccct tctccaacta gg            592
```

<210> SEQ ID NO 230
<211> LENGTH: 520
<212> TYPE: DNA
<213> ORGANISM: Oryza sativa

<400> SEQUENCE: 230

```
atgcaaaccc actccaacac tccacaatcc acatactctc tctctctctc tctctctgag     60
taggagtaca tgtgtgtgtg tgatatcaat atgcattcga tgttgatgct actgtagcca    120
tcttgtggct atataaaccc agcaggcagc agcacagctt agctagagag ccatattgca    180
tgcacactcg ctaatctctt ttctctactc tacttgcatt acaccacctc tgcattgcac    240
ttcagttcat tcattccact gatgcatgga tcgatgttgc taccttcttc tcttctcctc    300
```

```
atgcatccat gcatcgatct cacctagctt cttcctcatc ctctctcgat cgattacaag    360
agaaaagtgt tgctgttct tgctatcgat ctacaggtga gtaggttctt gttggagaag     420
cagggtacgt gcaaaatgca caccggttgg tcgagctaat aacaagctc tgacgaccat     480 ggtgatcgaa tgcacgtgct cccttctcc accatggcct                           520

<210> SEQ ID NO 231
<211> LENGTH: 501
<212> TYPE: DNA
<213> ORGANISM: Arabidopsis lyrata

<400> SEQUENCE: 231
ctagggttta ggaatgacga cttgtttctg ttgtgtctta ttaaaagccc atcttcgtct    60
ccgccactca tcattccctc atcataacac catcatcacc attcaccaac ctctctctct    120
ttctctctct cctctcgatc tacaacaaaa tgtgaatctg ctaagatcga ttatcatgag    180
aattaagcta tttcagttga ggggaatgtt gtctggatcg aggatattat acatatatac    240
atgtgtatgt tgatacatgt gatcatagag agtatcctcg gaccaggctt catccccccc    300
aacatgttat tgcctctgat caccatatat atgtcgttac atttcatggt taattacttg    360
cacaaatcac aaaagcttgg tttgtaactt tctatgacct tttttaatga ctttgaatct    420
ttcatgcatg acttcttaag agtagattta cacatttgcg gatccgttta tgcttttgc     480 ttttgtttcg tttatatata t                                              501

<210> SEQ ID NO 232
<211> LENGTH: 484
<212> TYPE: DNA
<213> ORGANISM: Arabidopsis thaliana

<400> SEQUENCE: 232
ctagggttta ggaatgacga cctgtttctg ttgtgtctta ttaaaagccc atcttcgtct    60
ccgccactca tcattccctc atcataacac catcatcacc attcaccaac ctctctctct    120
ctctcctcta tcactctcta caacaaaaat tgtgaatct gctaagatcg attatcatga     180
gggttaagct atttcagttg aggggaatgt tgtctggatc gaggatatta tagatatata    240
catgtgtatg ttaatgattc aagtgatcat agagagtatc ctcggaccag gcttcatccc    300
ccccaacatg ttattgcctc tgatcaccat ttattgttac atttttttt gttaattact     360 tgcgcaaatt acaaaagctt ggttttgtg atgactttga atcttcttg catggcttct      420 taagagtaga tttacggatc cgtctatgct ttttgctttt tgtttcgttt atttgtattt    480
aaac                                                                 484

<210> SEQ ID NO 233
<211> LENGTH: 552
<212> TYPE: DNA
<213> ORGANISM: Brassica carinata

<400> SEQUENCE: 233
gagatcaatg aaattatcct gccaaataaa acgtgtgacg tttattcaaa aatatatgca    60
ttagatgctt tgatattaaa atatttcctt ttaaaagcta gctagggttt aggaatgacg    120
agttgtgtct tattaaaagc ccttcttctc ctccgccact catcattccc tcatcataac    180
accatcatca ccattcaccc acctctcctc tttctctctc tctctctctc tctctctctc    240
tagaacaaca agtgagaatc tgctaaaata ttgtgactat tatcatgaga atgaagctat    300
ttcagttgag gggaatgttg tctggatcga ggatattata tatacacaaa tacgtatata    360
```

```
tgttaataca agtgtttgat catatatgta tatagattat tctcggacca ggcttcatcc    420
cccctaacat gttattgcct ctgatcacca gattctatca actcttcgct tattattttg    480
tcacaaacaa gtaataagct cataattttc tttgagtctt tcagcatcgt ttcattatgt    540
ttttcgaatc cg                                                        552

<210> SEQ ID NO 234
<211> LENGTH: 566
<212> TYPE: DNA
<213> ORGANISM: Brassica juncea

<400> SEQUENCE: 234
gagatcaatg aaattatcct gccaaataaa acgtgtgacg tttattcaaa aatatatgca     60
ttaaatgctt tgatattaaa atatttcctt ttaaaagcta gctagggttt aggaatgacg    120
agttgtgtct tattaaaagc ccttcttctc ctccgccact catcattccc tcatcataac    180
accatcatca ccattcatcc acctcttctc tcctctctct ctctctctct ctctctctct    240
ctctctctct ctctagaaca acaagtgaga atctgctaaa atattgtgat tattatcatg    300
agaatgaagc tatttcagtt gaggggaatg ttgtctggat cgaggatatt atatatacac    360
aaatatgtat atatatgtta atatcagtgt ttgatcatat atatgtatat agattattct    420
cggaccaggc ttcatccccc ctaacatgtt attgcctctg atcaccagat tctatcaact    480
cttagcttat tatttgtcac aaacaagtaa taagctcaat aatgtctttg agtctttcag    540
catcgtttca tatgttttcg aatccg                                         566

<210> SEQ ID NO 235
<211> LENGTH: 549
<212> TYPE: DNA
<213> ORGANISM: Brassica napus

<400> SEQUENCE: 235
gatatcaatg aaattatcct gccaaataaa acgtgtgacg tttattcaaa aatatatgct     60
ttaaatgctt tcatattaaa atatttcctt ttaaaagcta gctagggttt aggaatgacg    120
agttgtgtct tattaaaagc ccttcttctc ctccgccact catcattccc tcatcataac    180
accatcatca ccattcaccc acctctcctc tttctctctc tctctctctc tctctctctc    240
tagaacaaca agtgagaatc tgctaaaata ttgtgactat tatcatgaga atgaagctat    300
ttcagttgag gggaatgttg tctggatcga ggatattata tatacacaaa tacgtatata    360
tgataataca agtgtttgat catatatgta tatagattat tctcggacca ggcttcatcc    420
cccctaacat gttattgcct ctgatcacca gattctatca actcttcgct tattatttgt    480
cacaaacaag taataagctc aataatgtct ttgagtcttt cagcatcgtt tcatatgttt    540
tcgaatccg                                                            549

<210> SEQ ID NO 236
<211> LENGTH: 543
<212> TYPE: DNA
<213> ORGANISM: Brassica oleracea

<400> SEQUENCE: 236
gggatcaatg aaaattatcc tgccaaataa aaacgtgtga cgtttatcca aaaatatatg     60
cattaaatgc tgtgatatga agtatttcct ttaaaagcta gctagggttt aggaattacg    120
agttgtgttt tattaaaagc ccttcttctc ctccgccact catcattccc tcatcataac    180
```

```
accatcatca ccattcaccc acctctcctc tttctctctc tctctctctc tctctagaac    240
aacaagtgag aatctgctaa atattgtga  ctattatcat gagaatgaag ctatttcagt    300 tgagggaat  gttgtctgga tcgaggatat tatatataca caagtacgta tatatgttaa    360
tacaagtgtt tgatcatata tgtatataga ttattctcgg accaggcttc atccccccta    420
acatgttatt gcctctgatc accagattct atcaactctt cgcttattat ttgtcacaaa    480
caagtagtaa gctcaataat gtctttgagc cttttcagcat cgtttcatat gttttcgaat   540
ccg                                                                  543

<210> SEQ ID NO 237
<211> LENGTH: 566
<212> TYPE: DNA
<213> ORGANISM: Brassica rapa

<400> SEQUENCE: 237
gagatcaatg aaattatcct gccaaataaa acgtgtgacg tttattcaaa aatatatgca     60
ttaaatgctt tgatattaaa atatttcctt ttaaaagcta gctagggttt aggaatgacg    120
agttgtgtct tattaaaagc ccttcttctc ctccgccact catcattccc tcatcataac    180
accatcatca ccattcatcc acctcttctc tcctctctct ctctctctct ctctctctct    240
ctctctctct ctctagaaca acaagtgaga atctgctaaa atattgtgat tattatcatg    300
agaatgaagc tatttcagtt gaggggaatg ttgtctggat cgaggatatt atatatacac    360
aaatatgtat atatatgtta atatcagtgt ttgatcatat atatgtatat agattattct    420
cggaccaggc ttcatccccc ctaacatgtt attgcctctg atcaccagat tctatcaact    480
cttagcttat tatttgtcac aaacaagtaa taagctcaat aatgtctttg agtctttcag    540
catcgtttca tatgttttcg aatccg                                         566

<210> SEQ ID NO 238
<211> LENGTH: 414
<212> TYPE: DNA
<213> ORGANISM: Arabidopsis thaliana

<400> SEQUENCE: 238
catcatcacc actcacttat cttcttctcc atctctctct ctgcttctcc cttaatctta     60
gccgggtctc gtgggggacg aacatagaaa gagagagata taaagatata tattcagaaa    120
ccctagattc tataatttcg actgaaaaga aaaaggggct ttctcttttg aggggactgt    180
tgtctggctc gaggactctg gctcgctcta ttcatgttgg atctctttcg atctaacaat    240
cgaattgaac cttcagattt cagatttgat tagggtttta gcgtcttcgg accaggcttc    300
attcccccca attgttgctc cctgtttact ccatatttct tccttctttt caaattaggg    360
tttcagatcc agtgaatgaa cccttgttaa aggtttgatc tcttaccttta cttt         414

<210> SEQ ID NO 239
<211> LENGTH: 328
<212> TYPE: DNA
<213> ORGANISM: Arabidopsis thaliana

<400> SEQUENCE: 239
tctcatcatt ctcttcatca tcaccacatt catctctctc tctctctctc tctctctctc     60
tttctcttcc ttgatcttag ccggatctgt tggggacga  acacatgaga gatagataaa    120
atataagaaa tttctcgaaa aaacctaata gaaaaaggtc tgtttcttaa agaagaagaa    180
gaagaggatt taaagaggga ttttctcttt gaggggactg ttgtctggct cgaggactct    240
```

```
tattctaata caatctcatt tgaatacatt cagatctgat gattgattag ggttttagtg    300
tcgtcggacc aggcttcatt cccccaa                                       328

<210> SEQ ID NO 240
<211> LENGTH: 192
<212> TYPE: DNA
<213> ORGANISM: Arabidopsis thaliana

<400> SEQUENCE: 240
tgatgaacag aaaaatctct ctttctcttt cttgatctgc tacggtgaag tctatggtgc    60
accggcatct gatgaagctg ccagcatgat ctaattagct ttctttatcc tttgttgtgt   120
ttcatgacga tggttaagag atcagtctcg attagatcat gttcgcagtt tcacccgttg   180
actgtcgcac cc                                                       192

<210> SEQ ID NO 241
<211> LENGTH: 846
<212> TYPE: DNA
<213> ORGANISM: Arabidopsis thaliana

<400> SEQUENCE: 241
aaccacaaag taccgctgct attttctttt tacgtctttg tatttgcatc gtctaagaga    60
atgatgggtt gttttgtggg attttaatgc aggaggaaac atatgagggg tgattaaggc   120 aaaaaccta agatgtggtc atttagatac atggagtcaa actaagaatg gaccttggcg    180
aaagcttctt cacggtcaag atttaaaatc aggtacgaca ctgtgtacgt gagagagaga   240
gagagagaga gaaagagatt atagaaagaa agagatgtat cacaataaag gagtatattt   300
agggtcacag gtggtggaga taggtatg cagggccaag gctctaatct cttcatagcc     360
ctattgattt tgtccctctc tctctctctt tcttcctctc ttagctgtat gcattatgat   420 gcgtcttta attcactgtt tcaggcttct ttaattcgtg gtgtctctct cctttttacc    480
caaccatctc ttaaaatttt taacatctgt tcctcaaatc ctctctcatc tctttctata   540
agtatctata gcgcctctta aaccacaaag catcacctct gtcttctctc atctcctttc   600
tgtattctct ttcattgcct tcacgtcgt tgcaatttct ccacttcttg agcttccgtt    660
ttttacaatt attgatccgt caaatatgtg agatttgcac aacttgttgc tcaggtattt   720
tgaagacaag tccacaaggg aacaagtgaa gctgccagca tgatctatct ttggttaaga   780
gatgaatgtg gaaacatatt gcttaaaccc aagctaggtc atgctctgac agcctcactc   840
cttcct                                                              846

<210> SEQ ID NO 242
<211> LENGTH: 571
<212> TYPE: DNA
<213> ORGANISM: Arabidopsis thaliana

<400> SEQUENCE: 242
gagcaagaca atgccacata caaacttgaa agatctcttc atcttttctc caaatgtttt    60
tttttcgttt gctatttatc tccacaattc ttggaacaaa aactacattc acaaacgaga   120
gaattttcac aacacctctt ttgctctcat tttttttttt tcgtccatta tgagtattaa   180
ttatggttag ggaatcttac agaatgaaaa tgaaggtgtg aatggattgt ctcatctaaa   240
gccttgaatg tggaaaaaag gccattgttg ttcagccaag gatgacttgc cggtagcttg   300
tattatgatt actctatatt cgatttatat tatggagatg atggtttata tatatttact   360
```

| | |
|---|---|
| tatctacata gttttagttg attttttttc gtacgtaata taatacgaaa aagtatttac | 420 |
| ttatttatat atgtgtgttg gggcaagaag tgtaaccaag ctagcccggc aagtcatcta | 480 |
| tggctatgca actgtctctt cctctcattc taggcttacg atgacacgta aaaaatccca | 540 |
| aatatcacta atatgatatg aatatggatg a | 571 |

<210> SEQ ID NO 243
<211> LENGTH: 241
<212> TYPE: DNA
<213> ORGANISM: Arabidopsis thaliana

<400> SEQUENCE: 243

| | |
|---|---|
| aggcatgaga cataaagaga gttaaatata atgaagaaga gaggtctaat atggcgaaaa | 60 |
| gagtcatgtt taatagccaa ggatgacttg cctgatcttt tcacctcca tgattcaatt | 120 |
| ttaagttcgt ggattttgga ttattatgcg tttaaaaggt ataataattt gagatcatgt | 180 |
| tgaatcttgc gggttaggtt tcaggcagtc tctttggcta tcttgacatg ctttcttcat | 240 |
| c | 241 |

<210> SEQ ID NO 244
<211> LENGTH: 689
<212> TYPE: DNA
<213> ORGANISM: Arabidopsis thaliana

<400> SEQUENCE: 244

| | |
|---|---|
| gaattttgat ttatgaacct cctcaagaag gaaagacaga ggaggagaca aagaagtata | 60 |
| ggttcacatt gcatagccag tttagttttg aaggatggat atatgaaaaa aatatgaaga | 120 |
| gagagaagag agaagaagag gaggattaaa gagggtgagg ccagcttttg tgctttggta | 180 |
| gtagatgagg tttaaatgct ccatacctc catttccttc tctcttaccc taatttaatt | 240 |
| cttcctctcc tttataactc cccacagaca ttctcacttc tcctcctcac acttcacatc | 300 |
| aacacttctt tcttgttttt tcattttaca atgtttcctt tgatatccgc actttaagca | 360 |
| tgagagagtc cctttgatat tggcctggtt cactcagatc ttacctgacc acacacgtag | 420 |
| atatacatta ttctctctag attatctgat tgagccgcgc caatatctca gtactctctc | 480 |
| gtctctattt tggactttgt ggtcttgtag atcgatttgt atgtgtgtgt tgaaatggag | 540 |
| acaagtactt gtaacttctt tgttgttata ttgtttaccT ataggctgat gtcataaact | 600 |
| cttttgatct tgtttctaac ttccagattc ttgaaaaatc aagtcgtgtg tgtgtctcca | 660 |
| tggaagcctt ttccatttct tcctttcca | 689 |

<210> SEQ ID NO 245
<211> LENGTH: 452
<212> TYPE: DNA
<213> ORGANISM: Arabidopsis thaliana

<400> SEQUENCE: 245

| | |
|---|---|
| actcataaac tttgctactg gccgcatttc tattttctcc ttcgattctt ctaattcgta | 60 |
| ctttggtttc tgacgtccct aaaattttta gacagtaaga gtttctccag gatccgatgg | 120 |
| ttctctccgg taaattaaca ttttagtgtc aatagtcatt tatacatatt tttatttcac | 180 |
| tttttgtttt gtttattggt tttctggagc taagtggaga ttatagtcga acaagagtgg | 240 |
| ttttatgcaa ggtaacgcga gatattagtg cggttcaatc aaatagtcgt cctcttaact | 300 |
| catggagaac ggtgttgttc gattgagccg tgccaatatc acgcggtaaa ccaaaaatgg | 360 |
| caaagatagt tattataacc ttaaaggtat gtatcattat cgttttattg tttcaatttt | 420 |

```
gattaatggc tttgatattt cattttttt tt                                    452
```

<210> SEQ ID NO 246
<211> LENGTH: 767
<212> TYPE: DNA
<213> ORGANISM: Medicago truncatula

<400> SEQUENCE: 246

```
attggtcaaa catacataca gtagcactag ctggtttcat tattccacta tgcttcttca     60
taggctctcc aaattttgca aaattgaaag agacatagta tatatatctt agcaaggaga    120
aattcaggat attgaggatg aagattgaag agtaatcagt gatgaagaaa gcaagcaagg    180
tattggcgcg cctcaatttg aatacatggc tataaaaatg catcatatca gccatgtagt    240
ttgattgagc cgcgtcaata tcttgtttcc atctccaaat ttaccaatct catcaaatca    300
aattaacacc acaatcaagg ctttcattta atgcagtcaa ataggttga ccttatcatc    360
gaagaaattg ttttctcatt cctatcgaag ttggacttgc cgaaaatgct cgaaagcatg    420
tgttttagtt cgacaggcga aaaagttacc gaaggacaat ttggttgtgg ttcggataag    480
atcaagcaac ggatattttc aagacacgtt cgaaattcaa atcaaatgga taagtatcgt    540
tagtttactg cagttatagt tttaaattca aatctaggca gttgtttcta tttgtataaa    600
tagtagtttt tccctaggga aaggggtcg caattcaatc atacaaaaaa cttacaatca    660
aattatccgc atggaagaga gaacgagtc acaagttgca atgtatgaac atgtgtacca    720
atttacattc aatcagtaca atttaagttc atttccataa aaaaaaa                 767
```

<210> SEQ ID NO 247
<211> LENGTH: 854
<212> TYPE: DNA
<213> ORGANISM: Zea mays

<400> SEQUENCE: 247

```
accagggtta ggtatccatc cacacagcaa tgcatctgcc ttcaactccc tctcgccccc     60
caccccaaca cacatctctc tctttttctag ggaaggaaat gacgaagggg acgacgacgg    120
catgcttcgg ctagctcgtt ggtgctagga caagggcgga ggtattggcg cgcctcaatc    180
cgaaggcgtg gctgatagat tggcgcggca gccatgttct tggattgagc cgcgtcaata    240
tctccccttg cctgtcccgt acctagctag cttgcttgcc tcactgatcg atgtcgtccc    300
tatttcatgg agaagctgat gattgattat tctcacaagc aagaactgtc tgatctgttg    360
cctgcatcga tcaggatcta tatgctggag agttcacaag aacatggaca gaactcgctt    420
caacaaccga tcaatcgatt gattaggtat gtacctacct catatgcctc agctcttcgt    480
tatggatttc ttcaaccgaa gggtcagtaa gctcttggtt ccatgccact gcgtgaacta    540
agcgttcaca aaatccgttc cmcggcatga accaagcact caaaatcgca tgcagcatct    600
ttcgtttcaa aaaaaaattg acttytgaaa acaatagatg aatcagtttc aaacatatat    660
gattatccat tttctcaacc gggaatttat atctcgttgg gatgcaaaac cgttcagtag    720
taaaactact ccacgagtat aaactgtttc agttatttta ctattaatta gttacccgta    780
tgctgttatg gtttctatat atctataagt aaaccttact taaataagat agttatacaa    840
aaaaaaaaaa aaaa                                                       854
```

<210> SEQ ID NO 248
<211> LENGTH: 660
<212> TYPE: DNA

<213> ORGANISM: Arabidopsis thaliana

<400> SEQUENCE: 248

```
caagaaaaaa cattgaaata gctcatgttg tctctttctc attttcatat ctgctaaaaa    60
aagaaccgtg ttttctaaac tggtttaacg gtaagtacct gtctctagta acttacctat   120
caatttgttc caatcattta cttgctttga cttatttggt ttccttttgt tttgtttttc   180
tttaatatgt ggatggagtt tggtgtaata agcaactgaa gagtcgatga gcgcactatc   240
ggacatcaaa tacgagatat tggtgcggtt caatcagaaa accgtactct tttgttttaa   300
agatcggttt atttgattga gccgtgccaa tatcacgcgt ttaaatagtt taaagattct   360
atgttagttg atgtgatcaa tcaaggtatg aatctatatc aattctctta tgcatagttt   420
tatatttaca gagatgaggt attatcaatg tctatcgtcg aggatcacgc tcttacttat   480
gttatatttc tatataattt tattaattag ttttctaaaa gagaaggaca atttaaaatt   540
attttaaaga gttttttttta agtagttttg ttttcatgtt tatcttctgc aggctctgaa   600
gttaggatag taacaagaaa aaagacagaa aaaagaaga aaattcatat acattcgtga   660
```

<210> SEQ ID NO 249
<211> LENGTH: 225
<212> TYPE: DNA
<213> ORGANISM: Medicago truncatula

<400> SEQUENCE: 249

```
gaataagtga atattatcga tatttatatc atatatcaac ttttcttctg tgcttgcttg    60
caaatttgca attaagcttt tttgatctta tgtaagagaa tattattgat gatggtgttt   120
gggaagccga aaaaagcgat gttggtgagg ttcaatccga agacggattt acatgtatag   180
agttgtaaaa tacgatctca gattgagccg cgccaatatc acttt                    225
```

<210> SEQ ID NO 250
<211> LENGTH: 367
<212> TYPE: DNA
<213> ORGANISM: Medicago truncatula

<400> SEQUENCE: 250

```
ccacaaaact ataactagct agaagcttta atcgccttat ttattataat aataataata    60
aatatggctt cagctgcaaa agtatacatg gcgtgatatt gatccggctc atctatatct   120
tcaagttcaa tcatccatat tcatatcaat ttcagacgag ccgaatcaat atcactcttg   180
tttgcttcat tgcatattaa ttatatactt catttataag ttatagtttg ccatatatat   240
attagattga ttctgcagaa gtagacagga gtggtgttgt ttctgctcat cttattaaat   300
aatgaatgaa tgaatgacat ttgcttactt ataagacgag ccgaatcaat atcactccag   360
tacacct                                                              367
```

<210> SEQ ID NO 251
<211> LENGTH: 712
<212> TYPE: DNA
<213> ORGANISM: Arabidopsis thaliana

<400> SEQUENCE: 251

```
ctctctctct ctctctctct catctgtgtt ctagatctca ccaggtcttt ctctggttaa    60
tatatggctt ccaagatctg gtaatatgtt ataaatacgt catacttaag cttttttcaa   120
atcaaaaata gaaatttgtg ggtttgtctc gtttactact tttagcagta tatattaaga   180
agttcagatg ttattcgatc atctgttttt gcttcccctc tgccatcttt atcttttagg   240
```

```
gtttcaattc ttttcactt tttctctctg gtttggagat ggttaggttc caactaagta    300
tacgagatta aatttgacat cttagttact tcaaaattcc ttcaatcaaa acaagtcatc    360
tcgactattc cgccatgttt gtatatacat atttatatat tatatatatg aaggtacgag    420
tttctagtgt ctataaatta agaaggttaa gtaccatata gatgatattt gttaagtagt    480
aagtcactca aagtttgagt ttgggtttga gtttgagttt gagtttgagt ttgagagaca    540
aaagattact acaagaagat tgttaaacaa aaatggaaga ctaatttccg gagccacggt    600
cgttgttggc tgctgtggca tcatcaagat tcacatctgt tgatggacgg tggtgattca    660
ctctccacaa agttctctat gaaaatgaga atcttgatga tgctgcatcg gc            712
```

<210> SEQ ID NO 252
<211> LENGTH: 714
<212> TYPE: DNA
<213> ORGANISM: Arabidopsis thaliana

<400> SEQUENCE: 252

```
acttgcacct ctcactccct ttctctaact agtcttgtgt gcacccattt atgtgtacgt     60
actattatct cataaataaa tatttttaaa attagatgca tttattgata tgaaaaagtt    120
acaagattag tttgttgtgt gtgagacttt ggatcgacag atcgaaaaat taactaaccg    180
gtcagtattg aatatcaact attatatgct ccatgcattc gcttatagtt tcacacaatt    240
tgttttcttc acggtctaaa atcagaagat tccatatatt ttcttatgac gtaaaaggac    300
cacttataag ttgacacgtc agcccttgga ttcgtgaggt ttttctctct acttcaccta    360 tctactttc ctcatatccc actgcttttc tccttcttgt tcttgttttt ctcgtttttt    420
tcttcttctt ctccaagaaa atagagatcg aaaagattag atctattttg tgtagcaaga    480
aattatcatt ttcgtttctt cattcatata ttgttctatt atgttgtaca ataatagata    540
ctcgatctct tgtgcgtgcg taaatttat acaagttgtc ggcggatcca tggaagaaag    600
ctcatctgtc gttgtttgta ggcgcagcac cattaagatt cacatggaaa ttgataaata    660
ccctaaatta gggttttgat atgtatatga gaatcttgat gatgctgcat caac          714
```

<210> SEQ ID NO 253
<211> LENGTH: 324
<212> TYPE: DNA
<213> ORGANISM: Arabidopsis thaliana

<400> SEQUENCE: 253

```
tcaccaaata ggctcttctt tatcgcttca tatatataaa agtctacatc tatctctttc     60
taggtcacta gctagactct agattaagga ttgaaattag ggtttcatgt ttccagcaaa    120
atggtgccgt cttgagtctt gaaaagatcc aagacaaaac caaatcacta catacatccc    180
tatcatcaac cagctactgt tcgctgttgg agcatcatca agattcacaa atcatcaagt    240
attcgtgtaa ataaacccat ttatgattag atttttgatg tatgtatgag aatcttgatg    300
atgctgcagc tgcaatcagt ggct                                            324
```

<210> SEQ ID NO 254
<211> LENGTH: 531
<212> TYPE: DNA
<213> ORGANISM: Arabidopsis thaliana

<400> SEQUENCE: 254

```
tgtcatattg agaactcttt agcctttggc ttctgttcct gacacttgta tagtgaagtg     60
```

-continued

```
ggcttgtgtt atatagatgg gatctctctc tttatttaaa agtcaattag agatcttgat    120
gctacttctg tccctttcca agtgatttta cgtcgaccaa ctagcttttt tcatatgagt    180
gtatatattc atgtacctat ctctctcaat tgcttctcac caaaatcatc ttgctgattc    240
atttgctgtc tgaatcctct tgctttcctc tttgcttttt catttgttga tttaaaccat    300
gggagttccc aactttagac ctcgaaaccg ataaggatct ttctctgcgg ttgaaatagc    360
taggttctcg atgaataggc tagccttttgg tggatgttat cagccagtag tcgcagatgc    420
agcaccatta agattcacaa gagatgtggt tccctttgct ttcgcctctc gatccgcaga    480
aaagggttcc ttatcgagtg ggaatcttga tgatgctgca tcagcaaata c            531
```

<210> SEQ ID NO 255
<211> LENGTH: 618
<212> TYPE: DNA
<213> ORGANISM: Arabidopsis cebennensis

<400> SEQUENCE: 255

```
ttgtatccat agtgtatttc ctcgcatcta ccatccattt tctacgcctc tctctctctc     60
tttctccatc aaatcttgtt ttgttcaaac tctctctctc atcaattctc tccatacaat    120
acatgcatac atacatacat accatctcta atatttcatc aatcttcttt tgttccaaac    180
gctctttctc tccatttaca tacatacgaa tcattgttgt catagatccg tttagaattg    240
ctttaacttt tagatgagat ctagggtttc ttttcttttc ttcaaaatca tgcttttttcg    300 cttgctaggt tatagatcca tgtaagttta gagtagatgt acacacacac gctcggacac    360
ttattaaata catgttgata cacttaatac tcgctgtttt gaattgatgt tgtaggaata    420
tataaatgta gagagagctt ccttgagtcc attcacaggt cggatatgat ccaattagct    480
tccgactcat tcatccaaat accgagtcgc caaaattcaa attagactcg ttaaatgaat    540
gaatgatgcg gtagacaaat tggatcattg attctctttg attggactga agggagctcc    600
ctctctcttc tgtattcc                                                 618
```

<210> SEQ ID NO 256
<211> LENGTH: 660
<212> TYPE: DNA
<213> ORGANISM: Arabidopsis halleri

<400> SEQUENCE: 256

```
ttgtatccat agtgtatttc ctcgcatcta ccatccattt tctacgcctc actctctctt     60
tctccatcaa atcttgtttt gatcaaactc tctctctctc tctctcatca attgtctcca    120
tacaatacat acataccatc atctttccca tctctaatat ttcatcaatc ttcttttgtt    180
caaacgctct tcctctccat atacatatac atacatacga atcacattgg tgtcatagat    240
ccgtttagaa ttgctttaac ttttagatga gatctagggt ttctttgttt ctttcgtttt    300
cttcaaattt tgctgcatat tctccaagat catgatttttt cgcttgctag gttatagatc    360
catgcaaata tagagtagat ttacacacac acacgctcgg acacttatta catacatgtt    420
gatacactta atactcgctg tttttaattg atgttgtagg aatatatata tgtagagaga    480
gcttccttga gtccattcac aggtcgtgat atgatccaat tagcttccga ctcattcatc    540
caaataccga gtcgccaaaa ttcgaactag actcgttaaa tgaatgaatg atgcggtaga    600
caaattggat cattgattct ctttgattgg actgaaggga gctccctctc tcttctgtat    660
```

<210> SEQ ID NO 257
<211> LENGTH: 632

```
<212> TYPE: DNA
<213> ORGANISM: Arabidospis lyrata

<400> SEQUENCE: 257
ttgtatccat agtgtatttc ctcgcatcta ccatccattt tctacgcctc tctctttctc    60
catcaaatct tgttttgttc caactctctc tctcatcaat tcattccata caatacatgc   120
atacatacat accatcatca tcttttccca tctctaatat ttcatcagtc ttcttttgtt   180
acaaacgctc tttctcgcca tatacataca taagaatcat tgttgtcata gatccgttta   240
gaattgcttt aacttttaga tgagatctag ggtttctttc ttttcttca attttgctg    300 catattcttc aaaatcatga tttttcgctt gctaggttat agatccatgc aaatatagag   360
tagatgtaca cacattcacg ctcggacact tattacatac atgttgatac acttaatact   420
cgctgttttg aatggatgtt gtaggaatat atatgtagag agagcttcct tgagtccatt   480
cacaggtcgt gatatgatcc aattagcttc cgactcattc atccaaatac cgagtcgcca   540
aaattcgaac tagactcgtt aaatgaatga atgatgcggt agacaaattg gatcattgat   600
tctctttgat tggactgaag ggagctccct ct                                 632

<210> SEQ ID NO 258
<211> LENGTH: 646
<212> TYPE: DNA
<213> ORGANISM: Arabidopsis thaliana

<400> SEQUENCE: 258
ttgtatccgc agtgtatttc ctcgcatcta ccatccctt tctacgcctc tctccctctc     60
tctctttctc catcaaatct tgttttgttc aaactctctc tctctcatct attctctcca   120
tacaatacat gaatacatac atatacccatc atcttcttt cccatctcta gttttcatc    180 aatcttctga tgttccaaac gctctatctc ttcatataca tacatacgaa tatattattg   240
ttgtcataga tccatttaga atcactttag cttttagatg agatctaggg tttctttgtt   300
ttctttcaaa ttttgttgca tattcttcta aatcatggtt tttcgcttgc taggttatag   360
atccatgcaa atatggagta gatgtacaaa cacacgctcg gacgcatatt acacatgttc   420
atacacttaa tactcgctgt tttgaattga tgttttagga atatatatgt agagagagct   480
tccttgagtc cattcacagg tcgtgatatg attcaattag cttccgactc attcatccaa   540
ataccgagtc gccaaaattc aaactagact cgttaaatga atgaatgatg cggtagacaa   600
attggatcat tgattctctt tgattggact gaagggagct ccctct                  646

<210> SEQ ID NO 259
<211> LENGTH: 660
<212> TYPE: DNA
<213> ORGANISM: Brassica rapa

<400> SEQUENCE: 259
ttgtatccat tgtgtatttc cttgcatcca tcaataaatt ttatgttacg cctctctatt    60
atttctctct acatcacact gtcttatgtt taagctctac ttctcagcaa ttctctccac   120
ccaatacatg catacatacc atcatcgtat cgctctaatt tttctatcaa tcttgtatcc   180
ttccacaaat tatcttatgt ctcccatttt aaatcctaca tagatccaca catacgaatt   240
attcttgtct gaagatccat ccatttacga ttgctttaac ttttacatga gatctagggc   300 ttcttattt ttcttcaaat cttgctgcat atatttcaag atcatgcttt tcggcttgct    360
agggttctag atccatggat gtatagcgta catacataca cgcactaatt catacctgta   420
```

```
gtttgtacgg agaacatcat aaaatatcac tgtttggaat taatcgtgta ggaaatatag    480
ataggtaggg agcttccttt agtccattca cagatcatga tatgatccaa ttagcttccg    540
actcattcat ccaaataccg agtcacgaaa atttcaactt agactcgtta aatgaatgaa    600
tgatgcggta aacaaattgg atcattgatt ctctctgatt ggactgaagg gagctccctc    660
```

<210> SEQ ID NO 260
<211> LENGTH: 932
<212> TYPE: DNA
<213> ORGANISM: Carica papaya

<400> SEQUENCE: 260

```
ctatatccct gtcaaatagt acttggtttt gttttagcca caaatcttct ggtcttgcaa     60
agttccttct gatctctccc cctttctcat tttttcctcc tcttatatat ggatcatcaa    120
tttgctgtac acacacacac atttactgta gtgataatta gctagctaat ttgttagtat    180
gtaaattaga tcccaagtac cctgttatat ttttttaggc ttatcctatg catacctgat    240
agtacaagaa cttagtttgt aattaggtac ttggtagtag ggttagatta attactgtct    300
tgaaagagaa cttatccaac aaatagagct atgaagatta aattaggttt tagtcttatt    360
aagattatta tattactaga caaaaacagt taaattttt taattgggta attaggtact    420
tagcaatagg gttagattaa ttactgtttt gaaagagaac ctacctacaa atagagttga    480
aatgattatg ttttagtctt actaagattg tcatatttct ggaaaaaaac aaatcttgaa    540
acagataatt cagatagtca tgatcaatgg aaaaaacatc atgggtgtgt gcttaattaa    600
gctaatatat atatatatga agatataatg ttatgcacac tagctatgaa tttgtaagaa    660
taatgaagga taaagatgat atatttagat gttataagtg taagtaaggt ggaatgggtt    720
gatgggtagt agtagtagta gtagagatga ttggtggaga gagcttcctt cagcccactc    780
atggatgggt atgaaggggt agaagtagct gccgactcat tcattcagcc actcagtatg    840
taaactcgtc ccactgttga ctgtatgaat gatgcgggag atattttttac atccatcttt    900 ctctgtgctt ggactgaagg gagctccttc tt                                   932
```

<210> SEQ ID NO 261
<211> LENGTH: 702
<212> TYPE: DNA
<213> ORGANISM: Capsella rubella

<400> SEQUENCE: 261

```
ttgtatccat agtgtatttc ctcgcatcta ccatctacta ttttctacgc ctctctctct     60
ttatccctct atctctttct tcatcaaatc ttcttttgtt caaagtctct ctcatcattt    120
ttctctatac acatacatgc atccacatac atacatacat ataccatcat cttcttttct    180
catctctagt ttttgtttat aaattttgtt ccaaggatct gtatctctcc aataaagata    240
catacaaatt attgttgtca tagatctatt agaattgctt taacttttat atgagatcta    300
ggatttcttc cttttctttc aaaatttgct gcatattttt caaaatcatg atttatcgct    360
tgctaggttc tagatccatg caaatttaga gtatttttac acacacacac gcttggacac    420
aagtacatac atgtagtttt ctttatgtg gtgaaaagta cataacatgt agtttatagt    480
tactagtcgc tatataattt aaaattgatg ttataggaat atatgtacgg agagagcttc    540
cttgagtcca ttcacaggtc gtgatatgat ccaattagct tccgactcat tcatccaaat    600
accgagtctc accaaaattg gaacaagact tgttaaatga atgaatgatg cggtagacaa    660
attggatcat tgattctctt tgattggact gaagggagct cc                       702
```

<210> SEQ ID NO 262
<211> LENGTH: 767
<212> TYPE: DNA
<213> ORGANISM: Eucalyptus grandis

<400> SEQUENCE: 262

```
tcgtttccca tccccatttc atagaataat gccaccaaac aaagaagcat tagctcaaag      60
actaattacc atctgtttta ttgatagata cgtgcgaaac ggtgattgtt ttttcccaaa     120
taagaaacca aaatgaagca tattcaaagg tggagatatg gggagacttc cggaaggcaa     180
ggggattgga aaaggctcga gatcaaagtg catagcaacc cttcgctaaa ggtgaaaaag     240
aatacgaata acttcagtag ctcactttaa attccgaaac attaaacaaa tcaaatctcc     300
ctcgccctcc ttgcctcctc tctttaccta tataaagcca ccgccccttc aatgaaatcc     360
acgagtggaa ggtcacagta tagtagggtc ctgcaaaggg agagcgagag cggctccact     420
gtctacctat aagcagttcc tttcttttgt ttacatgtct gttgcacctc accgagtttt     480
tctattctct ttcctctggt tggttagcag atttctcagg ggacttccct cctcccttga     540
ggatccttct cttgaagcga tatgtctcga atgggtaaga gagagagagg aagggagctt     600
tcttcagtcc acccatggga cgtgttgggt tttaattagc tgccgactca ttcatccaaa     660
taccgagcga gagcaagtaa cagagctccg taaatgaatg gatgatgcgg gagtcttgtt     720
gattcccaag ctttccgtga ttggactgaa gggagctccc tctatct                  767
```

<210> SEQ ID NO 263
<211> LENGTH: 612
<212> TYPE: DNA
<213> ORGANISM: Gossypium raimondii

<400> SEQUENCE: 263

```
gcgtatcctt ccacttacgg attcaccata gctgctatag cccgagtttg cttgtcataa      60
tagaaataaa ctaagggaga aaaaagctct ccactctcgc cttttttcttc ttcgagtctc    120
tctctttgac tggcctttgt gcaaagatct cctttttta aacagtcgct ttctttactc     180
tcccttttccc ttctttctct taattgctaa agcagcttcc acttccactc actttaaccc    240
atgatccatt tcaacctgtc acagtggaga gcaatttgta tggctaattt ccatctcacc    300
tattcttttc tgtttggggt tctctagtct agggttgcat gacatgagag acatggctct    360
tttttttttt tttcagttca caggtgttta tatatgttgt tgtgttattt tgtcttaaag    420
ctttgtgatt gatgatctga taggtaagag agagctttct tcagtccact catgggatgg    480
ggatggggtt taattagctg ccgactcatt catccaaata ctgtgttaca aaacccagta    540
aatgagtgaa tgatgcggga gacaaattga atcctaatct tcctgtgctt ggactgaagg    600
gagctccctc cc                                                        612
```

<210> SEQ ID NO 264
<211> LENGTH: 675
<212> TYPE: DNA
<213> ORGANISM: Medicago truncatula

<400> SEQUENCE: 264

```
atttatccaa tcatgttgct ctcacttctt ttcagcagtt ctgttgatat cacccttta       60
gttgaagctt tggattcatg actttatgag atggtaaatc tttaaattaa gtttaagtat    120
gcacttgatt tgtttatata atttgtttat ttagatttta aaccctaagt tgacttttt     180
```

| | |
|---|---|
| aatttgattt aaattatgat atgattgtta tttggcttac catggtcata atttagggtt | 240 |
| tagaagatgc atgtatatct tgaattgttt atggtaataa aggggttagg atttctcctt | 300 |
| ttggtgaagt gagaaaatct cataattttg ttctgaaggt agttttaag atttaggg tt | 360 |
| atgggttctt tgtttgaatg cttttttcaag tcttttttcaa tgatatttgc ctagatctgt | 420 |
| tttaattttg aattaaaatt ctgggtttgg attaatatta ttgaagatta ttattaatta | 480 |
| atttattaga aatagatgaa gagagcttcc ttcagtccac tcatggaagg gtaaggggtt | 540 |
| tgaatttacc tgctgactca ttgattcaaa cacaatagac aattatgggg ttatgctatt | 600 |
| gtgaattgtg tgaatgatgc aggaggtgaa tttcttcctt ttcttctttg cttggactga | 660 |
| agggagtctc cctttt | 675 |

<210> SEQ ID NO 265
<211> LENGTH: 866
<212> TYPE: DNA
<213> ORGANISM: Oryza sativa

<400> SEQUENCE: 265

| | |
|---|---|
| ttatatctga cgcgttgtaa tcctgtttaa ttagggcttt gcccatttct tttgaccct | 60 |
| tccggacatt cgctagttgg aaccttgttt tactcctagc agtgtactgt gtagtactta | 120 |
| ttacgagcaa acgtaaaaat aaataaatgg aaatgataca aaggccgtgt ttaattttaa | 180 |
| aattttttt caaactttca acactttaca tcccataaaa agcttactat acatacaaac | 240 |
| ttccaacctt tcgtcacat cgtatctaat ttcaactaaa cttttaattt tagcgtgaac | 300 |
| taaacacagc cgaagcccgg ccacattctc actattttta ttcattttat catgcctgtg | 360 |
| atgtcacgcc ttggccctat ttaataggcc ttctccattt ctctccatat gatgtcttct | 420 |
| cttctctatc cctcttgcca tcttctatct tccctcttgc acccatcttt gtgataactt | 480 |
| ctactagctc ctctcctact accagtcata ccactctcac aaatcctcca agatccgcat | 540 |
| ggggagaagc tccaaaagtt tcgtggttag tttaatttca tgcttgtttg ctgccgtttt | 600 |
| tcatgttgat ctgatcttaa tatatgtaga ctgctgttaa catattcttt taatttgatg | 660 |
| gaagaagcga tcgatggatg gaagagagcg atccttcagt ccactcatgg gcggtgctag | 720 |
| ggtcgaatta gctgccgact cattcaccca caatgccaag caagaaacgc ttgagatagc | 780 |
| gaagcttagc agatgagtga atgaagcggg agagtaacgt tccgatctcg cgccgtcttt | 840 |
| gcttggactg aagggtgctc cctcct | 866 |

<210> SEQ ID NO 266
<211> LENGTH: 801
<212> TYPE: DNA
<213> ORGANISM: Physcomitrella patens

<400> SEQUENCE: 266

| | |
|---|---|
| tgggatccac acgagtaatt attccctctc tcatgcatca caacttggac ttgcccagct | 60 |
| tttacctctc tccatgttcc accgtcggag atcctcggtg ctgctacccc cgttcggcca | 120 |
| aacccaaccc aaccctaggt gtctgccgga cctccgcttc ccctcctgct tcacccctg | 180 |
| caccgcttaa atttgcacct cgtagtattt atctatgccc catttcagat gacttgcatg | 240 |
| acacccatct ggattcgtct ccaggcgcct tgtcgtatct attcgctatc agtctttctt | 300 |
| tcagtctgtc tttctgccaa gcacaccgtg ctggtggtgg tgctatcagt cgaagcagtc | 360 |
| gccgaagggt ccttgtatcc agccctcacc ggagacagtt cgcttcgggg tggggagaac | 420 |
| tgttgagacc gtcgatgttg catgcagcag cactggcgaa ggtgcttctg atactgggta | 480 |

```
ttccagcctc gccgctcggt gcactgcagg tacgtggtta catgacacta ctgtgtgggt    540
agtctgggca caagtagatc gacatgccag atttggcccg tatgcgtgta tgtgcggtta    600
tgttcccgtt tcgattgcgg ataccttgat tgtggagctc cgtttcggtc caatagtggc    660
tgcgacggaa ggtggtcccg ctgccgaatc acacgtccgg gttgcttatc ggggcagggc    720
cccgatacgg tatccgaacg tttgtcccgg gaactggtcg accttccgcc cggcgtctct    780
tggactgaag ggagctccac t                                              801
```

<210> SEQ ID NO 267
<211> LENGTH: 819
<212> TYPE: DNA
<213> ORGANISM: Thellungiella halophila

<400> SEQUENCE: 267

```
ttttatacaa ataatgttcg ataacactaa accctagcca tccaactaat agacaaaacc    60
ctacttgtaa tttacaaccg caaattccca gagaacagag taactacgag agagagatgg   120
agattcaaat taaaagaaa aacttatata taatgaatac acaaaagcta cctaatctgt    180
atatatatat atataaatat gtcttcatta aattaatggt cgtggaatag aaaaaggaaa   240
acctaatttg atcgctaggg cttatcagag taaagatggt taaccttcaa aagatgacta   300
attaaccggg gagataatta aaagattaaa tacgccaaca gagagttaag agataccaga   360
tttaaattcc acaatttggt catgttcttc ttcacgtatt catgacgatg tctgaattat   420
agagaaaccc aaaatataaa atgttaattt taccagacat ttacatacca ataactctat   480
gacgatatgt aaagtaagca aggcatgttt ttatgcaggg aagattgaaa attcaagatt   540
aatcaagaaa attggaatac caaaaagaga gggagctccc ttcagtccaa tcagagagaa   600
tcaatgaccc aatttgtcta ccgcatcatt cattcattta acaagtctag ctcgaattct   660
tggtgactcg gtatttggat gaatgagtcg gaagctaatt ggatcatatc acgacctatg   720
aatggactca aggaagctct ctacaaatgt attcctacca catcaaccca aatatagtga   780
ttacagatgc tgttctcact gtagactaca tttacgttt                          819
```

<210> SEQ ID NO 268
<211> LENGTH: 503
<212> TYPE: DNA
<213> ORGANISM: Arabidopsis thaliana

<400> SEQUENCE: 268

```
agacatctct tcttctctca tctctctttt cttctctctt ttcctcacat aaactctctt    60
tttttactat taaatccata tggtacctca aattaatcta tggtcatcta gggttatctt   120
gaagattaga attgattcta gcacgcacag agaggaagat cattgcatcc agaatcacaa   180
acatggccta tctttatct tttcttttg atctaagtca ctgttttatg ctatatatag    240
tataatcaaa ttcttacat gtgcttgtat gtatgcgtat atatagtaac ggaattgtta    300
atatgcttat agatgttgag ttggtggagg aagagagctt tcttcggtcc actcatggag    360
taatatgtga gatttaattg actctcgact cattcatcca ataccaaat gaaagaattt    420 gttctcatat ggtaaatgaa tgaatgatgc gagagacaaa ttgagtcttc acttctctat   480
gcttggactg aagggagctc cct                                           503
```

<210> SEQ ID NO 269
<211> LENGTH: 365
<212> TYPE: DNA

<213> ORGANISM: Arabidopsis thaliana

<400> SEQUENCE: 269

```
tcttattcca tcacaatcat ctagggtttt aagccaagct tatatagccc gtcataaaga        60
gaactcatct gcctctctct caataccaat aaatatcacc accgtccttc tctcctatca       120
ctattcaatc tatcgcaaac tcctttatgt ctctccaatt ttatgagagg gtttccttca       180
agaacacagt aaaatagatt ggatctttaa acttttgttc cttttcatga gggtttgaca       240
aagatttcct tacagtcatc tttggcattc tgtccacctc cttctataca tatatgcatg       300
tgtatatata tatgcgtttc gtgtgaaaga aggaggtggg tatactgcca atagagatct       360
gttag                                                                    365
```

<210> SEQ ID NO 270
<211> LENGTH: 134
<212> TYPE: DNA
<213> ORGANISM: Arabidopsis thaliana

<400> SEQUENCE: 270

```
ttgtatcatg acagagcaag aagaagaaag tcaaatgtcc acatgagttc cctttaacgc        60
ttcattgttg aatactcaaa gccacattgg tttgtatata acactgaagt gtttgggggg       120
actcttggtg tcat                                                          134
```

<210> SEQ ID NO 271
<211> LENGTH: 229
<212> TYPE: DNA
<213> ORGANISM: Arabidopsis thaliana

<400> SEQUENCE: 271

```
tttcaaaccc taacactctt ataaaccgat tcgccaaaat gtatctacaa tatattgata        60
atgtaatatc tatatattca aacaatcgtc gtgttggtcg gatgttttct agagttcctc       120
tgagcacttc attggagata caattttttta taaaatagtt ttctactgaa gtgtttgggg       180
gaactcccgg gctgattcgg tatttttaaat tcagtagact agctagctg                  229
```

<210> SEQ ID NO 272
<211> LENGTH: 220
<212> TYPE: DNA
<213> ORGANISM: Arabidopsis thaliana

<400> SEQUENCE: 272

```
tggtaataga aatgagcaag gagatatttt tttcccctgg gtttgaatga acatcattga        60
gtgcatcgtt gatgtaattt tacttatttt attccattgt tgaattaatt aaagaagtat       120
atatcagcgt tgcattcaat tatgttttttc taattttcag gaaatacaaa aaaaatgaaa       180
aaaaaaaatc acttaaaaga ccttgagagt tcttttgact                             220
```

<210> SEQ ID NO 273
<211> LENGTH: 225
<212> TYPE: DNA
<213> ORGANISM: Arabidopsis thaliana

<400> SEQUENCE: 273

```
ggatatcgaa actcaaactg taacagtcct tttattactg gtttagaaga tagataaata        60
ttgttaaggt agtggatctc gacagggttg atatgagaac acgagcaa tcaacggcta         120
taacgacgct acgtcattgt tacagctctc gtttcatgtg ttctcaggtc accctgctg        180
agctctttct ctaccgtcca tgttttatca acgccgtggc ccgtg                       225
```

<210> SEQ ID NO 274
<211> LENGTH: 165
<212> TYPE: DNA
<213> ORGANISM: Arabidopsis thaliana

<400> SEQUENCE: 274

| | | | | | |
|---|---|---|---|---|---|
| tcttatagag | atgaagagaa | acatgtaaac | tcactagttt | tagggcgcct | ctccattggc | 60 |
| aggtccttta | cttccaaata | tacacataca | tatatgaata | tcgaaaattt | ccgatgatcg | 120 |
| atttataaat | gacctgccaa | aggagagttg | ccctgaaact | ggttc | | 165 |

<210> SEQ ID NO 275
<211> LENGTH: 187
<212> TYPE: DNA
<213> ORGANISM: Arabidopsis thaliana

<400> SEQUENCE: 275

| | | | | | |
|---|---|---|---|---|---|
| caataactca | aaatgcaatg | tgaaatatga | agaatatatt | aaatagtagt | gaagatgcat | 60 |
| gtttatgaag | acagagagat | aatgtatggt | tggattactg | ggcgaatact | cctatggcag | 120 |
| atcgcattgg | ctagatatgc | aagtaaaatg | cttctctgcc | aaaggagatt | tgccccgcaa | 180 |
| ttcatcc | | | | | | 187 |

<210> SEQ ID NO 276
<211> LENGTH: 235
<212> TYPE: DNA
<213> ORGANISM: Arabidopsis thaliana

<400> SEQUENCE: 276

| | | | | | |
|---|---|---|---|---|---|
| atttaggtct | ctcttcttct | tcttcttttt | cttcttgagc | gccggcgaaa | aaagtctctg | 60 |
| tgagaaaaag | atacgacgat | tgtcattaga | agagtcgtat | tacatgtttt | gtgcttgaat | 120 |
| ctaattcaac | aggctttatg | taagagattc | tttaacaatt | cctataatct | ttgttgttgg | 180 |
| attagattca | cgcacaaact | cgtaatctgt | cttttcgatt | tttaccagat | ctgtc | 235 |

<210> SEQ ID NO 277
<211> LENGTH: 944
<212> TYPE: DNA
<213> ORGANISM: Arabidopsis thaliana

<400> SEQUENCE: 277

| | | | | | |
|---|---|---|---|---|---|
| aattatatcc | atggtcatgg | ctcatcatta | gtcgcactgc | tctccttttc | tcaaagttta | 60 |
| aattcgacat | ttggtaaaat | gatgaaacct | cgatggaact | gctctcttta | tggaatcacg | 120 |
| gaatggacaa | ataatcaaaa | tcagaaatcg | aagcgaaaag | ggaggagaaa | aacgcagatt | 180 |
| tggaggattg | gggacagatt | agatactgtt | gaatgcatca | ctctaatgct | atcagcctat | 240 |
| taatagcgtc | ctatattttc | gaagactttt | aatgtttagg | gttatggatt | tttcgagcga | 300 |
| agcatggaga | gatgttgaat | tggatactat | aggatttggt | acaacacata | catatgttct | 360 |
| gcttctgcaa | aactaacata | tcaagttcag | agaaaccagt | aagtcgttga | atattttatt | 420 |
| atccattcaa | cgctttcttc | ttttggatca | tgtcttgttt | gcttgaccac | ttcttcttgc | 480 |
| ttaagaggat | ggacaatata | taaaaactgg | agccttcttt | ttctatgaat | gcttatcatc | 540 |
| gcggagttga | tctgttcaat | tcacctgcca | ttggatgctt | tttttatata | tacttcactg | 600 |
| ttcaatttca | gatgctttag | aaggtttgcg | gagtagctag | agaatctggt | atcttcagtt | 660 |
| cttcaatttc | agctacttgg | tatcagcttc | gtcattgtat | atcaacacat | tcttaatata | 720 |

-continued

| taatactact | ttttcatcca | ttaaacccct | tacaatgtcg | agtaaacgaa | gcatctgtcc | 780 |
| cctggtattg | tcttcgagct | tggtgttttt | ttctagccaa | ctccaagttc | tcgagttgat | 840 |
| cattgtttgt | attcttgaga | cattatttgg | ggacgagatg | ttttgttgac | tcgatataag | 900 |
| aaggggcttt | atgaagaaa | ttgtagtatt | atatatcgag | agtg | | 944 |

<210> SEQ ID NO 278
<211> LENGTH: 420
<212> TYPE: DNA
<213> ORGANISM: Arabidopsis thaliana

<400> SEQUENCE: 278

| ctataaatgc | tgcttatcat | cgtggagttg | gttctgtaaa | catttgaaaa | ttctgaacag | 60 |
| tttcacctgc | cattggatgc | tttgtttcaa | tttcaggtgc | gttagaaggt | ttgcagagta | 120 |
| gctagagaat | ctcgtatctt | cactttctgc | tacttggtat | cagcttcgtc | actttatatc | 180 |
| aacacattct | taatatacaa | tactactttt | tcatccatta | atccccttac | aatgtcgagt | 240 |
| aaacgaagca | tctgtcccct | ggtattgtct | tcgagcttgg | tgtgttttc | tagccagccc | 300 |
| caagttctcg | agttgatcat | tgtttgtatt | ctgacacatt | atttggggac | gagatgtttt | 360 |
| gttgactcga | tataagaagg | ggctttatgg | aagaaattgt | agtattatat | attgagaatg | 420 |

<210> SEQ ID NO 279
<211> LENGTH: 383
<212> TYPE: DNA
<213> ORGANISM: Arabidopsis thaliana

<400> SEQUENCE: 279

| tagtataacc | gctgatgtac | acctaccagc | ttgataactc | tttttcgtgg | tttctgtgta | 60 |
| ctcgtttctg | tttgtacaga | tacttcttgt | tcaatttcag | atgctttaga | aggttttcgg | 120 |
| agtggctaga | gatctgttat | ctgtatgaac | agctacttgg | tatcagcttc | gtcattttat | 180 |
| caacacattc | ttaatataca | atacttcttt | tcatgcatt | aagcccctta | caatgtcgag | 240 |
| taaacaaagc | atgtgtccgc | taatattgtc | ttcgagcttg | gtattttgt | attctgatac | 300 |
| ggtatttggg | gacgacatct | tttgttgact | cgatataaga | aggggttg | tggaagaaat | 360 |
| tgtagtatta | tatatcaaga | atg | | | | 383 |

<210> SEQ ID NO 280
<211> LENGTH: 2164
<212> TYPE: DNA
<213> ORGANISM: Drosophila melanogaster

<400> SEQUENCE: 280

| tttgtggaac | acattcgacc | cactgaaaaa | ttgatataat | ttaatgaaag | tgcataaaaa | 60 |
| tggtggacag | tgcattaaac | tgagcattga | acacaaaggc | cgctcagcaa | attgctaatt | 120 |
| aaaattcacg | attgccattt | cacctgacac | gttgacgatt | tcattacaa | ttcgattatg | 180 |
| tttcgttgca | gggaatttta | aatgttaatt | gccaagaatg | tttcaacaaa | ttcatttctc | 240 |
| attaatgtgt | cttttcattt | aatttatgt | tgtatgagct | gcacgagaaa | tgagttgtac | 300 |
| ttttagttcg | acggcagagt | catgaatgtt | cggcaaagaa | tgtaataata | actatcctct | 360 |
| ttagacaaat | atagatacaa | atctatcaga | ttctaaaagt | agaataatca | attaatcaga | 420 |
| aagctaaaaa | taaataggca | tatttatatt | ttaatgcgga | ttttgaagt | tcaacgggag | 480 |
| aaatgaatcc | tttttaccag | ccacaggcgc | aatttgcaac | agaaagtgta | gcagaagtac | 540 |
| tcctcgaata | tttccctgct | ccaggagtca | tccatgtggt | ttcgaggcac | acatttgaca | 600 |

```
aactcatgcc ccgctatttg ttgtaaaaac acaatcgcac acatggccgc atttcggcga    660
cttccagaga gcggtacact taaggcggcc tgggaaacgc ctgcaatctg ctggtcgcga    720
actgcagatt gcatccatgt gccaggcgac catgcgacca tgtgaccatg tgcccgcccg    780
acgcctcgca gcccacatcc tgcccatcga gggcacaact cagcgtgggt attgccgctc    840
cggctgcttc aagtaggtaa aaaccgagaa gattgaggat gaatgtatga gtatgagaaa    900
atactcggcg gaacatatgc tgccgggctt gacctgaccc tgcctcatgt gtgggtctcc    960
gatttaattt taggcaccta tataaacgcg tgtttacact gcagccagaa cacagtcgcc   1020
gtcttcagtt cgcgccgtca actcctcgat cgatcgatcg catcgtctcg gatcgaatag   1080
agctgggctt ctgctccgga gctacatcgc cgtacttgtc ggacgagtgt ggtgatgaaa   1140
agtcgcttag tccgggattc ctgccagatc tctaagggat gagctggcat ccaggctgg    1200
ccatgtggcg cgaagtatgc gcacaaaaaa gtcaaacaaa aaggcgcaat tttattacgg   1260
gcaaccaacg acgaaacaaa acaaaagcca accgaaaagc agaaacaaag cagcaaaaag   1320
tttatgaatt ttttgtgcag gcgcgtgaaa gatgcaaaac gagaaaaaaa catgaaaaaa   1380
aaacattaaa aaaacaaaa aaaatccaaa acagataccg agctgtatcc gaaaacgagt   1440
ggggaaaggg gtttcccagt cacatataaa cacacttcag tgcgcttaaa aattgcttta   1500
ttgcagttgg actataaaaa cgcacggcag cgaacaccgc acaacaaaaa ggacgagcag   1560
aagtgggcaa ataaaacgaa agctcttaaa cgaaaaacag gaaaatttgc atgccacaaa   1620
aataagcata aggatttgcc gcgcacaaag tagaagcaaa aaggaattgc ccaaatgcag   1680
ccacaaaaga ctgtggcaaa tgttttgcag cttgccccctt tttccctgca attaccgtca   1740
gtcgttgtca ttattcagca gattatatgg ttttgcttat tccggaccac catcatcatc   1800
atcattatca tcatcttcgg taagttagac aatcccataa aaaactgtcc aagtgagtag   1860
tgccaccaaa agttagccgc gttgtggaaa atccaaaaca aagaccatcc catattcagc   1920
ctttgagagt tccatgcttc cttgcattca atagttatat tcaagcatat ggaatgtaaa   1980
gaagtatgga gcgaaatctg gcgagacatc ggagttgaaa ctaaaactga aatttgattg   2040
aaacagaagt agaaccgtaa tgaaatgaat gaaatattaa cccgtttcta caatccctga   2100
ataaaattat taattaatta tagagcgggc taattttaca atatatattg atttttttt    2160
gaag                                                                2164

<210> SEQ ID NO 281
<211> LENGTH: 919
<212> TYPE: DNA
<213> ORGANISM: Drosophila melanogaster

<400> SEQUENCE: 281 attcttttt ggtgctcgat cgtgacggtt tgctcgcgct ctccgctgcg ccgctctttc     60
cgttgcatat gtgtgcgggc gttattgtgc atgtttccgg tggccgaaaa aaatagtaa    120
aataaaatat agaaaacaga aaccaagaat aataacagcc atacgataaa cagtgtgcca   180
atgtgtgtgt ctgtgtgtgt gtgcatctcg cgtaacaaca ataattgcat ttatcggatg   240
gcgccagctt caatttaatt ataaataaca tgttcaactt tttatactat tttccctgcg   300
tcaaagtggg cgttgcaact gcccccggaa aatcacgcgc cccggttcaa agttaaagtt   360
tgctgggtaa cgcacacaca cacacacaca atcactcaca cgcggtcaca cgcacatttc   420
aataaactaa tggagcctgg ctttgttttt gttttatttc caacccactt gagcacacag   480
```

-continued

| | |
|---|---|
| cacacacaga gagaaaaatc aatactcgtt atgggattaa atttacaaag cgcaaagcaa | 540 |
| agcgacaaac aaaattcaaa agaaagaaaa aaaaacactc aaataaactc acaaagaatt | 600 |
| ccttatcgcc aaggggggcca atgttctaag gttctttcgc cttgagaact ttgagcttcc | 660 |
| tctggcaaag gagattataa tgtacaaata atgttgcaat aaccagttga aaccaatgga | 720 |
| ataccgaatc ttgctaatta gcaaggacat ctgttcacat cttaccgggc agcattagat | 780 |
| ccttttttata actctaatac tgtcaggtaa agatgtcgtc cgtgtcctta accttcagta | 840 |
| ccaccaacag cagcagcagc accaaaaaaa aaaaaaaaaa aatgcgtaaa aatccaaaca | 900 |
| aatcataaaa gtcgaagga | 919 |

<210> SEQ ID NO 282
<211> LENGTH: 20
<212> TYPE: RNA
<213> ORGANISM: Arabidopsis thaliana

<400> SEQUENCE: 282
ugacagaaga gagugagcac    20

<210> SEQ ID NO 283
<211> LENGTH: 20
<212> TYPE: RNA
<213> ORGANISM: Arabidopsis thaliana

<400> SEQUENCE: 283
ugacagaaga gagugagcac    20

<210> SEQ ID NO 284
<211> LENGTH: 20
<212> TYPE: RNA
<213> ORGANISM: Arabidopsis thaliana

<400> SEQUENCE: 284
ugacagaaga gagugagcac    20

<210> SEQ ID NO 285
<211> LENGTH: 20
<212> TYPE: RNA
<213> ORGANISM: Arabidopsis thaliana

<400> SEQUENCE: 285
ugacagaaga gagugagcac    20

<210> SEQ ID NO 286
<211> LENGTH: 21
<212> TYPE: RNA
<213> ORGANISM: Arabidopsis lyrata

<400> SEQUENCE: 286
uuuggauuga agggagcucu a    21

<210> SEQ ID NO 287
<211> LENGTH: 21
<212> TYPE: RNA
<213> ORGANISM: Arabidopsis thaliana

<400> SEQUENCE: 287
uuuggauuga agggagcucu a    21

<210> SEQ ID NO 288
<211> LENGTH: 21

```
<212> TYPE: RNA
<213> ORGANISM: Capsella rubella

<400> SEQUENCE: 288
uuuggauuga agggagcucu a                                              21

<210> SEQ ID NO 289
<211> LENGTH: 21
<212> TYPE: RNA
<213> ORGANISM: Arabidopsis thaliana

<400> SEQUENCE: 289
uuuggauuga agggagcucu u                                              21

<210> SEQ ID NO 290
<211> LENGTH: 21
<212> TYPE: RNA
<213> ORGANISM: Arabidopsis thaliana

<400> SEQUENCE: 290
ugccuggcuc ccuguaugcc a                                              21

<210> SEQ ID NO 291
<211> LENGTH: 21
<212> TYPE: RNA
<213> ORGANISM: Arabidopsis thaliana

<400> SEQUENCE: 291
ugccuggcuc ccuguaugcc a                                              21

<210> SEQ ID NO 292
<211> LENGTH: 21
<212> TYPE: RNA
<213> ORGANISM: Arabidopsis thaliana

<400> SEQUENCE: 292
ucaaugcauu gaaagugacu a                                              21

<210> SEQ ID NO 293
<211> LENGTH: 21
<212> TYPE: RNA
<213> ORGANISM: Arabidopsis thaliana

<400> SEQUENCE: 293
ucgauaaacc ucugcaucca g                                              21

<210> SEQ ID NO 294
<211> LENGTH: 21
<212> TYPE: RNA
<213> ORGANISM: Arabidopsis thaliana

<400> SEQUENCE: 294
ucgauaaacc ucugcaucca g                                              21

<210> SEQ ID NO 295
<211> LENGTH: 24
<212> TYPE: RNA
<213> ORGANISM: Arabidopsis thaliana

<400> SEQUENCE: 295
uugaagagga cuuggaacuu cgau                                           24

<210> SEQ ID NO 296
```

```
<211> LENGTH: 21
<212> TYPE: RNA
<213> ORGANISM: Arabidopsis lyrata

<400> SEQUENCE: 296
uggagaagca gggcacgugc a                                              21

<210> SEQ ID NO 297
<211> LENGTH: 21
<212> TYPE: RNA
<213> ORGANISM: Arabidopsis thaliana

<400> SEQUENCE: 297
uggagaagca gggcacgugc a                                              21

<210> SEQ ID NO 298
<211> LENGTH: 21
<212> TYPE: RNA
<213> ORGANISM: Brassica rapa

<400> SEQUENCE: 298
uggagaagca gggcacgugc a                                              21

<210> SEQ ID NO 299
<211> LENGTH: 21
<212> TYPE: RNA
<213> ORGANISM: Carica papaya

<400> SEQUENCE: 299
uggagaagca gggcacgugc a                                              21

<210> SEQ ID NO 300
<211> LENGTH: 21
<212> TYPE: RNA
<213> ORGANISM: Capsella rubella

<400> SEQUENCE: 300
uggagaagca gggcacgugc a                                              21

<210> SEQ ID NO 301
<211> LENGTH: 21
<212> TYPE: RNA
<213> ORGANISM: Gossypium raimondii

<400> SEQUENCE: 301
uggagaagca gggcacgugc a                                              21

<210> SEQ ID NO 302
<211> LENGTH: 21
<212> TYPE: RNA
<213> ORGANISM: Medicago truncatula

<400> SEQUENCE: 302
uggagaagca gggcacgugc a                                              21

<210> SEQ ID NO 303
<211> LENGTH: 21
<212> TYPE: RNA
<213> ORGANISM: Oryza sativa

<400> SEQUENCE: 303
uggagaagca ggguacgugc a                                              21
```

```
<210> SEQ ID NO 304
<211> LENGTH: 21
<212> TYPE: RNA
<213> ORGANISM: Arabidopsis lyrata

<400> SEQUENCE: 304
ucggaccagg cuucaucccc c                                              21

<210> SEQ ID NO 305
<211> LENGTH: 21
<212> TYPE: RNA
<213> ORGANISM: Arabidopsis thaliana

<400> SEQUENCE: 305
ucggaccagg cuucaucccc c                                              21

<210> SEQ ID NO 306
<211> LENGTH: 21
<212> TYPE: RNA
<213> ORGANISM: Brassica carinata

<400> SEQUENCE: 306
ucggaccagg cuucaucccc c                                              21

<210> SEQ ID NO 307
<211> LENGTH: 21
<212> TYPE: RNA
<213> ORGANISM: Brassica juncea

<400> SEQUENCE: 307
ucggaccagg cuucaucccc c                                              21

<210> SEQ ID NO 308
<211> LENGTH: 21
<212> TYPE: RNA
<213> ORGANISM: Brassica napus

<400> SEQUENCE: 308
ucggaccagg cuucaucccc c                                              21

<210> SEQ ID NO 309
<211> LENGTH: 21
<212> TYPE: RNA
<213> ORGANISM: Brassica oleracea

<400> SEQUENCE: 309
ucggaccagg cuucaucccc c                                              21

<210> SEQ ID NO 310
<211> LENGTH: 21
<212> TYPE: RNA
<213> ORGANISM: Brassica rapa

<400> SEQUENCE: 310
ucggaccagg cuucaucccc c                                              21

<210> SEQ ID NO 311
<211> LENGTH: 21
<212> TYPE: RNA
<213> ORGANISM: Arabidopsis thaliana

<400> SEQUENCE: 311
ucggaccagg cuucauuccc c                                              21
```

```
<210> SEQ ID NO 312
<211> LENGTH: 21
<212> TYPE: RNA
<213> ORGANISM: Arabidopsis thaliana

<400> SEQUENCE: 312
ucggaccagg cuucauuccc c                                              21

<210> SEQ ID NO 313
<211> LENGTH: 21
<212> TYPE: RNA
<213> ORGANISM: Arabidopsis thaliana

<400> SEQUENCE: 313
ugaagcugcc agcaugaucu a                                              21

<210> SEQ ID NO 314
<211> LENGTH: 21
<212> TYPE: RNA
<213> ORGANISM: Arabidopsis thaliana

<400> SEQUENCE: 314
ugaagcugcc agcaugaucu a                                              21

<210> SEQ ID NO 315
<211> LENGTH: 21
<212> TYPE: RNA
<213> ORGANISM: Arabidopsis thaliana

<400> SEQUENCE: 315
cagccaagga ugacuugccg g                                              21

<210> SEQ ID NO 316
<211> LENGTH: 21
<212> TYPE: RNA
<213> ORGANISM: Arabidopsis thaliana

<400> SEQUENCE: 316
uagccaagga ugacuugccu g                                              21

<210> SEQ ID NO 317
<211> LENGTH: 21
<212> TYPE: RNA
<213> ORGANISM: Arabidopsis thaliana

<400> SEQUENCE: 317
ugauugagcc gcgccaauau c                                              21

<210> SEQ ID NO 318
<211> LENGTH: 21
<212> TYPE: RNA
<213> ORGANISM: Arabidopsis thaliana

<400> SEQUENCE: 318
uugagccgug ccaauaucac g                                              21

<210> SEQ ID NO 319
<211> LENGTH: 21
<212> TYPE: RNA
<213> ORGANISM: Medicago truncatula

<400> SEQUENCE: 319
ugauugagcc gcgucaauau c                                              21
```

<210> SEQ ID NO 320
<211> LENGTH: 21
<212> TYPE: RNA
<213> ORGANISM: Zea mays

<400> SEQUENCE: 320
ggauugagcc gcgucaauau c                                          21

<210> SEQ ID NO 321
<211> LENGTH: 21
<212> TYPE: RNA
<213> ORGANISM: Arabidopsis thaliana

<400> SEQUENCE: 321
uugagccgug ccaauaucac g                                          21

<210> SEQ ID NO 322
<211> LENGTH: 21
<212> TYPE: RNA
<213> ORGANISM: Medicago truncatula

<400> SEQUENCE: 322
agauugagcc gcgccaauau c                                          21

<210> SEQ ID NO 323
<211> LENGTH: 21
<212> TYPE: RNA
<213> ORGANISM: Medicago truncatula

<400> SEQUENCE: 323
cgagccgaau caauaucacu c                                          21

<210> SEQ ID NO 324
<211> LENGTH: 21
<212> TYPE: RNA
<213> ORGANISM: Arabidopsis thaliana

<400> SEQUENCE: 324
agaaucuuga ugaugcugca u                                          21

<210> SEQ ID NO 325
<211> LENGTH: 20
<212> TYPE: RNA
<213> ORGANISM: Arabidopsis thaliana

<400> SEQUENCE: 325
gcagcaccau uaagauucac                                            20

<210> SEQ ID NO 326
<211> LENGTH: 21
<212> TYPE: RNA
<213> ORGANISM: Arabidopsis thaliana

<400> SEQUENCE: 326
agaaucuuga ugaugcugca g                                          21

<210> SEQ ID NO 327
<211> LENGTH: 21
<212> TYPE: RNA
<213> ORGANISM: Arabidopsis thaliana

<400> SEQUENCE: 327
ggaaucuuga ugaugcugca u                                              21

<210> SEQ ID NO 328
<211> LENGTH: 21
<212> TYPE: RNA
<213> ORGANISM: Arabidopsis cebennensis

<400> SEQUENCE: 328
uuggacugaa gggagcuccc u                                              21

<210> SEQ ID NO 329
<211> LENGTH: 21
<212> TYPE: RNA
<213> ORGANISM: Arabidopsis halleri

<400> SEQUENCE: 329
uuggacugaa gggagcuccc u                                              21

<210> SEQ ID NO 330
<211> LENGTH: 21
<212> TYPE: RNA
<213> ORGANISM: Arabidospis lyrata

<400> SEQUENCE: 330
uuggacugaa gggagcuccc u                                              21

<210> SEQ ID NO 331
<211> LENGTH: 21
<212> TYPE: RNA
<213> ORGANISM: Arabidopsis thaliana

<400> SEQUENCE: 331
uuggacugaa gggagcuccc u                                              21

<210> SEQ ID NO 332
<211> LENGTH: 21
<212> TYPE: RNA
<213> ORGANISM: Brassica rapa

<400> SEQUENCE: 332
uuggacugaa gggagcuccc u                                              21

<210> SEQ ID NO 333
<211> LENGTH: 21
<212> TYPE: RNA
<213> ORGANISM: Carica papaya

<400> SEQUENCE: 333
uuggacugaa gggagcuccu u                                              21

<210> SEQ ID NO 334
<211> LENGTH: 19
<212> TYPE: RNA
<213> ORGANISM: Capsella rubella

<400> SEQUENCE: 334
uuggacugaa gggagcucc                                                 19

<210> SEQ ID NO 335
<211> LENGTH: 21
<212> TYPE: RNA
<213> ORGANISM: Eucalyptus grandis

<400> SEQUENCE: 335

-continued

```
uuggacugaa gggagcuccc u                                                21

<210> SEQ ID NO 336
<211> LENGTH: 21
<212> TYPE: RNA
<213> ORGANISM: Gossypium raimondii

<400> SEQUENCE: 336
uuggacugaa gggagcuccc u                                                21

<210> SEQ ID NO 337
<211> LENGTH: 22
<212> TYPE: RNA
<213> ORGANISM: Medicago truncatula

<400> SEQUENCE: 337
uuggacugaa gggagucucc cu                                               22

<210> SEQ ID NO 338
<211> LENGTH: 21
<212> TYPE: RNA
<213> ORGANISM: Oryza sativa

<400> SEQUENCE: 338
uuggacugaa gggugcuccc u                                                21

<210> SEQ ID NO 339
<211> LENGTH: 20
<212> TYPE: RNA
<213> ORGANISM: Physcomitrella patens

<400> SEQUENCE: 339
cuuggacuga agggagcucc                                                  20

<210> SEQ ID NO 340
<211> LENGTH: 20
<212> TYPE: RNA
<213> ORGANISM: Thellungiella halophila

<400> SEQUENCE: 340
uggacucaag gaagcucucu                                                  20

<210> SEQ ID NO 341
<211> LENGTH: 21
<212> TYPE: RNA
<213> ORGANISM: Arabidopsis thaliana

<400> SEQUENCE: 341
uuggacugaa gggagcuccc u                                                21

<210> SEQ ID NO 342
<211> LENGTH: 20
<212> TYPE: RNA
<213> ORGANISM: Arabidopsis thaliana

<400> SEQUENCE: 342
uuggcauucu guccaccucc                                                  20

<210> SEQ ID NO 343
<211> LENGTH: 21
<212> TYPE: RNA
<213> ORGANISM: Arabidopsis thaliana
```

```
<400> SEQUENCE: 343
cugaaguguu uggggggacu c                                              21

<210> SEQ ID NO 344
<211> LENGTH: 21
<212> TYPE: RNA
<213> ORGANISM: Arabidopsis thaliana

<400> SEQUENCE: 344
cugaaguguu uggggggaacu c                                             21

<210> SEQ ID NO 345
<211> LENGTH: 21
<212> TYPE: RNA
<213> ORGANISM: Arabidopsis thaliana

<400> SEQUENCE: 345
ucauugagug caucguugau g                                              21

<210> SEQ ID NO 346
<211> LENGTH: 21
<212> TYPE: RNA
<213> ORGANISM: Arabidopsis thaliana

<400> SEQUENCE: 346
uguguucuca ggucacccu g                                               21

<210> SEQ ID NO 347
<211> LENGTH: 21
<212> TYPE: RNA
<213> ORGANISM: Arabidopsis thaliana

<400> SEQUENCE: 347
ugccaaagga gaguugcccu g                                              21

<210> SEQ ID NO 348
<211> LENGTH: 21
<212> TYPE: RNA
<213> ORGANISM: Arabidopsis thaliana

<400> SEQUENCE: 348
ugccaaagga gauuugcccc g                                              21

<210> SEQ ID NO 349
<211> LENGTH: 21
<212> TYPE: RNA
<213> ORGANISM: Arabidopsis thaliana

<400> SEQUENCE: 349
uuagauucac gcacaaacuc g                                              21

<210> SEQ ID NO 350
<211> LENGTH: 22
<212> TYPE: RNA
<213> ORGANISM: Arabidopsis thaliana

<400> SEQUENCE: 350
uuggggacga gauguuuugu ug                                             22

<210> SEQ ID NO 351
<211> LENGTH: 22
<212> TYPE: RNA
<213> ORGANISM: Arabidopsis thaliana
```

```
<400> SEQUENCE: 351
uuggggacga gauguuuugu ug                                              22

<210> SEQ ID NO 352
<211> LENGTH: 21
<212> TYPE: RNA
<213> ORGANISM: Arabidopsis thaliana

<400> SEQUENCE: 352
ccccuuacaa ugucgaguaa a                                               21

<210> SEQ ID NO 353
<211> LENGTH: 22
<212> TYPE: RNA
<213> ORGANISM: Drosophila melanogaster

<400> SEQUENCE: 353
uggaauguaa agaaguaugg ag                                              22

<210> SEQ ID NO 354
<211> LENGTH: 23
<212> TYPE: RNA
<213> ORGANISM: Drosophila melanogaster

<400> SEQUENCE: 354
uaauacuguc agguaaagau guc                                             23

<210> SEQ ID NO 355
<211> LENGTH: 17
<212> TYPE: PRT
<213> ORGANISM: Homo sapiens

<400> SEQUENCE: 355

Met Glu Met Ala Leu Met Val Ala Gln Thr Arg Lys Gly Lys Ser Val
1               5                   10                  15
Val

<210> SEQ ID NO 356
<211> LENGTH: 53
<212> TYPE: DNA
<213> ORGANISM: Homo sapiens

<400> SEQUENCE: 356
tggagatggc tctaatggtg gcacaaacca ggaaggggaa atctgtggtt taa           53

<210> SEQ ID NO 357
<211> LENGTH: 1500
<212> TYPE: DNA
<213> ORGANISM: Homo sapiens

<400> SEQUENCE: 357
gccgagcccg ggcccagcgc cgcctgcagc ctcgggaagg gagcggatag cggagccccg    60
agccgcccgc agagcaagcg cggggaacca aggagacgct cctggcactg cagataactt   120
gtctgcattt caagaacaac ctaccagaga ccttacctgt caccttggct ctcccaccca   180
atggagatgg ctctaatggt ggcacaaacc aggaagggga atctgtggt ttaaattctt    240 tatgcctcat cctctgagtg ctgaaggctt gctgtaggct gtatgctgtt aatgctaatc   300
gtgatagggg ttttttgcctc caactgactc ctacatatta gcattaacag tgtatgatgc  360
ctgttactag cattcacatg gaacaaattg ctgccgtggg aggatgacaa agaagcatga   420
```

-continued

```
gtcaccctgc tggataaact tagacttcag gctttatcat ttttcaatct gttaatcata    480
atctggtcac tgggatgttc aaccttaaac taagttttga agtaaggtt  atttaaaaga    540 tttatcagta gtatcctaaa tgcaaacatt ttcatttaaa tgtcaagccc atgtttgttt    600
ttatcattaa cagaaaatat attcatgtca ttcttaattg caggttttgg cttgttcatt    660
ataatgttca taaacacctt tgattcaact gttagaaatg tgggctaaac acaaatttct    720
ataatatttt tgtagttaaa aattagaagg actactaacc tccagttata tcatggattg    780
tctggcaacg ttttttaaaa gatttagaaa ctggtacttt ccccaggta  acgattttct    840 gttcaggcaa cttcagttta aaattaatac ttttatttga ctcttaaagg gaaactgaaa    900
ggctatgaag ctgaatttt  ttaatgaaat attttaaca  gttagcaggg taaataacat    960
ctgacagcta atgagatatt ttttccatac aagataaaaa gatttaatca aaaaatttca   1020
tatttgaaat gaagtcccaa atctaggttc aagttcaata gcttagccac ataatacggt   1080
tgtgcgagca gagaatctac ctttccactt ctaagcctgt ttcttcctcc atatggggat   1140
aatactttac aaggttgttg tgaggcttag atgagataga gaattattcc ataagataat   1200
caagtgctac attaatgtta tagttagatt aatccaagaa ctagtcaccc tactttatta   1260
gagaagagaa aagctaatga tttgatttgc agaatattta aggtttggat ttctatgcag   1320
tttttctaaa taaccatcac ttacaaatat gtaaccaaac gtaattgtta gtatatttaa   1380
tgtaaacttg ttttaacaac tcttctcaac attttgtcca ggttattcac tgtaaccaaa   1440
taaatctcat gagtctttag ttgatttaaa ataaaaaaaa aaaaaaaaaa aaaaaaaaa    1500
```

<210> SEQ ID NO 358
<211> LENGTH: 23
<212> TYPE: RNA
<213> ORGANISM: Homo sapiens

<400> SEQUENCE: 358

```
uaauacugu c agguaaagau guc                                             23
```

<210> SEQ ID NO 359
<211> LENGTH: 337
<212> TYPE: DNA
<213> ORGANISM: Medicago truncatula

<400> SEQUENCE: 359

```
ttagggtttt cagctcatgg taataaaaat gtcatctaat gtcttgcatg tgggaatgag     60
gtcatatatg cagccaagga tgacttgccg gcgagcctct ttcgatactt ttatgacata    120
attaatcatg tggatagcca aggtactaaa ctcactttgc actaaaacaa atattttgc    180 tttagtgcaa acttagttta ggcgcttcgc aacggctagt caaatgtcct agttccaatg    240
tgattggttg tccggcaagt cgtctctggc tacgtaaagg cctccttttt tcatgctaga    300
tttttgatga tttgatatag ccacacatat tttggaa                              337
```

<210> SEQ ID NO 360
<211> LENGTH: 121
<212> TYPE: DNA
<213> ORGANISM: Medicago truncatula

<400> SEQUENCE: 360

```
aagaggcaga gagagtaatg cagccaagga tgacttgccg acaacattgg cgaatgttca     60
tgtgatttct gcctcattgt gccggcaagt tgtccttggc tatgttagtc tctcatcttc    120
``` t                                                                         121

<210> SEQ ID NO 361
<211> LENGTH: 114
<212> TYPE: DNA
<213> ORGANISM: Medicago truncatula

<400> SEQUENCE: 361
tgaattcccc tccgcttttt gatgttggct tgtctcaatc aaatcaaagt tcttgaaatt    60
tgagttcttt agtctgattg agtcgtgcca atatcatatt aagcgataaa agtc         114

<210> SEQ ID NO 362
<211> LENGTH: 367
<212> TYPE: DNA
<213> ORGANISM: Medicago truncatula

<400> SEQUENCE: 362
ccacaaaact ataactagct agaagcttta atcgccttat ttattataat aataataata    60
aatatggctt cagctgcaaa agtatacatg gcgtgatatt gatccggctc atctatatct   120
tcaagttcaa tcatccatat tcatatcaat ttcagacgag ccgaatcaat atcactcttg   180
tttgcttcat tgcatattaa ttatatactt catttataag ttatagtttg ccatatatat   240
attagattga ttctgcagaa gtagacagga gtggtgttgt ttctgctcat cttattaaat   300
aatgaatgaa tgaatgacat ttgcttactt ataagacgag ccgaatcaat atcactccag   360
tacacct                                                              367

<210> SEQ ID NO 363
<211> LENGTH: 135
<212> TYPE: DNA
<213> ORGANISM: Medicago truncatula

<400> SEQUENCE: 363
aactgcaact tgaggaggca tccaaaggga tcgcattgat cctataatat ttcaacttta    60
gtcactttaa ttttctctca tataatactt aattgggatc atgccatccc tttggatttc   120
tcctttagta gctac                                                    135

<210> SEQ ID NO 364
<211> LENGTH: 119
<212> TYPE: DNA
<213> ORGANISM: Medicago truncatula

<400> SEQUENCE: 364
aggcatccaa agggatcgca ttgatcccaa atctaattaa gtccctagct acttaattaa    60
caacttaatt tccttaatat ctcataatat ttgggatcat gctatcccett tggattcat   119

<210> SEQ ID NO 365
<211> LENGTH: 93
<212> TYPE: DNA
<213> ORGANISM: Medicago truncatula

<400> SEQUENCE: 365
tgcttttcca cagctttctt gaacttcttt cgtatcttaa atctgttttc aagattaaaa    60
gtcctagaag ctcaagaaag ctgtgggaga ata                                93

<210> SEQ ID NO 366
<211> LENGTH: 95
<212> TYPE: DNA
<213> ORGANISM: Medicago truncatula

<400> SEQUENCE: 366
tattcttcca cagctttctt gaactgcatc caaattgagt tcctttgcat tgccatggcc    60
attgttttgc ggttcaataa agctgtggga agata    95

<210> SEQ ID NO 367
<211> LENGTH: 21
<212> TYPE: RNA
<213> ORGANISM: Medicago truncatula

<400> SEQUENCE: 367
cagccaagga ugacuugccg g    21

<210> SEQ ID NO 368
<211> LENGTH: 21
<212> TYPE: RNA
<213> ORGANISM: Medicago truncatula

<400> SEQUENCE: 368
cagccaagga ugacuugccg a    21

<210> SEQ ID NO 369
<211> LENGTH: 21
<212> TYPE: RNA
<213> ORGANISM: Medicago truncatula

<400> SEQUENCE: 369
ugauugaguc gugccaauau c    21

<210> SEQ ID NO 370
<211> LENGTH: 20
<212> TYPE: RNA
<213> ORGANISM: Medicago truncatula

<400> SEQUENCE: 370
gagccgaauc aauaucacuc    20

<210> SEQ ID NO 371
<211> LENGTH: 21
<212> TYPE: RNA
<213> ORGANISM: Medicago truncatula

<400> SEQUENCE: 371
uccaaaggga ucgcauugau c    21

<210> SEQ ID NO 372
<211> LENGTH: 21
<212> TYPE: RNA
<213> ORGANISM: Medicago truncatula

<400> SEQUENCE: 372
uccaaaggga ucgcauugau c    21

<210> SEQ ID NO 373
<211> LENGTH: 21
<212> TYPE: RNA
<213> ORGANISM: Medicago truncatula

<400> SEQUENCE: 373
uuccacagcu uucuugaacu u    21

<210> SEQ ID NO 374

```
<211> LENGTH: 21
<212> TYPE: RNA
<213> ORGANISM: Medicago truncatula

<400> SEQUENCE: 374
uuccacagcu uucuugaacu g                                              21

<210> SEQ ID NO 375
<211> LENGTH: 15
<212> TYPE: PRT
<213> ORGANISM: Arabidopsis thaliana

<400> SEQUENCE: 375

Met Met Leu His Ile Thr His Arg Phe Glu Ser Asp Val Gly Cys
1               5                   10                  15

<210> SEQ ID NO 376
<211> LENGTH: 4
<212> TYPE: PRT
<213> ORGANISM: Arabidopsis thaliana

<400> SEQUENCE: 376

Met Leu Tyr Val
1

<210> SEQ ID NO 377
<211> LENGTH: 14
<212> TYPE: PRT
<213> ORGANISM: Arabidopsis thaliana

<400> SEQUENCE: 377

Met Phe Met Arg Arg Gly Leu Val Tyr Asn Asn Ile Tyr Ile
1               5                   10

<210> SEQ ID NO 378
<211> LENGTH: 17
<212> TYPE: PRT
<213> ORGANISM: Arabidopsis thaliana

<400> SEQUENCE: 378

Met Met Lys Val Cys Asp Glu Gln Asp Gly Glu Ala Gly His Val His
1               5                   10                  15

Tyr

<210> SEQ ID NO 379
<211> LENGTH: 28
<212> TYPE: PRT
<213> ORGANISM: Arabidopsis thaliana

<400> SEQUENCE: 379

Met Lys Lys Arg Ile Thr Arg Ile Asn Leu Glu Glu Gln Ile Lys Lys
1               5                   10                  15

Thr Leu Asp Asp Ser Arg Thr Arg Leu His Ser Pro
            20                  25

<210> SEQ ID NO 380
<211> LENGTH: 10
<212> TYPE: PRT
<213> ORGANISM: Arabidopsis thaliana

<400> SEQUENCE: 380

Met Lys Lys Ile Gly Ser Ile Asp Ser Phe
1               5                   10
```

```
<210> SEQ ID NO 381
<211> LENGTH: 6
<212> TYPE: PRT
<213> ORGANISM: Arabidopsis thaliana

<400> SEQUENCE: 381

Met Thr Cys Arg Phe Lys
1               5

<210> SEQ ID NO 382
<211> LENGTH: 11
<212> TYPE: PRT
<213> ORGANISM: Arabidopsis thaliana

<400> SEQUENCE: 382

Met Lys Asn Glu Asn Leu Cys Gly Ser Gln Gly
1               5                   10

<210> SEQ ID NO 383
<211> LENGTH: 45
<212> TYPE: PRT
<213> ORGANISM: Arabidopsis thaliana

<400> SEQUENCE: 383

Met Lys Cys Met Met Lys Lys Arg Gly Leu Thr Trp Arg Lys Ala Ser
1               5                   10                  15

Cys Leu Val Ala Lys Asp Asp Leu Pro Asp Leu Phe Arg Leu His Asp
            20                  25                  30

Ser Ile Ser Asn Ser Cys Ile Leu Asp Tyr Tyr Thr Phe
        35                  40                  45

<210> SEQ ID NO 384
<211> LENGTH: 7
<212> TYPE: PRT
<213> ORGANISM: Arabidopsis thaliana

<400> SEQUENCE: 384

Met Phe Pro Arg Glu Ser Leu
1               5

<210> SEQ ID NO 385
<211> LENGTH: 29
<212> TYPE: PRT
<213> ORGANISM: Arabidopsis thaliana

<400> SEQUENCE: 385

Met Thr Leu Ser Val Phe Phe His Ser Phe Leu Glu Leu Gln Asn Phe
1               5                   10                  15

Phe Arg Phe Phe Phe Phe Ser Phe Asp Ile Ser Tyr Ala
            20                  25

<210> SEQ ID NO 386
<211> LENGTH: 23
<212> TYPE: PRT
<213> ORGANISM: Arabidopsis thaliana

<400> SEQUENCE: 386

Met Ser Leu Ala Lys Gly Glu Leu Pro Cys His Cys Phe Arg Leu Asn
1               5                   10                  15

Thr Val Tyr Asn Arg Phe Cys
            20
```

```
<210> SEQ ID NO 387
<211> LENGTH: 48
<212> TYPE: DNA
<213> ORGANISM: Arabidopsis thaliana

<400> SEQUENCE: 387
atgatgttgc atatcacaca taggtttgag agtgatgttg gttgttga                    48

<210> SEQ ID NO 388
<211> LENGTH: 15
<212> TYPE: DNA
<213> ORGANISM: Arabidopsis thaliana

<400> SEQUENCE: 388
atgctgtatg tatag                                                        15

<210> SEQ ID NO 389
<211> LENGTH: 45
<212> TYPE: DNA
<213> ORGANISM: Arabidopsis thaliana

<400> SEQUENCE: 389
atgttcatgc gtagaggttt ggtatacaac aatatataca tataa                       45

<210> SEQ ID NO 390
<211> LENGTH: 54
<212> TYPE: DNA
<213> ORGANISM: Arabidopsis thaliana

<400> SEQUENCE: 390
atgatgaagg tgtgtgatga gcaagatgga gaagcagggc acgtgcatta ctag             54

<210> SEQ ID NO 391
<211> LENGTH: 87
<212> TYPE: DNA
<213> ORGANISM: Arabidopsis thaliana

<400> SEQUENCE: 391
atgaagaaga gaatcactcg aattaatttg gaagaacaaa ttaagaaaac cctagatgat       60
tctcggacca ggcttcattc cccctaa                                           87

<210> SEQ ID NO 392
<211> LENGTH: 33
<212> TYPE: DNA
<213> ORGANISM: Arabidopsis thaliana

<400> SEQUENCE: 392
atgaagaaga tcggtagtat tgattcattt taa                                    33

<210> SEQ ID NO 393
<211> LENGTH: 21
<212> TYPE: DNA
<213> ORGANISM: Arabidopsis thaliana

<400> SEQUENCE: 393
atgacttgcc gatttaaatg a                                                 21

<210> SEQ ID NO 394
<211> LENGTH: 12
<212> TYPE: DNA
<213> ORGANISM: Arabidopsis thaliana

<400> SEQUENCE: 394
```

```
atggtgacat ga                                                            12

<210> SEQ ID NO 395
<211> LENGTH: 36
<212> TYPE: DNA
<213> ORGANISM: Arabidopsis thaliana

<400> SEQUENCE: 395
atgaagaatg agaacttgtg tggtagccaa ggatga                                  36

<210> SEQ ID NO 396
<211> LENGTH: 138
<212> TYPE: DNA
<213> ORGANISM: Arabidopsis thaliana

<400> SEQUENCE: 396
atgaagtgta tgatgaagaa gagaggtcta acatggcgga aagcgtcatg tttagtagcc        60
aaggatgact tgcctgatct ttttcgcctc cacgattcaa tttcaaattc atgcattttg       120
gattattata ccttttaa                                                     138

<210> SEQ ID NO 397
<211> LENGTH: 24
<212> TYPE: DNA
<213> ORGANISM: Arabidopsis thaliana

<400> SEQUENCE: 397
atgtttccga gagagtccct ctga                                               24

<210> SEQ ID NO 398
<211> LENGTH: 90
<212> TYPE: DNA
<213> ORGANISM: Arabidopsis thaliana

<400> SEQUENCE: 398
atgaccctct ctgtattctt ccacagcttt cttgaactgc aaaacttctt cagattttt        60 ttttttcttt tgatatctc ttacgcataa                                          90

<210> SEQ ID NO 399
<211> LENGTH: 72
<212> TYPE: DNA
<213> ORGANISM: Arabidopsis thaliana

<400> SEQUENCE: 399
atgtcacttg ccaaaggaga gttgccctgt cactgcttcc gcttaaacac agtctataac        60
cggttctgct aa                                                            72

<210> SEQ ID NO 400
<211> LENGTH: 331
<212> TYPE: DNA
<213> ORGANISM: Arabidopsis thaliana

<400> SEQUENCE: 400
ctttgtcact tcatacactc cctattgtct atatatatat atatacttac acatattcaa        60
acattataat acttaattac acatacatac tttatgatgt tgcatatcac acataggttt       120
gagagtgatg ttggttgttg acagaagata gagagcacta aggatgacat gcaagtacat       180
acatatatat catcacaccg catgtggatg ataaaatatg tataacaaat tcaaagaaag       240
agagggagag aaagagagag aacctgcatc tctactcttt tgtgctctct atacttctgt       300 caccacctttt atctcttctt ctctctaacc t                                     331
```

<210> SEQ ID NO 401
<211> LENGTH: 304
<212> TYPE: DNA
<213> ORGANISM: Arabidopsis thaliana

<400> SEQUENCE: 401

| atttactctt | caccgccctc | tctctatata | tagtctctat | cctcacatat | tatatatcaa | 60 |
| accgcaagaa | tgctgtatgt | atagtggagg | gtgatagtgt | ggttgctgac | agaagataga | 120 |
| gagcactaag | gatgctatgc | aaaacagaca | cagatatgtg | tttctaattg | tatttcatac | 180 |
| tttaacctca | aagttgatat | aaaaaaagaa | agaaagatag | aagagctaga | agactatctg | 240 |
| catctctatt | cctatgtgct | ctctatgctt | ctgtcatcac | cttctttct  | ctatttctct | 300 |
| ctac       |            |            |            |            |            | 304 |

<210> SEQ ID NO 402
<211> LENGTH: 245
<212> TYPE: DNA
<213> ORGANISM: Arabidopsis thaliana

<400> SEQUENCE: 402

| aaccaaaact | cttcaacatt | tctctctgac | tacttcattt | cctcttccca | acagttaaaa | 60 |
| aaagttctga | ttcgattcaa | gccaagatcc | acgtataaag | atatgttcat | gcgtagaggt | 120 |
| ttggtataca | acaatatata | catataatag | tttgtcgtta | tgcctggctc | cctgtatgcc | 180 |
| acgagtggat | accgattttg | gttttaaaat | cggctgccgg | tggcgtacaa | ggagtcaagc | 240 |
| atgac      |            |            |            |            |            | 245 |

<210> SEQ ID NO 403
<211> LENGTH: 240
<212> TYPE: DNA
<213> ORGANISM: Arabidopsis thaliana

<400> SEQUENCE: 403

| atacattctc | tctttctctc | tctctctctc | tctcatcccg | gcccagttat | gtggtcggag | 60 |
| agaatgatga | aggtgtgtga | tgagcaagat | ggagaagcag | ggcacgtgca | ttactagctc | 120 |
| atatatacac | tctcaccaca | aatgcgtgta | tatatgcgga | attttgtgat | atagatgtgt | 180 |
| gtgtgtgttg | agtgtgatga | tatggatgag | ttagttcttc | atgtgcccat | cttcaccatc | 240 |

<210> SEQ ID NO 404
<211> LENGTH: 280
<212> TYPE: DNA
<213> ORGANISM: Arabidopsis thaliana

<400> SEQUENCE: 404

| tcacacatac | ctttctttct | cttcttcttc | ttacgaaaag | tttcatcaca | ttcacattat | 60 |
| ctttaacttt | ggtctctttt | ctttttgtc  | tcttttctct | tcttgataac | gtggttctag | 120 |
| tcttgattaa | ttcattgttg | tgcgatttag | tgttgagagg | attgttgtct | ggctcgaggt | 180 |
| catgaagaag | agaatcactc | gaattaattt | ggaagaacaa | attaagaaaa | ccctagatga | 240 |
| ttctcggacc | aggcttcatt | cccctaacc  | tacttatcgc |            |            | 280 |

<210> SEQ ID NO 405
<211> LENGTH: 179
<212> TYPE: DNA
<213> ORGANISM: Arabidopsis thaliana -continued

```
<400> SEQUENCE: 405
atttagcttc ttcttcttct tcttcttctg tctacttaca taaagttatc cttgctttgg      60 tttaggggttg agaggaatat tgtctggctc gaggtcatga agaagatcgg tagtattgat    120
tcattttaaa gagtgaaatc cctaaatgat tctcggacca ggcttcattc cccccaacc     179

<210> SEQ ID NO 406
<211> LENGTH: 376
<212> TYPE: DNA
<213> ORGANISM: Arabidopsis thaliana

<400> SEQUENCE: 406
tagtattcat aagcaccaaa acaaatatgt agagatctcc tcttccattc tctattgtta     60
ctttcgagaa gaaacataca aaacacatac attttttcttt tgtttgtggt tttcatatat   120
acaagtgggt atagctagtg aaacgcgaat gtgacgaaag tagtgtgcag ccaaggatga   180
cttgccgatt taaatgatct ttcttttatac tctattaaga caatttagtt tcaaactttt   240 ttttttttt ttttttgaag gattcaggaa gaaattagga tatattattc cgtataaaat     300
acaagatata taaaaccaaa aagaaaaagt aacatgatcg gcaagttgtc cttggctaca   360
cgttactttg tgtcgc                                                    376

<210> SEQ ID NO 407
<211> LENGTH: 77
<212> TYPE: DNA
<213> ORGANISM: Arabidopsis thaliana

<400> SEQUENCE: 407
actcatcaac aacctcttca taaatacata atcatataa gagaaaatgg tgacatgaag      60
aatgagaact tgtgtgg                                                    77

<210> SEQ ID NO 408
<211> LENGTH: 248
<212> TYPE: DNA
<213> ORGANISM: Arabidopsis thaliana

<400> SEQUENCE: 408
aggcaaaaac atatagagag taatgaagtg tatgatgaag aagagaggtc taacatggcg      60
gaaagcgtca tgtttagtag ccaaggatga cttgcctgat cttttttcgcc tccacgattc    120 aatttcaaat tcatgcattt tggattatta taccttttaa agtataatag gtcaaatatc    180
atgttgaatc ttgcgggtta ggtttcaggc agtctctttg gctatcttga catgcttttt    240
ccatccat                                                              248

<210> SEQ ID NO 409
<211> LENGTH: 187
<212> TYPE: DNA
<213> ORGANISM: Arabidopsis thaliana

<400> SEQUENCE: 409
attcactccc ttcttcttct taatctcctt acagttacag acattctctc acttgcgttc      60 ttgtttctt tacaaaacag atacactatg tttccgagag agtccctctg atattggcct     120
ggttcactca gattctcttt tactaactca tctgattgag ccgtgtcaat atctcagtcc    180
tctctcg                                                              187

<210> SEQ ID NO 410
<211> LENGTH: 246
```

-continued

```
<212> TYPE: DNA
<213> ORGANISM: Arabidopsis thaliana

<400> SEQUENCE: 410
tctcacaact caacttccc tctttctcta tattacgctt ttgcccctca ctccctcttt      60
ccacaattag ggtttcgtct gctctacatg accctctctg tattcttcca cagctttctt    120
gaactgcaaa acttcttcag atttttttt ttttctttg atatctctta cgcataaaat     180
agtgattttc ttcatatctc tgctcgattg atttgcggtt caataaagct gtgggaagat    240
acagac                                                               246

<210> SEQ ID NO 411
<211> LENGTH: 631
<212> TYPE: DNA
<213> ORGANISM: Arabidopsis thaliana

<400> SEQUENCE: 411
gaataaccaa ccagccttct ctcaaagcaa accaaaaaga aaaccaaca ttgaaagagg      60 aagttacgat aagcggagca gtaatagggc atctttctat ggcaggcga cttggctatt    120 tgtatctttt gtgttcttga ctattggcta tgtcacttgc caaggagag ttgccctgtc    180 actgcttccg cttaaacaca gtctataacc ggttctgcta atatcaatcc ttcttttgga    240
catgtccaaa gccgagattg attgatagag aattggtctc tctggctaca aaactagtgc    300
ggttctctcg atttaagttt taatagcatt cactttgcac attgcatctt tcacatcaaa    360
tttccatttc atcaaccatc taaacctctt tgttagcttt gatataagca acgatctaaa    420
gtctaaaaac cattaatcct ctgaaaaaaa agacaatttc gatggttcta ttatgtttct    480
ccaatgcaga aattgtatcg tctgaattat agtagatttt ttctagacta aagtgtaaac    540
caagacgaat ctgcactaac aagacacacc aatagacttt acagagaaag gttacgagtt    600
ttgaaaatat taacggacca tagtcatcgc g                                   631

<210> SEQ ID NO 412
<211> LENGTH: 21
<212> TYPE: RNA
<213> ORGANISM: Arabidopsis thaliana

<400> SEQUENCE: 412
uugacagaag auagagagca c                                               21

<210> SEQ ID NO 413
<211> LENGTH: 20
<212> TYPE: RNA
<213> ORGANISM: Arabidopsis thaliana

<400> SEQUENCE: 413
ugacagaaga uagagagcac                                                 20

<210> SEQ ID NO 414
<211> LENGTH: 21
<212> TYPE: RNA
<213> ORGANISM: Arabidopsis thaliana

<400> SEQUENCE: 414
ugccuggcuc ccuguaugcc a                                               21

<210> SEQ ID NO 415
<211> LENGTH: 21
<212> TYPE: RNA
```

```
<213> ORGANISM: Arabidopsis thaliana

<400> SEQUENCE: 415
uggagaagca gggcacgugc a                                              21

<210> SEQ ID NO 416
<211> LENGTH: 21
<212> TYPE: RNA
<213> ORGANISM: Arabidopsis thaliana

<400> SEQUENCE: 416
ucggaccagg cuucauuccc c                                              21

<210> SEQ ID NO 417
<211> LENGTH: 21
<212> TYPE: RNA
<213> ORGANISM: Arabidopsis thaliana

<400> SEQUENCE: 417
ucggaccagg cuucauuccc c                                              21

<210> SEQ ID NO 418
<211> LENGTH: 21
<212> TYPE: RNA
<213> ORGANISM: Arabidopsis thaliana

<400> SEQUENCE: 418
cagccaagga ugacuugccg a                                              21

<210> SEQ ID NO 419
<211> LENGTH: 21
<212> TYPE: RNA
<213> ORGANISM: Arabidopsis thaliana

<400> SEQUENCE: 419
uagccaagga ugacuugccu g                                              21

<210> SEQ ID NO 420
<211> LENGTH: 21
<212> TYPE: RNA
<213> ORGANISM: Arabidopsis thaliana

<400> SEQUENCE: 420
uagccaagga ugacuugccu g                                              21

<210> SEQ ID NO 421
<211> LENGTH: 21
<212> TYPE: RNA
<213> ORGANISM: Arabidopsis thaliana

<400> SEQUENCE: 421
ugauugagcc gugucaauau c                                              21

<210> SEQ ID NO 422
<211> LENGTH: 21
<212> TYPE: RNA
<213> ORGANISM: Arabidopsis thaliana

<400> SEQUENCE: 422
uuccacagcu uucuugaacu g                                              21

<210> SEQ ID NO 423
<211> LENGTH: 21
```

```
<212> TYPE: RNA
<213> ORGANISM: Arabidopsis thaliana

<400> SEQUENCE: 423
ugccaaagga gaguugcccu g                                          21
```

MICROPEPTIDES AND USE OF SAME FOR MODULATING GENE EXPRESSION

RELATED APPLICATIONS

This application is a continuation of U.S. patent application Ser. No. 14/320,703, filed on Jul. 1, 2014; which claims priority under 35 U.S.C. § 119, to French Patent Application Nos. 1360727, filed Oct. 31, 2013, and U.S. Pat. No. 1,455,044, filed Jun. 3, 2014, the disclosures of which are incorporated by reference herein in their entireties. The disclosure of U.S. patent application Ser. No. 14/320,703, includes an ASCII text file named "U.S. Ser. No. 14/320, 703", created on and electronically submitted Jul. 1, 2014, 139.77 KB, which is incorporated herein by reference in its entirety.

FIELD OF THE INVENTION

The present invention relates to micropeptides (peptides encoded by microRNAs or "miPEPs") and use thereof for modulating gene expression.

BACKGROUND OF THE INVENTION

The microRNAs (miRNAs) are small non-coding RNAs, about 21 nucleotides in length after maturation, which control expression of target genes at the post-transcriptional level, by degrading the target mRNA or by inhibiting its translation. The miRNAs occur in plants and animals.

The target genes are often key genes in developmental processes. For example they encode transcription factors or proteins of the proteasome.

The regulation of expression of the miRNAs is very poorly understood, but it is known in particular that the latter involves, like most coding genes, an RNA polymerase II: this enzyme produces a primary transcript, called "pri-miRNA", which is then matured by a protein complex in particular containing the Dicer type enzymes. This maturation leads firstly to the formation of a precursor of miRNA called "pre-miRNA", having a stem-loop secondary structure containing the miRNA and its complementary sequence miRNA*. Then the precursor is matured, which leads to formation of a shorter double-stranded RNA containing the miRNA and the miRNA*. The miRNA is then manipulated by the RISC complex, which cleaves the mRNA of the target gene or inhibits its translation.

Moreover, it has been shown that the presence of introns in the primary transcript of the microRNA increases the expression of the mature microRNA (Schwab et al, *EMBO Rep.*, 14(7): 615-21, 2013). However, owing to experimental difficulties, the primary transcripts of microRNAs, or pri-miRNAs, have received very little study.

About 50% of eukaryotic genes have small open reading frames within their 5'UTR region (5' UnTranslated Region) upstream of the coding sequence. These small open reading frames (or "uORFs" for upstream ORFs) may perform a role of translation regulator, mainly in cis, by modulating the fixation and the rate of the ribosomes on the mRNA, but also in trans by an as yet unknown mechanism, by means of peptides encoded by said uORFs (Combier et al., *Gene Dev,* 22: 1549-1559, 2008). By definition, the uORFS are present upstream of coding genes.

Recently, small ORFs have also been discovered in long intergenic non-coding RNAs (lincRNAs), the putative function of which, if it exists, is not known (Ingolia et al., *Cell,* 147(4): 789-802, 2011; Guttman & Rinn, *Nature,* 482 (7385): 339-46, 2012).

However, no example has yet been reported concerning the existence of ORFs encoding peptides within non-coding microRNAs. Until now, the microRNAs, and by extension their primary transcript, have always been regarded, based on their particular mode of action, as non-coding regulatory RNAs that do not produce any peptide.

SUMMARY OF THE INVENTION

One of the aspects of the invention is to propose peptides capable of modulating the expression of microRNAs.

Another aspect of the invention is to propose a means for modulating the expression of one or more target genes of a microRNA.

The present invention offers the advantage of allowing easier and more effective control of the expression of genes targeted by the microRNAs, through a means other than the microRNA.

The invention thus relates to a process for detecting and identifying a micropeptide (miPEP) encoded by a nucleotide sequence contained in the sequence of the primary transcript of a microRNA, comprising:
  a) a step of detecting an open reading frame from 12 to 303 nucleotides in length contained in the sequence of the primary transcript of said microRNA, then
  b) a step of comparison between:
    the accumulation of said microRNA in a specified eukaryotic cell expressing said microRNA,
    in the presence of a peptide encoded by a nucleotide sequence that is identical or degenerate relative to that of said open reading frame, said peptide being present in the cell independently of transcription of the primary transcript of said microRNA, and
    the accumulation of said microRNA in a eukaryotic cell of the same type as the aforesaid specified eukaryotic cell expressing said microRNA, in the absence of said peptide,
in which a modulation of the accumulation of said microRNA in the presence of said peptide relative to the accumulation of said microRNA in the absence of said peptide indicates the existence of a micropeptide encoded by said open reading frame.

The invention relates in particular to a process for detecting and identifying a micropeptide (miPEP) encoded by a nucleotide sequence contained in the sequence of the primary transcript of a microRNA, comprising:
  a) a step of detecting an open reading frame from 15 to 303 nucleotides in length contained in the sequence of the primary transcript of said microRNA, then
  b) a step of comparison between:
    the accumulation of said microRNA in a specified eukaryotic cell expressing said microRNA,
    in the presence of a peptide encoded by a nucleotide sequence that is identical or degenerate relative to that of said open reading frame, said peptide being present in the cell independently of transcription of the primary transcript of said microRNA, and
    the accumulation of said microRNA in a eukaryotic cell of the same type as the aforesaid specified eukaryotic cell expressing said microRNA, in the absence of said peptide,
in which a modulation of the accumulation of said microRNA in the presence of said peptide relative to the accumulation of said microRNA in the absence of said peptide indicates the existence of a micropeptide encoded by said open reading frame.

BRIEF DESCRIPTION OF THE DRAWINGS

The following figures and examples will illustrate the invention better, but without limiting its scope.

(A) The y-axis indicates the relative expression of MtmiR171b (left-hand columns), of HAM1 (middle columns) or of HAM2 (right-hand columns) in a control plant (white columns) or in a plant in which MtmiR171b is overexpressed (black columns). The error bar corresponds to the standard error of the mean (number of individuals=10). The overexpression of MtmiR171b induces a decrease in the expression of the HAM1 and HAM2 genes.

(B) The y-axis indicates the mean number of lateral roots observed in a control plant (white column) or in a plant in which MtmiR171b is overexpressed (black column). The error bar corresponds to the standard error of the mean (number of individuals=100). The overexpression of MtmiR171b leads to a reduction in the number of lateral roots.

Figure 2:
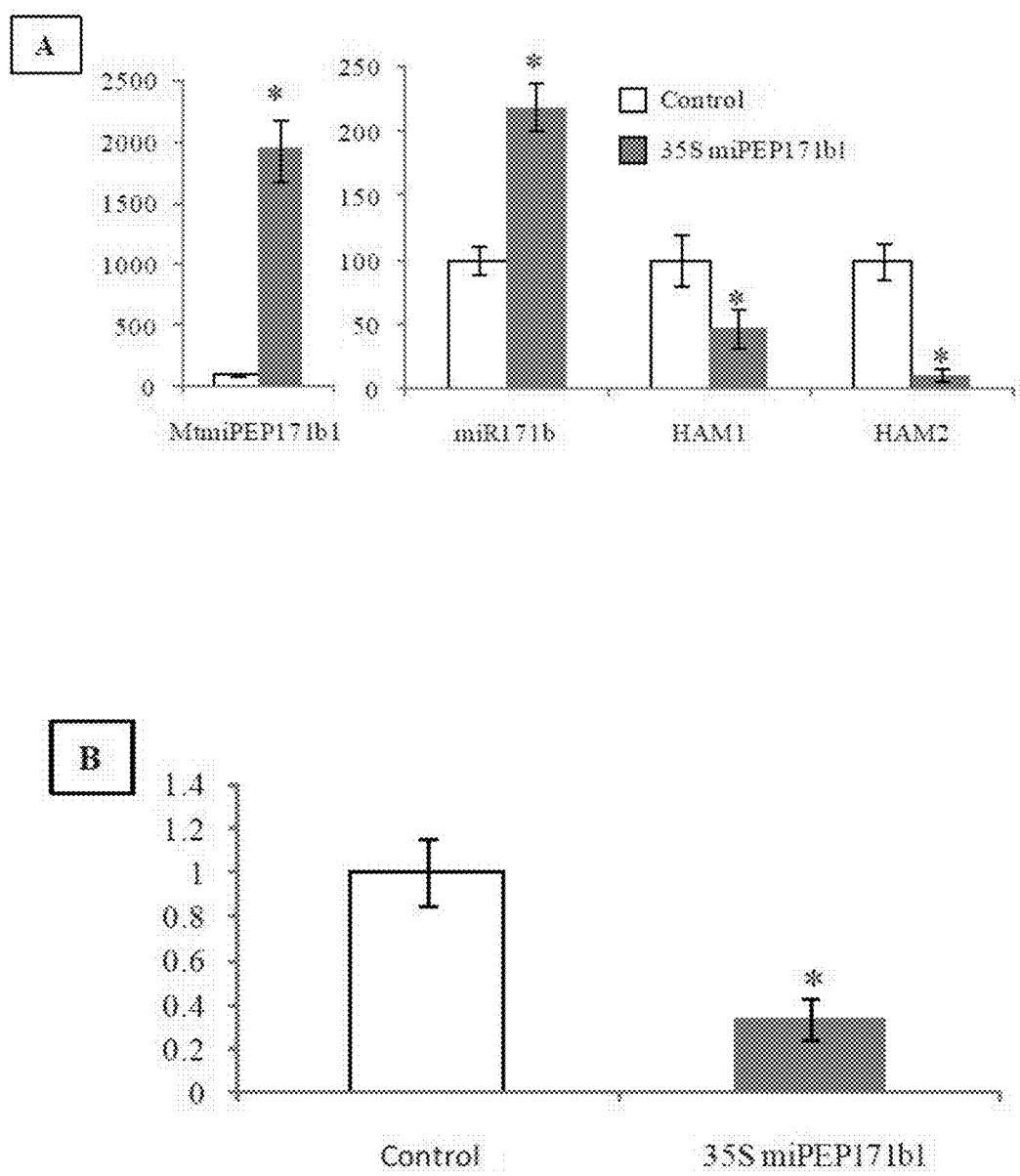

FIG. 2. Effects of overexpression of MtmiPEP171b1 on the expression of MtmiR171b and of the HAM1 and HAM2 genes (A) or on the number of lateral roots (B) in *M. truncatula*.

(A) The y-axis indicates the relative expression of MtmiPEP171b1 (graph on left), miR171b (graph on right, left-hand columns), of HAM1 (accession No. MtGI9-TC114268) (graph on right, middle columns) or of HAM2 (accession No. MtGI9-TC120850) (graph on right, right-hand columns) in a control plant (white columns) or in a plant in which MtmiPEP171b1 is overexpressed (black columns). The error bar corresponds to the standard error of the mean (number of individuals=10). The overexpression of MtmiPEP171b1 induces an increase in the accumulation of MtmiR171b, as well as a decrease in the expression of the HAM1 and HAM2 genes.

(B) The y-axis indicates the mean number of lateral roots observed in a control plant (white column) or in a plant in which MtmiPEP171b1 is overexpressed (black column). The error bar corresponds to the standard error of the mean (number of individuals=100). The overexpression of MtmiPEP171b1 leads to a reduction in the number of lateral roots.

Figure 3:
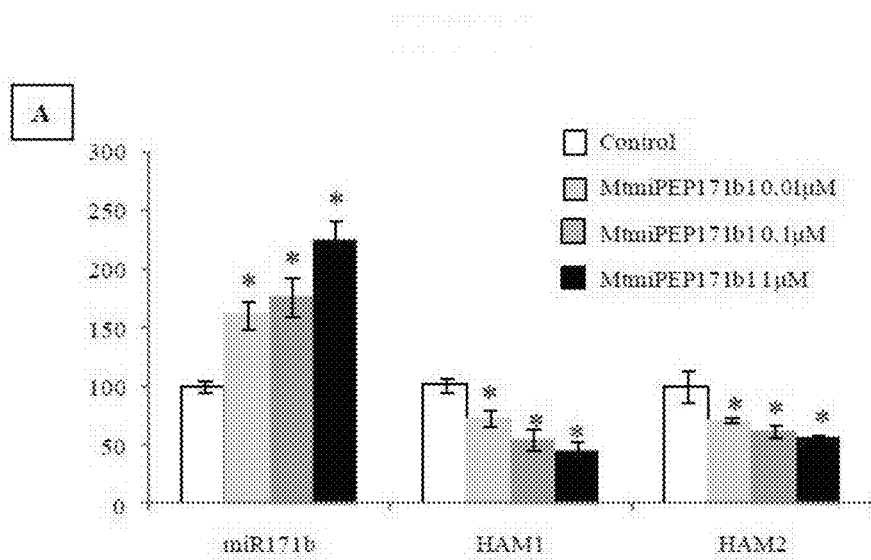
Figure 3:
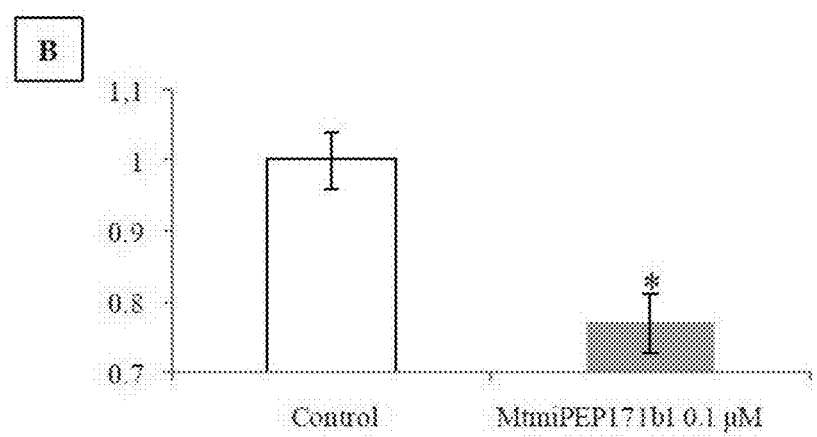
Figure 3:
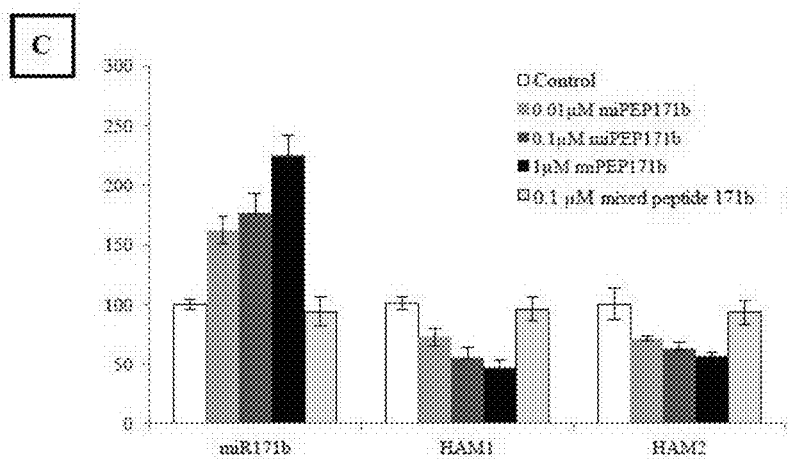

FIG. 3. Effects of MtmiPEP171b1 on the expression of MtmiR171b and the HAM1 and HAM2 genes (A) and on the number of lateral roots (B) in *M. truncatula*.

(A) The y-axis indicates the relative expression of MtmiR171b (left-hand columns), of HAM1 (middle columns) or of HAW (right-hand columns) in a control plant (white columns) or in a plant treated by watering once daily for 5 days with MtmiPEP171b1 at 0.01 µM (light grey columns), 0.1 µM (dark grey columns) or 1 µM (black columns). The error bar corresponds to the standard error of the mean (number of individuals=10). Application of MtmiPEP171b1 at different concentrations induces an increase in the accumulation of MtmiR171b, as well as a decrease in the expression of the HAM1 and HAM2 genes.

(B) The y-axis indicates the mean number of lateral roots observed in a control plant (white column) or in a plant treated by watering with MtmiPEP171b1 at 0.1 µM once daily for 5 days (black column). The error bar corresponds to the standard error of the mean (number of individuals=100). Application of MtmiPEP171b1 at 0.1 µM leads to a reduction in the number of lateral roots.

(C) The y-axis indicates the relative expression of MtmiR171b (left-hand columns), of HAM1 (middle columns) or of HAM2 (right-hand columns) in a control plant (white columns) or in a plant treated by watering once daily for 5 days with MtmiPEP171b1 at 0.01 µM (grey columns), 0.1 µM (dark grey columns) or 1 µM (black columns) or with 0.01 µM of a mixed peptide (light grey columns) the amino acid composition of which is identical to miPEP171b but the sequence of which is different. The error bar corresponds to the standard error of the mean (number of individuals=10).

Figure 4:
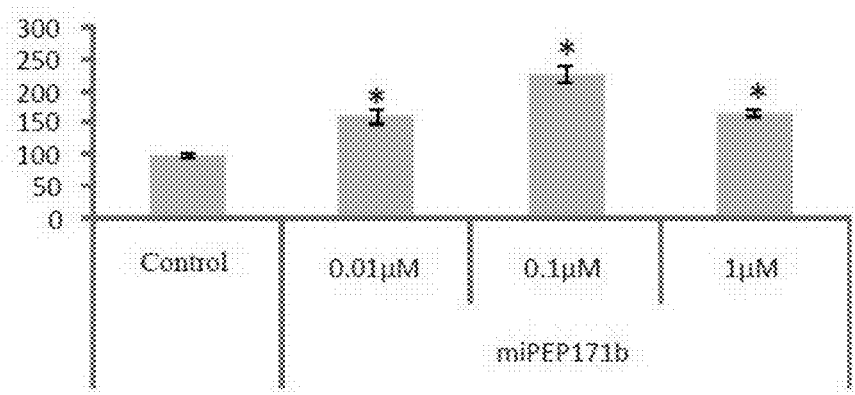
Figure 4:
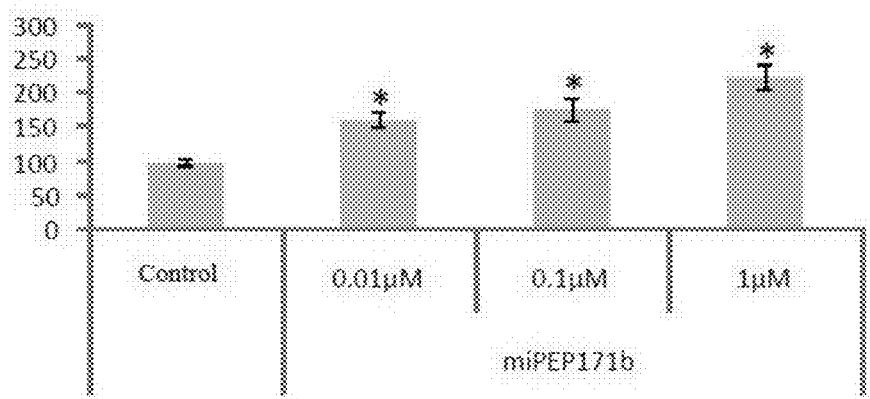

FIG. 4. Effects of MtmiPEP171b1 on the expression of pre-MtmiR171b (A) and of MtmiR171b (B) in *M. truncatula*.

The y-axis indicates the relative expression of the precursors of the different forms of the microRNA in control plants (left-hand column) or in plants treated by watering once daily for 5 days with MtmiPEP171b1 at 0.01 µM, 0.1 µM or 1 µM (right-hand columns). The error bar corresponds to the standard error of the mean (number of individuals=200). Application of MtmiPEP171b1 at different concentrations leads to an increase in the accumulation of pre-MtmiR171b (A) and of MtmiR171b (B).

Figure 5:
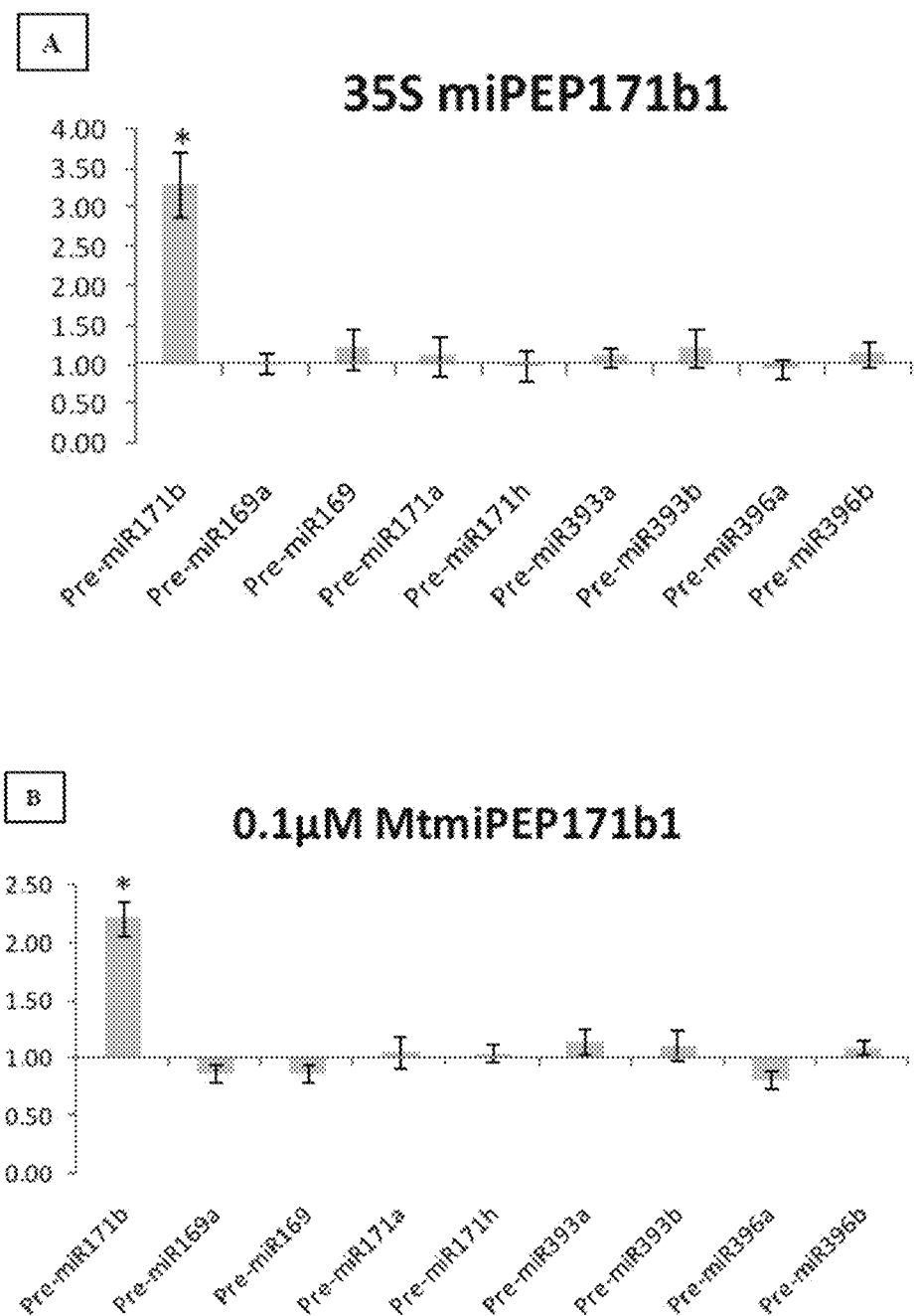

FIG. 5. Effects of overexpression of MtmiPEP171b1 (A) and effects of MtmiPEP171b1 (B) on the expression of different precursors of microRNAs in *M. truncatula*.

The y-axis indicates the ratio of the expression of the precursors of microRNAs in plants overexpressing MtmiPEP171b1 to the expression of these same precursors in control roots (A), or the ratio of the expression of the precursors of microRNAs in plants treated with MtmiPEP171b1 (0.1 µM) to the expression of these same precursors in control roots (B). The different precursors of microRNAs tested are indicated from left to right on the x-axis, namely pre-MtmiR171b (SEQ ID NO: 246), pre-MtmiR169 (SEQ ID NO: 359), pre-MtmiR169a (SEQ ID NO: 360), pre-MtmiR171a (SEQ ID NO: 361), pre-MtmiR171h (SEQ ID NO: 362), pre-MtmiR393a (SEQ ID NO: 363), pre-MtmiR393b (SEQ ID NO: 364), pre-MtmiR396a (SEQ ID NO: 365) and pre-MtmiR396b (SEQ ID NO: 366). The error bar corresponds to the standard error of the mean (number of individuals=10). It is noted that MtmiPEP171b1 only leads to an effect on the accumulation of MtmiR171b and not on the other miRNAs.

Figure 6:
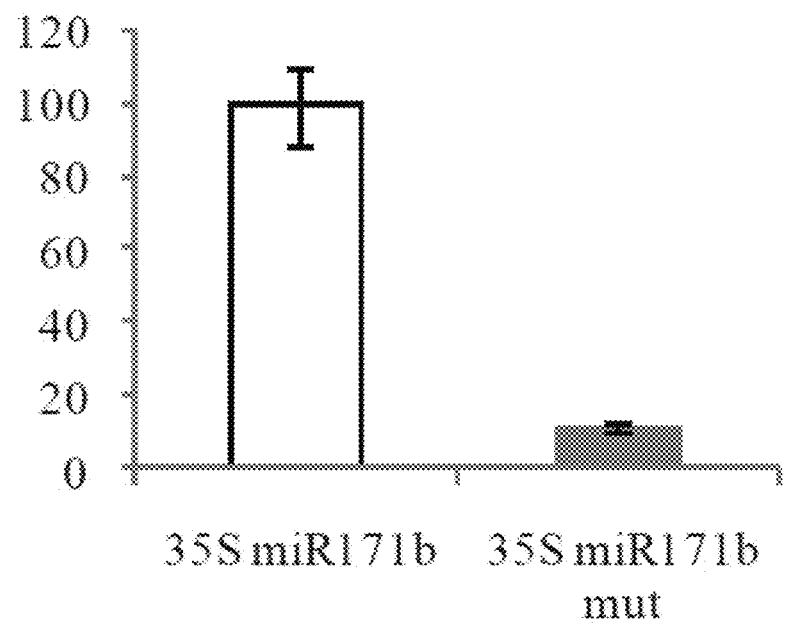

FIG. 6. Effects of translation of MtmiPEP171b1 on the expression of MtmiR171b demonstrated in the model plant *Nicotiana benthamiana*. The y-axis indicates the relative expression of MtmiR171b in tobacco plants transformed in order to express pri-MtmiR171b (white column) or a mutated pri-MtmiR171b in which the codon ATG has been replaced with ATT (black column). The mutated pri-MtmiR171b is therefore incapable of producing MtmiPEP171b1. The error bar corresponds to the standard error of the mean (number of individuals=30). It is noted that the absence of translation of MtmiPEP171b1 leads to a marked decrease in the accumulation of miR171b.

Figure 7:
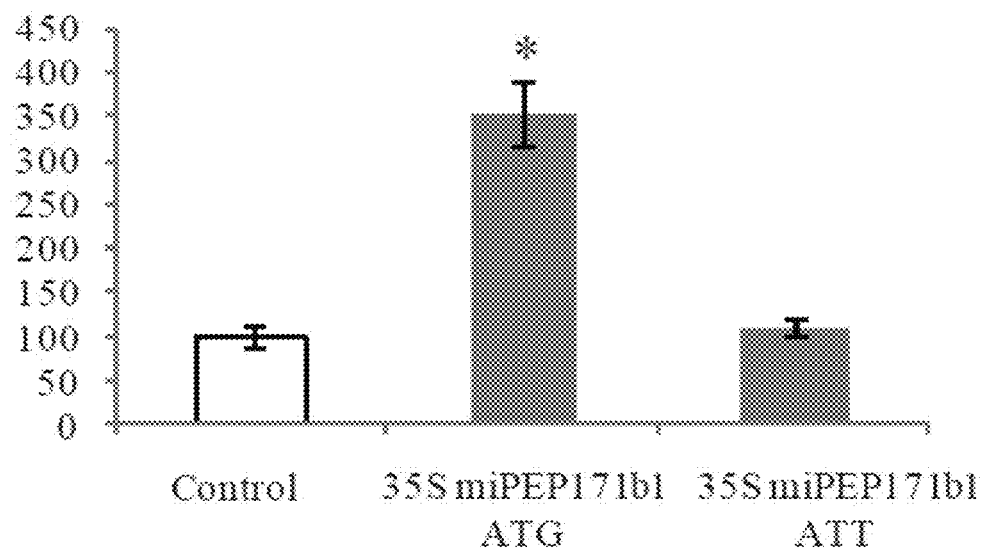

FIG. 7. Effects of overexpression of MtmiPEP171b1 on the expression of pre-MtmiR171b demonstrated in the model plant *Nicotiana benthamiana*.

The y-axis indicates the relative expression of pre-MtmiR171b in tobacco plants that have been transformed in order to express MtmiR171b (left-hand column), MtmiR171b and MtmiPEP171b1 (middle column), or MtmiR171b and a mutated version of MtmiORF171b in which the start codon ATG has been replaced with ATT (right-hand column). The error bar corresponds to the standard error of the mean (number of individuals=30). It is noted that the expression of MtmiPEP171b1 increases the expression of MtmiR171b, and this effect is dependent on the translation of MtmiORF171b to MtmiPEP171b1.

Figure 8:
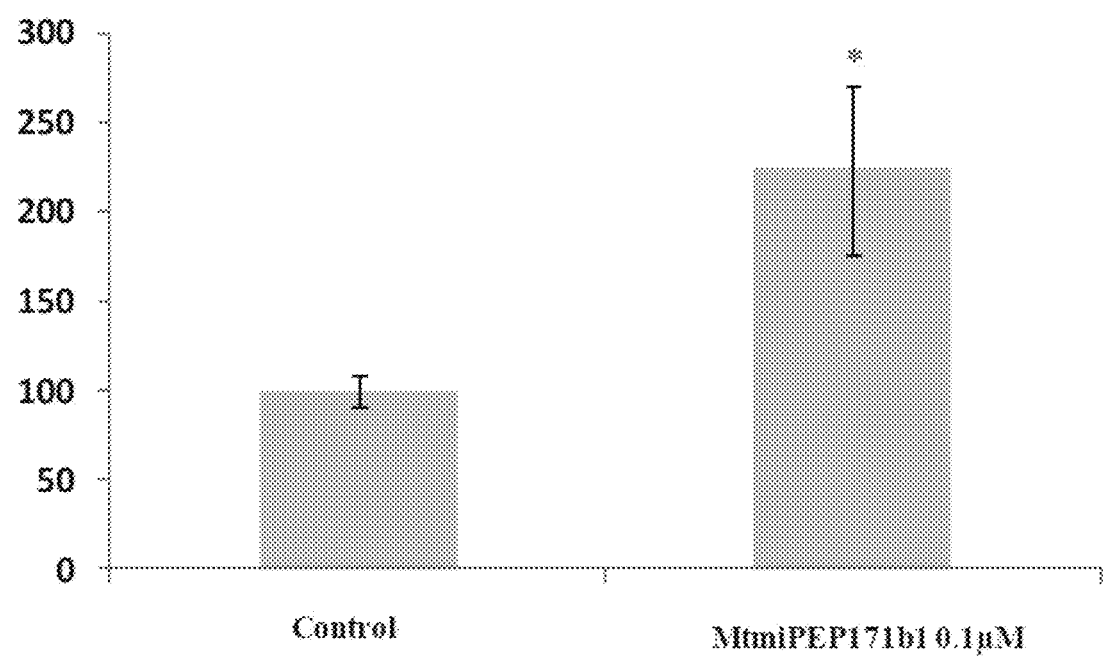

FIG. 8. Effects of MtmiPEP171b1 on the expression of pre-MtmiR171b demonstrated in the model plant *Nicotiana benthamiana*.

The y-axis indicates the relative expression of MtmiR171b in tobacco plants transformed in order to express MtmiR171b onto which MtmiPEP171b1 has been sprayed (0.1 µM) twice, 12 h and then 30 min before sampling (right-hand column) or not (left-hand column). The error bar corresponds to the standard error of the mean (number of individuals=6). The peptide MtmiPEP171b1 applied by spraying induces an increase in the accumulation of MtmiR171b.

Figure 9:
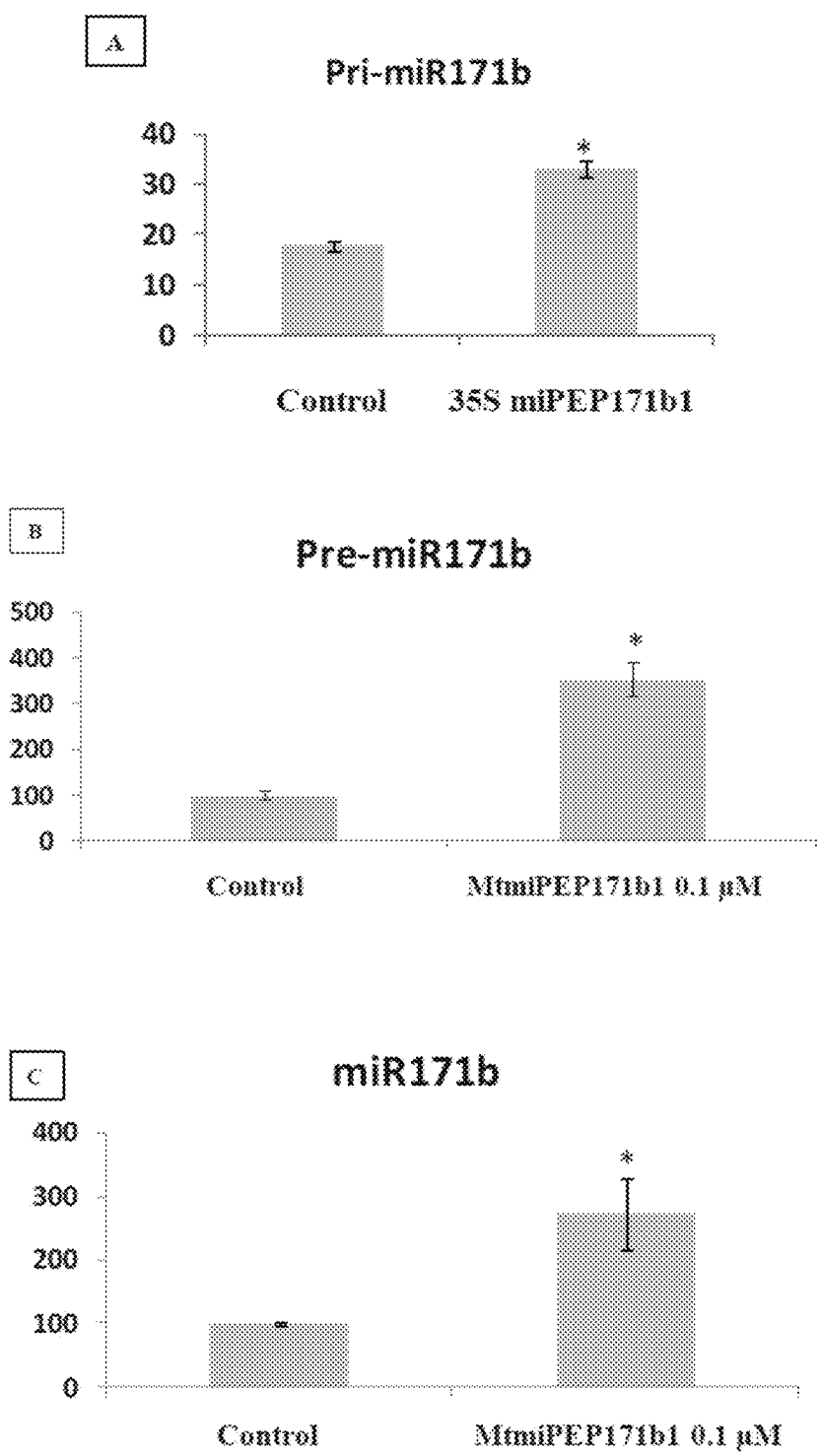

FIG. 9. Effects of MtmiPEP171b1 on the expression of pri-miR171b (A), pre-MtmiR171b (B) and MtmiR171b (C) demonstrated in the model plant *Nicotiana benthamiana*.

The y-axis indicates the relative expression of the precursors of the different forms of the microRNA in tobacco plants modified in order to express MtmiR171b (left-hand column) or modified in order to express MtmiR171b and overexpress MtmiPEP171b1 (right-hand columns, FIG. 9A) or treated with 0.1 µM of miPEP171b1 (FIGS. 9B and C). The error bar corresponds to the standard error of the mean (number of individuals=30). The overexpression of MtmiPEP171b1 or application of miPEP171b1 increases the accumulation of pri-MtmiR171b (A), pre-MtmiR171b (B) and MtmiR171b (C).

Figure 10:
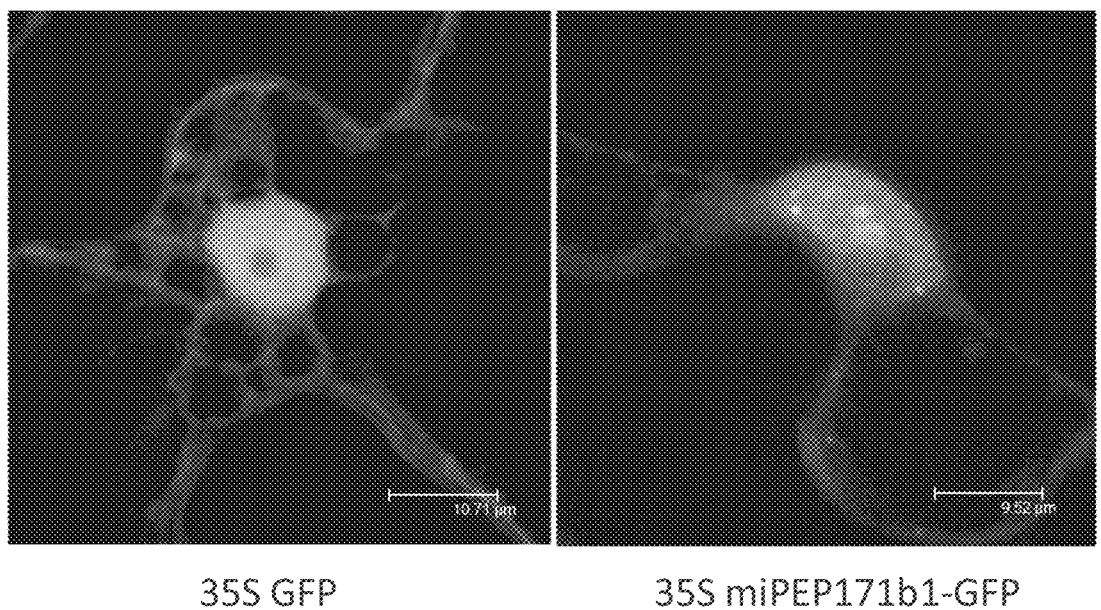

FIG. 10. Localization of MtmiPEP171b1 in tobacco leaf cells that have been modified in order to express MtmiPEP171b1.

The photographs show tobacco leaf cells modified in order to express the protein GFP alone (left panel) or the protein GFP fused to MtmiPEP171b1 (right panel). These observations indicate that MtmiPEP171b1 is localized in small nuclear bodies.

Figure 11:
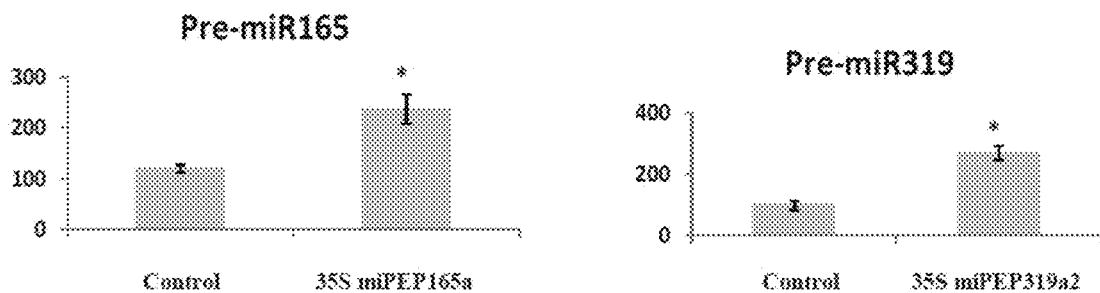

FIG. 11. Effects of the expression of AtmiPEP165a (identified in *Arabidopsis thaliana*) on the expression of AtmiR165a (A), and of the expression of AtmiPEP319a2 (identified in *Arabidopsis thaliana*) on AtmiR319a (B), demonstrated in the model plant of tobacco.

(A) The y-axis indicates the relative expression of AtmiR165a in tobacco plants modified in order to express AtmiR165a (left-hand column) or to express AtmiR165a and AtmiPEP165a (right-hand column).
(B) The y-axis indicates the relative expression of AtmiR319a in tobacco plants modified in order to express AtmiR319a (left-hand column) or in order to express AtmiR319a and AtmiPEP319a (right-hand column).

The error bar corresponds to the standard error of the mean (number of individuals=30). In both cases, it is noted that the expression of miORF, and therefore the production of miPEP, leads to an increase in the accumulation of pre-miRNA.

Figure 12:
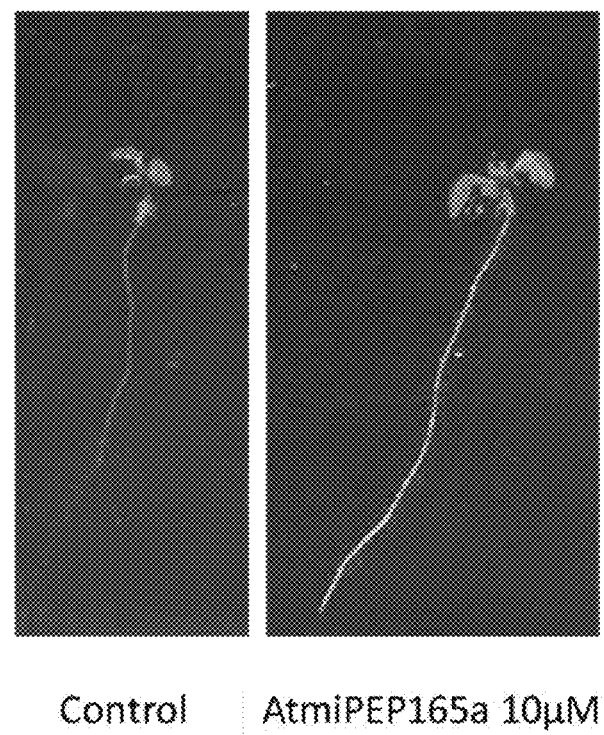
Figure 12:
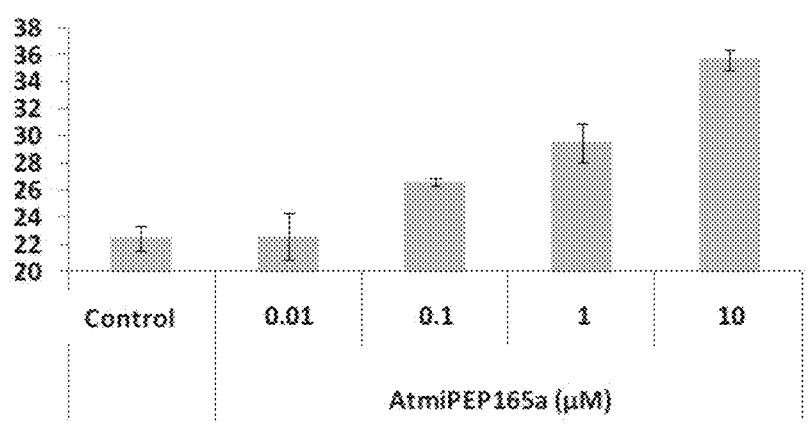

FIG. 12. Effects of treatment with AtmiPEP165a on root growth in *Arabidopsis thaliana*.

The photograph shows two plants of the same age: a control plant (plant on the left) and a plant treated with AtmiPEP165a (plant on the right). The treatment with AtmiPEP165a leads to a phenotype with greatly accelerated root growth in *Arabidopsis thaliana*. The graph shows the expression of pre-miR165 in response to treatment with increasing doses of AtmiPEP165a.

Figure 13:
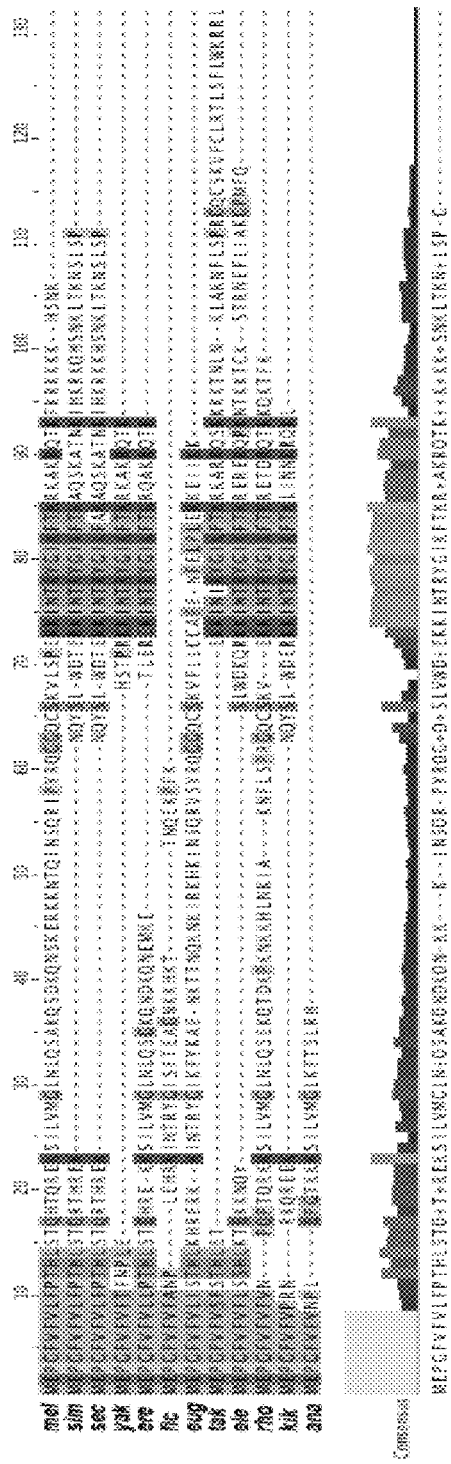

FIG. 13. Conservation of the sequence of miPEP8 identified in *Drosophila*.

The sequences of miPEP8 (SEQ ID NO: 104) were deduced from the sequences of miORF8 (SEQ ID NO: 208) of 12 different *Drosophila* species and were aligned. A histogram shows the conservation of each amino acid between the sequences of miORF8 in the 12 species analysed.

Figure 14:
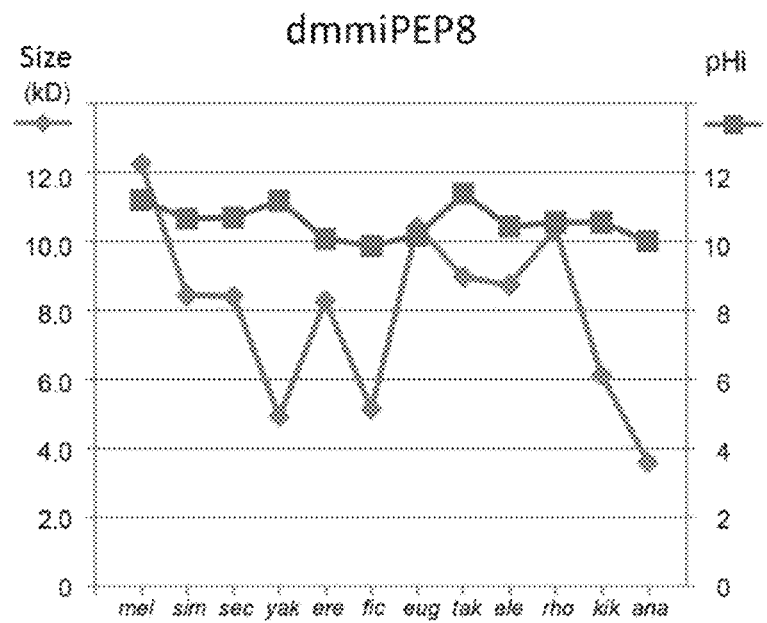

FIG. 14. Evolution of the mass (kDa) and isoelectric point (pI) of miPEP8 in the *Drosophila* species.

The y-axis on the left indicates the size of the miPEP8 (in kD). The y-axis on the right indicates the isoelectric point of the miPEP. The x-axis indicates the origin of the miPEP, i.e. the *Drosophila* species. It is noted that despite a significant change in their size (by more than a factor of 3), the charge of the miPEPs is still very basic (>9.8) in the 12 species studied.

Figure 15:
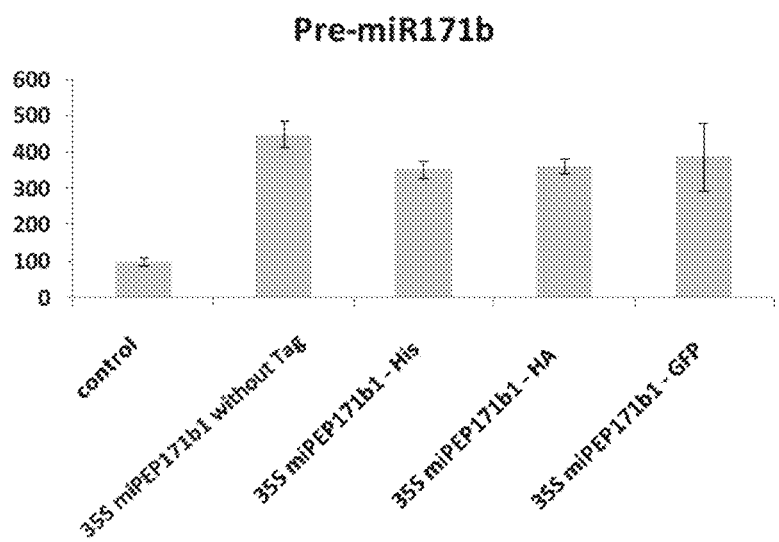

FIG. 15. Effect of the addition of sequences on the function of miPEP.

The tobacco leaves were transformed in order to overexpress miPEP171b. These graphs show that the addition of sequences (tag His, HA or GFP) does not alter the function of miPEP. The y-axis indicates the relative expression of pre-MtmiR171b in tobacco plants that have been transformed in order to express MtmiR171b (left-hand column), MtmiR171b and MtmiPEP171b1 with or without addition of protein tags (right-hand columns). The error bar corresponds to the standard error of the mean (number of individuals=6). It is noted that the expression of MtmiPEP171b1 increases the expression of MtmiR171b, and this effect is independent of the presence of tags.

Figure 16:
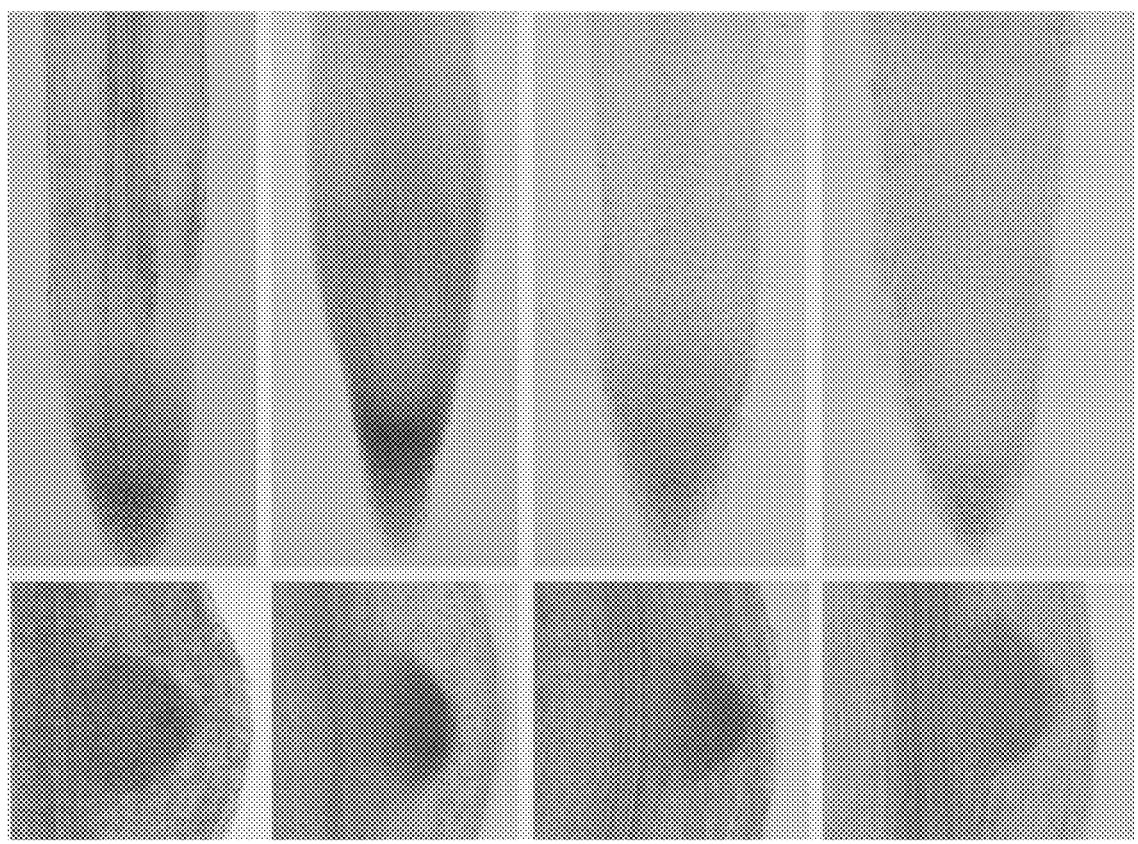

FIG. 16. Expression of MtmiPEP171b1 in the root system of *Medicago truncatula*. The roots of *Medicago truncatula* were transformed in order to express fusions between GUS protein (in blue) and the promoter of miR17b (A, E), the ATG of miPEP171b1 (B, F), whole miPEP (C, G) or ATG2 (second ATG located on the precursor, after miPEP) (D, H). It is clear that there is expression of miRNA in the root tips (A) as well as the lateral roots (E). The transcriptional (B, F) and translational (C, G) fusions show an expression of miPEP171b in the same tissues, whereas the next ATG is not active (D, H).

Figure 17:
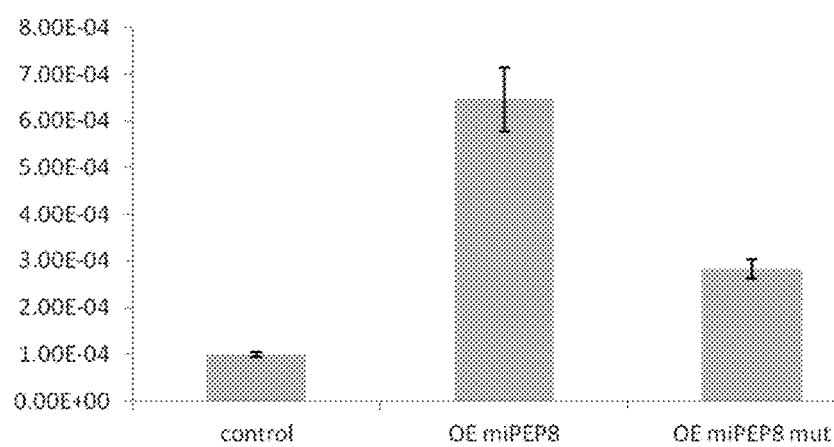

FIG. 17. Expression of DmmiPEP8 in cells of *Drosophila melanogaster*

The cells of *Drosphila melanogaster* were transfected in order to overexpress DmmiPEP8 (OE miPEP8) or miPEP8 of which the translation start codons have been mutated (OE miPEP8 mut). The y-axis indicates the relative expression of Pre-miR8. The error bar corresponds to the standard error of the mean (number of independent experiments=6). It is noted that the expression of DmmiPEP8 increases the expression of DmmiR8, and this effect is linked to the translation of the mRNA.

Figure 18:
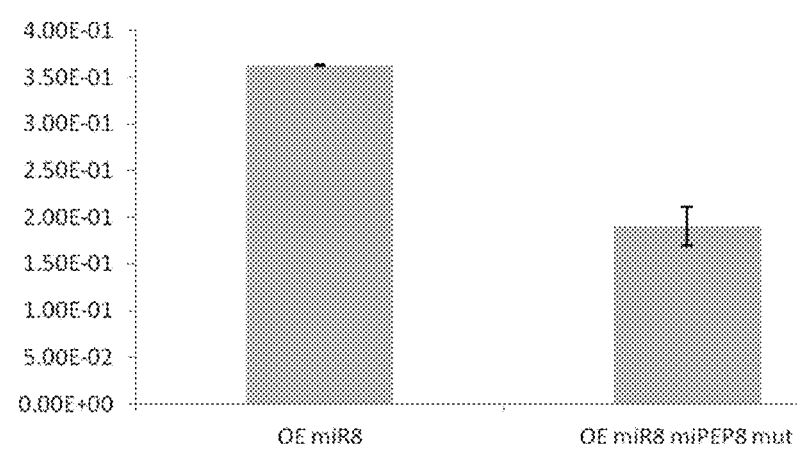

FIG. 18. Impact of DmmiPEP8 on accumulation of DmmiR8 in cells of *D. melanogaster*

The cells of *Drosophila melanogaster* were transfected in order to overexpress wild-type DmmiR8 (OE miR8) or DmmiR8 the translation start codons of which have been mutated (OE miR8 miPEP8 mut). The y-axis indicates the relative expression of Pre-miR8. The error bar corresponds to the standard error of the mean (number of independent experiments=2). It is noted that the presence of DmmiPEP8 increases the expression of DmmiR8.

Figure 19:
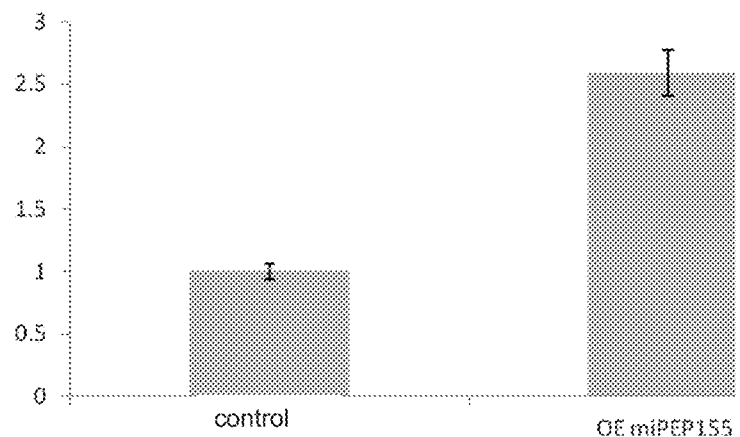

FIG. 19. Impact of HsmiPEP155 on accumulation of HsmiR155 in cells of *Homo sapiens*

HeLa cells of *Homo sapiens* had been transfected in order to overexpress HsmiPEP155 (OE miPEP155). The y-axis indicates the relative expression of Pre-miR155. The error bar corresponds to the standard error of the mean (number of independent experiments=2). It is noted that the expression of HsmiPEP155 increases the expression of HsmiR155.

Figure 20:
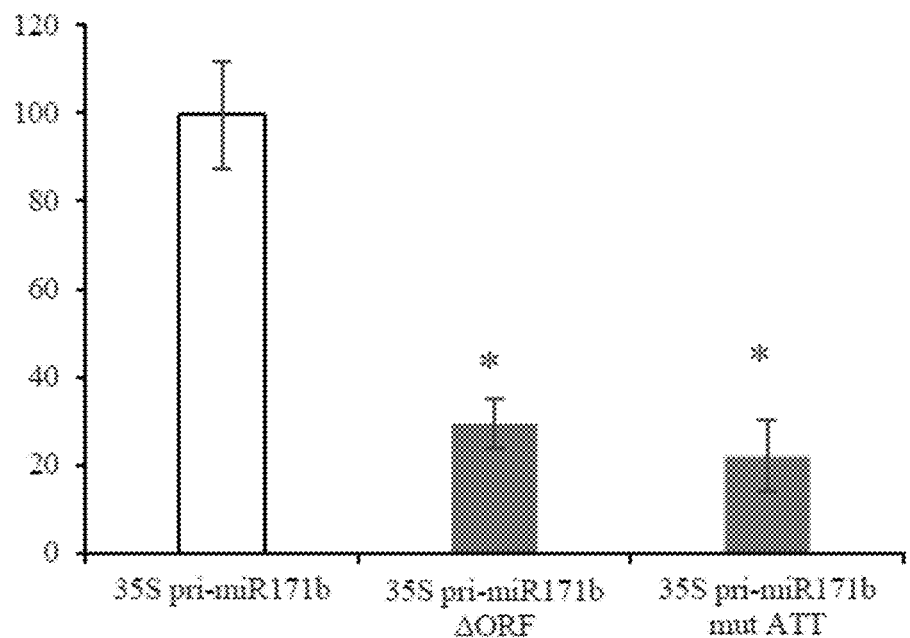

FIG. 20. Effects of translation of MtmiPEP171b1 on the expression of MtmiR171b demonstrated in the model plant *Nicotiana benthamiana*.

The y-axis indicates the relative expression of MtmiR171b in tobacco plants transformed in order to express pri-miR171b (left-hand column), a pri-miR171b in which the miORF171b has been deleted (middle column) or a mutated pri-miR171b in which the codon ATG has been replaced with ATT (right-hand column). The mutated pri-miR171b is therefore incapable of producing miPEP171b1. The error bar corresponds to the standard error of the mean (number of individuals=30). It is noted that the absence of translation of miPEP171b1 leads to a marked decrease in the accumulation of miR171b.

Figure 21:
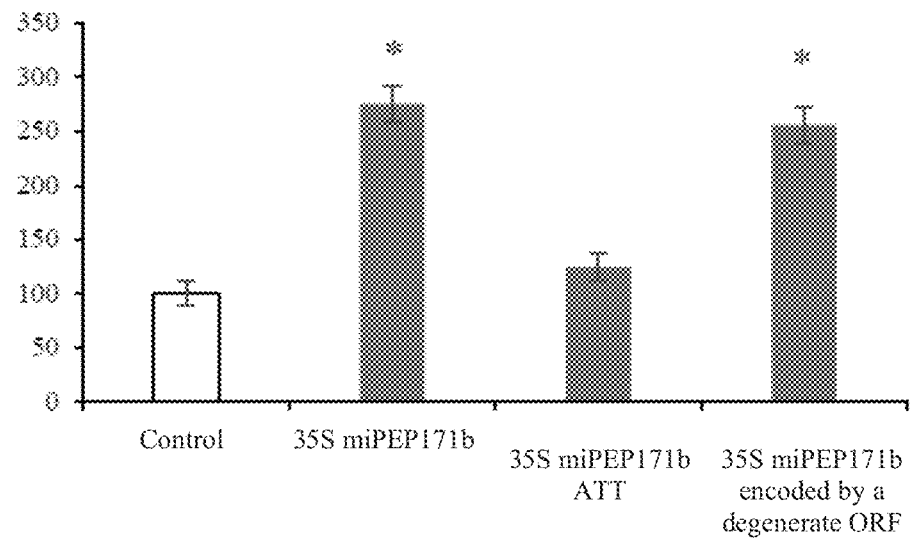

FIG. 21. Effects of overexpression of MtmiPEP171b1 on the expression of MtmiR171b demonstrated in the model plant *Nicotiana benthamiana*.

The y-axis indicates the relative expression of MtmiR171b in tobacco plants that had been transformed with a vector allowing the expression of miPEP171b and either a second empty vector (white column), or a vector allowing the expression of mtmiPEP171b (left black column), or a vector in which the codon ATG of the ORF encoding mtmiPEP171b has been replaced with ATT (middle black column), or a vector in which the nucleotide sequence of the ORF has been mutated without modifying the amino acid sequence of the translated peptide (miPEP encoded by a degenerate ORF) (right black column). The error bar corresponds to the standard error of the mean (number of individuals=30). It is noted that the expression of MtmiPEP171b1 increases the expression of MtmiR171b, and this effect is dependent on the translation of MtmiORF171b to MtmiPEP171b1.

Figure 22:
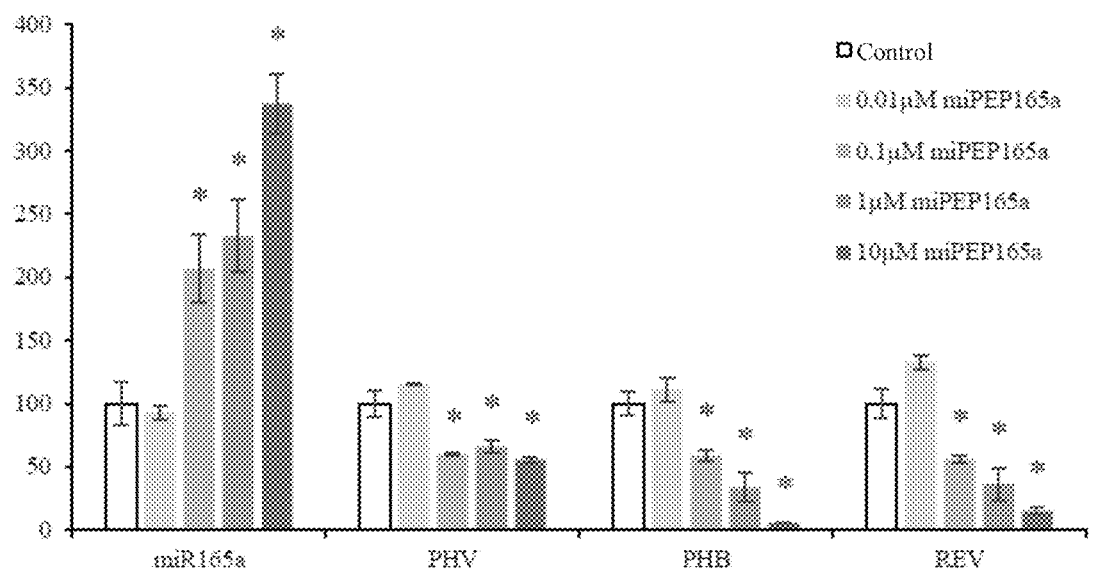

FIG. 22. Effects of AtmiPEP165a on accumulation of AtmiR165a and of its target genes (PHAVOLUTA: PHV, PHABOL USA: PHB and REVOLUTA: REV).

The y-axis indicates the relative expression of AtmiR165a, PHV, PHB and REV in roots of *Arabidopsis thaliana* treated with water (control) or different concentrations of AtmiPEP165a (0.01 µM, 0.1 µM, 1 µM or 10 µM). The error bar corresponds to the standard error of the mean (number of individuals=10).

The treatment of plants with higher and higher concentrations of AtmiPEP165a demonstrates a dose-dependent effect of the accumulation of AtmiR165a and the negative regulation of its target genes as a function of the quantity of AtmiPEP165a.

Figure 23:
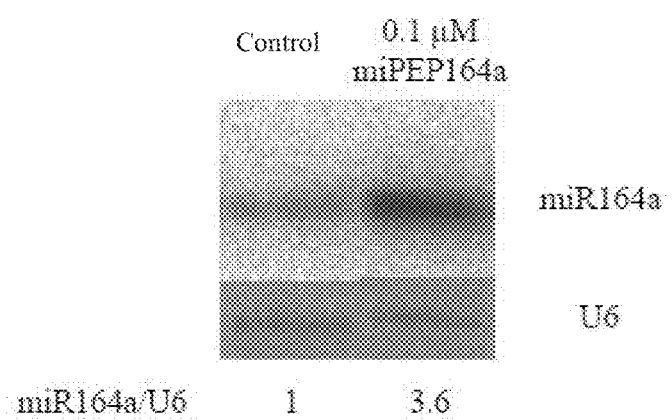

FIG. 23. Effects of treatment with AtmiPEP164a on the expression of AtmiR164a in *A. thaliana*.

The photographs show the results of a Northern blot analysis of the accumulation of AtmiR164a in roots treated with water (control, photograph on left) or with 0.1 µM of a synthetic peptide, having a sequence identical to that of AtmiPEP164a, dissolved in water (0.1 µM miPEP164a). The RNA U6 is used as loading control making it possible to quantify the quantity of AtmiR164a.

This experiment was repeated 4 times independently and led to similar results.

Treatment of shoots of *A. thaliana* with 0.1 µM of miPEP164a leads to an increase in the accumulation of miR164a.

Figure 24:
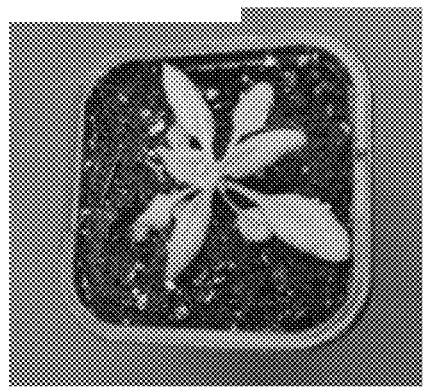
Figure 24:
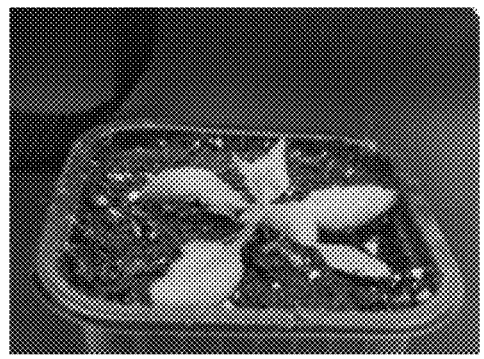
Figure 24:
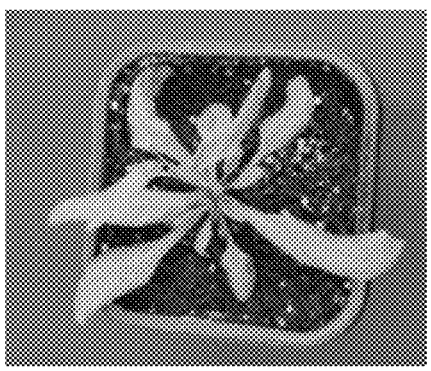
Figure 24:

FIG. 24. Effects of treatment with AtmiPEP164a on the growth of *Arabidopsis thaliana*.

The photographs show two plants (top views and side views) after 3 weeks of growth: a control plant watered with water (A), and a plant watered with a composition of 0.1 µM of synthetic peptide corresponding to AtmiPEP164a (B). Watering plants of *Arabidopsis thaliana* with AtmiPEP164a increases plant growth significantly.

Figure 25:
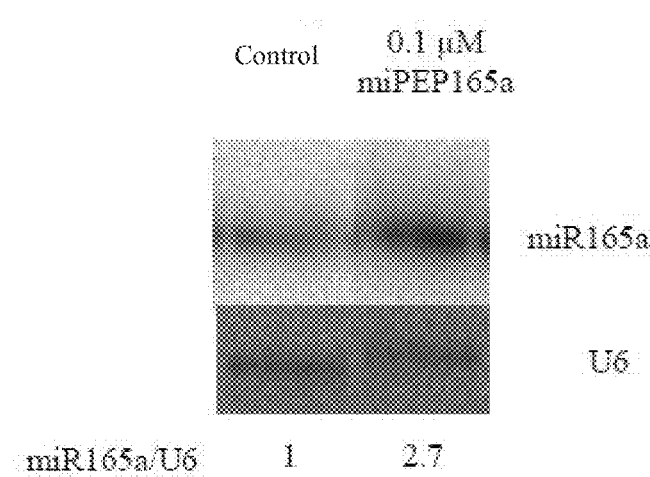

FIG. 25. Effects of treatment with AtmiPEP165a on the expression of AtmiR165a in *A. thaliana*.

The photographs show the results of a Northern blot analysis of the accumulation of AtmiR165a in roots treated with water (control, photograph on left) or with 0.1 µM of a synthetic peptide, having a sequence identical to that of AtmiPEP165a, dissolved in water (0.1 µM miPEP165a). The RNA U6 is used as loading control making it possible to quantify the quantity of AtmiR165a.

This experiment was repeated 4 times independently and led to similar results.

Treatment of *A. thaliana* shoots with 0.1 µM of miPEP leads to an increase in the accumulation of miR165a.

Figure 26:
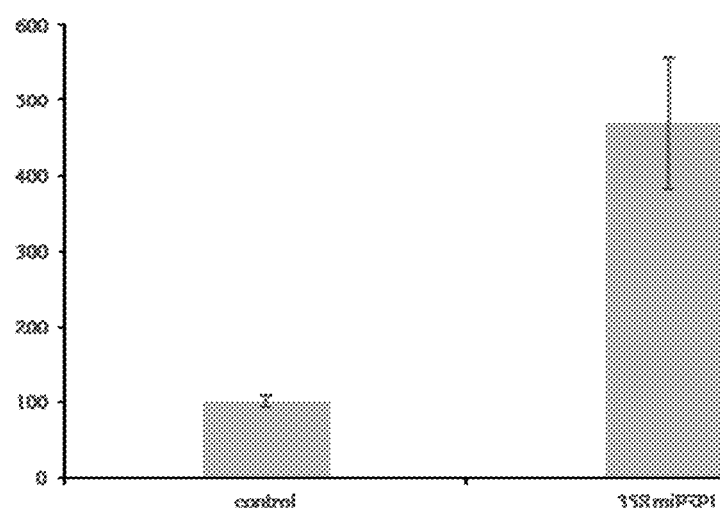

FIG. 26. Effects of overexpression of AtmiPEP319a1 on the expression of AtmiR319a in *A. thaliana*.

The y-axis indicates the relative expression of AtmiR319a in a control plant (left-hand column) or in a plant in which AtmiPEP319a1 is overexpressed (right-hand column). The error bar corresponds to the standard error of the mean (number of individuals=10). The overexpression of AtmiPEP319a1 induces an increase in the accumulation of AtmiR319a.

Figure 27:
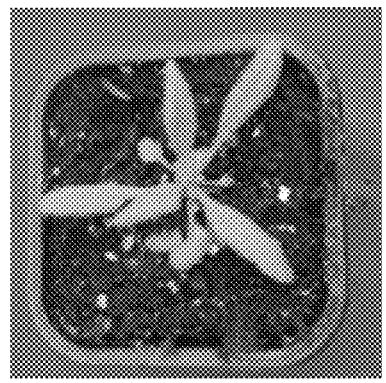
Figure 27:
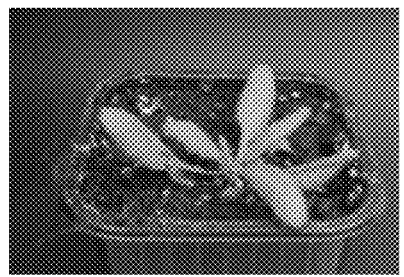
Figure 27:
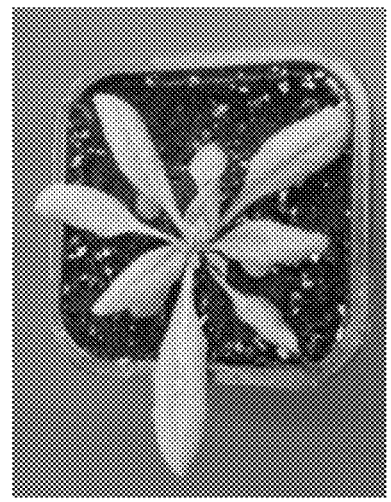
Figure 27:
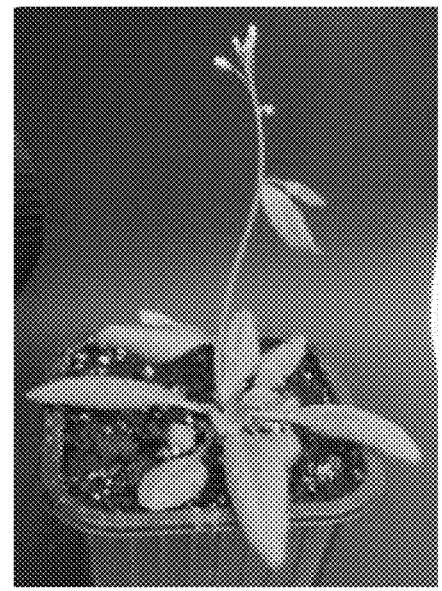

FIG. 27. Effects of treatment with AtmiPEP319a on the growth of *Arabidopsis thaliana*.

The photographs show two plants (top views and side views) after 3 weeks of growth: a control plant watered with water (A), and a plant watered with a composition of 0.1 µM of synthetic peptide corresponding to AtmiPEP319a1 (B). Watering of the plants of *Arabidopsis thaliana* with AtmiPEP319a1 increases plant growth significantly.

Figure 28:
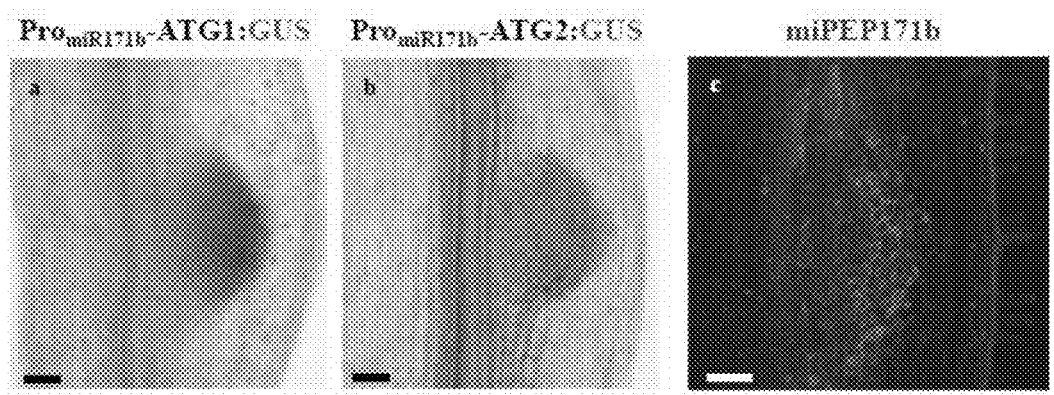

FIG. 28. Immunolocalization.

The roots of *Medicago truncatula* were transformed in order to express fusions between the GUS protein (in blue) and the ATG of miPEP171b ($Pro_{miR171b}$-ATG1:GUS) or ATG2 (second ATG located on the precursor, after miPEP) ($Pro_{miR171b}$-ATG2:GUS). Labelling was also carried out with an anti-miPEP171b antibody (miPEP171b). Immunolocalization of miPEP171b in the roots of *M. truncatula* reveals the presence of miPEP171b in the lateral root initiation sites, showing a co-localization between the microRNA and the corresponding miPEP.

DETAILED DESCRIPTION OF THE INVENTION

In a first step, the process for detecting and identifying a micropeptide therefore consists of detecting, on the primary transcript of a microRNA, the existence of an open reading frame potentially encoding a peptide.

For its part, the second step makes it possible to characterize said peptide, i.e. to determine whether said peptide corresponds to a peptide really produced in the cell, by searching for an effect of said peptide on the accumulation of said microRNA.

In order to demonstrate an effect of the peptide on the accumulation of the microRNA, a large quantity of peptide is introduced into a first cell expressing said microRNA. The accumulation of the microRNA in this first cell is then measured and compared with the accumulation of the microRNA in a second cell identical to the first, but not containing said peptide.

Observation of a variation of the quantities of microRNA between the cells in the presence and in the absence of the peptide thus indicates (i) that there is a peptide encoded on the primary transcript of said microRNA, (ii) that the sequence of this peptide is encoded by the open reading frame identified on the primary transcript of said microRNA, and (iii) that said peptide has an effect on the accumulation of said microRNA.

The invention is therefore based on the unexpected double observation made by the inventors that, on the one hand, there are open reading frames that are able to encode micropeptides present on the primary transcripts of microRNAs, and on the other hand that said micropeptides are capable of modulating the accumulation of said microRNAs.

In particular, the invention relates to a process for detecting and identifying a micropeptide (miPEP) encoded by a nucleotide sequence contained in the sequence of the primary transcript of a microRNA, comprising:
a) a step of detecting an open reading frame from 15 to 303 nucleotides in length contained in the sequence of the primary transcript of said microRNA, then
b) a step of comparison between:
the accumulation of said microRNA in a specified eukaryotic cell expressing the primary transcript of said microRNA,
in the presence of a peptide encoded by a nucleotide sequence that is identical or degenerate relative to that of said open reading frame, said peptide being present in the cell independently of transcription of the primary transcript of said microRNA, and
the accumulation of said microRNA in a eukaryotic cell of the same type as the aforesaid specified eukaryotic cell expressing the primary transcript of said microRNA,
in the absence of said peptide,
in which a modulation of the accumulation of said microRNA in the presence of said peptide relative to the accumulation of said microRNA in the absence of said peptide indicates the existence of a micropeptide encoded by said open reading frame.

In the invention, the terms "microRNA", "non-coding microRNA" and "miRNA" are equivalent and may be used interchangeably. They define small molecules of RNA of about 21 nucleotides, which are not translated and do not lead to a peptide or a protein. However, in this mature form, the microRNAs perform a function of regulation of certain genes via post-transcriptional mechanisms, for example by means of the RISC complex.

The primary transcript of the microRNA or "pri-miRNA" corresponds to the RNA molecule obtained directly from transcription of the DNA molecule. Generally, this primary transcript undergoes one or more post-transcriptional modifications, involving for example a particular structure of the RNA or cleavage of certain portions of the RNA by splicing phenomena, and which lead to the precursor form of the microRNA or "pre-miRNA", then to the mature form of the microRNA or "miRNA".

The terms "micropeptides" and "miPEPs" (microRNA encoded PEPtides) are equivalent and may be used interchangeably. They define a peptide that is encoded by an open reading frame present on the primary transcript of a microRNA, and which is capable of modulating the accumulation of said microRNA.

In view of the above definitions, it is important to distinguish on one side, the miRNA which does not encode any peptide and on the other side, the primary transcript of such a miRNA which may encode a miPEP.

This distinction derives from the teaching of the invention and is original in view of the current knowledge about miRNAs.

The micropeptides within the meaning of the present invention are not to be understood as necessarily being small peptides, as "micro" does not correspond to the size of the peptide.

Taking into account the degeneracy of the genetic code, one and the same micropeptide is or may be encoded by several nucleotide sequences. Nucleotide sequences of this kind, differing from one another by at least one nucleotide but encoding one and the same peptide, are called "degenerate sequences".

The terms "open reading frame" or "ORF" are equivalent and may be used interchangeably. They correspond to a nucleotide sequence in a DNA or RNA molecule that may potentially encode a peptide or a protein: said open reading frame begins with a start codon (the start codon generally encoding a methionine), followed by a series of codons (each codon encoding an amino acid), and ends with a stop codon (the stop codon not being translated).

In the invention, the ORFs may be called specifically "miORFs" when they are present on the primary transcripts of microRNA.

The miORFs as defined in the particular invention may have a size from 12 to 303 nucleotides and may encode peptides from 3 to 100 amino acids.

In particular, the miORFs as defined in the invention may have a size from 15 to 303 nucleotides. As an amino acid is encoded by a codon of 3 nucleotides, the miORFs from 15 to 303 nucleotides encode miPEPS from 4 to 100 amino acids.

In particular, the miORFs have a size of:
15, 18, 21, 24, 27, 30, 33, 36, 39, 42, 45, 47, 51, 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153, 156, 159, 162, 165, 168, 171, 174, 177, 180, 183, 186, 189, 192, 195, 198, 201, 204, 207, 210, 213, 216, 219, 222, 225, 228, 231, 234, 237, 240, 243, 246, 249, 252, 255, 258, 261, 264, 267, 270, 273, 276, 279, 282, 285, 288, 291, 294, 297, 300 or 303 nucleotides, and encode respectively miPEPs having a size of:
4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 amino acids.

In the invention, "accumulation" means the production of a molecule, such as a microRNA or a micropeptide, in the cell.

Thus, "modulation" of the accumulation of a molecule in a cell corresponds to a modification of the quantity of this molecule present in the cell.

In an embodiment, the invention relates to a process for detecting and identifying a miPEP as defined above, in which the modulation of the accumulation of said microRNA is a decrease or an increase in the accumulation of said microRNA, in particular an increase.

A "decrease in the accumulation" corresponds to a decrease in the quantity of said molecule in the cell.

Conversely, an "increase in the accumulation" corresponds to an increase in the quantity of said molecule in the cell.

In an advantageous embodiment, the invention relates to a process for detecting and identifying a miPEP as defined above, in which the modulation of the accumulation of said microRNA is an increase in the accumulation of said microRNA.

In an embodiment, the invention relates to a process for detecting and identifying a miPEP as defined above, in which the presence of said peptide in the cell results from:
the introduction of a nucleic acid encoding said peptide into the cell, or
the introduction of said peptide into the cell.

In order to characterize a miPEP, it is necessary to have a cellular model expressing a microRNA in which said peptide to be tested is present. For this, it is possible to introduce a peptide into the cell, either by bringing the cell into contact with said peptide, or by introducing a nucleic acid encoding said peptide into the cell, and this nucleic acid will then be translated into peptide within the cell.

In an embodiment, the invention relates to a process for detecting and identifying a miPEP as defined above, in which said open reading frame in step a) is contained in the 5' or 3' portion of said primary transcript of the microRNA, preferably in the 5' portion.

The 5' or 3' portions of the primary transcript of the microRNA correspond to the terminal portions of the RNA molecule that are cleaved during maturation of the microRNA.

In an embodiment, the invention relates to a process for detecting and identifying a miPEP as defined above, in which said microRNA is present in a wild-type plant cell.

In the invention, a wild-type plant cell corresponds to a plant cell that has not been genetically modified by humans.

In an embodiment, the invention relates to a process for detecting and identifying a miPEP as defined above, in which said microRNA is present in a wild-type animal cell, and in particular a wild-type human cell or a wild-type *Drosophila* cell.

In the invention, a wild-type animal cell corresponds to an animal cell, and in particular a human cell, that has not been modified genetically by humans.

In an embodiment, the invention relates to a process for detecting and identifying a miPEP as defined above, in which said specified eukaryotic cell and said eukaryotic cell of the same type as the aforesaid specified eukaryotic cell, used in step b, are plant cells of a cruciferous plant such as *Arabidopsis thaliana*, of a leguminous plant such as *Glycine max* (soya), *Medicago truncatula* and *Medicago sativa* (alfalfa) or of a plant of the Solanaceae family such as *Nicotiana benthamiana* (tobacco), *Solanum tuberosum* (potato), *Solanum lycopersicum* (tomato) or *Solanum melongena* (aubergine).

In an embodiment, the invention relates to a process for detecting and identifying a miPEP as defined above, in which said specified eukaryotic cell and said eukaryotic cell of the same type as the aforesaid specified eukaryotic cell, used in step b, are plant cells, preferably cells of *Medicago truncatula*, *Nicotiana benthamiana* or *Arabidopsis thaliana*.

In an embodiment, the invention relates to a process for detecting and identifying a miPEP as defined above, in which said specified eukaryotic cell and said eukaryotic cell of the same type as the aforesaid specified eukaryotic cell, used in step b, are animal cells, preferably human cells or *Drosophila* cells.

In the process for detecting and identifying a micropeptide as defined above, after identifying an ORF that is able to encode a peptide on the primary transcript of a microRNA, it is necessary to have a cellular model having said microRNA and said peptide, so as to be able to demonstrate a possible effect of the peptide on said microRNA.

Two options are therefore conceivable:
the cellular model in which the miORF has been identified and that in which the effect of the peptide on the miRNA has been demonstrated are identical, or
the cellular model in which the miORF has been identified and that in which the effect of the peptide on the miRNA has been demonstrated are different.

In the first option, the cellular model used for observing an effect of the peptide is the same as that in which the primary transcript of said microRNA was isolated. In this cellular model, the specified eukaryotic cells contain said microRNA naturally and only the peptide to be tested has to be introduced into these cells. In this context, said microRNA is qualified as "of endogenous origin" as it exists naturally in the cells. Nevertheless, other copies of a microRNA of endogenous origin may be added to a cell, for example by introducing a vector encoding said microRNA of endogenous origin into the cell.

In the second option, the cellular model used for observing an effect of the peptide is different from that in which the primary transcript of said microRNA was isolated. In this cellular model, the specified eukaryotic cells contain neither the microRNA, nor the peptide to be tested. These two elements must therefore be introduced into these cells. In this context, said microRNA is qualified as "of exogenous origin" as it does not exist naturally in the cells.

In an embodiment, the invention relates to a process for detecting and identifying a miPEP as defined above, in which said microRNA is of endogenous origin in said eukaryotic cell and in said eukaryotic cell of the same type as the aforesaid specified eukaryotic cell, used in step b).

In an embodiment, the invention relates to a process for detecting and identifying a miPEP as defined above in which said microRNA is of exogenous origin in said eukaryotic cell and in said eukaryotic cell of the same type as the aforesaid specified eukaryotic cell, used in step b), said eukaryotic cells containing a vector allowing the expression of said microRNA.

In an embodiment, the invention relates to a process for detecting and identifying a miPEP as defined above, in which the accumulation of said microRNA is determined using quantitative RT-PCR or Northern blot.

In an embodiment, the invention relates to a process for detecting and identifying a miPEP as defined above, in which the accumulation of said microRNA is determined using a DNA or RNA chip.

The accumulation of said microRNA may be determined using the techniques of molecular biology for assaying specific nucleic acid molecules.

In another aspect, the invention also relates to a process for detecting and identifying a microRNA in which the sequence of the primary transcript contains a nucleotide sequence encoding a miPEP, comprising:
a) a step of detecting an open reading frame from 15 to 303 nucleotides in length contained in the sequence of the primary transcript of said microRNA, then
b) a step of comparison between:
the accumulation of said microRNA in a specified eukaryotic cell expressing said microRNA,
in the presence of a peptide encoded by a nucleotide sequence that is identical or degenerate relative to that of said open reading frame, said peptide being present in the cell independently of transcription of the primary transcript of said microRNA, and the accumulation of said microRNA in a eukaryotic cell, of the same type as the aforesaid specified eukaryotic cell expressing said microRNA,
in the absence of said peptide,
in which a modulation of the accumulation of said microRNA in the presence of said peptide relative to the accumulation of said microRNA in the absence of said peptide indicates the existence of a microRNA the primary transcript of which contains a nucleotide sequence encoding a micropeptide.

In particular, the invention relates to a process for detecting and identifying a microRNA in which the sequence of the primary transcript contains a nucleotide sequence encoding a miPEP,
comprising:
a) a step of detecting an open reading frame from 15 to 303 nucleotides in length contained in the sequence of the primary transcript of said microRNA, then
b) a step of comparison between:
the accumulation of said microRNA in a specified eukaryotic cell expressing the primary transcript of said microRNA,
in the presence of a peptide encoded by a nucleotide sequence that is identical or degenerate relative to that of said open reading frame, said peptide being present in the cell independently of transcription of the primary transcript of said microRNA, and
the accumulation of said microRNA in a eukaryotic cell, of the same type as the aforesaid specified eukaryotic cell expressing the primary transcript of said microRNA,
in the absence of said peptide,
in which a modulation of the accumulation of said microRNA in the presence of said peptide relative to the accumulation of said microRNA in the absence of said peptide indicates the existence of a microRNA the primary transcript of which contains a nucleotide sequence encoding a micropeptide.

In an embodiment, the invention relates to a process for detecting and identifying a microRNA as defined above, in which the modulation of the accumulation of said microRNA is a decrease or an increase in the accumulation of said microRNA, in particular an increase.

In an embodiment, the invention relates to a process for detecting and identifying a microRNA as defined above, in which the presence of said peptide in the cell results from:
the introduction of a nucleic acid encoding said peptide into the cell, or
the introduction of said peptide into the cell.

In an embodiment, the invention relates to a process for detecting and identifying a microRNA as defined above, in which said open reading frame in step a) is contained in the 5' or 3' portion of said primary transcript of the microRNA, preferably in the 5' portion.

In an embodiment, the invention relates to a process for detecting and identifying a microRNA as defined above, in which said microRNA is present in a wild-type plant cell.

In an embodiment, the invention relates to a process for detecting and identifying a microRNA as defined above, in which said microRNA is present in a wild-type animal cell, and in particular a wild-type human cell.

In an embodiment, the invention relates to a process for detecting and identifying a microRNA as defined above, in which said eukaryotic cell, and said eukaryotic cell of the same type as the aforesaid specified eukaryotic cell, used in step b) are plant cells, preferably cells of *Medicago truncatula*.

In an embodiment, the invention relates to a process for detecting and identifying a microRNA as defined above, in which said eukaryotic cell, and said eukaryotic cell of the same type as the aforesaid specified eukaryotic cell, used in step b) are animal cells, preferably *Drosophila* cells.

In an embodiment, the invention relates to a process for detecting and identifying a microRNA as defined above, in which said microRNA is of endogenous origin in said eukaryotic cell and in said eukaryotic cell of the same type as the aforesaid specified eukaryotic cell, used in step b).

In an embodiment, the invention relates to a process for detecting and identifying a microRNA as defined above in which said microRNA is of exogenous origin in said eukaryotic cell and in said eukaryotic cell of the same type as the aforesaid specified eukaryotic cell, used in step b), said eukaryotic cells containing a vector allowing the expression of said microRNA.

In an embodiment, the invention relates to a process for detecting and identifying a microRNA as defined above, in which the accumulation of said microRNA is determined using quantitative RT-PCR or Northern blot.

In an embodiment, the invention relates to a process for detecting and identifying a microRNA as defined above, in which the accumulation of said microRNA is determined using a DNA or RNA chip.

In another aspect, the invention relates to a miPEP as obtained by implementing the process as defined above.

More particularly, the invention relates to a miPEP encoded by a nucleotide sequence as obtained by implementing the process as defined above. In other words, the invention relates to a miPEP encoded by a nucleotide sequence detected and identified by implementing the process as defined above.

Another aspect of the invention also relates to a miPEP of 3 to 100 amino acids, in particular of 4 to 100 amino acids, in particular of 4 to 60 amino acids, preferably of 4 to 40 amino acids, encoded by a nucleotide sequence contained in the primary transcript of a microRNA, said miPEP being capable of modulating the accumulation of said microRNA in a eukaryotic cell.

In particular, the miPEP as defined in the invention is encoded by a miORF of 15 to 303 nucleotides and has a size of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 amino acids, in particular 5, 8, 10, 18, 19, 23, 37, 50 or 59 amino acids.

In particular, the miPEP of the invention has a size in the range from 4 to 10 amino acids, 4 to 20 amino acids, 4 to 30 amino acids, 4 to 40 amino acids, 4 to 50 amino acids, 4 to 60 amino acids, 4 to 70 amino acids, 4 to 80 amino acids, 4 to 90 amino acids, or 4 to 100 amino acids.

Moreover, it should be noted that several miORFS may be identified on the primary transcript of a microRNA, indicating that a primary transcript of microRNA may potentially encode several miPEPs.

It should also be noted that the effect of a miPEP is generally specific to a single microRNA, namely that resulting from the primary transcript encoding said miPEP.

The modulation of the microRNA by said miPEP may be demonstrated after observing a variation in quantities of microRNA between the cells in the presence and in the absence of the miPEP.

In an embodiment, the invention relates to a miPEP as defined above, said nucleotide sequence being contained in the 5' or 3' portion of said primary transcript of a microRNA, preferably in the 5' portion.

In an embodiment, the invention relates to a miPEP as defined above, said nucleotide sequence corresponding to the first open reading frame present on said primary transcript of a microRNA.

In an embodiment, the invention relates to a miPEP as defined above, said miPEP having a basic isoelectric point, preferably above 8.

In an embodiment, the invention relates to a miPEP as defined above, said miPEP having an acidic isoelectric point.

In an embodiment, the invention relates to a miPEP as defined above, said miPEP being selected from the group of peptides consisting of SEQ ID NO: 1 to SEQ ID NO: 104, SEQ ID NO: 375 to SEQ ID NO: 386, and SEQ ID NO: 355 (Table 1).

In an embodiment, the invention relates to a miPEP as defined above, consisting of the amino acid sequence MVT.

In another aspect, the invention relates to a nucleic acid molecule encoding a miPEP as defined above.

In an embodiment, the invention relates to a nucleic acid molecule as defined above, said molecule being selected from the group of nucleic acids consisting of SEQ ID NO: 105 to SEQ ID NO 208, SEQ ID NO: 387 to SEQ ID NO: 399 and SEQ ID NO: 356 (Table 2).

In a particular embodiment, the invention relates to MtmiPEP171b1 (SEQ ID NO: 59) encoded by the nucleotide sequence (SEQ ID NO: 163) contained in the primary transcript of miR171b (SEQ ID NO: 319), said MtmiPEP171b1 being capable of modulating the accumulation of said miR171b in a eukaryotic cell.

In a particular embodiment, the invention relates to AtmiPEP164a1 (SEQ ID NO: 24) encoded by the nucleotide sequence (SEQ ID NO: 128) contained in the primary transcript of miR164a (SEQ ID NO: 297), said AtmiPEP164a1 being capable of modulating the accumulation of said miR164a in a eukaryotic cell.

In a particular embodiment, the invention relates to AtmiPEP165a (SEQ ID NO: 43) encoded by the nucleotide sequence (SEQ ID NO: 147) contained in the primary transcript of miR165a (SEQ ID NO: 305), said miPEP165a being capable of modulating the accumulation of said miR165a in a eukaryotic cell.

In a particular embodiment, the invention relates to AtmiPEP319a1 (SEQ ID NO: 76) encoded by the nucleotide sequence (SEQ ID NO: 180) contained in the primary transcript of miR319a (SEQ ID NO: 331), said AtmiPEP319a1 being capable of modulating the accumulation of said miR319a in a eukaryotic cell.

In a particular embodiment, the invention relates to AtmiPEP319a2 (SEQ ID NO: 77) encoded by the nucleotide sequence (SEQ ID NO: 181) contained in the primary transcript of miR319a (SEQ ID NO: 331), said AtmiPEP319a2 being capable of modulating the accumulation of said miR319a in a eukaryotic cell.

In a particular embodiment, the invention relates to DmmiPEP1a (SEQ ID NO: 102) encoded by the nucleotide sequence (SEQ ID NO: 206) contained in the primary transcript of miR1 (SEQ ID NO: 353), said dmmiPEP1a being capable of modulating the accumulation of said miR1 in a eukaryotic cell.

In a particular embodiment, the invention relates to DmmiPEP1b (SEQ ID NO: 103) encoded by the nucleotide sequence (SEQ ID NO: 207) contained in the primary transcript of miR1 (SEQ ID NO: 353), said dmmiPEP1b being capable of modulating the accumulation of said miR1 in a eukaryotic cell.

In a particular embodiment, the invention relates to dmmiPEP8 (SEQ ID NO: 104) encoded by the nucleotide sequence (SEQ ID NO: 208) contained in the primary transcript of miR8 (SEQ ID NO: 354), said dmmiPEP8 being capable of modulating the accumulation of said miR8 in a eukaryotic cell.

In a particular embodiment, the invention relates to HsmiPEP155 (SEQ ID NO: 355) encoded by the nucleotide sequence (SEQ ID NO: 356) contained in the primary transcript of miR155 (SEQ ID NO: 358), said HsmiPEP155 being capable of modulating the accumulation of said miR155 in a eukaryotic cell.

In another aspect, the invention relates to an isolated peptide, or an isolated and purified peptide, or a synthetic peptide or a recombinant peptide, comprising or consisting of a sequence identical to that of a miPEP, said miPEP in particular being present naturally in a plant, or in an animal, such as humans.

In another aspect, the invention relates to a vector comprising at least one nucleic acid molecule as defined above.

In another aspect, the invention also relates to the use of at least one:
miPEP as defined above,
nucleic acid encoding said miPEP, or
vector containing said nucleic acid,
for modulating the expression of at least one gene in a specified eukaryotic cell,
said specified eukaryotic cell being capable of expressing a microRNA, the primary transcript of which contains at least one nucleotide sequence encoding said at least one miPEP and the accumulation of which is modulated by said at least one miPEP,
the expression of said at least one gene being regulated by said microRNA.

In another aspect, the invention also relates to the use of at least one:
miPEP of 4 to 100 amino acids, preferably of 4 to 40 amino acids, encoded by a nucleotide sequence contained in the primary transcript of a microRNA, said miPEP being capable of modulating the accumulation of said microRNA in a eukaryotic cell,
nucleic acid encoding said miPEP, or
vector containing said nucleic acid,
for modulating the expression of at least one gene in a specified eukaryotic cell,
said specified eukaryotic cell being capable of expressing a microRNA, the primary transcript of which contains at least one nucleotide sequence encoding said at least one miPEP and the accumulation of which is modulated by said at least one miPEP,
the expression of said at least one gene being regulated by said microRNA.

The invention is based on the surprising observation made by the inventors that it is possible to modulate the expression of one or more target genes of one and the same microRNA by modulating the accumulation of said microRNA using a miPEP.

In an embodiment, the invention relates to the use as defined above in which said specified eukaryotic cell is a plant cell.

In an embodiment, the invention relates to the use as defined above in which said specified eukaryotic cell is a plant cell of a crucifer such as *Arabidopsis thaliana*, of a leguminous plant such as *Glycine max* (soya), *Medicago*

*truncatula* and *Medicago sativa* (alfalfa) or of a plant of the Solanaceae family such as *Nicotiana benthamiana* (tobacco), *Solanum tuberosum* (potato), *Solanum lycopersicuin* (tomato) or *Solanum melongena* (aubergine).

In an embodiment, the invention relates to the use as defined above in which said specified eukaryotic cell is an animal cell, in particular human.

In an embodiment, the invention relates to the use as defined above in which said specified eukaryotic cell is an animal cell, in particular human, said miPEP not being used for surgical or therapeutic treatment of the human body or animal body, nor for modifying the genetic identity of a human being.

In an embodiment, the invention relates to the use as defined above in which said specified eukaryotic cell is an animal cell, said miPEP being used for surgical or therapeutic treatment of the human body or animal body.

In an embodiment, the invention relates to the use as defined above in which said microRNA and said gene are of endogenous origin in said specified eukaryotic cell.

In an embodiment, the invention relates to the use as defined above in which said microRNA and said gene are of exogenous origin in said specified eukaryotic cell, said specified eukaryotic cell containing at least one vector allowing the expression of said microRNA and of said gene.

In the invention, the expressions "of endogenous origin" and "of exogenous origin" are used for distinguishing said microRNAs and/or the genes of different species, in view of the conservation of the sequences between species.

Thus, the term "of endogenous origin" indicates that the microRNA and/or gene may be present naturally in the cell in question. Other copies of the microRNA and/or of the gene of endogenous origin may nevertheless be added artificially to the cell in question, for example by cloning.

Conversely, the term "of exogenous origin" indicates that the microRNA and/or the gene are never present naturally in the cell in question. It is a microRNA and/or a gene identified in another cellular type or in an organism of another species; this microRNA and/or this gene are therefore necessarily introduced artificially into the cell in question.

In the invention, a genetically transformed cell may therefore contain 2 groups of microRNAs and/or of genes potentially similar in terms of sequence, one of endogenous origin and the other of exogenous origin.

In an embodiment, the invention relates to the use as defined above in which the primary transcript of the miRNA and said gene are of exogenous origin in said specified eukaryotic cell, said specified eukaryotic cell containing at least one vector allowing the expression of the primary transcript of the microRNA.

In an embodiment, the invention relates to the use as defined above in which the primary transcript of the miRNA is encoded by a vector introduced into the cell artificially.

In an embodiment, the invention relates to the use as defined above in which said miPEP is selected from the group of peptides consisting of SEQ ID NO: 1 to SEQ ID NO: 104, SEQ ID NO: 375 to SEQ ID NO: 386 and SEQ ID NO: 355 (Table 1).

In an embodiment, the invention relates to the use as defined above in which said miPEP is selected from MtmiPEP171b1 (SEQ ID NO: 59), AtmiPEP164a1 (SEQ ID NO: 24), AtmiPEP165a (SEQ ID NO: 43), AtmiPEP319a1 (SEQ ID NO: 76) and AtmiPEP319a2 (SEQ ID NO: 77).

In an embodiment, the invention relates to the use as defined above in which said miPEP is selected from DmmiPEP1a (SEQ ID NO: 102), DmmiPEP1b (SEQ ID NO: 103) and DmmiPEP8 (SEQ ID NO: 104).

In an embodiment, the invention relates to the use as defined above in which said miPEP is HsmiPEP155a (SEQ ID NO: 355).

In an embodiment, the invention relates to the use as defined above in which said nucleic acid is selected from the group of nucleic acids consisting of SEQ ID NO: 105 to SEQ ID NO: 208 and SEQ ID NO: 356 (Table 2).

In an embodiment, the invention relates to the use as defined above in which said nucleic acid is selected from miORF171b (SEQ ID NO: 163), miORF164a1 (SEQ ID NO: 128), miORF165a (SEQ ID NO: 147), miORF319a1 (SEQ ID NO: 180) and miORF319a2 (SEQ ID NO: 181).

In an embodiment, the invention relates to the use as defined above in which said nucleic acid is selected from miORF1a (SEQ ID NO: 206), miORF1b (SEQ ID NO: 207) and miORF8 (SEQ ID NO: 208).

In an embodiment, the invention relates to the use as defined above in which said nucleic acid is selected from miORF155 (SEQ ID NO: 356).

In an embodiment, the invention relates to the use as defined above in which said microRNA is selected from the group of nucleic acids consisting of SEQ ID NO: 282 to SEQ ID NO: 354 and SEQ ID NO: 358.

In an embodiment, the invention relates to the use as defined above in which said microRNA is selected from miR171b (SEQ ID NO: 319), miR165a (SEQ ID NO: 305) and miR319a (SEQ ID NO: 331).

In an embodiment, the invention relates to the use as defined above in which said microRNA is selected from miR1a (SEQ ID NO: 353) and miR8 (SEQ ID NO: 354).

In an embodiment, the invention relates to the use as defined above in which said microRNA is selected from miR155 (SEQ ID NO: 358).

In another aspect, the invention relates in particular to a process for modulating the expression of a gene regulated by a microRNA in a eukaryotic cell,
comprising carrying out a step of accumulation of a miPEP in said eukaryotic cell,
said miPEP having:
   a size from 3 to 100 amino acids, preferably 4 to 20 amino acids, and
   a peptide sequence identical to that encoded by a nucleotide sequence contained in the primary transcript of a microRNA regulating the expression of said gene, and
   being capable of modulating the accumulation of said microRNA,
in which the accumulation of said miPEP in said eukaryotic cell induces a modulation of the expression of said gene relative to the expression of said gene without accumulation of said miPEP.

In particular, the invention relates to a process for modulating the expression of a gene regulated by a microRNA in a eukaryotic cell,
comprising carrying out a step of accumulation of a miPEP in said eukaryotic cell,
   said miPEP having:
   a size from 4 to 100 amino acids, preferably 4 to 20 amino acids, and
   a peptide sequence identical to that encoded by a nucleotide sequence contained in the primary transcript of a microRNA regulating the expression of said gene, and
   being capable of modulating the accumulation of said microRNA, in which the accumulation of said miPEP in said eukaryotic cell induces a modulation of the expression of said gene relative to the expression of said gene without accumulation of said miPEP.

In an embodiment, the invention relates to a process for modulating the expression of a gene as defined above, in which the accumulation of said miPEP in the cell results from:
introduction of a nucleic acid encoding said miPEP into the cell, or
introduction of said miPEP into the cell.

In an embodiment, the invention relates to a process for modulating the expression of a gene as defined above in which said eukaryotic cell is a plant cell.

In an embodiment, the invention relates to a process for modulating the expression of a gene as defined above in which said eukaryotic cell is an animal cell and in particular a human cell.

In an embodiment, the invention relates to a process for modulating the expression of a gene as defined above in which said eukaryotic cell is an animal cell and in particular a human cell, said process not being used for surgical or therapeutic treatment of the human body or animal body, nor for modifying the genetic identity of a human being.

In an embodiment, the invention relates to a process for modulating the expression of a gene as defined above in which said microRNA and said gene are of endogenous origin in said eukaryotic cell.

In an embodiment, the invention relates to a process for modulating the expression of a gene as defined above in which said microRNA and said gene are of exogenous origin in said eukaryotic cell, said eukaryotic cell containing at least one vector allowing the expression of said microRNA and of said gene.

In an embodiment, the invention relates to a process for modulating the expression of a gene as defined above in which said miPEP is selected from the group of peptides consisting of SEQ ID NO: 1 to SEQ ID NO: 104, SEQ ID NO: 375 to SEQ ID NO: 386 and SEQ ID NO: 355.

In a particular embodiment, the invention relates to a process for modulating the expression of a gene regulated by miR171b (SEQ ID NO: 319) in a eukaryotic cell,
comprising carrying out a step of accumulation of MtmiPEP171b1 (SEQ ID NO: 59) in said eukaryotic cell,
in which the accumulation of said MtmiPEP171b1 in said eukaryotic cell induces a modulation of the expression of said gene relative to the expression of said gene without accumulation of said MtmiPEP171b1.

In a particular embodiment, the invention relates to a process for modulating the expression of a gene regulated by miR171b (SEQ ID NO: 319) in a eukaryotic cell,
comprising carrying out a step of accumulation of MtmiPEP171b1 (SEQ ID NO: 59) in said eukaryotic cell, in which the accumulation of said MtmiPEP171b1 in said eukaryotic cell induces a modulation of the expression of said gene relative to the expression of said gene without accumulation of said MtmiPEP171b1,
in which said gene is selected from the genes HAM1 (accession No. MtGI9-TC114268) and HAM2 (accession No. MtGI9-TC120850) (accession numbers according to the database *Medicago truncatula* Gene Expression Atlas "MtGEA").

In a particular embodiment, the invention relates to a process for modulating the expression of a gene regulated by miR164a (SEQ ID NO: 297) in a eukaryotic cell,
comprising carrying out a step of accumulation of AtmiPEP165a1 (SEQ ID NO: 24) in said eukaryotic cell,
in which the accumulation of said AtmiPEP164a1 in said eukaryotic cell induces a modulation of the expression of said gene relative to the expression of said gene without accumulation of said AtmiPEP164a1.

In a particular embodiment, the invention relates to a process for modulating the expression of a gene regulated by miR165a (SEQ ID NO: 305) in a eukaryotic cell,
comprising carrying out a step of accumulation of AtmiPEP165a (SEQ ID NO: 43) in said eukaryotic cell,
in which the accumulation of said AtmiPEP165a in said eukaryotic cell induces a modulation of the expression of said gene relative to the expression of said gene without accumulation of said AtmiPEP165a.

In a particular embodiment, the invention relates to a process for modulating the expression of a gene regulated by miR319a (SEQ ID NO: 331) in a eukaryotic cell,
comprising carrying out a step of accumulation of AtmiPEP319a1 (SEQ ID NO: 76) in said eukaryotic cell,
in which the accumulation of said AtmiPEP319a1 in said eukaryotic cell induces a modulation of the expression of said gene relative to the expression of said gene without accumulation of said AtmiPEP319a1.

In a particular embodiment, the invention relates to a process for modulating the expression of a gene regulated by miR319a (SEQ ID NO: 331) in a eukaryotic cell,
comprising carrying out a step of accumulation of AtmiPEP319a2 (SEQ ID NO: 77) in said eukaryotic cell,
in which the accumulation of said AtmiPEP319a2 in said eukaryotic cell induces a modulation of the expression of said gene relative to the expression of said gene without accumulation of said AtmiPEP319a2.

In a particular embodiment, the invention relates to a process for modulating the expression of a gene regulated by miR1 (SEQ ID NO: 353) in a eukaryotic cell,
comprising carrying out a step of accumulation of DmmiPEP1a (SEQ ID NO: 102) in said eukaryotic cell,
in which the accumulation of said DmmiPEP1a in said eukaryotic cell induces a modulation of the expression of said gene relative to the expression of said gene without accumulation of said DmmiPEP1a.

In a particular embodiment, the invention relates to a process for modulating the expression of a gene regulated by miR1 (SEQ ID NO: 353) in a eukaryotic cell,
comprising carrying out a step of accumulation of DmmiPEP1b (SEQ ID NO: 103) in said eukaryotic cell,
in which the accumulation of said DmmiPEP1b in said eukaryotic cell induces a modulation of the expression of said gene relative to the expression of said gene without accumulation of said DmmiPEP1b.

In a particular embodiment, the invention relates to a process for modulating the expression of a gene regulated by miR8 (SEQ ID NO: 354) in a eukaryotic cell,
comprising carrying out a step of accumulation of DmmiPEP8 (SEQ ID NO: 104) in said eukaryotic cell,
in which the accumulation of said DmmiPEP8 in said eukaryotic cell induces a modulation of the expression of said gene relative to the expression of said gene without accumulation of said DmmiPEP8.

In a particular embodiment, the invention relates to a process for modulating the expression of a gene regulated by miR155 (SEQ ID NO: 358) in a eukaryotic cell,
comprising carrying out a step of accumulation of hsmiPEP155 (SEQ ID NO: 355) in said eukaryotic cell,
in which the accumulation of said hsmiPEP155 in said eukaryotic cell induces a modulation of the expression of said gene relative to the expression of said gene without accumulation of said hsmiPEP155.

In another aspect, the invention relates to a modified eukaryotic cell containing a peptide identical to a miPEP as defined above, said peptide being present in said eukaryotic cell independently of transcription of the primary transcript of the microRNA bearing the nucleotide sequence encoding said miPEP.

In the invention, by the term "modified eukaryotic cell" is meant that said eukaryotic cell contains a miPEP introduced into the cell artificially, whether as a peptide, or via a vector encoding said miPEP.

In an embodiment, the invention relates to a modified eukaryotic cell as defined above, in which said microRNA is of endogenous origin.

In another embodiment, the invention relates to a modified eukaryotic cell as defined above in which said microRNA is of exogenous origin, said modified eukaryotic cell containing a vector allowing the expression of said microRNA.

In an embodiment, the invention relates to a modified eukaryotic cell as defined above, said cell being a plant cell.

In an embodiment, the invention relates to a modified eukaryotic cell as defined above, in which said plant cell is a cell of *Medicago truncatula* or of *Arabidopsis thaliana*, and said peptide is selected from the group of peptides consisting of SEQ ID NO: 43, SEQ ID NO: 59 and SEQ ID NO: 77.

In an embodiment, the invention relates to a modified eukaryotic cell as defined above, said cell being an animal cell.

In an embodiment, the invention relates to a modified eukaryotic cell as defined above, in which said animal cell is a *Drosophila* cell and said peptide is selected from the group of peptides consisting of SEQ ID NO: 102, SEQ ID NO: 103 and SEQ ID NO: 104.

In an embodiment, the invention relates to a modified eukaryotic cell as defined above, in which said animal cell is a human cell and said peptide consists of SEQ ID NO: 355.

In another aspect, the invention relates to a plant comprising at least one modified eukaryotic cell as defined above.

In another aspect, the invention also relates to a non-human animal organism comprising at least one modified eukaryotic cell as defined above.

In another aspect, the invention relates to a composition comprising at least one:
miPEP as defined above,
nucleic acid encoding said miPEP, or
vector containing said nucleic acid.

In another aspect, the invention relates to a pesticide composition comprising at least one:
miPEP as defined above,
nucleic acid encoding said miPEP, or
vector containing said nucleic acid.

In another aspect, the invention relates to a phytopharmaceutical composition comprising at least one:
miPEP as defined above,
nucleic acid encoding said miPEP, or
vector containing said nucleic acid.

In another aspect, the invention relates to an elicitor composition comprising at least one:
miPEP as defined above,
nucleic acid encoding said miPEP, or
vector containing said nucleic acid.

"Elicitor composition" denotes a composition capable of endowing the plant with better capacity for symbiosis or better resistance to different stresses whether they are of the nature of thermal stress, water stress or chemical stress.

For this purpose, the invention also relates to compositions acting on the growth (inhibition of growth or conversely growth promotion) and the physiology (better capacity for mycorrhization, nodule formation, better tolerance of different stresses) of the plant.

In particular, the invention relates to compositions for promoting plant growth.

In another aspect, the invention relates to a herbicide composition comprising at least one:
miPEP as defined above,
nucleic acid encoding said miPEP, or
vector containing said nucleic acid.

In another aspect, the invention relates to an insecticide composition comprising at least one:
miPEP as defined above,
nucleic acid encoding said miPEP, or
vector containing said nucleic acid.

In another aspect, the invention relates to a composition, in particular a phytosanitary composition, comprising miPEP164a as active ingredient, said miPEP164a preferably consisting of SEQ ID NO: 24.

In another aspect, the invention relates to a composition, in particular a phytosanitary composition, comprising miPEP319a as active ingredient, said miPEP319a preferably consisting of SEQ ID NO: 76.

In another aspect, the invention relates to a composition, in particular a phytosanitary composition, comprising miPEP171b as active ingredient, said miPEP171b preferably consisting of SEQ ID NO: 59.

The solubility properties of the miPEPs are in particular determined by their amino acid composition. The hydrophilic miPEPs can be dissolved and packaged in aqueous solutions, such as water. The hydrophobic miPEPs can be dissolved and packaged in solvents, such as organic solvents.

For treatment of plants with the miPEPS, the organic solvents are solvents that are non-toxic to the plants in small quantities, i.e. they do not have any harmful effect on the development of the plant. Non-limitatively, the organic solvents may be selected from acetonitrile and acetic acid.

The miPEPs can also be dissolved and packaged in mixtures of organic solvents, such as for example a mixture of acetonitrile and acetic acid. In particular, the miPEPs may be dissolved in a solution comprising 50% acetonitrile, 10% acetic acid and 40% water (volume/volume/volume).

Preferably, miPEPs 164a and 165a are dissolved in water, and miPEPs 171b and 319a are dissolved in a solution comprising 50% acetonitrile, 10% acetic acid and 40% water (volume/volume/volume).

Non-limitatively, the compositions, the pesticide compositions, the phytopharmaceutical compositions, the herbicide compositions and the insecticide compositions as defined above may comprise $10^{-9}$ M to $10^{-4}$ M of miPEP, in particular $10^{-9}$ M, $10^{-8}$ M, $10^{-7}$ M, $10^{-6}$ M, $10^{-5}$ M or $10^{-4}$ M of miPEP.

Compositions of higher or lower concentration may also be provided depending on the applications envisaged. For example, compositions comprising $10^{-1}$ M to $10^{-3}$ M of miPEP, in particular $10^{-1}$ M, $10^{-2}$ M or $10^{-3}$ M of miPEP, may be envisaged in the case where the miPEP has to be administered to the plant by spreading.

In another aspect, the invention relates to the use of a composition as defined above, as a herbicide for eradicating plants or slowing their growth, preferably as a herbicide specific to a species or to a genus of plants.

In another aspect, the invention relates to the use of a composition as defined above, as a phytopharmaceutical agent, for promoting the growth and/or development of plants, in particular for modulating the physiological parameters of a plant, in particular the biomass, foliar surface area, flowering, fruit size, production and/or selection of plant seeds, in particular for controlling the parthenocarpy or the monoecism of a plant, or for modifying the physiological parameters of plant seeds, in particular germination, establishment of the root system and resistance to water stress, or for preventing or treating plant diseases, in particular for promoting resistance to infectious diseases.

In another aspect, the invention relates to the use of a composition as defined above, for modulating the physiological parameters of a plant, in particular biomass, foliar surface area, or fruit size.

In an embodiment, the invention relates to the use of a composition as defined above, for thinning of orchards in order to increase fruit size.

In an embodiment, the invention relates to the use of a composition as defined above, for production and/or selection of plant seeds, said composition being used for controlling the parthenocarpy or the monoecism of a plant.

In an embodiment, the invention relates to the use of a composition as defined above, said composition being administered to said plant via the leaves or via the roots.

In an embodiment, the invention relates to the use of a composition as defined above, for production and/or selection of plant seeds.

In an embodiment, the invention relates to the use of a composition as defined above, in which said composition is used for modifying the physiological parameters of said plant seeds, in particular establishment of the root system, germination and resistance to water stress.

In an embodiment, the invention relates to the use of a composition as defined above, in which said composition is applied by dressing or film-coating of said plant seeds.

In another aspect, the invention relates to the use of a composition as defined above, as a pesticide, for eradicating organisms that are harmful to plants or that might be classified as such, in particular as insecticide, arachnicide, molluscicide or rodenticide.

In an embodiment, the invention relates to the use of a composition as defined above, as insecticide.

In an embodiment, the invention relates to the use of a composition as defined above, for eradicating insect pests.

In an embodiment, the invention relates to the use of a composition as defined above, for eradicating animal species classified as harmful or liable to be classified as such, in particular the Muridae, in particular the rat.

In an embodiment, the invention relates to the use of a composition as defined above, as pesticide for eradicating organisms harmful to plants or liable to be classified as such, in particular as insecticide, arachnicide, molluscicide, or rodenticide, in particular by application of said composition to a plant or to a support in contact with the plant.

In another aspect, the invention relates to the use of a composition as defined above, in which said composition is applied to a plant to protect it against insect pests.

In another aspect, the invention relates to the use of a peptide for promoting the growth of a plant, said peptide being introduced into the plant, said peptide having an amino acid sequence comprising or consisting of a sequence identical to that of a miPEP naturally present in said plant, said miPEP naturally present in said plant being a peptide of 4 to 100 amino acids the sequence of which is encoded by an open reading frame located on the primary transcript of a miRNA, said miPEP being capable of modulating the accumulation of said miRNA in said plant, said miRNA regulating the expression of at least one gene involved in the development of the vegetative or reproductive parts of the plant, in particular the roots, stem, leaves or flowers.

The inventors have surprisingly found that the use of peptides the sequence of which comprises or consists of a sequence identical to that of miPEPs encoded on the primary transcripts of miRNAs makes it possible to promote the growth of the plants.

In the invention, the term "plant" refers generally to the whole or part of a plant irrespective of its stage of development (including the plant in the form of a seed or a young shoot), to one or more organs of the plant (for example the leaves, roots, stem, flowers), to one or more cells of the plant, or to a cluster of cells of the plant.

In the invention, the term "growth" refers to the development of the whole or part of a plant over time. The growth of the plant may thus be determined and quantified by monitoring developmental parameters observable for certain parts, cells or organs of the plant, such as the leaves, roots, stems or flowers.

Non-limitatively, the parameters for determining and quantifying the growth of a plant may in particular be:

the size, surface area, volume, mass and the number of leaves, the size and number of flowers, the size of the stem (or spike), the length and number of roots, the earliness of germination, the earliness of budding, the earliness of floral induction (or floral transition), or also the number of cells.

In the case of leguminous plants, plant growth may also be linked to the rate of nodulation, or also to the size and number of nodules on the roots.

Moreover, in the invention, the expression "promote plant growth", or "improve plant growth", indicates:

either an acceleration of development (such as for example a larger leaf size for a plant at a given point in time relative to a reference plant), or an increase in development (such as for example a larger leaf size for a plant that cannot be attained by a reference plant), or an acceleration and an increase in the development of the plant.

It is important to note that the use according to the invention has the advantage of being ecological, in comparison with the chemical methods used conventionally in horticulture or in agriculture, as the miPEP is a peptide that is present naturally in the plant.

The invention also relates to the use of a miPEP introduced into a plant for promoting its growth, said miPEP introduced being a peptide comprising, or consisting of, a sequence identical to that of a miPEP naturally present in said plant, said miPEP naturally present is a peptide of 4 to 100 amino acids, the sequence of which is encoded by an open reading frame located at 5' on the primary transcript of a miRNA, said miPEP being capable of modulating the accumulation of said miRNA in said plant, said miRNA regulating the expression of at least one gene involved in the development of the vegetative or reproductive parts of the plant, in particular the roots, stem, leaves or flowers, the sum total of the quantity of said miPEP introduced and that of said miPEP naturally present being strictly greater than the quantity of said miPEP naturally present.

In the invention, the expression "miPEP introduced" refers to a miPEP introduced into the plant artificially as opposed to the "miPEP present naturally in the plant". The introduction of a miPEP into the plant therefore involves a technological step, which is not a natural phenomenon and corresponds neither to crossing, nor to selection.

The miPEP introduced may be either a peptide produced outside of the plant (for example an isolated and/or purified peptide, a synthetic peptide or a recombinant peptide), or a peptide produced in the plant following the non-natural introduction of a nucleic acid encoding said miPEP into said plant.

The plant into which the miPEP has not been introduced has a basal quantity of said miPEP, which corresponds to the quantity of said miPEP naturally present. The use of a miPEP comprising, or consisting of, a sequence identical to that of said miPEP leads to an increase in the total quantity of miPEP, which modulates the accumulation of the miRNA the primary transcript of which contains the sequence encoding said miPEP.

Moreover, the miPEP introduced is present in the plant and its introduction has no impact on its stability.

In an embodiment, the invention relates to the use as defined above, in which said gene, involved in the development of the vegetative or reproductive parts of the plant, is selected from the group consisting of: NAC1 (Accession No. AT1G56010.1), NAC4 (Accession No. AT5G07680.1), NAC5 (Accession No. AT5G61430.1), CUC1 (Accession No. AT3G15170.1), CUC2 (Accession No. AT5G53950.1), TCP3 (Accession No. AT1G53230.1) and TCP4 (Accession No. AT3G15030.1) (accession numbers according to the database The *Arabidopsis* Information Resource "TAIR").

In particular, the invention relates to the use as defined above, in which said gene involved in the development of the vegetative or reproductive parts of the plant is selected from the group consisting of: NAC1, NAC4, NAC5, CUC1 and CUC2.

In an embodiment, the invention relates to the use as defined above, in which said gene involved in the development of the vegetative or reproductive parts of the plant is selected from the group consisting of: TCP3 and TCP4, In an embodiment, the invention relates to the use as defined above, in which said miRNA is selected from miR164a and mir319a.

In particular, the invention relates to the use as defined above, in which said miR164a has a nucleotide sequence consisting of SEQ ID NO: 297.

In particular, the invention relates to the use as defined above, in which said miR164a has a nucleotide sequence having at least 80% identity, preferably at least 90% identity, with the nucleotide sequence SEQ ID NO: 297.

In an embodiment, the invention relates to the use as defined above, in which said miPEP is AtmiPEP164a1, in particular in which said AtmiPEP164a1 has an amino acid sequence consisting of SEQ ID NO: 24.

In particular, the invention relates to the use as defined above, in which said miR319a has a nucleotide sequence consisting of SEQ ID NO: 331.

In particular, the invention relates to the use as defined above, in which said miR319a has a nucleotide sequence having at least 80% identity, preferably at least 90% identity, with the nucleotide sequence SEQ ID NO: 331.

In an embodiment, the invention relates to the use as defined above, in which said miPEP is AtmiPEP319a1, in particular in which said AtmiPEP319a1 has an amino acid sequence consisting of SEQ ID NO: 76.

In an embodiment, the invention relates to the use as defined above, in which said plant is a crucifer such as *Arabidopsis thaliana*, a leguminous plant such as *Glycine max* (soya), *Medicago truncatula* and *Medicago sativa* (alfalfa) or a plant of the Solanaceae family such as *Nicotiana benthamiana* (tobacco), *Solanum tuberosum* (potato), *Solanum lycopersicum* (tomato) or *Solanum melongena* (aubergine).

In an embodiment, the invention relates to the use as defined above, in which said plant is a crucifer.

In an embodiment, the invention relates to the use as defined above, in which said plant is *Arabidopsis thaliana*.

In an embodiment, the invention relates to the use as defined above, for promoting the growth of an *Arabidopsis thaliana* plant, in which AtmiPEP164a1 is introduced into said *Arabidopsis thaliana* plant, said AtmiPEP164a1 also being naturally present in said *Arabidopsis thaliana* plant, said AtmiPEP164a1 introduced being a peptide the sequence of which comprises or consists of a sequence identical to that of said AtmiPEP164a1 naturally present, said sequence of AtmiPEP164a1 naturally present being encoded by an open reading frame located at 5' on the primary transcript of the miR164a, which miR164a controls the expression of at least one gene involved in the development of the vegetative or reproductive parts of *Arabidopsis thaliana*, the sum total of the quantity of said AtmiPEP164a1 introduced and that of said AtmiPEP164a1 naturally present being strictly greater than the quantity of said AtmiPEP164a1 naturally present in said *Arabidopsis thaliana* plant.

In an embodiment, the invention relates to the use as defined above, for promoting the growth of an *Arabidopsis thaliana* plant, in which the AtmiPEP319a1 is introduced into said *Arabidopsis thaliana* plant, said AtmiPEP319a1 also being naturally present in said *Arabidopsis thaliana* plant, said AtmiPEP319a1 introduced being a peptide the sequence of which comprises or consists of a sequence identical to that of said AtmiPEP319a1 naturally present, said sequence of the AtmiPEP319a1 naturally present being encoded by an open reading frame located at 5' on the primary transcript of the miR319a, which miR319a controls the expression of at least one gene involved in the development of the vegetative or reproductive parts of *Arabidopsis thaliana*, the sum total of the quantity of said AtmiPEP319a1 introduced and that of said AtmiPEP319a1 naturally present being strictly greater than the quantity of said AtmiPEP319a1 naturally present in said *Arabidopsis thaliana* plant.

In an embodiment, the invention relates to the use as defined above, in which said miPEP is introduced into the plant externally, preferably by watering, by spraying or by adding a fertilizer, a compost, a culture substrate or an inert support.

In an embodiment, the invention relates to the use as defined above, in which said miPEP is introduced by watering and by spraying.

In an embodiment, the invention relates to the use as defined above, in which said miPEP is introduced by watering and by adding a fertilizer.

In an embodiment, the invention relates to the use as defined above, in which said miPEP is introduced by spraying and by adding a fertilizer.

In an embodiment, the invention relates to the use as defined above, in which said miPEP is introduced, by watering, by spraying and by adding a fertilizer.

The inventors have in fact unexpectedly found that it is possible to apply a composition comprising a miPEP directly to the plant in order to modulate the accumulation of the corresponding miRNA in the plant, which indicates that the miPEP is captured by the plant.

In an embodiment, the invention relates to the use as defined above, in which the plant is treated with a composition comprising $10^{-9}$ M to $10^{-4}$ M of said miPEP, in particular $10^{-9}$ M, $10^{-8}$ M, $10^{-7}$ M, $10^{-6}$ M, M or $10^{-4}$ M of said miPEP.

Preferably, the compositions have a concentration from $10^{-8}$ M to $10^{-5}$ M for application by watering or by spraying on the plant.

In addition, compositions of higher or lower concentration may be envisaged for treating the plant with the miPEP. As a non-limitative example, compositions of higher concentration comprising $10^{-1}$ M to $10^{-3}$ M, in particular $10^{-2}$ M of miPEP, may be used in the case where the miPEP introduced exogenously is administered to the plant by spreading.

In an embodiment, the invention relates to the use as defined above, in which said miPEP is introduced into the plant by means of a nucleic acid encoding said miPEP, said nucleic acid being introduced into the plant.

In an embodiment, the invention relates to the use as defined above, in which the size of the stem is increased in the plant into which said miPEP has been introduced relative to the size of the stem of an identical plant of the same age into which no miPEP has been introduced, or relative to the size of the stem of an identical plant of the same age into which said miPEP has not been introduced.

In an embodiment, the invention relates to the use as defined above, in which the number of leaves is increased in the plant into which said miPEP has been introduced relative to the number of leaves of an identical plant of the same age into which no miPEP has been introduced, or relative to the number of leaves of an identical plant of the same age into which said miPEP has not been introduced.

In an embodiment, the invention relates to the use as defined above, in which the size of the leaves is increased in the plant into which said miPEP has been introduced relative to the size of the leaves of an identical plant of the same age into which no miPEP has been introduced, or relative to the size of the leaves of an identical plant of the same age into which said miPEP has not been introduced.

In an embodiment, the invention relates to the use as defined above, in which the number of roots is increased in the plant into which said miPEP has been introduced relative to the number of roots of an identical plant of the same age into which no miPEP has been introduced, or relative to the number of roots of an identical plant of the same age into which said miPEP has not been introduced.

In an embodiment, the invention relates to the use as defined above, in which the length of the roots is increased in the plant into which said miPEP has been introduced relative to the length of the roots of an identical plant of the same age into which no miPEP has been introduced, or relative to the length of the roots of an identical plant of the same age into which said miPEP has not been introduced.

In an embodiment, the invention relates to the use as defined above, in which the rate of nodulation is increased in the plant into which said miPEP has been introduced relative to the rate of nodulation of an identical plant of the same age into which no miPEP has been introduced, or relative to the rate of nodulation of an identical plant of the same age into which said miPEP has not been introduced.

In an embodiment, the invention relates to the use as defined above, in which the number of nodules is increased in the plant into which said miPEP has been introduced relative to the number of nodules of an identical plant of the same age into which no miPEP has been introduced, or relative to the number of nodules of an identical plant of the same age into which said miPEP has not been introduced.

The increase in the parameters for determining and quantifying growth in the plant into which the miPEP has been introduced (such as the size of the stem, the number and size of the leaves, the number and length of the roots, the rate of nodulation or also the number of nodules on the roots) is preferably demonstrated by comparison with an identical plant (i.e. a plant of the same species and/or variety), of the same age and grown under the same conditions but into which no miPEP has been introduced.

In another aspect, the invention relates to a process for promoting the growth of a plant, comprising a step of introducing a miPEP into a plant, said miPEP also being present naturally in said plant, said miPEP introduced being a peptide of 4 to 100 amino acids the sequence of which comprises or consists of a sequence identical to that of said miPEP naturally present, said sequence of the miPEP naturally present being encoded by an open reading frame located at 5' on the primary transcript of a miRNA, said miPEP being capable of modulating the accumulation of said miRNA, said miRNA regulating the expression of at least one gene involved in the development of the vegetative or reproductive parts of the plant, in particular the roots, stem, leaves or flowers, the sum total of the quantity of said miPEP introduced and that of said miPEP naturally present being strictly greater than the quantity of said miPEP naturally present.

In an embodiment, the invention relates to a process as defined above, in which said gene involved in the development of the vegetative or reproductive parts of the plant is selected from the group consisting of: NAC1 (Accession No. AT1G56010.1), NAC4 (Accession No. AT5G07680.1), NAC5 (Accession No. AT5G61430.1), CUC1 (Accession No. AT3G15170.1), CUC2 (Accession No. AT5G53950.1), TCP3 (Accession No. AT1G53230.1) and TCP4 (Accession No. AT3G15030.1).

In particular, the invention relates to a process as defined above, in which said gene involved in the development of the vegetative or reproductive parts of the plant is selected from the group consisting of: NAC1, NAC4, NAC5, CUC1 and CUC2.

In an embodiment, the invention relates to a process as defined above, in which said gene involved in the development of the vegetative or reproductive parts of the plant is selected from the group consisting of: TCP3 and TCP4.

In an embodiment, the invention relates to a process as defined above, in which said miRNA is miR164a, in particular in which said miR164a has a nucleotide sequence consisting of SEQ ID NO: 297.

In an embodiment, the invention relates to a process as defined above, in which said miPEP is AtmiPEP164a1, in particular in which said AtmiPEP164a1 has an amino acid sequence consisting of SEQ ID NO: 24.

In an embodiment, the invention relates to a process as defined above, in which said miRNA is miR319a, in particular in which said miR319a has a nucleotide sequence consisting of SEQ ID NO: 331.

In an embodiment, the invention relates to a process as defined above, in which said miPEP is AtmiPEP319a1, in particular in which said AtmiPEP319a1 has an amino acid sequence consisting of SEQ ID NO: 76.

In an embodiment, the invention relates to a process as defined above, in which said plant is a crucifer such as *Arabidopsis thaliana*, a leguminous plant such as *Glycine max* (soya), *Medicago truncatula* and *Medicago sativa* (alfalfa) or a plant of the Solanaceae family such as *Nicotiana benthamiana* (tobacco), *Solanum tuberosum* (potato), *Solanum lycopersicum* (tomato) or *Solanum melongena* (aubergine).

In an embodiment, the invention relates to a process as defined above, in which said plant is a crucifer.

In an embodiment, the invention relates to a process as defined above, in which said plant is *Arabidopsis thaliana*.

In an embodiment, the invention relates to a process as defined above, for promoting the growth of an *Arabidopsis thaliana* plant, in which AtmiPEP164a1 is introduced into said *Arabidopsis thaliana* plant, said AtmiPEP164a1 also being naturally present in said *Arabidopsis thaliana* plant, said AtmiPEP164a1 introduced being a peptide comprising or consisting of a sequence identical to that of said AtmiPEP164a1 naturally present, where the AtmiPEP164a1 naturally present is a peptide of 4 to 100 amino acids the sequence of which is encoded by an open reading frame located at 5' on the primary transcript of the miR164a,
said AtmiPEP164a1 being capable of increasing the accumulation of said miR164a, where said miR164a regulates the expression of at least one gene involved in the development of the vegetative or reproductive parts of *Arabidopsis thaliana*,
the sum total of the quantity of said AtmiPEP164a1 introduced and that of said AtmiPEP164a1 naturally present being strictly greater than the quantity of said AtmiPEP164a1 naturally present.

In an embodiment, the invention relates to a process as defined above, for promoting the growth of an *Arabidopsis thaliana* plant, in which AtmiPEP319a1 is introduced into said *Arabidopsis thaliana* plant, said AtmiPEP319a1 also being naturally present in said *Arabidopsis thaliana* plant, said AtmiPEP319a1 introduced being a peptide comprising or consisting of a sequence identical to that of said AtmiPEP319a1 naturally present, where the AtmiPEP319a1 naturally present is a peptide of 4 to 100 amino acids the sequence of which is encoded by an open reading frame located at 5' on the primary transcript of the miR319a,
said AtmiPEP319a1 being capable of increasing the accumulation of said miR319a, where miR319a regulates the expression of at least one gene involved in the development of the vegetative or reproductive parts of *Arabidopsis thaliana*,
the sum total of the quantity of said AtmiPEP319a1 introduced and that of said AtmiPEP319a1 naturally present being strictly greater than the quantity of said AtmiPEP319a1 naturally present.

In an embodiment, the invention relates to a process as defined above, in which said miPEP is introduced into the plant externally, preferably by watering, by spraying or by adding a fertilizer, a compost, a culture substrate or an inert support.

In an embodiment, the invention relates to a process as defined above, in which said miPEP is administered to the plant in the form of a composition comprising $10^{-9}$ M to $10^{-4}$ M of said miPEP, in particular $10^{-9}$, $10^{-8}$, $10^{-7}$, $10^{-6}$, $10^{-5}$ or $10^{-4}$ M of said miPEP.

In an embodiment, the invention relates to a process as defined above, in which said miPEP is introduced into the plant by means of a nucleic acid encoding said miPEP, said nucleic acid being introduced into the plant.

In an embodiment, the invention relates to a process as defined above, in which the size of the stem is increased in the plant into which said miPEP has been introduced relative to the size of the stem of an identical plant of the same age into which no miPEP has been introduced, or relative to the size of the stem of an identical plant of the same age into which said miPEP has not been introduced.

In an embodiment, the invention relates to a process as defined above, in which the number of leaves is increased in the plant into which said miPEP has been introduced relative to the number of leaves of an identical plant of the same age into which no miPEP has been introduced, or relative to the number of leaves of an identical plant of the same age into which said miPEP has not been introduced.

In an embodiment, the invention relates to a process as defined above, in which the size of the leaves is increased in the plant into which said miPEP has been introduced relative to the size of the leaves of an identical plant of the same age into which no miPEP has been introduced, or relative to the size of the leaves of an identical plant of the same age into which said miPEP has not been introduced.

In an embodiment, the invention relates to a process as defined above, in which the number of roots is increased in the plant into which said miPEP has been introduced relative to the number of roots of an identical plant of the same age into which no miPEP has been introduced, or relative to the number of roots of an identical plant of the same age into which said miPEP has not been introduced.

In an embodiment, the invention relates to a process as defined above, in which the length of the roots is increased in the plant into which said miPEP has been introduced relative to the length of the roots of an identical plant of the same age into which no miPEP has been introduced, or relative to the length of the roots of an identical plant of the same age into which said miPEP has not been introduced.

In an embodiment, the invention relates to a process as defined above, in which the rate of nodulation is increased in the plant into which said miPEP has been introduced relative to the rate of nodulation of an identical plant of the same age into which no miPEP has been introduced, or relative to the rate of nodulation of an identical plant of the same age into which said miPEP has not been introduced.

In an embodiment, the invention relates to a process as defined above, in which the number of nodules is increased in the plant into which said miPEP has been introduced relative to the number of nodules of an identical plant of the same age into which no miPEP has been introduced, or relative to the number of nodules of an identical plant of the same age into which said miPEP has not been introduced.

In another aspect, the invention relates to a plant into which a miPEP has been introduced according to the use or the process for promoting the growth of a plant described above.

In another aspect, the invention relates to a process for producing a transgenic plant comprising:
a) a step of introducing a nucleic acid encoding a miPEP of 4 to 100 amino acids into a plant, or into at least one cell of said plant, under conditions allowing the expression of said miPEP,
said miPEP also being naturally present in said plant, said miPEP naturally present being a peptide the sequence of which is encoded by an open reading frame located at 5' on the primary transcript of a miRNA, said miPEP being capable of modulating the accumulation of said miRNA in the plant, said miRNA regulating the expression of at least one gene involved in the development of the vegetative or reproductive parts of the plant, in particular the roots, stem, leaves or flowers, and b) a step of culturing the plant, or at least one cell of said plant, obtained in step a) under conditions allowing a transgenic plant to be obtained.

In an embodiment, the invention relates to a process for producing a transgenic plant as defined above, in which said transgenic plant obtained in step b) has improved growth relative to an identical plant in which said nucleic acid has not been introduced.

In an embodiment, the invention relates to a process for producing a transgenic plant as defined above, in which step a) is carried out using a vector containing said nucleic acid, preferably a plasmid.

In an embodiment, the invention relates to a process for producing a transgenic plant as defined above, in which the expression of said nucleic acid of step a) is placed under the control of a strong promoter, preferably a constitutive strong promoter such as the 35S promoter.

In an embodiment, the invention relates to a process for producing a transgenic plant as defined above, in which said gene involved in the development of the vegetative or reproductive parts of the plant is selected from the group consisting of: NAC1 (Accession No. AT1G56010.1), NAC4 (Accession No. AT5G07680.1), NAC5 (Accession No. AT5G61430.1), CUC1 (Accession No. AT3G15170.1), CUC2 (Accession No. AT5G53950.1), TCP3 (Accession No. AT1G53230.1) and TCP4 (Accession No. AT3G15030.1).

In an embodiment, the invention relates to a process for producing a transgenic plant as defined above, in which said miPEP has an amino acid sequence comprising or consisting of a sequence selected from the group consisting of SEQ ID NO: 1 to SEQ ID NO: 101 and SEQ ID NO: 375 to SEQ ID NO: 386.

In an embodiment, the invention relates to a process for producing a transgenic plant as defined above, in which said miRNA is miR164a, in particular in which said miR164a has a nucleotide sequence consisting of SEQ ID NO: 297.

In an embodiment, the invention relates to a process for producing a transgenic plant as defined above, in which said miPEP is AtmiPEP164a1, in particular in which said AtmiPEP164a1 has an amino acid sequence consisting of SEQ ID NO: 24.

In an embodiment, the invention relates to a process for producing a transgenic plant as defined above, in which said miRNA is miR319a, in particular in which said miR319a has a nucleotide sequence consisting of SEQ ID NO: 331.

In an embodiment, the invention relates to a process for producing a transgenic plant as defined above, in which said miPEP is AtmiPEP319a1, in particular in which said AtmiPEP319a1 has an amino acid sequence consisting of SEQ ID NO: 76.

In an embodiment, the invention relates to a process for producing a transgenic plant as defined above, in which said nucleic acid introduced in step a) comprises a nucleotide sequence selected from SEQ ID NO: 128 and SEQ ID NO: 180.

In an embodiment, the invention relates to a process for producing a transgenic plant as defined above, in which said plant is a crucifer such as Arabidopsis thaliana, a leguminous plant such as Glycine max (soya), Medicago truncatula and Medicago sativa (alfalfa) or a plant of the Solanaceae family such as Nicotiana benthamiana (tobacco), Solanum tuberosum (potato), Solanum lycopersicum (tomato) or Solanum melongena (aubergine).

In an embodiment, the invention relates to a process for producing a transgenic plant as defined above, in which said transgenic plant is a crucifer.

In an embodiment, the invention relates to a process for producing a transgenic plant as defined above, in which said transgenic plant is Arabidopsis thaliana.

In an embodiment, the invention relates to a process for producing a transgenic plant as defined above, comprising:

a) a step of introducing a nucleic acid containing the nucleotide sequence SEQ ID NO: 128, encoding AtmiPEP164a1 consisting of the amino acid sequence SEQ ID NO: 24, into an Arabidopsis thaliana plant, or into at least one cell of said Arabidopsis thaliana plant, under conditions allowing the expression of AtmiPEP164a1, said AtmiPEP164a1 also being naturally present in said Arabidopsis thaliana plant, said miPEP naturally present being a peptide the sequence of which is encoded by an open reading frame located at 5' on the primary transcript of miR164a, said AtmiPEP164a1 being capable of modulating the accumulation of said miR164, where miR164a controls the expression of at least one gene involved in the development of the vegetative or reproductive parts of Arabidopsis thaliana, and b) a step of culturing the plant, or at least one cell of said plant, obtained in step a) under conditions allowing a transgenic Arabidopsis thaliana plant to be obtained.

In an embodiment, the invention relates to a process for producing a transgenic plant as defined above, comprising:

a) a step of introducing a nucleic acid containing the nucleotide sequence SEQ ID NO: 180, encoding AtmiPEP319a1 consisting of the amino acid sequence SEQ ID NO: 76, into an Arabidopsis thaliana plant, or into at least one cell of said Arabidopsis thaliana plant, under conditions allowing the expression of AtmiPEP319a1, said AtmiPEP319a1 also being naturally present in said Arabidopsis thaliana plant, said miPEP naturally present being a peptide the sequence of which is encoded by an open reading frame located at 5' on the primary transcript of the miR319a, said AtmiPEP319a1 being capable of modulating the accumulation of said miR319, which miR319a regulates the expression of at least one gene involved in the development of the vegetative or reproductive parts of Arabidopsis thaliana, and b) a step of culturing the plant, or at least one cell of said plant, obtained in step a) under conditions allowing a transgenic Arabidopsis thaliana plant to be obtained.

In an embodiment, the invention relates to a process of production as defined above, in which said miPEP is introduced into the plant by means of a nucleic acid encoding said miPEP, said nucleic acid being introduced into the plant.

In an embodiment, the invention relates to a process for producing a transgenic plant as defined above, in which the size of the stem is increased in the plant into which said miPEP has been introduced relative to the size of the stem of an identical plant of the same age into which no miPEP has been introduced, or relative to the size of the stem of an identical plant of the same age into which said miPEP has not been introduced.

In an embodiment, the invention relates to a process for producing a transgenic plant as defined above, in which the number of leaves is increased in the plant into which said miPEP has been introduced relative to the number of leaves of an identical plant of the same age into which no miPEP has been introduced, or relative to the number of leaves of an identical plant of the same age into which said miPEP has not been introduced.

In an embodiment, the invention relates to a process for producing a transgenic plant as defined above, in which the size of the leaves is increased in the plant into which said miPEP has been introduced relative to the size of the leaves of an identical plant of the same age into which no miPEP has been introduced, or relative to the size of the leaves of an identical plant of the same age into which said miPEP has not been introduced.

In an embodiment, the invention relates to a process for producing a transgenic plant as defined above, in which the number of roots is increased in the plant into which said miPEP has been introduced relative to the number of roots of an identical plant of the same age into which no miPEP has been introduced, or relative to the number of roots of an identical plant of the same age into which said miPEP has not been introduced.

In an embodiment, the invention relates to a process for producing a transgenic plant as defined above, in which the length of the roots is increased in the plant into which said miPEP has been introduced relative to the length of the roots of an identical plant of the same age into which no miPEP has been introduced, or relative to the length of the roots of an identical plant of the same age into which said miPEP has not been introduced.

In an embodiment, the invention relates to a process for producing a transgenic plant as defined above, in which the rate of nodulation is increased in the plant into which said miPEP has been introduced relative to the rate of nodulation of an identical plant of the same age into which no miPEP has been introduced, or relative to the rate of nodulation of an identical plant of the same age into which said miPEP has not been introduced.

In an embodiment, the invention relates to a process for producing a transgenic plant as defined above, in which the number of nodules is increased in the plant into which said miPEP has been introduced relative to the number of nodules of an identical plant of the same age into which no miPEP has been introduced, or relative to the number of nodules of an identical plant of the same age into which said miPEP has not been introduced.

In an aspect, the invention also relates to a transgenic plant as obtained by the process of production as defined above.

In another aspect, the invention relates to a composition comprising, in combination, a quantity of seeds of a plant and a quantity of a peptide the sequence of which comprises or consists of a sequence identical to that of a miPEP naturally present in said plant.

In an embodiment, the invention relates to a composition comprising, in combination, a quantity of seeds of a plant, in particular *A. thaliana*, and a quantity of a peptide the sequence of which comprises or consists of a sequence identical to that of AtmiPEP164a1.

In an embodiment, the invention relates to a composition comprising, in combination, a quantity of seeds of a plant, in particular *A. thaliana*, and a quantity of a peptide the sequence of which comprises or consists of a sequence identical to that of AtmiPEP319a1.

In an embodiment, the invention relates to a composition comprising, in combination, a quantity of seeds of a plant, in particular *M. truncatula*, and a quantity of a peptide the sequence of which comprises or consists of a sequence identical to that of MtmiPEP171b.

In an embodiment, the invention relates to a composition as defined above, formulated so as to form a dressed seed.

Dressing may be carried out by the processes used conventionally in the agri-food industry and may be obtained using a material able to disaggregate in a solvent or in the ground, such as a binder or clay.

According to the invention, dressing may be used for example for conferring particular properties on a composition of miPEP, or on a composition of seeds in combination with a miPEP.

In an embodiment, the invention relates to a composition as defined above, formulated so as to form a dressed seed comprising MtmiPEP171b.

In an embodiment, the invention relates to a composition as defined above, formulated so as to form a dressed seed comprising AtmiPEP164a1.

In an embodiment, the invention relates to a composition as defined, above formulated so as to form a dressed seed comprising AtmiPEP319a1.

In another aspect, the invention relates to a composition comprising at least one:
 miPEP as defined above
 nucleic acid encoding said miPEP, or
 vector containing said nucleic acid.
for use as a medicament, in particular for humans or for animals.

The use of the compositions of the invention is applicable in human medicine and in veterinary medicine.

In another aspect, the invention relates to a composition comprising at least one:
 miPEP as defined above
 nucleic acid encoding said miPEP, or
 vector containing said nucleic acid,
for use in the prevention and/or treatment of a disease involving deregulation of the expression of a gene of the patient,
the expression of said gene being regulated by a microRNA the accumulation of which is modulated by said miPEP.

In an embodiment, the invention relates to the composition as defined above in which said disease is selected from cancer, diabetes, obesity, infectious diseases and neurodegenerative diseases.

In another aspect, the invention relates to a composition comprising at least one:
 miPEP as defined above,
 nucleic acid encoding said miPEP, or
 vector containing said nucleic acid,
for use in the prevention and/or treatment of an infection of an animal or of a human with a parasitic organism,
said parasitic organism having a gene the expression of which is regulated by a microRNA the accumulation of which is modulated by said miPEP.

In another aspect, the invention relates to an antibody specifically recognizing a miPEP.

In particular, the invention relates to an antibody specifically recognizing AtmiPEP165a.

In particular, the invention relates to an antibody specifically recognizing MtmiPEP171b.

In particular, the invention relates to an antibody specifically recognizing AtmiPEP164a1.

In particular, the invention relates to an antibody specifically recognizing AtmiPEP319a1.

Such an antibody may be obtained by a process known to a person skilled in the art, such as for example by injecting said miPEP into a non-human animal in order to trigger an immunization reaction and the production of antibodies by said animal.

In another aspect, the invention relates to a process of immunolocalization of a miPEP comprising a step of labelling a biological sample from a plant with an antibody specifically recognizing a miPEP.

In particular, the invention relates to a process of immunolocalization of AtmiPEP165a using an antibody specifically recognizing AtmiPEP165a.

In particular, the invention relates to a process of immunolocalization of MtmiPEP171b using an antibody specifically recognizing MtmiPEP171b.

In particular, the invention relates to a process of immunolocalization of AtmiPEP164a1 using an antibody specifically recognizing AtmiPEP164a1.

In particular, the invention relates to a process of immunolocalization of MtmiPEP319a1 using an antibody specifically recognizing AtmiPEP319a1.

In another aspect, the invention relates to a protocol for producing a recombinant peptide, the sequence of which comprises or consists of a sequence identical to that of a miPEP as defined above, comprising a step of transforming an organism with an expression vector encoding said recombinant peptide.

In an embodiment, said organism is selected from the group comprising bacteria, yeasts, fungi (other than yeasts), animal cells, plants and animals.

In an embodiment, said organism is *Escherichia coli*.

In particular, the invention relates to a protocol for producing a recombinant peptide as defined above, comprising the following steps:
- binding the nucleic acid encoding said recombinant peptide to a nucleic acid encoding a tag, such as GST,
- introducing the expression vector containing said nucleic acid encoding said recombinant peptide into the bacterium *E. coli*,
- culturing the bacterium *E. coli* containing the expression vector in LB medium preferably up to an OD between 0.2 and 0.4,
- inducing production of the recombinant peptide with IPTG, preferably for 4 to 5 hours,
- centrifuging and lysing the *E. coli* bacteria,
- filtering the supernatant,
- purifying said recombinant peptide on a glutathione sepharose affinity column,
- if necessary, cleaving the GST with a protease.

All the sequences of the miPEPs, miORFs, miRNAs and primary transcripts of miRNAs are presented in Tables 1, 2, 3, 4, 5 and 6.

Table 7 presents an analysis of the polymorphism of the DNA sequence of the different regions of pri-miR171b (a haplotype is defined when it differs by at least one amino acid from the other haplotypes).

TABLE 1

List of potential miPEPs (miPEPs)

| miPEP (pI / size MW) | miRNA | Organism | Target genes of the miRNA | Sequence of the miPEP | SEQ ID |
|---|---|---|---|---|---|
| AtmiPEP156a1 (10.57 / 3824) | miR156a | Arabidopsis thaliana | SPL gene family, involved in development of the stem and flowering | MFCSIQCVARHLFPLHVREIKKATRAI KKGKTL | SEQ ID NO: 1 |
| AtmiPEP156a2 | miR156a | Arabidopsis thaliana | | MRRQTSVPFACKRDKESDKSHKER | SEQ ID NO: 2 |
| AtmiPEP156a3 | miR156a | Arabidopsis thaliana | | MVMFFLDLDKNPRFDLLKGLKWNLF SSHISPSLPPSL | SEQ ID NO: 3 |
| AtmiPEP156e1 (8.5 / 1359) | miR156c | Arabidopsis thaliana | | MKDNFPLLLRL | SEQ ID NO: 4 |
| AtmiPEP156e2 | miR156c | Arabidopsis thaliana | | MSDD | SEQ ID NO: 5 |
| AtmiPEP156e1 (4.03 / 1818) | miR156c | Arabidopsis thaliana | | MIYINKYGSISAVEDD | SEQ ID NO: 6 |
| AtmiPEP156f1 (9.5 / 520) | miR156f | Arabidopsis thaliana | | MSQR | SEQ ID NO: 7 |
| AlmiPEP159a1 (8.34 / 1898) | miR159a | Arabidopsis lyrata | MYB gene family, involved in germination and flowering | MTCPLLSLSFLLSKYI | SEQ ID NO: 8 |
| AtmiPEP159a1 | miR159a | Arabidopsis thaliana | | MTWPLLSLSFLLSKYV | SEQ ID NO: 9 |
| CrmiPEP159a | miR159a | Capsella rubella | | MTCTLSALSLSLNMFRVN | SEQ ID NO: 10 |
| AtmiPEP159b1 (5.27 / 659) | miR159b | Arabidopsis thaliana | | MFYLS | SEQ ID NO: 11 |
| AtmiPEP159b2 | miR159b | Arabidopsis thaliana | | MVNTSSFISSFILPLVLSESNCLLFRTI YKFSMVLY | SEQ ID NO: 12 |
| AtmiPEP160a1 (8.02 / 2936) | miR160a | Arabidopsis thaliana | ARF gene family, involved in germination, development and flowering | MFCLLIPIFSFVFSPNRHLRLQEQ | SEQ ID NO: 13 |
| AtmiPEP160b1 (5.28 / 608) | miR160b | Arabidopsis thaliana | | MFSPQ | SEQ ID NO: 14 |
| AtmiPEP160b2 | miR160b | Arabidopsis thaliana | | MKYIHILILFKSRSTYKLSTNHI | SEQ ID NO: 15 |
| AtmiPEP161 (10/ 1199) | miR161 | Arabidopsis thaliana | PPR gene family DCL1 gene, involved in development | MKIPLFLPKL | SEQ ID NO: 16 |
| AtmiPEP162a1 (4.03 / 3045) | miR162a | Arabidopsis thaliana | | MVSGQEDSWLKLSSLCFLFLSLLDSLI | SEQ ID NO: 17 |
| AtmiPEP162b1 (5.71 /4114) | miR162b | Arabidopsis thaliana | | MFLLIFLRLIMICVCSSTDFLRSVNYFC LFIYDL | SEQ ID NO: 18 |
| AtmiPEP163-1 (6.5 / 1076) | miR163 | Arabidopsis thaliana | SAMT gene family, involved in the production of secondary metabolites | MSTTQEHRS | SEQ ID NO: 19 |
| AtmiPEP163-2 | miR163 | Arabidopsis thaliana | | MILKCWSRFLRVSPYQNAHSLSLG | SEQ ID NO: 20 |
| AlmiPEP164a1 | miR164a | Arabidopsis lyrata | NAC gene family, involved in root, foliar and floral development | MPLAVIRQGIVWP | SEQ ID NO: 21 |
| AlmiPEP164a2 | miR164a | Arabidopsis lyrata | | MPSWHDMVLLPYVKHTHANTRHIT | SEQ ID NO: 22 |
| AlmiPEP164a3 | miR164a | Arabidopsis lyrata | | MTWFFCLT | SEQ ID NO: 23 |
| AtmiPEP164a1 (7.05 / 4256) | miR164a | Arabidopsis thaliana | | MPSWHGMVLLPYVKHTHASTHTHTH NIYGCACELVFH | SEQ ID NO: 24 |
| AtmiPEP164a2 | miR164a | Arabidopsis thaliana | | MAWYGSFALRKTHSRQHTHTHT | SEQ ID NO: 25 |

TABLE 1-continued

List of potential miPEPs (miPEPs)

| miPEP (pI / size MW) | miRNA | Organism | Target genes of the miRNA | Sequence of the miPEP | SEQ ID |
|---|---|---|---|---|---|
| AtmiPEP164a3 | miR164a | Arabidopsis thaliana | | MWFFCLT | SEQ ID NO: 26 |
| BrmiPEP164a1 | miR164a | Brassica rapa | | MMILWK | SEQ ID NO: 27 |
| BrmiPEP164a2 | miR164a | Brassica rapa | | MLWAKLVSFSTLHSLVFLLSPSFA | SEQ ID NO: 28 |
| BrmiPEP164a3 | miR164a | Brassica rapa | | MPSWHGIVILPFVKHTHANIHYSYSCVCI | SEQ ID NO: 29 |
| CpmiPEP164a1 | miR164a | Carica papaya | | MIACHPYLPFPLFLSLTFYSIFFSPSPPSPSLPL | SEQ ID NO: 30 |
| CpmiPEP164a2 | miR164a | Carica papaya | | MPSLLAFSPFPSNILLNLLPLPPFPLSAITTIIKPLSLSLPLSLSGFSV | SEQ ID NO: 31 |
| CrmiPEP164a1 | miR164a | Capsella rubella | | MELKGLRTWQLLDKV | SEQ ID NO: 32 |
| CrmiPEP164a2 | miR164a | Capsella rubella | | MPSWHGMACFYCLT | SEQ ID NO: 33 |
| CrmiPEP164a3 | miR164a | Capsella rubella | | MAWHGMFLLPYVKHTHANTYSLYM | SEQ ID NO: 34 |
| GrmiPEP164a1 | miR164a | Gossypium raimondii | | MMRSRILKFQYRPGMGIGGRKQLKNQLCQIQGRIS | SEQ ID NO: 35 |
| GrmiPEP164a2 | miR164a | Gossypium raimondii | | MSNSRSYQLK | SEQ ID NO: 36 |
| GrmiPEP164a3 | miR164a | Gossypium raimondii | | MNEDLEISTRKRTPQLC | SEQ ID NO: 37 |
| MtmiPEP164a1 | miR164a | Medicago truncatula | | MPKFDIFFYIFV | SEQ ID NO: 38 |
| MtmiPEP164a2 | miR164a | Medicago truncatula | | MSYISLSPKLLPINTKPPWLVQFNFYFSSNTKCNKLHFLGEKLLVGEAGHVQILFLIHSLIMHINIFCTCSPSPTRLPHPSL | SEQ ID NO: 39 |
| OsmiPEP164a1 | miR164a | Oryza sativa | | MQTHSNTPQSTYSLSLSLSE | SEQ ID NO: 40 |
| OsmiPEP164a2 | miR164a | Oryza sativa | | MCVCDINMHSMLMLL | SEQ ID NO: 41 |
| AlmiPEP165a | miR165a | Arabidopsis lyrata | HD-ZIPIII gene family, involved in vascular, root, foliar and floral development, and nodulation | MRIKLFQLRGMLSGSRILYIYTCVC | SEQ ID NO: 42 |
| AtmiPEP165a (12.3 /2105) | miR165a | Arabidopsis thaliana | | MRVKLFQLRGMLSGSRIL | SEQ ID NO: 43 |
| BcmiPEP165a | miR165a | Brassica carinata | | MRMKLFQLRGMLSGSRILYIHKYVYMLIQVFDHICI | SEQ ID NO: 44 |
| BjmiPEP165a | miR165a | Brassica juncea | | MRMKLFQLRGMLSGSRILYIHKYVYIC | SEQ ID NO: 45 |
| BnmiPEP165a | miR165a | Brassica napus | | MRMKLFQLRGMLSGSRILYIHKYVYMIIQVFDHICI | SEQ ID NO: 46 |
| BomiPEP165a | miR165a | Brassica oleracea | | MRMKLFQLRGMLSGSRILYIHKYVYMLIQVFDHICI | SEQ ID NO: 47 |
| BrmiPEP165a | miR165a | Brassica rapa | | MRMKLFQLRGMLSGSRILYIHKYVYIC | SEQ ID NO: 48 |
| AtmiPEP166a (4.68 / 2372) | miR166a | Arabidopsis thaliana | | MLDLFRSNNRIEPSDFRFD | SEQ ID NO: 49 |
| AtmiPEP166b (9.35 / 576) | miR166b | Arabidopsis thaliana | | MRDR | SEQ ID NO: 50 |
| AtmiPEP167a (11 / 1148) | miR167a | Arabidopsis thaliana | ARF gene family, involved in root and floral development gene family of | MNRKISLSLS | SEQ ID NO: 51 |
| AtmiPEP167b1 (5.27 / 891) | miR167b | Arabidopsis thaliana | | MMGCFVGF | SEQ ID NO: 52 |

TABLE 1-continued

List of potential miPEPs (miPEPs)

| miPEP (pI / size MW) | miRNA | Organism | Target genes of the miRNA | Sequence of the miPEP | SEQ ID |
|---|---|---|---|---|---|
| AtmiPEP167b2 | miR167b | Arabidopsis thaliana | CCAAT-bing factor, involved in nodulation, drought resistance, resistance to nitrogen deficiency | MQEETYEG | SEQ ID NO: 53 |
| AtmiPEP169c1 (9.3 / 7110) | miR169c | Arabidopsis thaliana | | MPHTNLKDLFIFSPNVFFSFAIYLHNS WNKNYIHKRENFHNTSFALIFFSSIM SINYG | SEQ ID NO: 54 |
| AtmiPEP169c2 | miR169c | Arabidopsis thaliana | | MFFFRLLFISTILGTKTFTNERIFTTPL LLSFFFFRPL | SEQ ID NO: 55 |
| AtmiPEP169l (8.52 / 786) | miR169l | Arabidopsis thaliana | | MRHKES | SEQ ID NO: 56 |
| AtmiPEP171a1 (11.05 / 4057) | miR171a | Arabidopsis thaliana | GRAS gene family, involved in floral, foliar, and root development, mycorrhization, nodulation | MNLLKKERQRRRQRSIGSHCIASLVL KDGYMKKI | SEQ ID NO: 57 |
| AtmiPEP17 1b (8.5 / 995) | miR171b | Arabidopsis thaliana | | MVLSGKLTF | SEQ ID NO: 58 |
| MtmiPEP171b1 | miR171b | Medicago truncatula | | MLLHRLSKFCKIERDIVYIS | SEQ ID NO: 59 |
| MtmiPEP171b2 | miR171b | Medicago truncatula | | MKIEE | SEQ ID NO: 60 |
| ZmmiPEP171b | miR171b | Zea mays | | MHLPSTPSRPPPQHTSLSFLGKEMTKG TTTACFG | SEQ ID NO: 61 |
| AtmiPEP171c1 (6.68 / 1187) | miR171c | Arabidopsis thaliana | | MLSLSHFHIC | SEQ ID NO: 62 |
| MtmiPEP171e | miR171e | Medicago truncatula | | MMVFGKPKKAMLVRFNPKTDLHV | SEQ ID NO: 63 |
| MtmiPEP171h | miR171h | Medicago truncatula | | MASAAKVYMA | SEQ ID NO: 64 |
| AtmiPEP172a1 (8.5 / 734) | miR172a | Arabidopsis thaliana | AP2 gene family, involved in floral development | MASKIw | SEQ ID NO: 65 |
| AtmiPEP172a3 | miR172a | Arabidopsis thaliana | | MVRFQLSIRD | SEQ ID NO: 66 |
| AtmiPEP172b1 (7.9 / 1621) | miR172b | Arabidopsis thaliana | | MCTYYYLINKYF | SEQ ID NO: 67 |
| AtmiPEP172c1 (7.98 / 1367) | miR172c | Arabidopsis thaliana | | MFPAKWCRLES | SEQ ID NO: 68 |
| AtmiPEP172e1 (8.35 / 2452) | miR172e | Arabidopsis thaliana | | MGSLSLFKSQLEILMLLLSLSK | SEQ ID NO: 69 |
| AtmiPEP172e2 | miR172e | Arabidopsis thaliana | | MSVYIHVPISLNCFSPKSSC | SEQ ID NO: 70 |
| AtmiPEP172e3 | miR172e | Arabidopsis thaliana | | MGVPNFRPRNR | SEQ ID NO: 71 |
| AcmiPEP319a1 | miR319a | Arabidopsis cebennensis | TCP gene family, involved in floral and foliar development | MRSRVSFFFKIMLFRLLGYRSM MHTYIHTISNISSIFFCCSKRSFSPFTYIRI IVVIDPFRIALTFR | SEQ ID NO: 72 |
| AcmiPEP319a2 | miR319a | Arabidopsis cebennensis | | | SEQ ID NO: 73 |
| AhmiPEP319a | miR319a | Arabidopsis halleri | | MRSRVSLFLSFSSNFAAYSPRS | SEQ ID NO: 74 |
| AlmiPEP319a | miR319a | Arabidopsis lyrata | | MHTYIPSSSFPISNISSVFFCYKRSFSPY TYIRIVVIDPFRIALTFR | SEQ ID NO: 75 |
| AtmiPEP319a1 (6.56 / 5917) | miR319a | Arabidopsis thaliana | | MNIHTYHHLLFPSLVFHQSSDVPNALS LHIHTYEYIIVVIDPFRITLAFR | SEQ ID NO: 76 |
| AtmiPEP319a2 | miR319a | Arabidopsis thaliana | | MFQTLYLFIYIHTNILLS | SEQ ID NO: 77 |
| BrmiPEP319a | miR319a | Brassica rapa | | MFKLYFSAILSTQYMHTYHHRIALIFL SILYPSTNYLMSPILNPT | SEQ ID NO: 78 |
| CpmiPEP319a | miR319a | Carica papaya | | MKIKLGFSLIKIIILLDKNS | SEQ ID NO: 79 |
| CrmiPEP319a | miR319a | Capsella rubella | | MHPHTYIHIPSSSFLISSFCL | SEQ ID NO: 80 |

TABLE 1-continued

List of potential miPEPs (miPEPs)

| miPEP (pI / size MW) | miRNA | Organism | Target genes of the miRNA | Sequence of the miPEP | SEQ ID |
|---|---|---|---|---|---|
| EgmiPEP319a | miR319a | Eucalyptus grandis | | MKHIQRWRYGETSGRQDMKRLEIK VHSNPSLKVKKNTNNFSSSL | SEQ ID NO: 81 |
| GrmiPEP319a | miR319a | Gossypium raimondii | | MIHFNLSQWRAICMANFHLTYSFLFG VL | SEQ ID NO: 82 |
| MtmiPEP319a | miR319a | Medicago truncatula | | MHVYLELFMVIKGLGFLLVK | SEQ ID NO: 83 |
| OsmiPEP319a | miR319a | Oryza sativa | | MEMIQRPCLILKFFFKLSTLYIP | SEQ ID NO: 84 |
| PpmiPEP319a | miR319a | Physcomitrella patens | | MFHRRSSVLLPPFGQTQPNPRCLPDL RFPSCFTPCTA | SEQ ID NO: 85 |
| ThmiPEP319a1 | miR319a | Thellungiella halophila | | MTICKVSKACFYAGKIENSRLIKKIGIP KREGAPFSPIRENQ | SEQ ID NO: 86 |
| ThmiPEP319a2 | miR319a | Thellungiella halophila | | MEIQIKKKNLYIMNTQKLPNLYIYIYK YVFIKLMVVE | SEQ ID NO: 87 |
| AtmiPEP319b1 (8.04 / 5120) | miR319b | Arabidopsis thaliana | | MVPQINLWSSRVILKIRIDSSTHREED HCIQNHKHGLSFIFSF | SEQ ID NO: 88 |
| AtmiPEP394 a1 (9.7 / 1977) | miR394a | Arabidopsis thaliana | F-box gene family, involved in foliar development and drought resistance | MSLQFYERVSFKNTVK | SEQ ID NO: 89 |
| AtmiPEP395e1 (3.58 / 1429) | miR395c | Arabidopsis thaliana | Family of the APS and AST genes, involved in germination and sulphur metabolism | MTEQEEESQMST | SEQ ID NO: 90 |
| AtmiPEP395e1 (9.98 / 4700) | miR395e | Arabidopsis thaliana | | MYLQYIDNVISIYSNNRRVGRMFSRV PLSTSLEIQFFIK | SEQ ID NO: 91 |
| AtmiPEP397b1 (4.53 / 1418) | miR397b | Arabidopsis thaliana | Family of the genes of laccases, involved in copper metabolism, their overexpression improves growth | MSKEIFFSPGFE | SEQ ID NO: 92 |
| AtmiPEP398c1 | miR398c | Arabidopsis thaliana | CSD gene family, involved in copper metabolism, its overexpression improves growth | MIRTHEQSTAITTLRHCYSSRFMCSQV TPAELFLYRPCFINAVAR | SEQ ID NO: 93 |
| AtmiPEP399b (11 /678) | miR399b | Arabidopsis thaliana | PHO2 gene family, involved in phosphorus metabolism | MKRNM | SEQ ID NO: 94 |
| AtmiPEP399d1 (4 / 622) | miR399d | Arabidopsis thaliana | | MQCEI | SEQ ID NO: 95 |
| AtmiPEP403 (5.27470) | miR403 | Arabidopsis thaliana | AGO gene family | MFCA | SEQ ID NO: 96 |
| AtmiPEP447a1 | miR447a | Arabidopsis thaliana | Family of the genes of | MVMAHH | SEQ ID NO: 97 |

TABLE 1-continued

List of potential miPEPs (miPEPs)

| miPEP (pI / size MW) | miRNA | Organism | Target genes of the miRNA | Sequence of the miPEP | SEQ ID |
|---|---|---|---|---|---|
| (6.69 / 724) AtmiPEP447a2 | miR447a | Arabidopsis thaliana | phosphoglycerate kinase | MMKPRWNCSLYGITEWTNNQNQKSK RKGRRKTQIWRIGDRLDTVECITLML SAY | SEQ ID NO: 98 |
| AtmiPEP447b1 (4 / 1155) | miR447b | Arabidopsis thaliana | | MLLIVELVL | SEQ ID NO: 99 |
| AtmiPEP447b2 | miR447b | Arabidopsis thaliana | | MLCFNFRCVRRFAE | SEQ ID NO: 100 |
| AtmiPEP447c | miR447c | Arabidopsis thaliana | | MTYQLDNSFSWFLCTRFCLYRYFLF NFRCFRRFSE | SEQ ID NO: 101 |
| DmmiPEP1a | miR1 | Drosophila melanogaster | Muscular differentiation | MWREVCAQKSQTKRRNFITGNQRRN KTKANRKAETKQQKVYEFFVQARER CKTRKKHEKKTLKKTKKIQNRYRAV SENEWGKGFPSHI | SEQ ID NO: 102 |
| DmmiPEP1b | miR1 | Drosophila melanogaster | Muscular differentiation | MRTKKSNKKAQFYYGQPTTKQNKSQ PKSRNKAAKSL | SEQ ID NO: 103 |
| DmmiPEP8 | miR8 | Drosophila melanogaster | Growth | MEPGFVFVLFPTHLSTQHTQREKSILV MGLNLQSAKQSDKQNSKERKKNTQI NSQRIPYRQGGQCSKVLSP | SEQ ID NO: 104 |
| HsmiPEP155 | miR155 | Homo sapiens | inflammation | MEMALMVAQTRKGKSVV | SEQ ID NO: 355 |
| AtmiPEP157c (5.95 / 1776) | miR157c | Arabidopsis thaliana | SPL gene family, involved in development of the stem and flowering | MMLHITHRFESDVGC | SEQ ID NO: 375 |
| AtmiPEP157d (5.27 / 524) | miR157d | Arabidopsis thaliana | | MLYV | SEQ ID NO: 376 |
| AtmiPEP160c (9.98 / 1790) | miR160c | Arabidopsis thaliana | ARF gene family, involved in germination, development and flowering | MFMRRGLVYNNIYI | SEQ ID NO: 377 |
| AtmiPEP164b (4.72 / 1949) | miR164b | Arabidopsis thaliana | NACgene family, involved in root, foliar and floral development | MMKVCDEQDGEAGHVHY | SEQ ID NO: 378 |
| AtmiPEP166c (10.42 / 3407) | miR166c | Arabidopsis thaliana | HD-ZIPIII gene family, involved in vascular, root, foliar and floral development and nodulation | MKKRITRINLEQIKKTLDDSRTRLHS P | SEQ ID NO: 379 |
| AtmiPEP166d (8.35 / 1125) | miR166d | Arabidopsis thaliana | | MKKIGSIDSF | SEQ ID NO: 380 |

TABLE 1-continued

List of potential miPEPs (miPEPs)

| miPEP (pI / size MW) | miRNA | Organism | Target genes of the miRNA | Sequence of the miPEP | SEQ ID |
|---|---|---|---|---|---|
| AtmiPEP169a (9.5 / 784) | miR169a | Arabidopsis thaliana | Gene family of CCAAT-bing factor, involved in nodulation, drought resistance, resistance to nitrogen deficiency | MTCRFK | SEQ ID NO: 381 |
| AtmiPEP169h1 (5.28 / 349) | miR169h | Arabidopsis thaliana | | MVT | SEQ ID NO: 382 |
| AtmiPEP169h2 | miR169h | Arabidopsis thaliana | | MKNENLCGSQG | SEQ ID NO: 383 |
| AtmiPEP169n (8.96 /5315) | miR169n | Arabidopsis thaliana | | MKCMMKKRGLTWRKASCLVAKDDL PDLFRLHDSISNSCILDYYTF | |
| AtmiPEP170 (5.75 / 879) | miR170 | Arabidopsis thaliana | GRAS gene family, involved in floral, foliar, and root development, mycorrhization, nodulation | MFPRESL | SEQ ID NO: 384 |
| AtmiPEP396a (5.3 / 3636) | miR396a | Arabidopsis thaliana | Family of the GRF genes involved in root development and cellular proliferation, mycorrhization | MTLSVFPHSFLELQNFRFFFSFDISY A | SEQ ID NO: 385 |
| AtmiPEP399c (8.66/2703) | miR399c | Arabidopsis thaliana | PHO2 gene family, involved in phosphorus metabolism | MSLAKGELPCHCFRLNTVYNRFC | SEQ ID NO: 386 |

TABLE 2

List of the miORFs

| miPEP | Organism | Sequence of the miORF | SEQ ID |
|---|---|---|---|
| AtmiPEP156a1 | Arabidopsis thaliana | ATGTTCTGTTCAATTCAATGCGTCGCCAGACATCTGTTCCCTTTGC ATGTAAGAGAGATAAAGAAAGCGACAAGAGCCATAAAGAAAGG TAA | SEQ ID NO: 105 |
| AtmiPEP156a2 | Arabidopsis thaliana | ATGCGTCGCCAGACATCTGTTCCCTTTGCATGTAAGAGAGATAAA GAAAGCGACAAGAGCCATAAAGAAAGGTAA | SEQ ID NO: 106 |
| AtmiPEP156a3 | Arabidopsis thaliana | ATGGTTATGTTTTTTCTCGATTTAGACAAAAACCCTAGATTTGATC TTCTAAAGGGTCTCAAATGGAATCTCTTCTCTTCTCATATCTCTCC CTCTCTCCCTCCCTCTCTTTGA | SEQ ID NO: 107 |
| AtmiPEP156c1 | Arabidopsis thaliana | ATGAAGGACAACTTTCCTCTTCTCCTTCGGTTATAA | SEQ ID NO: 108 |
| AtmiPEP156c2 | Arabidopsis thaliana | ATGAGTGATGACTGA | SEQ ID NO: 109 |
| AtmiPEP156e1 | Arabidopsis thaliana | ATGATATATATAAATAAATATGGGTCGATATCGGCTGTGGAGGAC GACTAG | SEQ ID NO: 110 |
| AtmiPEP156f1 | Arabidopsis thaliana | ATGAGCCAAAGATAA | SEQ ID NO: 111 |
| AlmiPEP159a | Arabidopsis lyrata | ATGACGTGTCCTCTTCTCTCTCTCTCTTTCCTTCTCTCTAAGTATAT TTAG | SEQ ID NO: 112 |
| AtmiPEP159a1 | Arabidopsis thaliana | ATGACGTGGCCTCTTCTCTCTCTCTCTTTCCTTCTCTCTAAGTATGT TTAG | SEQ ID NO: 113 |
| CrmiPEP159a | Capsella rubella | ATGACGTGTACTCTCTCTGCTCTATCTCTCTCTAAATATGTTTA GGGTTAA | SEQ ID NO: 114 |
| AtmiPEP159b1 | Arabidopsis thaliana | ATGTTTTATCTTTCATAA | SEQ ID NO: 115 |
| AtmiPEP159b2 | Arabidopsis thaliana | ATGGTTAATACTAGTAGCTTTTTCATTTCAAGTTTTATCCTTCCAT TGGTTCTTTCTGAGTCAAATTGTCTCCTGTTTCGAACCATATATAA GTTTTCAATGGTTTTGTATTAA | SEQ ID NO: 116 |
| AtmiPEP160a1 | Arabidopsis thaliana | ATGTTTTGTTTGTTGATTCCCATCTTCTCTTTTGTCTTTTCACCAAA TCGTCATTTAAGGCTTCAAGAACAGTAA | SEQ ID NO: 117 |
| AtmiPEP160b1 | Arabidopsis thaliana | ATGTTTTCCCCTCAATGA | SEQ ID NO: 118 |
| AtmiPEP160b2 | Arabidopsis thaliana | ATGAAATACATACACATTTTGATTTTATTTAAATCAAGATCGACG TATAAGCTATCCACCAATCATATTTAA | SEQ ID NO: 119 |
| AtmiPEP161 | Arabidopsis thaliana | ATGAAAATTCCATTGTTTCTGCCGAAGCTTTGA | SEQ ID NO: 120 |
| AtmiPEP162a1 | Arabidopsis thaliana | ATGGTATCTGGTCAAGAAGATTCCTGGTTAAAACTTTCATCTCTCT GTTTCCTTTTTCTTTCTTTGTTGGATTCATTAATTTGA | SEQ ID NO: 121 |
| AtmiPEP162b1 | Arabidopsis thaliana | ATGTTTCTTTTAATCTTTTTGAGATTAATAATGATTTGTGTTTGTTC ATCAACCGATTTTCTCAGATCTGTCAATTATTTTTGTTTATTTATTT ATGATTTATGA | SEQ ID NO: 122 |
| AtmiPEP163-1 | Arabidopsis thaliana | ATGTCCACTACTCAAGAGCATAGGTCTTGA | SEQ ID NO: 123 |
| AtmiPEP163-2 | Arabidopsis thaliana | ATGATACTAAAGTGCTGGAGTTCCCGGTTCCTGAGAGTGAGTCCA TATCAAAATGCGCATTCGTTATCACTTGGTTGA | SEQ ID NO: 124 |
| AlmiPEP164a1 | Arabidopsis lyrata | ATGCCCTTAGCAGTTATTAGACAAGGGATTGTTTGGCCCTAG | SEQ ID NO: 125 |
| AlmiPEP164a2 | Arabidopsis lyrata | ATGCCATCATGGCATGACATGGTTCTTTTGCCTTACGTAAAACAC ACTCACGCCAACACACGCCACATAACATAA | SEQ ID NO: 126 |
| AlmiPEP164a3 | Arabidopsis lyrata | ATGACATGGTTCTTTTGCCTTACGTAA | SEQ ID NO: 127 |
| AtmiPEP164a1 | Arabidopsis thaliana | ATGCCATCATGGCATGGTATGGTTCTTTTGCCTTACGTAAAACAC ACTCACGCCAGCACACACACACACACATAACATATACGGATG TGCGTGTGAGCTAGTCTTCCATTAA | SEQ ID NO: 128 |
| AtmiPEP164a2 | Arabidopsis thaliana | ATGGCATGGTATGGTTCTTTTGCCTTACGTAAAACACACTCACGC CAGCACACACACACACACACATAA | SEQ ID NO: 129 |
| AtmiPEP164a3 | Arabidopsis thaliana | ATGGTATGGTTCTTTTGCCTTACGTAA | SEQ ID NO: 130 |

TABLE 2-continued

List of the miORFs

| miPEP | Organism | Sequence of the miORF | SEQ ID |
|---|---|---|---|
| BrmiPEP164a1 | Brassica rapa | ATGATGATAATTTTGTGGAAATAA | SEQ ID NO: 131 |
| BrmiPEP164a2 | Brassica rapa | ATGCTTTGGGCCAAGCTAGTTTCTTTTAGCACTCTTCACTCACTAG TTTTTCTTCTCAGCCCTTCTTTTGCGTGA | SEQ ID NO: 132 |
| BrmiPEP164a3 | Brassica rapa | ATGCCATCATGGCATGGCATTGTCATTTTGCCTTTCGTAAAACAC ACTCACGCCAACATACATTATTCATATTCATGTGTATGTATATGA ATGCCATCATGGCATATGCCATCATGGCAT | SEQ ID NO: 133 |
| CpmiPEP164a1 | Carica papaya | ATGATTGCATGCCATCCCTACTTGCCTTTTCCCCTTTTCCTTTCTCT AACATTTTACTCAATCTTCTTCTCCCCCTCCCCCCCTTCCCCCTCTC TGCCATTATAA | SEQ ID NO: 134 |
| CpmiPEP164a2 | Carica papaya | ATGCCATCCCTACTTGCCTTTTCCCCTTTTCCTTTCTCTAACATTTT ACTCAATCTTCTTCTCCCCCTCCCCCCCTTCCCCCTCTCTGCCATTA TAACCATAATTAAACCTCTCTCCCTCTCTCTCCCTCTCTCTCTCT CTCTCTGGGTTCTCAGTATAA | SEQ ID NO: 135 |
| CrmiPEP164a1 | Capsella rubella | ATGGAATTAAAAGGTTTGAGAACTTGGCAGTTATTAGACAAGGTA TAG | SEQ ID NO: 136 |
| CrmiPEP164a2 | Capsella rubella | ATGCCATCATGGCATGGCATGGCATGTTTCTATTGCCTTACGTAA | SEQ ID NO: 137 |
| CrmiPEP164a3 | Capsella rubella | ATGGCATGGCATGTTTCTATTGCCTTACGTAAAACACACTCACGC CAACACATACTCACTATACATGTAAATAAGTATGTGCGCGTGTGA | SEQ ID NO: 138 |
| GrmiPEP164a1 | Gossypium raimondii | ATGATGAGATCAAGAATTTTAAAGTTTCAATATAGATTTGGCATG GGTATTGGCGGCAGAAAGCAATTAAAAAAACCAGTTATGTCAAAT TCAAGGTCGTATCAGTTAA | SEQ ID NO: 139 |
| GrmiPEP164a2 | Gossypium raimondii | ATGTCAAATTCAAGGTCGTATCAGTTAAAATGA | SEQ ID NO: 140 |
| GrmiPEP164a3 | Gossypium raimondii | ATGAATGAAGATTTAGAAATTTCAACAAGGAAGAGGACCCCACA GCTTTGTTAA | SEQ ID NO: 141 |
| MtmiPEP164a1 | Medicago truncatula | ATGCCCAAATTTGATATTTTTTTTATATATTTGTATAG | SEQ ID NO: 142 |
| MtmiPEP164a2 | Medicago truncatula | ATGTCATATATCTCTCTCTCCTAAGTTGCTACCTATAAATACTA AGCTTTTCCCTTGGTTGGTCAATTCAACTTCTACTTCTCATCAAA CACAAAGTGCAATAAGCTTCATTTCCTGGGTGAGAAGCTCCTTGT TGGAGAAGCAGGGCACGTGCAAATCCTCTTTCTGATTCATTCTCT CATAATGCATATCAATATCTTTTGCACGTGCTCCCCTTCTCCAACT AGG | SEQ ID NO: 143 |
| OsmiPEP164a1 | Oryza sativa | ATGCAAACCCACTCCAACACTCCACAATCCACATACTCTCTCTCT CTCTCTCTCTCTGAGTAG | SEQ ID NO: 144 |
| OsmiPEP164a2 | Oryza sativa | ATGTGTGTGTGTGATATCAATATGCATTCGATGTTGATGCTACTGT AG | SEQ ID NO: 145 |
| AlmiPEP165a | Arabidopsis lyrata | ATGAGAATTAAGCTATTTCAGTTGAGGGGAATGTTGTCTGGATCG AGGATATTACATATATACATGTGTATGTTGA | SEQ ID NO: 146 |
| AtmiPEP165a | Arabidopsis thaliana | ATGAGGGTTAAGCTATTTCAGTTGAGGGGAATGTTGTCTGGATCG AGGATATTATAG | SEQ ID NO: 147 |
| BcmiPEP165a | Brassica carinata | ATGAGAATGAAGCTATTTCAGTTGAGGGGAATGTTGTCTGGATCG AGGATATTATATATACACAAATACGTATATATGTTAATACAAGTG TTTGATCATATATGTATATAG | SEQ ID NO: 148 |
| BjmiPEP165a | Brassica juncea | ATGAGAATGAAGCTATTTCAGTTGAGGGGAATGTTGTCTGGATCG AGGATATTATATATACACAAATATGTATATATATGTTAA | SEQ ID NO: 149 |
| BnmiPEP165a | Brassica napus | ATGAGAATGAAGCTATTTCAGTTGAGGGGAATGTTGTCTGGATCG AGGATATTATATATACACAAATACGTATATATGATAATACAAGTG TTTGATCATATATGTATATAG | SEQ ID NO: 150 |
| BomiPEP165a | Brassica oleracea | ATGAGAATGAAGCTATTTCAGTTGAGGGGAATGTTGTCTGGATCG AGGATATTATATATACACAAGTACGTATATATGTTAATACAAGTG TTTGATCATATATGTATATAG | SEQ ID NO: 151 |
| BrmiPEP165a | Brassica rapa | ATGAGAATGAAGCTATTTCAGTTGAGGGGAATGTTGTCTGGATCG AGGATATTATATATACACAAATATGTATATATATGTTAA | SEQ ID NO: 152 |
| AtmiPEP166a | Arabidopsis thaliana | ATGTTGGATCTCTTTCGATCTAACAATCGAATTGAACCTTCAGATT TCAGATTTGATTAG | SEQ ID NO: 153 |

TABLE 2-continued

List of the miORFs

| miPEP | Organism | Sequence of the miORF | SEQ ID |
|---|---|---|---|
| AtmiPEP166b | Arabidopsis thaliana | ATGAGAGATAGATAA | SEQ ID NO: 154 |
| AtmiPEP167a | Arabidopsis thaliana | ATGAACAGAAAAATCTCTCTTTCTCTTTCTTGA | SEQ ID NO: 155 |
| AtmiPEP167b1 | Arabidopsis thaliana | ATGATGGGTTGTTTTGTGGGATTTTAA | SEQ ID NO: 156 |
| AtmiPEP167b2 | Arabidopsis thaliana | ATGCAGGAGGAAACATATGAGGGGTGA | SEQ ID NO: 157 |
| AtmiPEP169c1 | Arabidopsis thaliana | ATGCCACATACAAACTTGAAAGATCTCTTCATCTTTTCTCCAAATG TTTTTTTTTCGTTTGCTATTTATCTCCACAATTCTTGGAACAAAAA CTACATTCACAAACGAGAGAATTTTCACAACACCTCTTTTGCTCTC ATTTTTTTTTTTTCGTCCATTATGAGTATTAATTATGGTTAG | SEQ ID NO: 158 |
| AtmiPEP169c2 | Arabidopsis thaliana | ATGTTTTTTTTTCGTTTGCTATTTATCTCCACAATTCTTGGAACAA AAACTACATTCACAAACGAGAGAATTTTCACAACACCTCTTTTGC TCTCATTTTTTTTTTTCGTCCATTATGA | SEQ ID NO: 159 |
| AtmiPEP16911 | Arabidopsis thaliana | ATGAGACATAAAGAGAGTTAA | SEQ ID NO: 160 |
| AtmiPEP171a1 | Arabidopsis thaliana | ATGAACCTCCTCAAGAAGGAAAGACAGAGGAGGAGACAAAGAA GTATAGGTTCACATTGCATAGCCAGTTTAGTTTTGAAGGATGGAT ATATGAAAAAAATATGA | SEQ ID NO: 161 |
| AtmiPEP171b | Arabidopsis thaliana | ATGGTTCTCTCCGGTAAATTAACATTTTAG | SEQ ID NO: 162 |
| MtmiPEP171b1 | Medicago truncatula | ATGCTTCTTCATAGGCTCTCCAAATTTTGCAAAATTGAAAGAGAC ATAGTATATATATCTTAG | SEQ ID NO: 163 |
| MtmiPEP171b2 | Medicago truncatula | ATGAAGATTGAAGAGTAA | SEQ ID NO: 164 |
| ZmmiPEP171b | Zea mays | ATGCATCTGCCTTCAACTCCCTCTCGCCCCCCACCCCAACACACAT CTCTCTCTTTTCTAGGGAAGGAAATGACGAAGGGGACGACGACG GCATGCTTCGGCTAG | SEQ ID NO: 165 |
| AtmiPEP171c1 | Arabidopsis thaliana | ATGTTGTCTCTTTCTCATTTTCATATCTGCTAA | SEQ ID NO: 166 |
| MtmiPEP171e | Medicago truncatula | ATGATGGTGTTTGGGAAGCCGAAAAAAGCGATGTTGGTGAGGTT CAATCCGAAGACGGATTTACATGTATAG | SEQ ID NO: 167 |
| MtmiPEP171h | Medicago truncatula | ATGGCTTCAGCTGCAAAAGTATACATGGCGTGA | SEQ ID NO: 168 |
| AtmiPEP172a1 | Arabidopsis thaliana | ATGGCTTCCAAGATCTGGTAA | SEQ ID NO: 169 |
| AtmiPEP172a3 | Arabidopsis thaliana | ATGGTTAGGTTCCAACTAAGTATACGAGATTAA | SEQ ID NO: 170 |
| AtmiPEP172b1 | Arabidopsis thaliana | ATGTGTACGTACTATTATCTCATAAATAAATATTTTTAA | SEQ ID NO: 171 |
| AtmiPEP172c1 | Arabidopsis thaliana | ATGTTTCCAGCAAAATGGTGCCGTCTTGAGTCTTGA | SEQ ID NO: 172 |
| AtmiPEP172e1 | Arabidopsis thaliana | ATGGGATCTCTCTCTTTATTTAAAAGTCAATTAGAGATCTTGATGC TACTTCTGTCCCTTTCCAAGTGA | SEQ ID NO: 173 |
| AtmiPEP172e2 | Arabidopsis thaliana | ATGAGTGTATATATTCATGTACCTATCTCTCTCAATTGCTTCTCAC CAAAATCATCTTGCTGA | SEQ ID NO: 174 |
| AtmiPEP172e3 | Arabidopsis thaliana | ATGGGAGTTCCCAACTTTAGACCTCGAAACCGATAA | SEQ ID NO: 175 |
| AcmiPEP319a1 | Arabidopsis cebennensis | ATGAGATCTAGGGTTTCTTCTTTTTCTTCAAAATCATGCTTTTTC GCTTGCTAGGTTATAGATCCATGTAA | SEQ ID NO: 176 |
| AcmiPEP319a2 | Arabidopsis cebennensis | ATGCATACATACATACATACCATCTCTAATATTTCATCAATCTTCT TTTGTTCCAAACGCCTTTCTCTCCATTTACATACATACGAATCATT GTTGTCATAGATCCGTTTAGAATTGCTTTAACTTTTAGATGA | SEQ ID NO: 177 |
| AhmiPEP319a | Arabidopsis halleri | ATGAGATCTAGGGTTTCTTGTTTCTTTCGTTTTCTTCAAATTTTGC TGCATATTCTCCAAGATCATGA | SEQ ID NO: 178 |
| AlmiPEP319a | Arabidopsis lyrata | ATGCATACATACATACCATCATCATCTTTTCCCATCTCTAATATTT CATCAGTCTTCTTTTTGTTACAAACGCTCTTTCTCGCCATATACATA CATAAGAATCATTGTTGTCATAGATCCGTTTAGAATTGCTTTAACT TTTAGATGA | SEQ ID NO: 179 |

TABLE 2-continued

List of the miORFs

| miPEP | Organism | Sequence of the miORF | SEQ ID |
|---|---|---|---|
| AtmiPEP319a1 | Arabidopsis thaliana | ATGAATATACATACATACCATCATCTTCTTTTCCCATCTCTAGTTT TTCATCAATCTTCTGATGTTCCAAACGCTCTATCTCTTCATATACA TACATACGAATATATTATTGTTGTCATAGATCCATTTAGAATCACT TTAGCTTTTAGATGA | SEQ ID NO: 180 |
| AtmiPEP319a2 | Arabidopsis thaliana | ATGTTCCAAACGCTCTATCTCTTCATATACATACATACGAATATAT TATTGTTGTCATAG | SEQ ID NO: 181 |
| BrmiPEP319a | Brassica rapa | ATGTTTAAGCTCTACTTCTCAGCAATTCTCTCCACCCAATACATGC ATACATACCATCATCGTATCGCTCTAATTTTTCTATCAATCTTGTA TCCTTCCACAAATTATCTTATGTCTCCCATTTTAAATCCTACATAG | SEQ ID NO: 182 |
| CpmiPEP319a | Carica papaya | ATGAAGATTAAATTAGGTTTTAGTCTTATTAAGATTATTATATTAC TAGACAAAAACAGTTAA | SEQ ID NO: 183 |
| CrmiPEP319a | Capsella rubella | ATGCATCCACATACATACATACATATACCATCATCTTCTTTTCTCA TCTCTAGTTTTTGTTTATAA | SEQ ID NO: 184 |
| EgmiPEP319a | Eucalyptus grandis | ATGAAGCATATTCAAAGGTGGAGATATGGGGAGACTTCCGGAAG GCAAGGGGATTGGAAAAGGCTCGAGATCAAAGTGCATAGCAACC CTTCGCTAAAGGTGAAAAAGAATACGAATAACTTCAGTAGCTCAC TTTAA | SEQ ID NO: 185 |
| GrmiPEP319a | Gossypium raimondii | ATGATCCATTTCAACCTGTCACAGTGGAGAGCAATTTGTATGGCT AATTTCCATCTCACCTATTCTTTTCTGTTTGGGGTTCTCTAG | SEQ ID NO: 186 |
| MtmiPEP319a | Medicago truncatula | ATGCATGTATATCTTGAATTGTTTATGGTAATAAAGGGGTTAGGA TTTCTCCTTTTGGTGAAGTGA | SEQ ID NO: 187 |
| OsmiPEP319a | Olyza sativa | ATGGAAATGATACAAAGGCCGTGTTTAATTTTAAAATTTTTTTCA AACTTTCAACACTTTACATCCCATAA | SEQ ID NO: 188 |
| PpmiPEP319a | Physcomitrella patens | ATGTTCCACCGTCGGAGATCCTCGGTGCTGCTACCCCCGTTCGGC CAAACCCAACCCAACCCTAGGTGTCTGCCGGACCTCCGCTTCCCC TCCTGCTTCACCCCCTGCACCGCTTAA | SEQ ID NO: 189 |
| ThmiPEP319a1 | Thellungiella halophila | ATGACGATATGTAAAGTAAGCAAGGCATGTTTTTATGCAGGGAA GATTGAAAATTCAAGATTAATCAAGAAAATTGGAATACAAAAA GAGAGGGAGCTCCCTTCAGTCCAATCAGAGAATCAATGA | SEQ ID NO: 190 |
| ThmiPEP319a2 | Thellungiella halophila | ATGGAGATTCAAATTAAAAAGAAAAACTTATATATAATGAATAC ACAAAAGCTACCTAATCTGTATATATATATATATATAAATATGTCTT CATTAAATTAATGGTCGTGGAATAG | SEQ ID NO: 191 |
| AtmiPEP319b1 | Arabidopsis thaliana | ATGGTACCTCAAATTAATCTATGGTCATCTAGGGTTATCTTGAAG ATTAGAATTGATTCTAGCACGCACAGAGAGGAAGATCATTGCATC CAGAATCACAAACATG3GCCTATCTTTTATCTTTTCTTTTTGA | SEQ ID NO: 192 |
| AtmiPEP394a1 | Arabidopsis thaliana | ATGTCTCTCCAATTTTATGAGAGGGTTTCCTTCAAGAACACAGTA AAATAG | SEQ ID NO: 193 |
| AtmiPEP395c1 | Arabidopsis thaliana | ATGACAGAGCAAGAAGAAGAAAGTCAAATGTCCACATGA | SEQ ID NO: 194 |
| AtmiPEP395e1 | Arabidopsis thaliana | ATGTATCTACAATATATTGATAATGTAATATCTATATATTCAAAC AATCGTCGTGTTGGTCGGATGTTTTCTAGAGTTCCTCTGAGCACTT CATTGGAGATACAATTTTTTATAAAATAG | SEQ ID NO: 195 |
| AtmiPEP397b1 | Arabidopsis thaliana | ATGAGCAAGGAGATATTTTTTTCCCCTGGGTTTGAATGA | SEQ ID NO: 196 |
| AtmiPEP398c1 | Arabidopsis thaliana | ATGAGAACACACGAGCAATCAACGGCTATAACGACGCTACGTCA TTGTTACAGCTCTCGTTTCATGTGTTCTCAGGTCACCCCTGCTGAG CTCTTTCTCTACCGTCCATGTTTTATCAACGCCGTGGCCCGTG | SEQ ID NO: 197 |
| AtmiPEP399b | Arabidopsis thaliana | ATGAAGAGAAACATGTAA | SEQ ID NO: 198 |
| AtmiPEP399d1 | Arabidopsis thaliana | ATGCAATGTGAAATATGA | SEQ ID NO: 199 |
| AtmiPEP403 | Arabidopsis thaliana | ATGTTTTGTGCTTGA | SEQ ID NO: 200 |
| AtmiPEP447a1 | Arabidopsis thaliana | ATGGTCATGGCTCATCATTAG | SEQ ID NO: 201 |
| AtmiPEP447a2 | Arabidopsis thaliana | ATGATGAAACCTCGATGGAACTGCTCTCTTTATGGAATCACGGAA TGGACAAATAATCAAATCAGAAATCGAAGCGAAAAGGGAGGA GAAAAACGCAGATTTGGAGGATTGGGGACAGATTAGATACTGTT GAATGCATCACTCTAATGCTATCAGCCTATTAA | SEQ ID NO: 202 |

TABLE 2-continued

List of the miORFs

| miPEP | Organism | Sequence of the miORF | SEQ ID |
|---|---|---|---|
| AtmiPEP447b1 | Arabidopsis thaliana | ATGCTGCTTATCATCGTGGAGTTGGTTCTGTAA | SEQ ID NO: 203 |
| AtmiPEP447b2 | Arabidopsis thaliana | ATGCTTTGTTTCAATTTCAGGTGCGTTAGAAGGTTTGCAGAGTAG | SEQ ID NO: 204 |
| AtmiPEP447c | Arabidopsis thaliana | ATGTACACCTACCAGCTTGATAACTCTTTTTCGTGGTTTCTGTGTA CTCGTTTCTGTTTGTACAGATACTTCTTGTTCAATTTCAGATGCTTT AGAAGGTTTTCGGAG | SEQ ID NO: 205 |
| dmmiPEP1a | Drosophila melanogaster | ATGTGGCGCGAAGTATGCGCACAAAAAAGTCAAACAAAAAGGCG CAATTTTATTACGGGCAACCAACGACGAAACAAAACAAAAGCCA ACCGAAAAGCAGAAACAAAGCAGCAAAAAGTTTATGAATTTTTTT GTGCAGGCGCGTGAAAGATGCAAAACGAGAAAAAAACATGAAA AAAAAACATTAAAAAAAACAAAAAAAATCCAAAACAGATACCG AGCTGTATCCGAAAACGAGTGGGGAAAGGGGTTTCCCAGTCACA TATAA | SEQ ID NO: 206 |
| DmmiPEP1b | Drosophila melanogaster | ATGCGCACAAAAAAGTCAAACAAAAAGGCGCAATTTTATTACGG GCAACCAACGACGAAACAAAACAAAAGCCAACCGAAAAGCAGA AACAAAGCAGCAAAAAGTTTATGA | SEQ ID NO: 207 |
| DmmiPEP8 | Drosophila melanogaster | ATGGAGCCTGGCTTTGTTTTTGTTTTATTTCCAACCCACTTGAGCA CACAGCACACAGAGAGAAAAATCAATACTCGTTATGGGATTA AATTTACAAAGCGCAAAGCAAAGCGACAAACAAAATTCAAAGA AAGAAAAAAAAACACTCAAATAAACTCACAAAGAATTCCTTATC GCCAAGGGGGCCAATGTTCTAAGGTTCTTTCGCCTTGA | SEQ ID NO: 208 |
| HsmiPEP155 | Homo sapiens | TGGAGATGGCTCTAATGGTGGCACAAACCAGGAAGGGGAAATCT GTGGTTTAA | SEQ ID NO: 356 |
| AtmiPEP157c | Arabidopsis thaliana | ATGATGTTGCATATCACACATAGGTTTGAGAGTGATGTTGGTTGT TGA | SEQ ID NO: 387 |
| AtmiPEP 157d | Arabidopsis thaliana | ATGCTGTATGTATAG | SEQ ID NO: 388 |
| AtmiPEP160c | Arabidopsis thaliana | ATGTTCATGCGTAGAGGTTTGGTATACAACAATATATACATATAA | SEQ ID NO: 389 |
| AtmiPEP164b | Arabidopsis thaliana | ATGATGAAGGTGTGTGATGAGCAAGATGGAGAAGCAGGGCACGT GCATTAC | SEQ ID NO: 390 TAG |
| AtmiPEP166c | Arabidopsis thaliana | ATGAAGAAGAGAATCACTCGAATTAATTTGGAAGAACAAATTAA GAAAACCCTAGATGATTCTCGGACCAGGCTTCATTCCCCCTAA | SEQ ID NO: 391 |
| AtmiPEP166d | Arabidopsis thaliana | ATGAAGAAGATCGGTAGIATTGATTCATTTTAA | SEQ ID NO: 392 |
| AtmiPEP169a | Arabidopsis thaliana | ATGACTTGCCGATTTAAATGA | SEQ ID NO: 393 |
| AtmiPEP169h1 | Arabidopsis thaliana | ATGGTGACATGA | SEQ ID NO: 394 |
| AtmiPEP169h2 | Arabidopsis thaliana | ATGAAGAATGAGAACTTGTGTGGTAGCCAAGGATGA | SEQ ID NO: 395 |
| AtmiPEP169n | Arabidopsis thaliana | ATGAAGTGTATGATGAAGAAGAGAGGTCTAACATGGCGGAAAGC GTCATGTTTAGTAGCCAAGGATGACTTGCCTGATCTTTTTCGCCTC CACGATTCAATTTCAAATTCATGCATTTTGGATTATTATACCTTTT AA | SEQ ID NO: 396 |
| AtmiPEP170 | Arabidopsis thaliana | ATGTTTCCGAGAGAGTCCCTCTGA | SEQ ID NO: 397 |
| AtmiPEP396a | Arabidopsis thaliana | ATGACCCTCTCTGTATTCTTCCACAGCTTTCTTGAACTGCAAAACT TCTTCAGATTTTTTTTTTTTCTTTTGATATCTCTTACGCATAA | SEQ ID NO: 398 |
| AtmiPEP399c | Arabidopsis thaliana | ATGTCACTTGCCAAGGAGAGTTGCCCTGTCACTGCTTCCGCTTA AACACAGTCTATAACCGGTTCTGCTAA | SEQ ID NO: 399 |

TABLE 3

List of the primary transcripts (pri-miRNAs)

| miPEP | Organism | Sequence of the Pri-miRNA | SEQ ID |
|---|---|---|---|
| AtmiPEP156a1 AtmiPEP156a2 AtmiPEP156a3 | Arabidopsis thaliana | ATTCATTGTTCACTCTCAAATCTCAAGTTCATTGCCATTTTTAGGTCTCTC TATAAATTCAAATGTTCTGTTCAATTCAATGCGTCGCCAGACATCTGTTC CCTTTGCATGTAAGAGAGATAAAGAAAGCGACAAGAGCCATAAAGAAA GGTAAGACTCTTTGAAATAGAGAGAGATAAGGTTTTCTCTTATCTTCTTC | SEQ ID NO: 209 |

TABLE 3-continued

List of the primary transcripts (pri-miRNAs)

| miPEP | Organism | Sequence of the Pri-miRNA | SEQ ID |
|---|---|---|---|
| | | TCATCAGATCTTTGTTTCTTTACCCTCTTTCTTTCTTTTTTTGCTTTTTATG<br>GTTATGTTTTTTCTCGATTTAGACAAAAACCCTAGATTTGATCTTCTAAAG<br>GGTCTCAAATGGAATCTCTTCTCTTCTCATATCTCTCCCTCTCTCCCTCCC<br>TCTCTTTGATTCTTTGTCTTCTCCAGTTAAAACTCAGATCTAACACAAAGC<br>TTAAAAGATTCTCATCGTTTCTTGTTTTCTTTGTTTCATCTTGTAGATCTCT<br>GAAGTTGGACTAATTGTGAATGAAAGAGTTGGGACAAGAGAAACGCAA<br>AGAAACTGACAGAAGAGAGTGAGCACACAAAGGCAATTTGCATATCATT<br>GCACTTGCTTCTCTTGCGTGCTCACTGCTCTTTCTGTCAGATTCCGGTGCT<br>GATCTCTTT | |
| AtmiPEP156c1<br>AtmiPEP156c2 | Arabidopsis thaliana | CTCTGCCTTTAGTTCTTTCTTTTTTGGTAATATATTTATTTTTCGTTACGAT<br>TTGGTCAAACCCTAGATTTGTTTTCCAAAAGCATATCTGAAAATGAAGG<br>ACAACTTTCCTCTTCTCCTTCGGTTATAAATATTCTCTCCGGTTTTGCTTGT<br>TTAACCTAAAAGCCTCAGATCTAACTCCAACACCTTCAAAGTCTGCCTCC<br>TTTCCAATCTTCTTTCTTCTGTTCGATCTCTAATCTCAGAATTTGTGTCGGT<br>AAGGTAAAGGTGATAATGAGTGATGACTGATGAGGGAGTTTTGGGACAA<br>ATTTTAAGAGAAACGCATAGAAACTGACAGAAGAGAGTGAGCACACAA<br>AGGCACTTTGCATGTTCGATGCATTTGCTTCTCTTGCGTGCTCACTGCTCT<br>ATCTGTCAGATTCCGGCT | SEQ ID NO: 210 |
| AtmiPEP156e1 | Arabidopsis thaliana | TCCCACATCCAAAGATAGAAAGATGTAAGGTCTAGAGTCTTGTTCTTAAT<br>CCCCTAACAGAACAATGATATATATAAATAAATATGGGTCGATATCGGC<br>TGTGGAGGACGACTAGCTACGGTTTCGAGCCTGGTCACATGCGTAGAGT<br>GTGAAAGGTAATTAGGAGGTGACAGAAGAGAGTGAGCACACATGGTGG<br>TTTCTTGCATGCTTTTTTGATTAGGGTTTCATGCTTGAAGCTATGTGTGCT<br>TACTCTCTCTCTGTCACCCCT | SEQ ID NO: 211 |
| AtmiPEP156f1 | Arabidopsis thaliana | TCCCACAGCCAATGAGCCAAAGATAAAGAAACACCTATCCTATAATAAT<br>TTAGAGCAATATACCTCCATAATGGAACATCTATATATATAAAGGTATCC<br>GTATATCTCTATATATTATATTCATTGAGTTTAAAGTGGCTAGGGTTTATA<br>GATGTATGTGATATTAAGAGATATGAAACATATTTGTCGACGGTTTGAGT<br>GGTGAGGAATTGATGGTGACAGAAGAGAGTGAGCACACATGGTGGCTTT<br>CTTGCATATTTGAAGGTTCCATGCTTGAAGCTATGTGTGCTCACTCTCTAT<br>CCGTCACCCCCTTCTCTCCCTCTCCCTC | SEQ ID NO: 212 |
| AlmiPEP159a | Arabidopsis lyrata | AAAAAATGACGTGTCCTCTTCTCTCTCTCTCTTTCCTTCTCTCTAAGTATA<br>TTTAGGGTTAATTATTAGGGTTCTTTATCTCTTTCTTCAGTCTTTGAAGTTT<br>CTTCAATAGCTTTAATTGAAGTGATTTACCTCTCTGGGTGTTTTTAGTATA<br>TATATCATGTACATGATCGAATTTCTTTCTATCCAAGTTCTCATCAAACCT<br>TCTCATGTTTTGAAGAGTTAAAGGCTTTATAGTTTGCTTAGGTCAGATCC<br>ATAACATACTGTATTTGACAAGTTTCTTTGTCTCACGATAGATCTTGGTCT<br>GACCAAAATGATTTTCTCGAGAAAAAAAAAGATGGAAGTAGAGCTCCTT<br>GAAGTTCAAACGAGAGTTGAGCAGGGTAAAGAAAAGCTGCTAAGCTATG<br>GATCCCATAAGCCCTAATCCTTATAAAGAAAAAAAAGGATTTGGTTATAT<br>GGCTTGCATATCTCAGGAGCTTTAACTTGCCCTTTAATGGCTTTTACTCTT<br>CTTTGGATTGAAGGGAGCTCTACATCTTCTTTCACCTTCTCTATTTTTCTTT<br>CTTTATTTTCTCCTCTACAGTAATTTATTTGGATT | SEQ ID NO: 213 |
| AtmiPEP159a1 | Arabidopsis thaliana | TTCCAAAACATGACGTGGCCTCTTCTCTCTCTCTCTTTCCTTCTCTCTAAG<br>TATGTTTAGGGTTAATAATTAGGGTTCCTCCTCTCTTTTGTTCTGTCTTTAT<br>ATCTCCTTCATAGCTCTAATGTAAGAGATTTACCTCTTTTGGTGTTTTTGT<br>TAATCCACGTTCTCATCAAAACTTTCTCATTGTTTTATGAAGAGTTAAAG<br>GTCTTTACAGTTTGCTTATGTCAGATCCATAATATATTTGACAAGATACTT<br>TGTTTTTCGATAGATCTTGATCTGACGATGGAAGTAGAGCTCCTTAAAGT<br>TCAAACATGAGTTGAGCAGGGTAAAGAAAAGCTGCTAAGCTATGGATCC<br>CATAAGCCCTAATCCTTGTAAAGTAAAAAAGGATTTGGTTATATGGATTG<br>CATATCTCAGGAGCTTTAACTTGCCCTTTAATGGCTTTTACTCTTCTTTGG<br>ATTGAAGGGAGCTCTACATCTTCTTTCACCTTCTCTATTTTTATTTTCTT<br>TATTTCTACTCAACAATTATTTATTCGGATTCATCTTTAATTTTCCGTTAT<br>AATTTCTTTTTGGTAAGGATTATTCGCTATAATTTGAGAAT | SEQ ID NO: 214 |
| CrmiPEP159a | Capsella rubella | TTCCAACGAATGACGTGTACTCTCTCTGCTCTATCTCTCTCTCTAAATATG<br>TTTAGGGTTAATTAGGGTTCTTCATCTGTCTCTCTCTCTCTCTCTTCAG<br>AGTCTTTATAGCTTCTTCCAAGATTTTTAATTGAAAGTAATTTACCTCTTT<br>TGGAGTTCTGTACATATAGAATATCAGGAGTCGTGTTTCTTTTTTATCAA<br>GGTTCTCATCTAACCTTTATAGTATTTTCATTAGTTGATAAAGGTCTTCAT<br>AGTTTGCTTAGATCAGATCTTGTCTTCGTCTTTTCGATAGATCTTGTTCTG<br>TCCAATATACAGTGATTTTATTTCGAGAGCAAAAAGATGAGAGGTAGA<br>GCTCCTTGAAGTCAAACGAGAGTTTAGCAGGGTAGAGAAAAGCTGCTA<br>AGCTATGGATCCCATAAGCCCTAATCCTTGTTAATGATAAAGGATTTGGT<br>TATATGGCTTGCATATCTCAGGAGCTTTAACTTGCCCTTTAATTGCTTTTA<br>CTCTTCTTTGGATTGAAGGGAGCTCTACATCTTCTTTGACTTCTCTCTCTA<br>TTAAGTCTTTCTTTATTTTCTTCTCTACAATAGTTGTTTTGGATCGGAAGA<br>TCTTTAAGTTTCCCTTA | SEQ ID NO: 215 |

TABLE 3-continued

List of the primary transcripts (pri-miRNAs)

| miPEP | Organism | Sequence of the Pri-miRNA | SEQ ID |
|---|---|---|---|
| AtmiPEP159b1<br>AtmiPEP159b2 | Arabidopsis thaliana | TTTCACTTTTGTTCTCCTCCTCCCTTTTTTTCTTTTCAGGATTCTTCTTTTCT<br>ATGTTTTATCTTTCATAATAGATCTGATAATTTTGATTTTTCACTATATAT<br>ATTATGGTTAATACTAGTAGCTTTTTCATTTCAAGTTTTATCCTTCCATTG<br>GTTCTTTCTGAGTCAAATTGTCTCCTGTTTCGAACCATATATAAGTTTTCA<br>ATGGTTTTGTATTAACTCAAGTATTCAACATTATGTCTCTCTTTTTCTTGC<br>TTGGATCTCTAATGCTGTTCATATTTTAAAGCATAGGTTTAGGTTAGATG<br>CATGTAACTGCCAATTAAAAGAAGGTCAAGAGTTTTTTGATTGTATGAAT<br>ATATGAGTTAGTCAAAGCAGATCCACACGATTATATAGAAAAACAAAGG<br>AAGAAGAAGAGGAAGAGCTCCTTGAAGTTCAATGGAGGGTTTAGCAGGG<br>TGAAGTAAAGCTGCTAAGCTATGGATCCCATAAGCCTTATCAAATTCAAT<br>ATAATTGATGATAAGGTTTTTTTTATGGATGCCATATCTCAGGAGCTTTC<br>ACTTACCCCTTTAATGGCTTCACTCTTCTTTGGATTGAAGGGAGCTCTTCA<br>TCTCTC | SEQ ID NO: 216 |
| AtmiPEP160a1 | Arabidopsis thaliana | CATCCCACCCTTAATTGTTTTATATAAACCATTTCTCCTCCTCTCTCCATC<br>ACCTTCAATCTCTCTCGATCTCTCTCTGGATCCCCAATCTCACCTCCATGT<br>TTTGTTTGTTGATTCCCATCTTCTCTTTTTGTCTTTTCACCAAATCGTCATTT<br>AAGGCTTCAAGAACAGTAACCCCAATTCCTCCACAAGAGGGAGAGAAAA<br>CAAAAGATCTTCCAATTCCATTCTCGTACATGCAAATCACAATCCATGCC<br>ATAGATTGTTTCTATTCCTCCTTATTTATTGCTTGTATCTGTTCATGCATG<br>GACCAGGTGGAGAGAGCATTACTTAAAAATAGAATTAGCTATCTGTTTTA<br>GGCGAATTAGTTTCCTTACATAACCATGTATATGTCATGACGCATATACA<br>TATGTAGATGTATATGTATTATATATGTATGCCTGGCTCCCTGTATGCCAT<br>ATGCTGAGCCCATCGAGTATCGATGACCTCCGTGGATGGCGTATGAGGA<br>GCCATGCATAT | SEQ ID NO: 217 |
| AtmiPEP160b1<br>AtmiPEP160b2 | Arabidopsis thaliana | ACTCATAACTCTCCCCAAATTCTTGACCAAAAATATCCGCCACTTTCTCTC<br>TGGTTCATGTTTTCCCCTCAATGAAATACATACACATTTTGATTTTATTTA<br>AATCAAGATCGACGTATAAGCTATCCACCAATCATATTTAAGGGTTCCCG<br>TATACATATATACTATATATATATATGGAATAATAGTCGTGCCTGGCTCC<br>CTGTATGCCACAAGAAAACATCGATTTAGTTTCAAAATCGATCACTAGTG<br>GCGTACAGAGTAGTCAAGCATGAC | SEQ ID NO: 218 |
| AtmiPEP161 | Arabidopsis thaliana | CTCTAACTCATCCTTCTCTTCTATGAAAATTCCATTGTTTCTGCCGAAGCT<br>TTGATCAGTACTTCTCTTTTGCTTGATCTCGGTTTTTGACCAGTTTATTGC<br>GTCGATCAATGCATTGAAAGTGACTACATCGGGGTTCCGATTTTTTTTGT<br>TCTTCATATGATGAAGCGGAAACAGTAATCAACCCTGGTTTAGTCACTTT<br>CACTGCATTAATCAATGCATTTGTAAAAGAGGGAAAAGCA | SEQ ID NO: 219 |
| AtmiPEP162a1 | Arabidopsis thaliana | CTAGAAGAAAAACCAGATCTATAAAGTTTGTTATTAAAGATAGAGAG<br>AGAGGAGGGATGTAGTAGGCCAATAGGCAAATCAGAGAATCACAAATG<br>GTATCTGGTCAAGAAGATTCCTGGTTAAAACTTTCATCTCTCTGTTTCCTT<br>TTTCTTTCTTTGTTGGATTCATTAATTTGACATATCTCTATCATCACACTG<br>ATTCTCTTTCTCCCAGTTTGTCTGCAGATGCATGTGTGTAATCTAGGGTAT<br>ATGTTTTTGTCCATTTGGTTTCATAAGGCAATAAAGATCCAGCTATTTACT<br>ACTTGTGGTATAGATTTTGACTGTTGAATTTTCAGATCTGATGTGTTTCGT<br>TTGATCCGATTCGGAAAATTTATGTTTCGTTGACATTTTGGAGTTTAGTTG<br>GAAGAAGAGTGAGAGTCGCTGGAGGCAGCGGTTCATCGATCTCTTCCTG<br>TGAACACATTAAAAATGTAAAAGCATGAATAGATCGATAAACCTCTGCA<br>TCCAGCGTTTGCCTCTTGTATCTTTCTTATTGACTT | SEQ ID NO: 220 |
| AtmiPEP162b1 | Arabidopsis thaliana | CTGCATCTATCCACCTCTCTCTGTAAATTTATCTAAATGTTTCTTTTAATC<br>TTTTTGAGATTAATAATGATTTGTGTTTGTTCATCAACCGATTTTCTCAGA<br>TCTGTCAATTATTTTTGTTTATTTATTTATGATTTATGAATGAGGAAAGAG<br>TGAAGTCGCTGGAGGCAGCGGTTCATCGATCAATTCCTGTGAATATTTAT<br>TTTGTTTACAAAAGCAAGAATCGATCGATAAACCTCTGCATCCAGCGCT<br>GCTTGCTC | SEQ ID NO: 221 |
| AtmiPEP163- 1<br>AtmiPEP163- 2 | Arabidopsis thaliana | TATCACAGTTCTCATCAAATATTTGAAAGTATCAAACAAAAAAGGAGA<br>GTGAGAAAATAAAGAGAGAGATAGAGAGAGATCATGTCCACTACTCA<br>AGAGCATAGGTCTTGATTGGTGGAAGCAAGTACCTTAGATAAACCGAC<br>CAAAACCCGGTGGATAAAATCGAGTTCCAACCTCTTCAACGACAACGAT<br>TTCAACACTCTCTTCCAGGAACAACTTCCTCCAGGCAGATGATACTAAAG<br>TGCTGGAGTTCCCGGTTCCTGAGAGTGAGTCCATATCAAAATGCGCATTC<br>GTTATCACTTGGTTGAACCCATTTGGGGATTTAAATTTGGAGGTGAAATG<br>GAACGCGTAATTGATGACTCCTACGTGGAACCTCTTCTTAGGAAGAGCAC<br>GGTCGAAGAAGTAACTGCGCAGTGCTTAAATCGTAGATGCTAAAGTCGT<br>TGAAGAGGACTTGGAACTTCGATATTATCCCCCGTGT | SEQ ID NO: 222 |
| AlmiPEP164a1<br>AlmiPEP164a2<br>AlmiPEP164a3 | Arabidopsis lyrata | AGTAGGGTTGGAAAATTTTTTACATTTTTACTCTAAAATAGAATAGAGT<br>TGGAGATGCCCTTAGCAGTTATTAGACAAGGGATTGTTTGGCCCTAGCGA<br>TCCTCTCTTCACTCTCTCACTTTTGTAGTTCAACCCTTCTTTTGCGTGAGAT<br>GCCATCATGGCATGACATGGTTCTTTTGCCTTACGTAAAACACACTCACG<br>CCAACACACGCCACATAACATAAATAAATTATATATACATATACGTATGT<br>GCGTGTGAGTCTTCCATTAATGCAATCTTTGGGCCTATATATATATACAA<br>ACCTTCCATAACCAAAGTTATCATACTACAAAAGCTCTCTCGTACTTGGA | SEQ ID NO: 223 |

TABLE 3-continued

List of the primary transcripts (pri-miRNAs)

| miPEP | Organism | Sequence of the Pri-miRNA | SEQ ID |
|---|---|---|---|
| | | AATGCGGGTGAGAATCTCCATGTTGGAGAAGCAGGGCACGTGCAAACCA ACAAACACGAAATCCGTCTCATGTGTTTTGCACGTACTCCCCTTCTCCAA CATGAGCTCCTGACCCATTG | |
| AtmiPEP164a1 AtmiPEP164a2 AtmiPEP164a3 | Arabidopsis thaliana | AGACAAGCCCCCACACTAAAAAAACAGTAATATGGAATAAAAAAAAGC TTTCAAAACTTAGCAGTTATTAGACAAGGTATTGTTTGGCCCTAGCTAGC GATCGTTTAGCTCTCTTCACTCTCTCACTTTTTTAGTTCAACCCTTCTTTTG CGTGAGATGCCATCATGGCATGGTATGGTTCTTTTGCCTTACGTAAAACA CACTCACGCCAGCACACACACACACACACATAACATATACGGATGTGCG TGTGAGCTAGTCTTCCATTAATGCAATCTTTGGGCCTATATATACAAACC TTTCCATAACCAAAGTTCTCATACTACAAACGCCCCTCATGTGCTTGGAA ATGCGGGTGAGAATCTCCATGTTGGAGAAGCAGGGCACGTGCAAACCAA CAAACACGAAATCCGTCTCATTTGCTTATTTGCACGTACTTAACTTCTCCA ACATGAGCTCTTCACCC | SEQ ID NO: 224 |
| BrmiPEP164a1 BrmiPEP164a2 BrmiPEP164a3 | Brassica rapa | AGACAACCCCACGTTTTAAAATAAGAAATGATGATAATTTTGTGGAAAT AAAAGCTAGTATACTTTTGCAATAATTAGACAAGGTATTGATGCTTTGGG CCAAGCTAGTTTCTTTTAGCACTCTTCACTCACTAGTTTTTCTTCTCAGCC CTTCTTTTGCGTGAAATGCCATCATGGCATGGCATTGTCATTTTGCCTTTC GTAAAACACACTCACGCCAACATACATTATTCATATTCATGTGTATGTAT ATGAATGTTCCATTAATGCAATCTTTGGGGCCTATATATACGAAGCTTAC ATCACCAAAGCTCTCATATTACAAAAGCTCACATATATACTTGGAAATGT AGGTGAGAACCTCCATGTTGGAAGCAGGGCACGTGCAAACCAAAAA ACATGAAATCTGTTTCATATGCTTTGCACGTGCTCCCCTCCTCCAACATG A | SEQ ID NO: 225 |
| CpmiPEP164a1 CpmiPEP164a2 | Carica papaya | AGACAACACTCCTCTTTGTTCCCTTCCTCACGTATCCACTTTTGAAATTTG TAATTTGTGTGCACCACCATGATTGCATGCCATCCCTACTTGCCTTTTCCC CTTTTCCTTTCTCTAACATTTTACTCAATCTTCTTCTCCCCCTCCCCCCCTT CCCCCTCTCTGCCATTATAACCATAATTAAACCTCTCTCCCTCTCTCTCCC TCTCTCTCTCTCTCTGGGTTCTCAGTATAAATGCAGCTCTGCTTATA CTTCCACACCTATATATATATACCTGACCCTTCTTCACCTCCTTCATCCAC CTCCTCCTTCTTCCCCAAAACTTTCTTAACTGTTCTCTGCATACATATATA TCCACATACATATATATATATATAGAGAGAGAGTGAGACAGAGAGGTTA CCGAGGCAATTGGGTGAGTAGCTCCCTGTTGGAGAAGCAGGGCACGTGC AAATTCTCCATGGCTTTCCCCTCTTTGCACGTGCTCCCCTTCTCCAACATG GGTTCC | SEQ ID NO: 226 |
| CrmiPEP164a1 CrmiPEP164a2 CrmiPEP164a3 | Capsella rubella | CGGCCACCCCCACATTTAACAAGAAAAAAACTGATGGAATTAAAAGGTT TGAGAACTTGGCAGTTATTAGACAAGGTATAGTTTGGCCCTAGCTTCTTT TAATTTAGCTCTCTCCACTCTCACACTTTTCAACTTTCACCCTTCTCTTGC GTGAGTCGCGAGATGCCATCATGGCATGGCATGGCATGTTTCTATTGCCT TACGTAAAACACACTCACGCCAACACATACTCACTATACATGTAAATAA GTATGTGCGCGTGTGAGTCTTCCATCCATCAATGCAATCTTTGGGCTAT ATATATACAAACCTTTTCCATAACCAAAGCTCTCATATAAACTACAAAAG GCTCACTTGGGAAATGCGGTGAGAATCTCCACGTTGGGAGAAGCAGGGC ACGTGCAAACCAACAAACACGAAACCCTCCTCATGTGCTTTGCACGTACT CCCCTTCTCCAACATG | SEQ ID NO: 227 |
| GrmiPEP164a1 GrmiPEP164a2 GrmiPEP164a3 | Gossypium raimondii | GAAAACCCAAGTTCAGGCTAACAAGTTATCTGATGATGAGATCAAGAAT TTTAAAGTTTCAATATAGATTTGGCATGGGTATTGGCGGCAGAAAGCAAT TAAAAAACCAGTTATGTCAAATTCAAGGTCGTATCAGTTAAAATGAATG AAGATTTAGAAATTTCAACAAGGAAGAGGACCCCACAGCTTTGTTAAAT TAAGTGTGTGGTTTTTATAATTATCATCTCGAAAGTTTCATAAATATCAATT AGATTAAAACATCTCTGAATTTCATAATTACAAACCAGATAGATAGATAC ATGAAAACTTAGACCCCAGAGATCTGTCTTTAAAGAATGCCCACTTCTAG ACTCAATCTCTATTACTCTCTTTTTTTCTCTCTCTCTCTTCGGAAAAACT TGTATATAAATAAATGACACTTTCTTTGCTTTCTGCACTCAACTCATGAAC TTGAAAAGCTTTACTTGGATGGGTTGGTTGGGGGTGAGTATCTCTTGTTG GAGAAGCAGGGCACGTGCAAGTTCCTATGTTTAAGTGAACTTTGCACGT GCTCCCCTTCTCCACCGTGAG | SEQ ID NO: 228 |
| MtmiPEP164a1 MtmiPEP164a2 | Medicago truncatula | GAAGAGAAAAACCTAGTGTAAAATTTGATATACTCTTTATGTATAGTAC GAATGTTTTTTTAAAAATTATGTAAAAAATGATAAAATAATAACTAACTA AATTAACAGTAAAATTAGAAAAGTAAAATACTATGCCCAAATTTGATAT TTTTTTTTATATATTTGTATAGATTATTATTATTTGATATGTAAAGTCCAA TTAAAAATTTGTTTTAACTAAGATTTGAACTAGGTTTTCTTAAAAGACTC ATCTTTTACTTCAAATTTATTTATCATTTGAATTCAATCACTTTCTAATATT ATTATTATTTTCCACCATACTCATTGCTTCTGCCACGTTACTTTAGTTA GATCTCTTATGTCATATATCTCTCTCTCCTAAGTTGCTACCTATAAATA CTAAGCCTTTCCCTTGGTTGGTTCAATTCAACTTCTACTTCTCATCAAACA CAAAGTGCAATAAGCTTCATTTCCTGGGTGAGAAGCTCCTTGTTGGAGAA GCAGGGCACGTGCAAATCCTCTTTCTGATTCATTCTCTCATAATGCATAT CAATATCTTTTGCACGTGCTCCCCTTCTCCAACTAGG | SEQ ID NO: 229 |

TABLE 3-continued

List of the primary transcripts (pri-miRNAs)

| miPEP | Organism | Sequence of the Pri-miRNA | SEQ ID |
|---|---|---|---|
| osmiPEP164a1 osmiPEP164a2 | Oryza sativa | ATGCAAACCCACTCCAACACTCCACAATCCACATACTCTCTCTCTCTCT CTCTCTGAGTAGGAGTACATGTGTGTGTGATATCAATATGCATTCGAT GTTGATGCTACTGTAGCCATCTTGTGGCTATATAAACCCAGCAGGCAGCA GCACAGCTTAGCTAGAGAGCCATATTGCATGCACACTCGCTAATCTCTTT TCTCTACTCTACTTGCATTACACCACCTCTGCATTGCACTTCAGTTCATTC ATTCCACTGATGCATGGATCGATGTTGCTACCTTCTTCTCTTCTCCTCATG CATCCATGCATCGATCTCACCTAGCTTCTTCCTCATCCTCTCTCGATCGAT TACAAGAGAAAAGTGTTTGCTGTTCTTGCTATCGATCTACAGGTGAGTAG GTTCTTGTTGGAGAAGCAGGGTACGTGCAAAATGCACACCGGTTGGTCG AGCTAATTAACAAGCTCTGACGACCATGGTGATCGAATGCACGTGCTCCC CTTCTCCACCATGGCCT | SEQ ID NO: 230 |
| AlmiPEP165a | Arabidopsis lyrata | CTAGGGTTTAGGAATGACGACTTGTTTCTGTTGTGTCTTATTAAAAGCCC ATCTTCGTCTCCGCCACTCATCATTCCCTCATCATAACACCATCATCACCA TTCACCAACCTCTCTCTCTTTCTCTCTCCTCTCGATCTACAACAAAATG TGAATCTGCTAAGATCGATTATCATGAGAATTAAGCTATTTCAGTTGAGG GGAATGTTGTCTGGATCGAGGATATTATACATATATACATGTGTATGTTG ATACATGTGATCATAGAGAGTATCCTCGGACCAGGCTTCATCCCCCCCAA CATGTTATTGCCTCTGATCACCATATATATGTCGTTACATTTCATGGTTAA TTACTTGCACAAATCACAAAAGCTTGGTTTGTAACTTTCTATGACCTTTTT TAATGACTTTGAATCTTTCATGCATGACTTCTTAAGAGTAGATTTACACA TTTGCGGATCCGTTTATGCTTTTTGCTTTTGTTTCGTTTATATATAT | SEQ ID NO: 231 |
| AtmiPEP165a | Arabidopsis thaliana | CTAGGGTTTAGGAATGACGACCTGTTTCTGTTGTGTCTTATTAAAAGCCC ATCTTCGTCTCCGCCACTCATCATTCCCTCATCATAACACCATCATCACCA TTCACCAACCTCTCTCTCTCTCCTCTATCACTCTCTACAACAAAAATTT GTGAATCTGCTAAGATCGATTATCATGAGGGTTAAGCTATTTCAGTTGAG GGGAATGTTGTCTGGATCGAGGATATTATAGATATATACATGTGTATGTT AATGATTCAAGTGATCATAGAGAGTATCCTCGGACCAGGCTTCATCCCCC CCAACATGTTATTGCCTCTGATCACCATTTATTGTTACATTTTTTTTGTTA ATTACTTGCGCAAATTACAAAAGCTTGGTTTTTGTGATGACTTTGAATCTT TCTTGCATGGCTTCTTAAGAGTAGATTTACGGATCCGTCTATGCTTTTTGC TTTTTGTTCGTTTATTTGTATTTAAAC | SEQ ID NO: 232 |
| BcmiPEP165a | Brassica carinata | GAGATCAATGAAATTATCCTGCCAAATAAAACGTGTGACGTTTATTCAAA AATATATGCATTAGATGCTTTGATATTAAAATATTTCCTTTTAAAAGCTA GCTAGGGTTTAGGAATGACGAGTTGTGTCTTATTAAAAGCCCTTCTTCTC CTCCGCCACTCATCATTCCCTCATCATAACACCATCATCACCATTCACCC ACCTCTCCTCTTTCTCTCTCTCTCTCTCTCTCTCTCTCTAGAACAACAAG TGAGAATCTGCTAAAATATTGTGACTATTATCATGAGAATGAAGCTATTT CAGTTGAGGGGAATGTTGTCTGGATCGAGGATATTATATATACACAAAT ACGTATATATGTTAATACAAGTGTTTGATCATATATATGTATATAGATTATT CTCGGACCAGGCTTCATCCCCCCTAACATGTTATTGCCTCTGATCACCAG ATTCTATCAACTCTTCGCTTATTATTTGTCACAAACAAGTAATAAGCTCA TAATTTTCTTTGAGTCTTTCAGCATCGTTTCATTATGTTTTTCGAATCCG | SEQ ID NO: 233 |
| BjmiPEP165a | Brassica juncea | GAGATCAATGAAATTATCCTGCCAAATAAAACGTGTGACGTTTATTCAAA AATATATGCATTAAATGCTTTGATATTAAAATATTTCCTTTTAAAAGCTA GCTAGGGTTTAGGAATGACGAGTTGTGTCTTATTAAAAGCCCTTCTTCTC CTCCGCCACTCATCATTCCCTCATCATAACACCATCATCACCATTCATCCA CCTCTTCTCCTCTCTCTCTCTCTCTCTCTCTCTCTCTCTCTCTCTCTCT AGAACAACAAGTGAGAATCTGCTAAAATATTGTGATTATTATCATGAGA ATGAAGCTATTTCAGTTGAGGGGAATGTTGTCTGGATCGAGGATATTATA TACACAAATATGTATATATATGTTAATATCAGTGTTTGATCATATATA TGTATATAGATTATTCTCGGACCAGGCTTCATCCCCCCTAACATGTTATTG CCTCTGATCACCAGATTCTATCAACTCTTAGCTTATTATTTGTCACAAACA AGTAATAAGCTCAATAATGTCTTTGAGTCTTTCAGCATCGTTTCATATGTT TTCGAATCCG | SEQ ID NO: 234 |
| BnmiPEP165a | Brassica napus | GATATCAATGAAATTATCCTGCCAAATAAAACGTGTGACGTTTATTCAAA AATATATGCTTTAAATGCTTTCATATTAAAATATTTCCTTTTAAAAGCTAG CTAGGGTTTAGGAATGACGAGTTGTGTCTTATTAAAAGCCCTTCTTCTCC TCCGCCACTCATCATTCCCTCATCATAACACCATCATCACCATTCACCCA CCTCTCCTCTTTCTCTCTCTCTCTCTCTCTCTCTCTAGAACAACAAGT GAGAATCTGCTAAAATATTGTGACTATTATCATGAGAATGAAGCTATTTC AGTTGAGGGGAATGTTGTCTGGATCGAGGATATTATATATACACAAATA CGTATATATGATAATACAAGTGTTTGATCATATATGTATATAGATTATTC TCGGACCAGGCTTCATCCCCCCTAACATGTTATTGCCTCTGATCACCAGA TTCTATCAACTCTTCGCTTATTATTTGTCACAAACAAGTAATAAGCTCAAT AATGTCTTTGAGTCTTTCAGCATCGTTTCATATGTTTTCGAATCCG | SEQ ID NO: 235 |
| BomiPEP165a | Brassica oleracea | GGGATCAATGAAAATTATCCTGCCAAATAAAACGTGTGACGTTTATCC AAAAATATATGCATTAAATGCTGTGATATGAAGTATTTCCTTTAAAAGCT AGCTAGGGTTTAGGAATTACGAGTTGTGTTTTATTAAAAGCCCTTCTTCT CCTCCGCCACTCATCATTCCCTCATCATAACACCATCATCACCATTCACCC ACCTCTCCTCTTTCTCTCTCTCTCTCTCTCTCTCTAGAACAACAAGTGAGA | SEQ ID NO: 236 |

TABLE 3-continued

List of the primary transcripts (pri-miRNAs)

| miPEP | Organism | Sequence of the Pri-miRNA | SEQ ID |
|---|---|---|---|
| | | ATCTGCTAAAATATTGTGACTATTATCATGAGAATGAAGCTATTTCAGTT<br>GAGGGGAATGTTGTCTGGATCGAGGATATTATATATACACAAGTACGTA<br>TATATGTTAATACAAGTGTTTGATCATATATGTATATAGATTATTCTCGG<br>ACCAGGCTTCATCCCCCCTAACATGTTATTGCCTCTGATCACCAGATTCT<br>ATCAACTCTTCGCTTATTATTTGTCACAAACAAGTAGTAAGCTCAATAAT<br>GTCTTTGAGCCTTTCAGCATCGTTTCATATGTTTTCGAATCCG | |
| BrmiPEP165a | Brassica rapa | GAGATCAATGAAATTATCCTGCCAAATAAAACGTGTGACGTTTATTCAAA<br>AATATATGCATTAAATGCTTTGATATTAAAATATTTCCTTTTAAAAGCTA<br>GCTAGGGTTTAGGAATGACGAGTTGTGTCTTATTAAAAGCCCTTCTTCTC<br>CTCCGCCACTCATCATTCCTCATCATAACACCATCATCACCATTCATCCA<br>CCTCTTCTCTCCTCTCTCTCTCTCTCTCTCTCTCTCTCTCTCTCTCTCT<br>AGAACAACAAGTGAGAATCTGCTAAAATATTGTGATTATTATCATGAGA<br>ATGAAGCTATTTCAGTTGAGGGGAATGTTGTCTGGATCGAGGATATTATA<br>TATACACAAATATGTATATATATGTTAATATCAGTGTTTGATCATATATA<br>TGTATATAGATTATTCTCGGACCAGGCTTCATCCCCCCTAACATGTTATTG<br>CCTCTGATCACCAGATTCTATCAACTCTTAGCTTATTATTTGTCACAAACA<br>AGTAATAAGCTCAATAATGTCTTTGAGTCTTTCAGCATCGTTTCATATGTT<br>TTCGAATCCG | SEQ ID NO: 237 |
| AtmiPEP166a | Arabidopsis thaliana | CATCATCACCACTCACTTATCTTCTTCTCCATCTCTCTCTCTGCTTCTCCCT<br>TAATCTTAGCCGGGTCTCGTGGGGACGAACATAGAAAGAGAGAGATAT<br>AAAGATATATATTCAGAAACCCTAGATTCTATAATTTCGACTGAAAAGA<br>AAAAGGGGCTTTCTCTTTTGAGGGGACTGTTGTCTGGCTCGAGGACTCTG<br>GCTCGCTCTATTCATGTTGGATCTCTTTCGATCTAACAATCGAATTGAACC<br>TTCAGATTTCAGATTTGATTAGGGTTTTAGCGTCTTCGGACCAGGCTTCAT<br>TCCCCCCAATTGTTGCTCCCTGTTTACTCCATATTTCTTCCTTCTTTTCAAA<br>TTAGGGTTTCAGATCCAGTGAATGAACCCTTGTTAAAGGTTTGATCTCTT<br>ACCTTACTTT | SEQ ID NO: 238 |
| AtmiPEP166b | Arabidopsis thaliana | TCTCATCATTCTCTTCATCATCACCACATTCATCTCTCTCTCTCTCTCTC<br>TCTCTCTCTTTCTCTTCCTTGATCTTAGCCGGATCTGTTGGGGGACGAACA<br>CATGAGAGATAGATAAAATATAAGAAATTTCTCGAAAAAACCTAATAGA<br>AAAAGGTCTGTTTCTTAAAGAAGAAGAAGAGGATTTAAAGAGGGAT<br>TTTTCTTTTGAGGGGACTGTTGTCTGGCTCGAGGACTCTTATTCTAATACA<br>ATCTCATTTGAATACATTCAGATCTGATGATTGATTAGGGTTTTAGTGTC<br>GTCGGACCAGGCTTCATTCCCCCCAA | SEQ ID NO: 239 |
| AtmiPEP167a | Arabidopsis thaliana | TGATGAACAGAAAAATCTCTCTTTCTCTTTCTTGATCTGCTACGGTGAAG<br>TCTATGGTGCACCGGCATCTGATGAAGCTGCCAGCATGATCTAATTAGCT<br>TTCTTTATCCTTTGTTGTGTTTCATGACGATGGTTAAGAGATCAGTCTCGA<br>TTAGATCATGTTCGCAGTTTCACCCGTTGACTGTCGCACCC | SEQ ID NO: 240 |
| AtmiPEP167b1<br>AtmiPEP167b2 | Arabidopsis thaliana | AACCACAAAGTACCGCTGCTATTTTCTTTTTACGTCTTTGTATTTGCATCG<br>TCTAAGAGAATGATGGGTTGTTTTGTGGGATTTTAATGCAGGAGGAAAC<br>ATATGAGGGGTGATTAAGGCAAAAACCTTAAGATGTGGTCATTTAGATA<br>CATGGAGTCAAACTAAGAATGGACCTTGGCGAAAGCTTCTTCACGGTCA<br>AGATTTAAAATCAGGTACGACACTGTGTACGTGAGAGAGAGAGAGAGAG<br>AGAGAAAGAGATTATAGAAAGAAAGAGATGTATCACAATAAAGGAGTA<br>TATTTAGGGTCACAGGTGGTGGAGATATAGGTATGCAGGGCCAAGGCTC<br>TAATCTCTTCATAGCCCTATTGATTTTGTCCCTCTCTCTCTCTCTTTCTTCC<br>TCTCTTAGCTGTATGCATTATGATGCGTCTTTTAATTCACTGTTTCAGGCT<br>TCTTTAATTCGTGGTGTCTCTCTCCTTTTTACCCAACCATCTCTTAAAATTT<br>TTAACATCTGTTCCTCAAATCCTCTCTCCATCTCTTTCTATAAGTATCTATA<br>GCGCCTCTTAAACCACAAAGCATCACCTCTGTCTTCTCTCATCTCCTTTCT<br>GTATTCTCTTTCATTGCCTTCACGTCTGTTGCAATTTCTCCACTTCTTGAG<br>CTTCCGTTTTTTACAATTATTGATCCGTCAAATATGTGAGATTTGCACAAC<br>TTGTTGCTCAGGTATTTTGAAGACAAGTCCACAAGGGAACAAGTGAAGC<br>TGCCAGCATGATCTATCTTTGGTTAAGAGATGAATGTGGAAACATATTGC<br>TTAAACCCAAGCTAGGTCATGCTCTGACAGCCTCACTCCTTCCT | SEQ ID NO: 241 |
| AtmiPEP169c1<br>AtmiPEP169c2 | Arabidopsis thaliana | GAGCAAGACAATGCCACATACAAACTTGAAAGATCTCTTCATCTTTTCTC<br>CAAATGTTTTTTTTCGTTTGTATTTATCTCCACAATTCTTGGAACAAAA<br>ACTACATTCACAAACGAGAGAATTTTCACAACACCTCTTTTGCTCTCATT<br>TTTTTTTTTTCGTCCATTATGAGTATTAATTATGGTTAGGGAATCTTACAG<br>AATGAAAATGAAGGTGTGAATGGATTGTCTCATCTAAAGCCTTGAATGT<br>GGGAAAAAGGCCATTGTTGTTCAGCCAAGGATGACTTGCCGGTAGCTTG<br>TATTATGATTACTCTATATTCGATTTATATTATGGAGATGATGGTTTATAT<br>ATATTTACTTATCTACATAGTTTTAGTTGATTTTTTTTCGTACGTAATATA<br>ATACGAAAAGTATTTACTTATTTATATATGTGTGTTGGGGCAAGAAGTG<br>TAACCAAGCTAGCCCGGCAAGTCATCTATGGCTATGCAACTGTCTCTTCC<br>TCTCATTCTAGGCCTTACGATGACACGTAAAAAATCCCAAATATCACTAAT<br>ATGATATGAATATGGATGA | SEQ ID NO: 242 |
| AtmiPEP169l | Arabidopsis thaliana | AGGCATGAGACATAAAGAGAGTTAAATATAATGAAGAAGAGAGGTCTA<br>ATATGGCGAAAAGAGTCATGTTTAATAGCCAAGGATGACTTGCCTGATCT | SEQ ID NO: 243 |

TABLE 3-continued

List of the primary transcripts (pri-miRNAs)

| miPEP | Organism | Sequence of the Pri-miRNA | SEQ ID |
|---|---|---|---|
| | | TTTTCACCTCCATGATTCAATTTTAAGTTCGTGGATTTTGGATTATTATGC<br>GTTTAAAAGGTATAATAATTTGAGATCATGTTGAATCTTGCGGGTTAGGT<br>TTCAGGCAGTCTCTTTGGCTATCTTGACATGCTTTCTTCATC | |
| AtmiPEP171a1 | Arabidopsis thaliana | GAATTTTGATTTATGAACCTCCTCAAGAAGGAAAGACAGAGGAGGAGAC<br>AAAGAAGTATAGGTTCACATTGCATAGCCAGTTTAGTTTTGAAGGATGG<br>ATATATGAAAAAAATATGAAGAGAGAGAAGAGAGAAGAAGAGGAGGAT<br>TAAAGAGGGTGAGGCCAGCTTTTGTGCTTTGGTAGTAGATGAGGTTTAAA<br>TGCTCCATACCTTCCATTTCCTTCTCTCTTACCCTAATTTAATTCTTCCTCT<br>CCTTTATAACTCCCCACAGACATTCTCACTTCTCCTCCTCACACTTCACAT<br>CAACACTTCTTTCTTGTTTTTTCATTTTACAATGTTTCCTTTGATATCCGCA<br>CTTTAAGCATGAGAGAGTCCCTTTGATATTGGCCTGGTTCACTCAGATCT<br>TACCTGACCACACACGTAGATATACATTATTCTCTAGATTATCTGATT<br>GAGCCGCGCCAATATCTCAGTACTCTCCGTCTCTATTTTGGACTTTGTGG<br>TCTTGTAGATCGATTTGTATGTGTGTGTTGAAATGGAGACAAGTACTTGT<br>AACTTCTTTGTTGTATATTGTTTACCTATAGGCTGATGTCATAAACTCTT<br>TTGATCTTGTTTCTAACTTCCAGATTCTTGAAAAATCAAGTCGTGTGTGTG<br>TCTCCATGGAAGCCTTTTCCATTTCTTCCTTTCCA | SEQ ID NO: 244 |
| AtmiPEP171b | Arabidopsis thaliana | ACTCATAAACTTTGCTACTGGCCGCATTTCTATTTTCTCCTTCGATTCTTC<br>TAATTCGTACTTTGGTTTCTGACGTCCCTAAAATTTTTAGACAGTAAGAG<br>TTTCTCCAGGATCCGATGGTTCTCTCCGGTAAATTAACATTTTAGTGTCAA<br>TAGTCATTTATACATATTTTATTTCACTTTTTGTTTTGTTTATTGGTTTTC<br>TGGAGCTAAGTGGAGATTATAGTCGAACAAGAGTGGTTTTATGCAAGGT<br>AACGCGAGATATTAGTGCGGTTCAATCAAATAGTCGTCCTCTTAACTCAT<br>GGAGAACGGTGTTGTTCGATTGAGCCGTGCCAATATCACGCGGTAAACC<br>AAAAATGGCAAAGATAGTTATTATAACCTTAAAGGTATGTATCATTATCG<br>TTTTATTGTTTCAATTTTGATTAATGGCTTTGATATTTCATTTTTTTTT | SEQ ID NO: 245 |
| MtmiPEP171b1<br>MtmiPEP171b2 | Medicago truncatula | ATTGGTCAAACATACATACAGTAGCACTAGCTGGTTTCATTATTCCACTA<br>TGCTTCTTCATAGGCTCTCCAAATTTTGCAAAATTGAAAGAGACATAGTA<br>TATATATCTTAGCAAGGAGAAATTCAGGATATTGAGGATGAAGATTGAA<br>GAGTAATCAGTGATGAAGAAAGCAAGCAAGGTATTGGCGCGCCTCAATT<br>TGAATACATGGCTATAAAAATGCATCATATCAGCCATGTAGTTTGATTGA<br>GCCGCGTCAATATCTTGTTTCCATCTCCAAATTTACCAATCTCATCAAATC<br>AAATTAACACCACAATCAAGGCTTTCATTTAATGCAGTCAAAATAGGTTG<br>ACCTTATCATCGAAGAAATTGTTTTCTCATTCCTATCGAAGTTGGACTTGC<br>CGAAAATGCTCGAAAGCATGTGTTTTAGTTCGACAGGCGAAAAAGTTAC<br>CGAAGGACAATTTGGTTGTGGTTCGGATAAGATCAAGCAACGGATATTTT<br>CAAGCACGTTCGAAATTCAAATCAAATGGATAAGTATCGTTAGTTTACT<br>GCAGTTATAGTTTTAAATTCAAATCTAGGCAGTTGTTTCTATTTGTATAAA<br>TAGTAGTTTTTCCCTAGGGAAAAGGGGTGCGCAATTCAATCATACAAAAA<br>ACTTACAATCAAATTATCCGCATGGAAGAGAGAAACGAGTCACAAGTTG<br>CAATGTATGAACATGTGTACCAATTTACATTCAATCAGTACAATTTAAGT<br>TCATTTCCATAAAAAAAAA | SEQ ID NO: 246 |
| ZmmiPEP171b | Zea mays | ACCAGGGTTAGGTATCCATCCACACAGCAATGCATCTGCCTTCAACTCCC<br>TCTCGCCCCCCACCCCAACACACATCTCTCTTTTCTAGGGAAGGAAAT<br>GACGAAGGGGACGACGACGGCATGCTTCGGCTAGCTCGTTGGTGCTAGG<br>ACAAGGGCGGAGGTATTGGCGCGCCTCAATCCGAAGGCGTGGCTGATAG<br>ATTGGCGCGGCAGCCATGTTCTTGGATTGAGCCGCGTCAATATCTCCCCT<br>TGCCTGTCCCGTACCTAGCTAGCTTGCTTGCCTCACTGATCGATGTCGTCC<br>CTATTTCATGGAGAAGCTGATGATTGATTATTCTCACAAGCAAGAACTGT<br>CTGATCTGTTGCCTGCATCGATCAGGATCTATATGCTGGAGAGTTCACGA<br>GAACATGGACAGAACTCGCTTCAACAACCGATCAATCGATTGATTAGGT<br>ATGTACCTACCTCATATGCCTCAGCTCTTCGTTATGGATTCTTCAACCGA<br>AGGGTCAGTAAGCTCTTGGTTCCATGCCACTGCGTGAACTAAGCGTTCAC<br>AAAATCCGTTCCMCGGCATGAACCAAGCACTCAAAATCGCATGCAGCAT<br>CTTTCGTTTCAAAAAAAAATTGACTTYTGAAAACAATAGATGAATCAGTT<br>TCAAACATATATGATTATCCATTTTCTCAACCGGGAATTTATATCTCGTTG<br>GGATGCAAAACCGTTCAGTAGTAAAACTACTCCACGAGTATAAACTGTTT<br>CAGTTATTTTACTATTAATTAGTTACCCGTATGCTGTTATGGTTTCTATAT<br>ATCTATAAGTAAACCTTACTTAAATAAGATAGTTATACAAAAAAAAAAA<br>AAAAA | SEQ ID NO: 247 |
| AtmiPEP171c1 | Arabidopsis thaliana | CAAGAAAAAACATTGAAATAGCTCATGTTGTCTCTTTCTCATTTTCATAT<br>CTGCTAAAAAAAGAACCGTGTTTTCTAAACTGGTTTAACGGTAAGTACCT<br>GTCTCTAGTAACTTACCTATCAATTTGTTCCAATCATTTACTTGCTTTGAC<br>TTATTTGGTTTCCTTTTGTTTGTTTTCTTTAATATGTGGATGGAGTTTGG<br>TGTAATAAGCAACTGAAGAGTCGATGAGCGCACTATCGGACATCAAATA<br>CGAGATATTGGTGCGGTTCAATCAGAAAACCGTACTCTTTTGTTTTAAAG<br>ATCGGTTTATTTGATTGAGCCGTGCCAATATCACGCGTTTAAAGTAGTTTA<br>AAGATTCTATGTTAGTTGATGTGATCAATCAAGGTATGAATCTATATCAA<br>TTCTCTTATGCATAGTTTTATATTTACAGAGATGAGGTATTATCAATGTCT<br>ATCGTCGAGGATCACGCTCTTACTTATGTTATATTTCTATATAATTTTATT<br>AATTAGTTTTCTAAAAGAGAAGGACAATTTAAAATTATTTTAAAGAGTTT | SEQ ID NO: 248 |

TABLE 3-continued

List of the primary transcripts (pri-miRNAs)

| miPEP | Organism | Sequence of the Pri-miRNA | SEQ ID |
|---|---|---|---|
| | | TTTTTAAGTAGTTTTGTTTTCATGTTTATCTTCTGCAGGCTCTGAAGTTAG GATAGTAACAAGAAAAAAGACAGAAAAAAAGAAGAAAATTCATATACA TTCGTGA | |
| MtmiPEP171e | Medicago truncatula | GAATAAGTGAATATTATCGATATTTATATCATATATCAACTTTTCTTCTGT GCTTGCTTGCAAATTTGCAATTAAGCTTTTTTGATCTTATGTAAGAGAAT ATTATTGATGATGGTGTTTGGGAAGCCGAAAAAAGCGATGTTGGTGAGG TTCAATCCGAAGACGGATTTACATGTATAGAGTTGTAAAATACGATCTCA GATTGAGCCGCGCCAATATCACTTT | SEQ ID NO: 249 |
| MtmiPEP171h | Medicago truncatula | CCACAAAACTATAACTAGCTAGAAGCTTTAATCGCCTTATTTATTATAAT AATAATAAATATGGCTTCAGCTGCAAAAGTATACATGGCGTGATATT GATCCGGCTCATCTATATCTTCAAGTTCAATCATCCATATTCATATCAATT TCAGACGAGCCGAATCAATATCACTCTTGTTTGCTTCATTGCATATTAATT ATATACTTCATTTATAAGTTATAGTTTGCCATATATATATTAGATTGATTC TGCAGAAGTAGACAGGAGTGGTGTTGTTTCTGCTCATCTTATTAAATAAT GAATGAATGAATGACATTTGCTTACTTATAAGACGAGCCGAATCAATATC ACTCCAGTACACCT | SEQ ID NO: 250 |
| AtmiPEP172a1 AtmiPEP172a3 | Arabidopsis thaliana | CTCTCTCTCTCTCTCTCTCATCTGTGTTCTAGATCTCACCAGGTCTTTCT CTGGTTAATATATGGCTTCCAAGATCTGGTAATATGTTATAAATACGTCA TACTTAAGCTTTTTTCAAATCAAAAATAGAAATTTGTGGGTTTGTCTCGTT TTACTATTTTAGCAGTATATATTAAGAAGTTCAGATGTTATTCGATCATCT GTTTTTGCTTCCCCTCTGCCATCTTTATCTTTTAGGGTTTCAATTCTTTTC ACTTTTTTCTTCTGGTTTGGAGATGGTTAGGTTCCAACTAAGTATACGAG ATTAAATTTGACATCTTAGTTACTTCAAAATTCCTTCAATCAAAACAAGT CATCTCGACTATTCCGCCATGTTTGTATATACATATTTATATATTATATAT ATGAAGGTACGAGTTTCTAGTGTCTATAAATTAAGAAGGTTAAGTACCAT ATAGATGATATTTGTTAAGTAGTAAGTCACTCAAAGTTTGAGTTTGGGTT TGAGTTTGAGTTTGAGTTTGAGTTTGAGAGACAAAAGATTACTACAAGA AGATTGTTAAACAAAAATGGAAGACTAATTTCCGGAGCCACGGTCGTTG TTGGCTGCTGTGGCATCATCAAGATTCACATCTGTTGATGGACGGTGGTG ATTCACTCTCCACAAAGTTCTCTATGAAAATGAGAATCTTGATGATGCTG CATCGGC | SEQ ID NO: 251 |
| AtmiPEP172b1 | Arabidopsis thaliana | ACTTGCACCTCTCACTCCCTTTCTCTAACTAGTCTTGTGTGCACCCATTTA TGTGTACGTACTATTATCTCATAAATAAATATTTTTAAAATTAGATGCATT TATTGATATGAAAAAGTTACAAGATTAGTTTGTTGTGTGTGAGACTTTGG ATCGACAGATCGAAAAATTAACTAACCGGTCAGTATTGAATATCAACTA TTATATGCTCCATGCATTCGCTTATAGTTTCACACAATTTGTTTTCTTCAC GGTCTAAAATCAGAAGATTCCATATATTTTCTTATGACGTAAAAGGACCA CTTATAAGTTGACACGTCAGCCCTTGGATTCGTGAGGTTTTTCTCTCTACT TCACCTATCTACTTTTCCTCATATCCCACTGCTTTTCTCCTTCTTGTTCTTG TTTTTTCTCGTTTTTTTCTTCTTCTTCTCCAAGAAAATAGAGATCGAAAGA TTAGATCTATTTTGTGTAGCAAGAAATTATCATTTTCGTTTCTTCATTCAT ATATTGTTCTATTATGTTGTACAATAATAGATACTCGATCTCTTGTGCGTG CGTAAATTTTATACAAGTGTCGGCGGATCCATGGAAGAAAGCTCATCTG TCGTTGTTTGTAGGCGCAGCACCATTAAGATTCACATGGAAATTGATAAA TACCCTAAATTAGGGTTTTGATATGTATATGAGAATCTTGATGATGCTGC ATCAAC | SEQ ID NO: 252 |
| AtmiPEP172c1 | Arabidopsis thaliana | TCACCAAATAGGCTCTTCTTTATCGCTTCATATATATAAAAGTCTACATCT ATCTCTTTCTAGGTCACTAGCTAGACTCTAGATTAAGGATTGAAATTAGG GTTTCATGTTTCCAGCAAAATGGTGCCGTCTTGAGTCTTGAAAAGATCCA AGACAAAACCAAATCACTACATACATCCCTATCATCAACCAGCTACTGTT CGCTGTTGGAGCATCATCAAGATTCACAAATCATCAAGTATTCGTGTAAA TAAACCCATTTATGATTAGATTTTTGATGTATGTATGAGAATCTTGATGA TGCTGCAGCTGCAATCAGTGGCT | SEQ ID NO: 253 |
| AtmiPEP172e1 AtmiPEP172c2 AtmiPEP172e3 | Arabidopsis thaliana | TGTCATATTGAGAACTCTTTAGCCTTTGGCTTCTGTTCCTGACACTTGTAT AGTGAAGTGGGCTTGTGTTATATAGATGGGATCTCTCTCTTTATTTAAAA GTCAATTAGAGATCTTGATGCTACTTCTGTCCCTTTCCAAGTGATTTTACG TCGACCAACTAGCTTTTTTCATATGAGTGTATATATTCATGTACCTATCTC TCTCAATTGCTTCTCACCAAAATCATCTTGCTGATTCATTTGCTGTCTGAA TCCTCTTGCTTTCCTCTTTGCTTTTTCATTTGTTGATTTAAACCATGGGAGT TCCCAACTTTAGACCTCGAAACCGATAAGGATCTTTCTCTGCGGTTGAAA TAGCTAGGTTCTCGATGAATAGGCTAGCCTTTGGTGGATGTTATCAGCCA GTAGTCGCAGATGCAGCACCATTAAGATTCACAAGAGATGTGGTTCCCTT TGCTTTCGCCTCTCGATCCGCAGAAAAGGGTTCCTTATCGAGTGGGAATC TTGATGATGCTGCATCAGCAAATAC | SEQ ID NO: 254 |
| AcmiPEP319a1 AcmiPEP319a2 | Arabidopsis cebennensis | TTGTATCCATAGTGTATTTCCTCGCATCTACCATCCATTTTCTACGCCTCT CTCTCTCTCTTTCTCCATCAAATCTTGTTTTGTTCAAACTCTCTCTCTCATC AATTCTCTCCATACAATACATGCATACATACATACATACCATCTCTAATA TTTCATCAATCTTCTTTTGTTCCAAACGCTCTTTCTCTCCATTTACATACAT ACGAATCATTGTTGTCATAGATCCGTTTAGAATTGCTTTAACTTTTAGATG | SEQ ID NO: 255 |

TABLE 3-continued

List of the primary transcripts (pri-miRNAs)

| miPEP | Organism | Sequence of the Pri-miRNA | SEQ ID |
|---|---|---|---|
| | | AGATCTAGGGTTTCTTTCTTTTTCTTCAAAATCATGCTTTTTCGCTTGCTA<br>GGTTATAGATCCATGTAAGTTTAGAGTAGATGTACACACACACGCTCGG<br>ACACTTATTAAATACATGTTGATACACTTAATACTCGCTGTTTTGAATTG<br>ATGTTGTAGGAATATATAAATGTAGAGAGAGCTTCCTTGAGTCCATTCAC<br>AGGTCGGATATGATCCAATTAGCTTCCGACTCATTCATCCAAATACCGAG<br>TCGCCAAAATTCAAATTAGACTCGTTAAATGAATGATGCGGTAGA<br>CAAATTGGATCATTGATTCTCTTTGATTGGACTGAAGGGAGCTCCCTCTC<br>TCTTCTGTATTCC | |
| AhmiPEP319a | Arabidopsis halleri | TTGTATCCATAGTGTATTTCCTCGCATCTACCATCCATTTTCTACGCCTCA<br>CTCTCTCTTTCTCCATCAAATCTTGTTTTGATCAAACTCTCTCTCTCTCT<br>CTCATCAATTGTCTCCATACAATACATACATACCATCATCTTTCCCATCTC<br>TAATATTTCATCAATCTTCTTTTGTTCAAACGCTCTTCCTCTCCATATACA<br>TATACATACATACGAATCACATTGGTGTCATAGATCCGTTTAGAATTGCT<br>TTAACTTTTAGATGAGATCTAGGGTTTCTTTGTTTCTTTCGTTTTCTTCAA<br>ATTTTGCTGCATATTCTCCAAGATCATGATTTTTCGCTTGCTAGGTTATAG<br>ATCCATGCAAATATAGAGTAGATTTACACACACACACGCTCGGACACTT<br>ATTACATACATGTTGATACACTTAATACTCGCTGTTTTTAATTGATGTTGT<br>AGGAATATATATGTAGAGAGAGCTTCCTTGAGTCCATTCACAGGTCGT<br>GATATGATCCAATTAGCTTCCGACTCATTCATCCAAATACCGAGTCGCCA<br>AAATTCGAACTAGACTCGTTAAATGAATGATGCGGTAGACAAATT<br>GGATCATTGATTCTCTTTGATTGGACTGAAGGGAGCTCCCTCTCTCTTCTG<br>TAT | SEQ ID NO: 256 |
| ALmiPEP319a | Arabidopsis lyrata | TTGTATCCATAGTGTATTTCCTCGCATCTACCATCCATTTTCTACGCCTCT<br>CTCTTTCTCCATCAAATCTTGTTTTGTTCCAACTCTCTCTCTCATCAATTCA<br>TTCCATACAATACATGCATACATACATACCATCATCATCTTTTCCCATCTC<br>TAATATTTCATCAGTCTTCTTTTGTTACAAACGCTCTTTCTCGCCATATAC<br>ATACATAAGAATCATTGTTGTCATAGATCCGTTTAGAATTGCTTTAACTTT<br>TAGATGAGATCTAGGGTTTCTTTCTTTTTCTTCAATTTTTGCTGCATATTCT<br>TCAAAATCATGATTTTTCGCTTGCTAGGTTATAGATCCATGCAAATATAG<br>AGTAGATGTACACACATTCACGCTCGGACACTTATTACATACATGTTGAT<br>ACACTTAATACTCGCTGTTTTGAATGGATGTTGTAGGAATATATATGTAG<br>AGAGAGCTTCCTTGAGTCCATTCACAGGTCGTGATATGATCCAATTAGCT<br>TCCGACTCATTCATCCAAATACCGAGTCGCCAAAATTCGAACTAGACTCG<br>TTAAATGAATGATGCGGTAGACAAATTGGATCATTGATTCTCTTTG<br>ATTGGACTGAAGGGAGCTCCCTCT | SEQ ID NO: 257 |
| AtmiPEP319a1<br>AtmiPEP319a2 | Arabidopsis thaliana | TTGTATCCGCAGTGTATTTCCTCGCATCTACCATCCCTTTTCTACGCCTCT<br>CTCCCTCTCTCTCTTTCTCCATCAAATCTTGTTTTGTTCAAACTCTCTCTCT<br>CTCATCTATTCTCTCCATACAATACATGAATATACATACATACCATCATCT<br>TCTTTTCCCATCTCTAGTTTTTCATCAATCTTCTGATGTTCCAAACGCTCT<br>ATCTCTTCATATACATACATACGAATATATATTATTGTTGTCATAGATCCATT<br>TAGAATCACTTTAGCTTTTAGATGAGATCTAGGGTTTCTTTGTTTTCTTTC<br>AAATTTTGTTGCATATTCTTCTAAATCATGGTTTTTCGCTTGCTAGGTTAT<br>AGATCCATGCAAATATGGAGTAGATGTACAAACACACGCTCGGACGCAT<br>ATTACACATGTTCATACACTTAATACTCGCTGTTTTGAATTGATGTTTTAG<br>GAATATATATGTAGAGAGAGCTTCCTTGAGTCCATTCACAGGTCGTGATA<br>TGATTCAATTAGCTTCCGACTCATTCATCCAAATACCGAGTCGCCAAAAT<br>TCAAACTAGACTCGTTAAATGAATGATGCGGTAGACAAATTGGAT<br>CATTGATTCTCTTTGATTGGACTGAAGGGAGCTCCCTCT | SEQ ID NO: 258 |
| BrmiPEP319a | Brassica rapa | TTGTATCCATTGTGTATTTCCTTGCATCCATCAATAAATTTTATGTTACGC<br>CTCTCTATTATTTCTCTCTACATCACACTGTCTTATGTTTAAGCTCTACTTC<br>TCAGCAATTCTCTCCACCCAATACATGCATACATACCATCATCGTATCGC<br>TCTAATTTTTCTATCAATCTTGTATCCTTCCACAAATTATCTTATGTCTCCC<br>ATTTTAAATCCTACATAGATCCACACATACGAATTATTCTTGTCTGAAGA<br>TCCATCCATTTACGATTGCTTTAACTTTTACATGAGATCTAGGGCTTCTTT<br>ATTTTTCTTCAAATCTTGCTGCATATATTTCAAGATCATGCTTTTCGGCTT<br>GCTAGGGTTCTAGATCCATGGATGTATAGCGTACATACATACACGCACTA<br>ATTCATACCTGTAGTTTGTACGGAGAACATCATAAAATATCACTGTTTGG<br>AATTAATCGTGTAGGAAATATAGATAGGTAGGGAGCTTCCTTTAGTCCAT<br>TCACAGATCATGATATGATCCAATTAGCTTCCGACTCATTCATCCAAATA<br>CCGAGTCACGAAAATTTCAACTTAGACTCGTTAAATGAATGATGC<br>GGTAAACAAATTGGATCATTGATTCTCTCTGATTGGACTGAAGGGAGCT<br>CCTC | SEQ ID NO: 259 |
| CpmiPEP319a | Carica papaya | CTATATCCCTGTCAAATAGTACTTGGTTTTGTTTTAGCCACAAATCTTCTG<br>GTCTTGCAAAGTTCCTTCTGATCTCTCCCCCTTTTCTCATTTTTTCCTCCTCT<br>TATATATGGATCATCAATTTGCTGTACACACACACATTTACTGTAGTG<br>ATAATTAGCTAGCTAATTGTTAGTATGTAAATTAGATCCCAAGTACCCT<br>GTTATATTTTTTAGGCTTATCCTATGCATACCTGATAGTACAAGAACTTA<br>GTTTGTAATTAGGTACTTGGTAGTAGGGTTAGATTAATTACTGTCTTGAA<br>AGAGAACTTATCCAACAAATAGAGCTATGAAGATTAAATTAGGTTTTAG<br>TCTTATTAAGATTATTATATTACTAGACAAAAACAGTTAAATTTTTTAAT<br>TGGGTAATTAGGTACTTAGCAATAGGGTTAGATTAATTACTGTTTTGAAA | SEQ ID NO: 260 |

TABLE 3-continued

List of the primary transcripts (pri-miRNAs)

| miPEP | Organism | Sequence of the Pri-miRNA | SEQ ID |
|---|---|---|---|
| | | GAGAACCTACCTACAAATAGAGTTGAAATGATTATGTTTTAGTCTTACTA<br>AGATTGTCATATTTCTGGAAAAAAACAAATCTTGAAACAGATAATTCAG<br>ATAGTCATGATCAATGGAAAAAACATCATGGGTGTGTGCTTAATTAAGCT<br>AATATATATATATATGAAGATATAATGTTATGCACACTAGCTATGAATTT<br>GTAAGAATAATGAAGGATAAAGATGATATATTTAGATGTTATAAGTGTA<br>AGTAAGGTGGAATGGGTTGATGGGTAGTAGTAGTAGTAGTAGAGATGAT<br>TGGTGGAGAGAGCTTCCTTCAGCCCACTCATGGATGGGTATGAAGGGGT<br>AGAAGTAGCTGCCGACTCATTCATTCAGCCACTCAGTATGTAAACTCGTC<br>CCACTGTTGACTGTATGAATGATGCGGGAGATATTTTTACATCCATCTTT<br>CTCTGTGCTTGGACTGAAGGGAGCTCCTTCTT | |
| CrmiPEP319a | Capsella rubella | TTGTATCCATAGTGTATTTCCTCGCATCTACCATCTACTATTTTCTACGCC<br>TCTCTCTCTTTATCCCTCTATCTCTTTCTTCATCAAATCTTCTTTTGTTCAA<br>AGTCTCTCTCATCATTTTTCTCTATACACATACATGCATCCACATACATAC<br>ATACATATACCATCATCTTCTTTTCTCATCTCTAGTTTTTGTTTATAAATTT<br>TGTTCCAAGGATCTGTATCTCTCCAATAAAGATACATACAAATTATTGTT<br>GTCATAGATCTATTAGAATTGCTTTAACTTTTATATGAGATCTAGGATTTC<br>TTCCTTTTCTTTCAAAATTTGCTGCATATTTTTCAAAATCATGATTTATCG<br>CTTGCTAGGTTCTAGATCCATGCAAATTTAGAGTATTTTACACACACAC<br>ACGCTTGGACACAAGTACATACATGTAGTTTTCTTTTATGTGGTGAAAAG<br>TACATAACATGTAGTTTATAGTTACTAGTCGCTATATAATTTAAAATTGA<br>TGTTATAGGAATATATGTACGGAGAGAGCTTCCTTGAGTCCATTCACAGG<br>TCGTGATATGATCCAATTAGCTTCCGACTCATTCATCCAAATACCGAGTC<br>TCACCAAAATTGGAACAAGACTTGTTAAATGAATGAATGATGCGGTAGA<br>CAAATTGGATCATTGATTCTCTTTGATTGGACTGAAGGGAGCTCC | SEQ ID NO: 261 |
| EgmiPEP319a | Eucalyptus grandis | TCGTTTCCCATCCCCATTTCATAGAATAATGCCACCAAACAAAGAAGCAT<br>TAGCTCAAAGACTAATTACCATCTGTTTTATTGATAGATACGTGCGAAAC<br>GGTGATTGTTTTTTCCCAAATAAGAAACCAAAATGAAGCATATTCAAAG<br>GTGGAGATATGGGGAGACTTCCGGAAGGCAAGGGGATTGGAAAAGGCT<br>CGAGATCAAAGTGCATAGCAACCCTTCGCTAAAGGTGAAAAAGAATACG<br>AATAACTTCAGTAGCTCACTTTAAATTCCGAAACATTAAACAAATCAAAT<br>CTCCCTCGCCCTCCTTGCCTCCTCTCTTTACCTATATAAAGCCACCGCCCC<br>TTCAATGAAATCCACGAGTGGAAGGTCACAGTATAGTAGGGTCCTGCAA<br>AGGGAGAGCGAGAGCGGCTCCACTGTCTACCTATAAGCAGTTCCTTTCTT<br>TTGTTTACATGTCTGTTGCACCTCACCGAGTTTTTCTATTCTCTTTCCTCTG<br>GTTGGTTAGCAGATTTCTCAGGGGACTTCCCTCCTCCCTTGAGGATCTTC<br>TCTTGAAGCGATATGTCTCGAATGGGTAAGAGAGAGAGAGGAAGGGAGC<br>TTTCTTCAGTCCACCCATGGGACGTGTTGGGTTTTAATTAGCTGCCGACTC<br>ATTCATCCAAATACCGAGCGAGAGCAAGTAACAGAGCTCCGTAAATGAA<br>TGGATGATGCGGGAGTCTTGTTGATTCCCAAGCTTTCCGTGATTGGACTG<br>AAGGGAGCTCCCTCTATCT | SEQ ID NO: 262 |
| GrmiPEP319a | Gossypium raimondii | GCGTATCCTTCCACTTACGGATTCACCATAGCTGCTATAGCCCGAGTTTG<br>CTTGTCATAATAGAAATAAACTAAGGGAGAAAAAAGCTCTCCACTCTCG<br>CCTTTTTCTTCTTCGAGTCTCTCTCTTTGACTGGCCTTTGTGCAAAGATCTT<br>CCTTTTTTAAACAGTCGCTTTCTTTACTCTCCCTTTCCCTTCTTTCTCTTAA<br>TTGCTAAAGCAGCTTCCACTTCCACTCACTTTAACCCATGATCCATTTCAA<br>CCTGTCACAGTGGAGAGCAATTTGTATGGCTAATTTCCATCTCACCTATT<br>CTTTTCTGTTTGGGGTTCTCTAGTCTAGGGTTGCATGACATGAGAGACAT<br>GGCTCTTTTTTTTTTTTTCAGTTCACAGGTGTTTATATATGTTGTTGTGTT<br>ATTTTGTCTTAAAGCTTTGTGATTGATGATCTGATAGGTAAGAGAGAGCT<br>TTCTTCAGTCCACTCATGGGATGGGGATGGGGTTTAATTAGCTGCCGACT<br>CATTCATCCAAATACTGTGTTACAAAACCCAGTAAATGAGTGAATGATGC<br>GGGAGACAAATTGAATCCTAATCTTCCTGTGCTTGGACTGAAGGGAGCTC<br>CCTCCC | SEQ ID NO: 263 |
| MtmiPEP319a | Medicago truncatula | ATTTATCCAATCATGTTGCTCTCACTTCTTTTCAGCAGTTCTGTTGATATC<br>ACCCTTTTAGTTGAAGCTTTGGATTCATGACTTTATGAGATGGTAAATCTT<br>TAAATTAAGTTTAAGTATGCACTTGATTTGTTTATATAATTTGTTTATTTA<br>GATTTAAACCCTAAGTTGACTTTTTTAATTTGATTTAAATTATGATATGA<br>TTGTTATTTGGCTTACCATGGTCATAATTTAGGGTTTAGAAGATGCATGT<br>ATATCTTGAATTGTTTATGGTAATAAAGGGGTTAGGATTTCTCCTTTTGGT<br>GAAGTGAGAAAATCTCATAATTTTGTTCTGAAGGTAGTTTTTAAGATTTA<br>GGGTTATGGGTTCTTGTTTGAATGCTTTTTCAAGTCTTTTTTCAATGATAT<br>TTGCCTAGATCTGTTTTAATTTTGAATTAAAATTCTGGGTTTGGATTAATA<br>TTATTGAAGATTATTATTAATTAATTTATTAGAAATAGATGAAGAGAGCT<br>TCCTTCAGTCCACTCATGGAAGGGTAAGGGGTTTGAATTTACCTGCTGAC<br>TCATTGATTCAAACACAATAGACAATTATGGGGTTATGCTATTGTGAATT<br>GTGTGAATGATGCAGGAGGTGAATTTCTTCCTTTTCTTCTTTGCTTGGACT<br>GAAGGGAGTCTCCCTTT | SEQ ID NO: 264 |
| OsmiPEP319a | Oryza sattva | TTATATCTGACGCGTTGTAATCCTGTTTAATTAGGGCTTTGCCCATTTCTT<br>TTGACCCCTTCCGGACATTCGCTAGTTGGAACCTTGTTTTACTCCTAGCAG<br>TGTACTGTGTAGTACTTATTACGAGCAAACGTAAAAATAAATAAATGGA<br>AATGATACAAAGGCCGTGTTTAATTTTAAAATTTTTTTTCAAACTTTCAAC | SEQ ID NO: 265 |

TABLE 3-continued

List of the primary transcripts (pri-miRNAs)

| miPEP | Organism | Sequence of the Pri-miRNA | SEQ ID |
|---|---|---|---|
| | | ACTTTACATCCCATAAAAAGCTTACTATACATACAAACTTCCAACCTTTT<br>CGTCACATCGTATCTAATTTCAACTAAACTTTTAATTTTAGCGTGAACTA<br>AACACAGCCGAAGCCCGGCCACATTCTCACTATTTTTATTCATTTTATCAT<br>GCCTGTGATGTCACGCCTTGGCCCTATTTAATAGGCCTTCTCCATTTCTCT<br>CCATATGATGTCTTCTCTTCTCTATCCCTCTTGCCATCTTCTATCTTCCCTC<br>TTGCACCCATCTTTGTGATAACTTCTACTAGCTCCTCTCCTACTACCAGTC<br>ATACCACTCTCACAAATCCTCCAAGATCCGCATGGGAGAAGCTCCAAA<br>AGTTTCGTGGTTAGTTTAATTTCATGCTTGTTTGCTGCCGTTTTTCATGTT<br>GATCTGATCTTAATATATGTAGACTGCTGTTAACATATTCTTTTAATTTGA<br>TGGAAGAAGCGATCGATGGATGGAAGAGAGCGATCCTTCAGTCCACTCA<br>TGGGCGGTGCTAGGGTCGAATTAGCTGCCGACTCATTCACCCACAATGCC<br>AAGCAAGAAACGCTTGAGATAGCGAAGCTTAGCAGATGAGTGAATGAA<br>GCGGGAGAGTAACGTTCCGATCTCGCGCCGTCTTTGCTTGGACTGAAGGG<br>TGCTCCCTCCT | |
| PpmiPEP319a | Physcomitrella patens | TGGGATCCACACGAGTAATTATTCCCTCTCTCATGCATCACAACTTGGAC<br>TTGCCCAGCTTTTACCTCTCTCCATGTTCCACCGTCGGAGATCCTCGGTGC<br>TGCTACCCCCGTTCGGCCAAACCCAACCCAACCCTAGGTGTCTGCCGGAC<br>CTCCGCTTCCCCTCCTGCTTCACCCCCTGCACCGCTTAAATTTGCACCTCG<br>TAGTATTTATCTATGCCCCATTTCAGATGACTTGCATGACACCCATCTGG<br>ATTCGTCTCCAGGCGCCTTGTCGTATCTATTCGCTATCAGTCTTTCTTTCA<br>GTCTGTCTTTCTGCCAAGCACACCGTGCTGGTGGTGGTGCTATCAGTCGA<br>AGCAGTCGCCGAAGGGTCCTTGTATCCAGCCCTCACCGGAGACAGTTCG<br>CTTCGGGGTGGGGAGAACTGTTGAGACCGTCGATGTTGCATGCAGCAGC<br>ACTGGCGAAGGTGCTTCTGATACTGGGTATTCCAGCCTCGCCGCTCGGTG<br>CACTGCAGGTACGTGGTTACATGACACTACTGTGTGGGTAGTCTGGGCAC<br>AAGTAGATCGACATGCCAGATTTGGCCCGTATGCGTGTATGTGCGGTTAT<br>GTTCCCGTTTCGATTGCGGATACCTTGATTGTGGAGCTCCGTTTCGGTCCA<br>ATAGTGGCTGCGACGGAAGGTGGTCCCGCTGCCGAATCACACGTCCGGG<br>TTGCTTATCGGGGCAGGGCCCCGATACGGTATCCGAACGTTTGTCCCGGG<br>AACTGGTCGACCTTCCGCCCGGCGTCTCTTGGACTGAAGGGAGCTCCACT | SEQ ID NO: 266 |
| ThmiPEP319a1<br>ThmiPEP319a2 | Thellungiella<br>halophila | TTTTATACAAATAATGTTCGATAACACTAAACCCTAGCCATCCAACTAAT<br>AGACAAAACCCTACTTGTAATTTACAACCGCAAATTCCCAGAGAACAGA<br>GTAACTACGAGAGAGAGATGGAGATTCAAATTAAAAAGAAAAACTTATA<br>TATAATGAATACACAAAAGCTACCTAATCTGTATATATATATATATAAAT<br>ATGTCTTCATTAAATTAATGGTCGTGGAATAGAAAAAGGAAAACCTAAT<br>TTGATCGCTAGGGCTTATCAGAGTAAAGATGGTTAACCTTCAAAAGATG<br>ACTAATTAACCGGGGAGATAATTAAAAGATTAAATACGCCAACAGAGAG<br>TTAAGAGATACCAGATTTAAATTCCACAATTTGGTCATGTTCTTCTTCAC<br>GTATTCATGACGATGTCTGAATTATAGAGAAACCCAAAATATAAAATGTT<br>AATTTTACCAGACATTTACATACCAATAACTCTATGACGATATGTAAAGT<br>AAGCAAGGCATGTTTTTATGCAGGGAAGATTGAAAATTCAAGATTAATC<br>AAGAAAATTGGAATACCAAAAAGAGAGGGAGCTCCCTTCAGTCCAATCA<br>GAGAGAATCAATGACCCAATTTGTCTACCGCATCATTCATTCATTTAACA<br>AGTCTAGCTCGAATTCTTGGTGACTCGGTATTTGGATGAATGAGTCGGAA<br>GCTAATTGGATCATATCACGACCTATGAATGGACTCAAGGAAGCTCTCTA<br>CAAATGTATTCCTACCACATCAACCCAAATATAGTGATTACAGATGCTGT<br>TCTCACTGTAGACTACATTTACGTTT | SEQ ID NO: 267 |
| AtmiPEP319b1 | Arabidopsis thaliana | AGACATCTCTTCTTCTCTCATCTCTCTTTTCTTCTCTCTTTTCCTCACATAA<br>ACTCTCTTTTTTACTATTAAATCCATATGGTACCTCAAATTAATCTATGG<br>TCATCTAGGGTTATCTTGAAGATTAGAATTGATTCTAGCACGCACAGAGA<br>GGAAGATCATTGCATCCAGAATCACAAACATGGCCTATCTTTTATCTTTT<br>CTTTTTGATCTAAGTCACTGTTI TATGCTATATATAGTATAATCAAATTCT<br>TTACATGTGCTTGTATGTATGCGTATATATAGTAACGGAATTGTTAATAT<br>GCTTATAGATGTTGAGTTGGTGGAGGAAGAGAGCTTTCTTCGGTCCACTC<br>ATGGAGTAATATGTGAGATTTAATTGACTCTCGACTCATTCATCCAAATA<br>CCAAATGAAAGAATTTGTTCTCATATGGTAAATGAATGAATGATGCGAG<br>AGACAAATTGAGTCTTCACTTCTCTATGCTTGGACTGAAGGGAGCTCCCT | SEQ ID NO: 268 |
| AtmiPEP394a1 | Arabidopsis thaliana | TCTTATTCCATCACAATCATCTAGGGTTTTAAGCCAAGCTTATATAGCCC<br>GTCATAAAGAGAACTCATCTGCCTCTCTCAATACCAATAAATATCACC<br>ACCGTCCTTCTCTCCTATCACTATTCAATCTATCGCAAACTCCTTTATGTC<br>TCTCCAATTTTATGAGAGGGTTTCCTTCAAGAACACAGTAAAATAGATTG<br>GATCTTTAAACTTTTGTTCCTTTTCATGAGGGTTTGACAAAGATTTTCTTA<br>CAGTCATCTTTGGCATTCTGTCCACCTCCTTCTATACATATATGCATGTGT<br>ATATATATATGCGTTTCGTGTGAAAGAAGGAGGTGGGTATACTGCCAAT<br>AGAGATCTGTTAG | SEQ ID NO: 269 |
| AtmiPEP395c1 | Arabidopsis thaliana | TTGTATCATGACAGAGCAAGAAGAAGAAAGTCAAATGTCCACATGAGTT<br>CCCTTTAACGCTTCATTGTTGAATACTCAAAGCCACATTGGTTTGTATATA<br>ACACTGAAGTGTTTGGGGGGACTCTTGGTGTCAT | SEQ ID NO: 270 |
| AtmiPEP395e1 | Arabidopsis thaliana | TTTCAAACCCTAACACTCTTATAAACCGATTCGCCAAAATGTATCTACAA<br>TATATTGATAATGTAATATCTATATATTCAAACAATCGTCGTGTTGGTCG | SEQ ID NO: 271 |

TABLE 3-continued

List of the primary transcripts (pri-miRNAs)

| miPEP | Organism | Sequence of the Pri-miRNA | SEQ ID |
|---|---|---|---|
| | | GATGTTTTCTAGAGTTCCTCTGAGCACTTCATTGGAGATACAATTTTTTAT<br>AAAATAGTTTTCTACTGAAGTGTTTGGGGGAACTCCCGGGCTGATTCGGT<br>ATTTTAAATTCAGTAGACTAGCTAGCTG | |
| AtmiPEP397b1 | Arabidopsis thaliana | TGGTAATAGAAATGAGCAAGGAGATATTTTTTTCCCCTGGGTTTGAATGA<br>ACATCATTGAGTGCATCGTTGATGTAATTTTACTTATTTTATTCCATTGTT<br>GAATTAATTAAAGAAGTATATATCAGCGTTGCATTCAATTATGTTTTTCT<br>AATTTTCAGGAAATACAAAAAAAATGAAAAAAAAAAATCACTTAAAAG<br>ACCTTGAGAGTTCTTTTGACT | SEQ ID NO: 272 |
| AtmiPEP398c1 | Arabidopsis thaliana | GGATATCGAAACTCAAACTGTAACAGTCCTTTTATTACTGGTTTAGAAGA<br>TAGATAAATATTGTTAAGGTAGTGGATCTCGACAGGGTTGATATGAGAA<br>CACACGAGCAATCAACGGCTATAACGACGCTACGTCATTGTTACAGCTCT<br>CGTTTCATGTGTTCTCAGGTCACCCCTGCTGAGCTCTTTCTCTACCGTCCA<br>TGTTTTATCAACGCCGTGGCCCGTG | SEQ ID NO: 273 |
| AtmiPEP399b | Arabidopsis thaliana | TCTTATAGAGATGAAGAGAAACATGTAAACTCACTAGTTTTAGGGCGCCT<br>CTCCATTGGCAGGTCCTTTACTTCCAAATATACACATACATATATGAATA<br>TCGAAAATTTCCGATGATCGATTTATAAATGACCTGCCAAAGGAGAGTTG<br>CCCTGAAACTGGTTC | SEQ ID NO: 274 |
| AtmiPEP399d1 | Arabidopsis thaliana | CAATAACTCAAAATGCAATGTGAAATATGAAGAATATATTAAATAGTAG<br>TGAAGATGCATGTTTATGAAGCAGAGAGATAATGTATGGTTGGATTAC<br>TGGGCGAATACTCCTATGGCAGATCGCATTGGCTAGATATGCAAGTAAA<br>ATGCTTCTCTGCCAAAGGAGATTTGCCCCGCAATTCATCC | SEQ ID NO: 275 |
| AtmiPEP403 | Arabidopsis thaliana | ATTTAGGTCTCTCTTCTTCTTCTTTTTCTTCTTGAGCGCCGGCGAAAA<br>AAGTCTCTGTGAGAAAAAGATACGACGATTGTCATTAGAAGAGTCGTAT<br>TACATGTTTTGTGCTTGAATCTAATTCAACAGGCTTTATGTAAGAGATTCT<br>TTAACAATTCCTATAATCTTTGTTGTTGGATTAGATTCACGCACAAACTC<br>GTAATCTGTCTTTTCGATTTTTACCAGATCTGTC | SEQ ID NO: 276 |
| AtmiPEP447a1<br>AtmiPEP447a2 | Arabidopsis thaliana | AATTATATCCATGGTCATGGCTCATCATTAGTCGCACTGCTCTCCTTTTCT<br>CAAAGTTTAAATTCGACATTTGGTAAAATGATGAAACCTCGATGGAACT<br>GCTCTCTTTATGGAATCACGGAATGGACAAATAATCAAAATCAGAAATC<br>GAAGCGAAAAGGGAGGAGAAAAACGCAGATTTGGAGGATTGGGGACAG<br>ATTAGATACTGTTGAATGCATCACTCTAATGCTATCAGCCTATTAATAGC<br>GTCCTATATTTTCGAAGACTTTTAATGTTTAGGGTTATGGATTTTTCGAGC<br>GAAGCATGGAGAGATGTTGAATTGGATACTATAGGATTTGGTACAACAC<br>ATACATATGTTCTGCTTCTGCAAAACTAACATATCAAGTTCAGAGAAACC<br>AGTAAGTCGTTGAATATTTTATTATCCATTCAACGCTTTCTTCTTTTGGAT<br>CATGTCTTGTTTGCTTGACCACTTCTTCTTGCTTAAGAGGATGGACAATAT<br>ATAAAACTGGAGCCTTCTTTTTCTATGAATGCTTATCATCGCGGAGTTG<br>ATCTGTTCAATTCACCTGCCATTGGATGCTTTTTTTATATATACTTCACTG<br>TTCAATTTCAGATGCTTTAGAAGGTTTGCGGAGTAGCTAGAGAATCTGGT<br>ATCTTCAGTTCTTCAATTTCAGCTACTTGGTATCAGCTTCGTCATTGTATA<br>TCAACACATTCTTAATATATAATACTACTTTTTCATCCATTAAACCCCTTA<br>CAATGTCGAGTAAACGAAGCATCTGTCCCCTGGTATTGTCTTCGAGCTTG<br>GTGTTTTTTTCTAGCCAACTCCAAGTTCTCGAGTTGATCATTGTTTGTATT<br>CTTGAGACATTATTTGGGGACGAGATGTTTTGTTGACTCGATATAAGAAG<br>GGGCTTTATGGAAGAAATTGTAGTATTATATATCGAGAGTG | SEQ ID NO: 277 |
| AtmiPEP447b1<br>AtmiPEP447b2 | Arabidopsis thaliana | CTATAAATGCTGCTTATCATCGTGGAGTTGGTTCTGTAAACATTTGAAAA<br>TTCTGAACAGTTTCACCTGCCATTGGATGCTTTGTTTCAATTTCAGGTGCG<br>TTAGAAGGTTTGCAGAGTAGCTAGAGAATCTCGTATCTTCACTTTCTGCT<br>ACTTGGTATCAGCTTCGTCACTTTATATCAACACATTCTTAATATACAATA<br>CTACTTTTTCATCCATTAATCCCCTTACAATGTCGAGTAAACGAAGCATC<br>TGTCCCCTGGTATTGTCTTCGAGCTTGGTGTGTTTTTCTAGCCAGCCCCAA<br>GTTCTCGAGTTGATCATTGTTTGTATTCTGACACATTATTTGGGGACGAG<br>ATGTTTTGTTGACTCGATATAAGAAGGGGCTTTATGGAAGAAATTGTAGT<br>ATTATATATTGAGAATG | SEQ ID NO: 278 |
| AtmiPEP447c | Arabidopsis thaliana | TAGTATAACCGCTGATGTACACCTACCAGCTTGATAACTCTTTTTCGTGG<br>TTTCTGTGTACTCGTTTCTGTTTGTACAGATACTTCTTGTTCAATTTCAGA<br>TGCTTTAGAAGGTTTTCGGAGTGGCTAGAGATCTGTTATCTGTATGAACA<br>GCTACTTGGTATCAGCTTCGTCATTTTATCAACACATTCTTAATATACAAT<br>ACTTCTTTTCATGCATTAAGCCCCTTACAATGTCGAGTAAACAAAGCAT<br>GTGTCCGCTAATATTGTCTTCGAGCTTGGTATTTTTGTATTCTGATACGGT<br>ATTTGGGGACGACATCTTTTGTTGACTCGATATAAGAAGGGGGTTTGTGG<br>AAGAAATTGTAGTATTATATATCAAGAATG | SEQ ID NO: 279 |
| DmmiPEP1a<br>DmmiPEP1b | Drosophila<br>melanogaster | TTTGTGGAACACATTCGACCCACTGAAAAATTGATATAATTTAATGAAAG<br>TGCATAAAATGGTGGACAGTGCATTAAACTGAGCATTGAACACAAAGG<br>CCGCTCAGCAAATTGCTAATTAAAATTCACGATTGCCATTTCACCTGACA<br>CGTTGACGATTTTCATTACAATTCGATTATGTTTCGTTGCAGGGAATTTTA<br>AATGTTAATTGCCAAGAATGTTTCAACAAATTCATTTCTCATTAATGTGT | SEQ ID NO: 280 |

TABLE 3-continued

List of the primary transcripts (pri-miRNAs)

| miPEP | Organism | Sequence of the Pri-miRNA | SEQ ID |
|---|---|---|---|
| | | CTTTTCATTTAATTTTATGTTGTATGAGCTGCACGAGAAATGAGTTGTACT<br>TTTAGTTCGACGGCAGAGTCATGAATGTTCGGCAAAGAATGTAATAATA<br>ACTATCCTCTTTAGACAAATATAGATACAAATCTATCAGATTCTAAAAGT<br>AGAATAATCAATTAATCAGAAAGCTAAAAATAAATAGGCATATTTATAT<br>TTTAATGCGGATTTTTGAAGTTCAACGGGAGAAATGAATCCTTTTTACCA<br>GCCACAGGCGCAATTTGCAACAGAAAGTGTAGCAGAAGTACTCCTCGAA<br>TATTTCCCTGCTCCAGGAGTCATCCATGTGGTTTCGAGGCACACATTTGA<br>CAAACTCATGCCCCGCTATTTGTTGTAAAAACACAATCGCACACATGGCC<br>GCATTTCGGCGACTTCCAGAGAGCGGTACACTTAAGGCGGCCTGGGAAA<br>CGCCTGCAATCTGCTGGTCGCGAACTGCAGATTGCATCCATGTGCCAGGC<br>GACCATGCGACCATGTGACCATGTGCCCGCCCGACGCCTCGCAGCCCAC<br>ATCCTGCCCATCGAGGGCACAACTCAGCGTGGGTATTGCCGCTCCGGCTG<br>CTTCAAGTAGGTAAAAACCGAGAAGATTGAGGATGAATGTATGAGTATG<br>AGAAAATACTCGGCGGAACATATGCTGCCGGGCTTGACCTGACCCTGCC<br>TCATGTGTGGGTCTCCGATTTAATTTTAGGCACCTATATAAACGCGTGTTT<br>ACACTGCAGCCAGAACACAGTCGCCGTCTTCAGTTCGCGCCGTCAACTCC<br>TCGATCGATCGATCGCATCGTCTCGGATCGAATAGAGCTGGGCTTCTGCT<br>CCGGAGCTACATCGCCGTACTTGTCGGACGAGTGTGGTGATGAAAAGTC<br>GCTTAGTCCGGGATTCCTGCCAGATCTCTAAGGGATGAGCTGGCATCCCA<br>GGCTGGCCATGTGGCGCGAAGTATGCGCACAAAAAAGTCAAACAAAAA<br>GGCGCAATTTTATTACGGGCAACCAACGACGAAACAAAACAAAAGCCAA<br>CCGAAAAGCAGAAACAAAGCAGCAAAAAGTTTATGAATTTTTTGTGCAG<br>GCGCGTGAAAGATGCAAAACGAGAAAAAAACATGAAAAAAAAACATTA<br>AAAAAAACAAAAAAAATCCAAAACAGATACCGAGCTGTATCCGAAAAC<br>GAGTGGGGAAGGGGTTTCCCAGTCACATATAAACACACTTCAGTGCGC<br>TTAAAAATTGCTTTATTGCAGTTGGACTATAAAAACGCACGGCAGCGAA<br>CACCGCACAACAAAAGGACGAGCAGAAGTGGGCAAATAAAACGAAAG<br>CTCTTAAACGAAAACAGGAAAATTTGCATGCCACAAAAATAAGCATAA<br>GGATTTGCCGCGCACAAAGTAGAAGCAAAAAGGAATTGCCCAAATGCAG<br>CCACAAAAGACTGTGGCAAATGTTTTGCAGCTTGCCCCTTTTTCCCTGCA<br>ATTACCGTCAGTCGTTGTCATTATTCAGCAGATTATATGGTTTTGCTTATT<br>CCGGACCACCATCATCATCATCATTATCATCATCTTCGGTAAGTTAGACA<br>ATCCCATAAAAACTGTCCAAGTGAGTAGTGCCACCAAAAGTTAGCCGC<br>GTTGTGGAAAATCCAAAACAAAGACCATCCCATATTCAGCCTTTGAGAG<br>TTCCATGCTTCCTTGCATTCAATAGTTATATTCAAGCATATGGAATGTAA<br>AGAAGTATGGAGCGAAATCTGGCGAGACATCGGAGTTGAAACTAAAACT<br>GAAATTTGATTGAAACAGAAGTAGAACCGTAATGAAATGAATGAAATAT<br>TAACCCGTTTCTACAATCCCTGAATAAAATTATTAATTAATTATAGAGCG<br>GGCTAATTTTACAATATATATTGATTTTTTTTGAAG | |
| DmmiPEP8 | *Drosophila melanogaster* | ATTCTTTTTTGGTGCTCGATCGTGACGGTTTGCTCGCGCTCTCCGCTGCGC<br>CGCTCTTTCCGTTGCATATGTGTGCGGGCGTTATTGTGCATGTTTTCCGGTG<br>GCCGAAAAAAATAGTAAAATAAAATATAGAAAACAGAAACCAAGAAT<br>AATAACAGCCATACGATAAACAGTGTGCCAATGTGTGTGTCTGTGTGTGT<br>GTGCATCTCGCGTAACAACAATAATTGCATTTATCGGATGGCGCCAGCTT<br>CAATTTAATTATAAATAACATGTTCAACTTTTTATACTATTTTCCCTGCGT<br>CAAAGTGGGCGTTGCAACTGCCCCCGGAAAATCACGCGCCCCGGTTCAA<br>AGTTAAAGTTTGCTGGGTAACGCACACACACACACACACAATCACTCAC<br>ACGCGGTCACACGCACATTTCAATAAACTAATG¹GAGCCTGGCTTTGTTTT<br>TGTTTTATTTCCAACCCACTTGAGCACCACAGCACACACACAGAGAGAAAA<br>TCAATACTCGTTATGGGATTAAATTTACAAAGCGCAAAGCAAAGCGACA<br>AACAAAATTCAAAAGAAAGAAAAAAAAACACTCAAATAAACTCACAAA<br>GAATTCCTTATCGCCAAGGGGGCCAATGTTCTAAGGTTCTTTCGCCTTGA¹<br>GAACTTTGAGCTTCCTCTGGCAAAGGAGATTATAATGTACAAATAATGTT<br>GCAATAACCAGTTGAAACCAATGGAATACCGAATCTTGCTAATTAGCAA<br>GGACATCTGTTCACATCTTACCGGGCAGCATTAGATCCTTTTTATAACTCT<br>AATACTGTCAGGTAAAGATGTCGTCCGTGTCCTTAACCTTCAGTACCACC<br>AACAGCAGCAGCAGCACCAAAAAAAAAAAAAAAAAAATGCGTAAAAAT<br>CCAAACAAATCATAAAAGTCGAAGGA | SEQ ID NO: 281 |
| HsmiPEP155 | *Homo sapiens* | GCCGAGCCCGGGCCCAGCGCCGCCTGCAGCCTCGGGAAGGGAGCGGATA<br>GCGGAGCCCCGAGCCGCCCGCAGAGCAAGCGCGGGGAACCAAGGAGAC<br>GCTCCTGGCACTGCAGATAACTTGTCTGCATTTCAAGAACAACCTACCAG<br>AGACCTTACCTGTCACCTTGGCTCTCCCACCCAATGGAGATGGCTCTAAT<br>GGTGGCACAAACCAGGAAGGGGAAATCTGTGGTTTAAATTCTTTATGCCT<br>CATCCTCTGAGTGCTGAAGGCTTGCTGTAGGCTGTATGCTGTTAATGCTA<br>ATCGTGATAGGGGTTTTTGCCTCCAACTGACTCCTACATATTAGCATTAA<br>CAGTGTATGATGCCTGTTACTAGCATTCACATGGAACAAATTGCTGCCGT<br>GGGAGGATGACAAAGAAGCATGAGTCACCCTGCTGGATAAACTTAGACT<br>TCAGGCTTTATCATTTTTCAATCTGTTAATCATAATCTGGTCACTGGGATG<br>TTCAACCTTAAACTAAGTTTTGAAAGTAAGGTTATTTAAAAGATTTATCA<br>GTAGTATCCTAAATGCAAACATTTTCATTTAAATGTCAAGCCCATGTTTG<br>TTTTTATCATTAACAGAAATATATTCATGTCATTCTTAATTGCAGGTTTT<br>GGCTTGTTCATTATAATGTTCATAAACACCTTTGATTCAACTGTTAGAAA<br>TGTGGGCTAAACACAAATTTCTATAATATTTTTGTAGTTAAAAATTAGAA<br>GGACTACTAACCTCCAGTTATATCATGGATTGTCTGGCAACGTTTTTTAA | SEQ ID NO: 357 |

TABLE 3-continued

List of the primary transcripts (pri-miRNAs)

| miPEP | Organism | Sequence of the Pri-miRNA | SEQ ID |
|---|---|---|---|
| | | AAGATTTAGAAACTGGTACTTTCCCCCAGGTAACGATTTTCTGTTCAGGC<br>AACTTCAGTTTAAAATTAATACTTTTATTTGACTCTTAAAGGGAAACTGA<br>AAGGCTATGAAGCTGAATTTTTTTAATGAAATATTTTTAACAGTTAGCAG<br>GGTAAATAACATCTGACAGCTAATGAGATATTTTTTCCATACAAGATAAA<br>AAGATTTAATCAAAAAATTTCATATTTGAAATGAAGTCCCAAATCTAGGT<br>TCAAGTTCAATAGCTTAGCCACATAATACGGTTGTGCGAGCAGAGAATCT<br>ACCTTTCCACTTCTAAGCCTGTTTCTTCCTCCATATGGGGATAATACTTTA<br>CAAGGTTGTTGTGAGGCTTAGATGAGATAGAGAATTATTCCATAAGATA<br>ATCAAGTGCTACATTAATGTTATAGTTAGATTAATCCAAGAACTAGTCAC<br>CCTACTTTATTAGAGAAGAGAAAAGCTAATGATTTGATTTGCAGAATATT<br>TAAGGTTTGGATTTCTATGCAGTTTTTCTAAATAACCATCACTTACAAAT<br>ATGTAACCAAACGTAATTGTTAGTATATTTAATGTAAACTTGTTTTAACA<br>ACTCTTCTCAACATTTTGTCCAGGTTATTCACTGTAACCAAATAAATCTCA<br>TGAGTCTTTAGTTGATTTAAAATAAAAAAAAAAAAAAAAAAAAAAAAA<br>AA | |
| AtmiPEP157c | Arabidopsis thaliana | CTTTGTCACTTCATACACTCCCTATTGTCTATATATATATATATACTTACA<br>CATATTCAAACATTATAATACTTAATTACACATACATACTTTATGATGTT<br>GCATATCACACATAGGTTTGAGAGTGATGTTGGTTGTTGACAGAAGATA<br>GAGAGCACTAAGGATGACATGCAAGTACATACATATATATCATCACACC<br>GCATGTGGATGATAAAATATGTATAACAAATTCAAAGAAAGAGAGGGAG<br>AGAAAGAGAGAGAACCTGCATCTCTACTCTTTTGTGCTCTCTATACTTCT<br>GTCACCACCTTTATCTCTTCTTCTCTAACCT | SEQ ID NO: 400 |
| AtmiPEP157d | Arabidopsis thaliana | ATTTACTCTTCACCGCCCTCTCTCTATATATAGTCTCTATCCTCACATATT<br>ATATATCAAACCGCAAGAATGCTGTATGTATAGTGGAGGGTGATAGTGT<br>GGTTGCTGACAGAAGATAGAGAGCACTAAGGATGCTATGCAAAACAGAC<br>ACAGATATGTGTTTCTAATTGTATTTCATACTTTAACCTCAAAGTTGATAT<br>AAAAAAAGAAAGAAGATAGAAGAGCTAGAAGACTATCTGCATCTCTAT<br>TCCTATGTGCTCTCTATGCTTCTGTCATCACCTTTCTTTCTCTATTTCTCTC<br>TAC | SEQ ID NO: 401 |
| AtmiPEP160c | Arabidopsis thaliana | AACCAAAACTCTTCAACATTTCTCTCTGACTACTTCATTTCCTCTTCCCAA<br>CAGTTAAAAAAAGTTCTGATTCGATTCAAGCCAAGATCCACGTATAAAG<br>ATATGTTCATGCGTAGAGGTTTGGTATACAACAATATATACATATAATAG<br>TTTGTCGTTATGCCTGGCTCCCTGTATGCCACGAGTGGATACCGATTTTG<br>GTTTTAAAATCGGCTGCCGGTGGCGTACAAGGAGTCAAGCATGAC | SEQ ID NO: 402 |
| AtmiPEP164b | Arabidopsis thaliana | ATACATTCTCTCTTTCTCTCTCTCTCTCTCATCCCGGCCCAGTTATGT<br>GGTCGGAGAGAATGATGAAGGTGTGTGATGAGCAAGATGGAGAAGCAG<br>GGCACGTGCATTACTAGCTCATATATACACTCTCACCACAAATGCGTGTA<br>TATATGCGGAATTTTGTGATATAGATGTGTGTGTGTTGAGTGTGATGA<br>TATGGATGAGTTAGTTCTTCATGTGCCCATCTTCACCATC | SEQ ID NO: 403 |
| AtmiPEP166c | Arabidopsis thaliana | TCACACATACCTTTCTTTCTCTTCTTCTTCTTACGAAAAGTTTCATCACAT<br>TCACATTATCTTTAACTTTGGTCTCTIITTCTTTTTTGTCTCTTTTCTCTTCTT<br>GATAACGTGGTTCTAGTCTTGATTAATTCATTGTTGTGCGATTTAGTGTTG<br>AGAGGATTGTTGTCTGGCTCGAGGTCATGAAGAAGAGAATCACTCGAAT<br>TAATTTGGAAGAACAAATTAAGAAAACCCTAGATGATTCTCGGACCAGG<br>CTTCATTCCCCCTAACCTACTTATCGC | SEQ ID NO: 404 |
| AtmiPEP166d | Arabidopsis thaliana | ATTTAGCTTCTTCTTCTTCTTCTTCTGTCTACTTACATAAAGTTATCCTt<br>GCTTTGGTTTAGGGTTGAGAGGAATATTGTCTGGCTCGAGGTCATGAAGA<br>AGATCGGTAGtATTGATTCATTTTAAAGAGTGAAATCCCTAAATGATTCTC<br>GGACCAGGCTTCATTCCCCCCAACC | SEQ ID NO: 405 |
| AtmiPEP169a | Arabidopsis thaliana | TAGTATTCATAAGCACCAAAACAAATATGTAGAGATCTCCTCTTCCATTC<br>TCTATTGTTACTTTCGAGAAGAAACATACAAAACACATACATTTTTCTTTT<br>GTTTGTGGTTTTCATATATACAAGTGGGTATAGCTAGTGAAACGCGAATG<br>TGACGAAAGTAGTGTGCAGCCAAGGATGACTTGCCGATTTAAATGATCTT<br>TCTTTATACTCTATTAAGACAATTTAGTTTCAAACTTTTTTTTTTTTTTT<br>TTTGAAGGATTCAGGAAGAAATTAGGATATATTATTCCGTATAAAATACA<br>AGATATATAAAACCAAAAAGAAAAAGTAACATGATCGGCAAGTTGTCCT<br>TGGCTACACGTTACTTTGTGTCGC | SEQ ID NO: 406 |
| AtmiPEP169h1<br>AtmiPEP169h2 | Arabidopsis thaliana | ACTCATCAACAACCTCTTCATAAATACATAAATCATATAAGAGAAAATG<br>GTGACATGAAGAATGAGAACTTGTGTGG | SEQ ID NO: 407 |
| AtmiPEP169n | Arabidopsis thaliana | AGGCAAAACATATAGAGAGTAATGAAGTGTATGATGAAGAAGAGAGG<br>TCTAACATGGCGGAAAGCGTCATGTTTAGTAGCCAAGGATGACTTGCCTG<br>ATCTTTTTCGCCTCCACGATTCAATTTCAAATTCATGCATTTTGGATTATT<br>ATACCTTTTAAAGTATAATAGGTCAAATATCATGTTGAATCTTGCGGGTT<br>AGGTTTCAGGCAGTCTCTTTGGCTATCTTGACATGCTTTTTCCATCCAT | SEQ ID NO: 408 |
| AtmiPEP170 | Arabidopsis thaliana | ATTCACTCCCTTCTTCTTCTTAATCTCCTTACAGTTACAGACATTCTCTCA<br>CTTGCGTTCTTGTTTCTTTTACAAAACAGATACACTATGTTTCCGAGAGA | SEQ ID NO: 409 |

TABLE 3-continued

List of the primary transcripts (pri-miRNAs)

| miPEP | Organism | Sequence of the Pri-miRNA | SEQ ID |
|---|---|---|---|
|  |  | GTCCCTCTGATATTGGCCTGGTTCACTCAGATTCTCTTTTACTAACTCATC<br>TGATTGAGCCGTGTCAATATCTCAGTCCTCTCTCG |  |
| AtmiPEP396a | Arabidopsis thaliana | TCTCACAACTTCAACTTCCCTCTTTCTCTATATTACGCTTTTGCCCCTCACT<br>CCCTCTTTCCACAATTAGGGTTTCGTCTGCTCTACATGACCCTCTCTGTAT<br>TCTTCCACAGCTTTCTTGAACTGCAAAACTTCTTCAGATTTTTTTTTTTTC<br>TTTTGATATCTCTTACGCATAAAATAGTGATTTTCTTCATATCTCTGCTCG<br>ATTGATTTGCGGTTCAATAAAGCTGTGGGAAGATACAGAC | SEQ ID NO: 410 |
| AtmiPEP399c | Arabidopsis thaliana | GAATAACCAACCAGCCTTCTCTCAAAGCAAACCAAAAAGAAAAACCAAC<br>ATTGAAAGAGGAAGTTACGATAAGCGGAGCAGTAATAGGGCATCTTTCT<br>ATTGGCAGGCGACTTGGCTATTTGTATCTTTTGTGTTCTTGACTATTGGCT<br>ATGTCACTTGCCAAAGGAGAGTTGCCCTGTCACTGCTTCCGCTTAAACAC<br>AGTCTATAACCGGTTCTGCTAATATCAATCCTTCTTTTGGACATGTCCAA<br>AGCCGAGATTGATTGATAGAGAATTGGTCTCTCTGGCTACAAAACTAGTG<br>CGGTTCTCTCGATTTAAGTTTTAATAGCATTCACTTTGCACATTGCATCTT<br>TCACATCAAATTTCCATTTCATCAACCATCTAAACCTCTTTGTTAGCTTTG<br>ATATAAGCAACGATCTAAAGTCTAAAAACCATTAATCCTCTGAAAAAAA<br>AGACAATTTCGATGGTTCTATTATGTTTCTCCAATGCAGAAATTGTATCG<br>TCTGAATTATAGTAGATTTTTTCTAGACTAAAGTGTAAACCAAGACGAAT<br>CTGCACTAACAAGACACACCAATAGACTTTACAGAGAAAGGTTACGAGT<br>TTTGAAAATATTAACGGACCATAGTCATCGCG | SEQ ID NO: 411 |

TABLE 4

List of the microRNAs (miRNAs)

| miPEP | Organism | Sequence of the miRNA | SEQ ID |
|---|---|---|---|
| AtmiPEP156a1<br>AtmiPEP156a2<br>AtmiPEP156a3 | Arabidopsis thaliana | ugacagaagagagugagcac | SEQ ID NO: 282 |
| AtmiPEP156c1<br>AtmiPEP156c2 | Arabidopsis thaliana | ugacagaagagagugagcac | SEQ ID NO: 283 |
| AtmiPEP156e1 | Arabidopsis thaliana | ugacagaagagagugagcac | SEQ ID NO: 284 |
| AtmiPEP156f1 | Arabidopsis thaliana | ugacagaagagagugagcac | SEQ ID NO: 285 |
| AlmiPEP159a | Arabidopsis lyrata | uuuggauugaagggagcucua | SEQ ID NO: 286 |
| AtmiPEP159a1 | Arabidopsis thaliana | uuuggauugaagggagcucua | SEQ ID NO: 287 |
| CrmiPEP159a | Capsella rubella | uuuggauugaagggagcucua | SEQ ID NO: 288 |
| AtmiPEP159b1<br>AtmiPEP159b2 | Arabidopsis thaliana | uuuggauugaagggagcucuu | SEQ ID NO: 289 |
| AtmiPEP160a1 | Arabidopsis thaliana | ugccuggcucccuguaugcca | SEQ ID NO: 290 |
| AtmiPEP160b1<br>AtmiPEP160b2 | Arabidopsis thaliana | ugccuggcucccuguaugcca | SEQ ID NO: 291 |
| AtmiPEP161 | Arabidopsis thaliana | ucaaugcauugaaagugacua | SEQ ID NO: 292 |
| AtmiPEP162a1 | Arabidopsis thaliana | ucgauaaaccucugcauccag | SEQ ID NO: 293 |
| AtmiPEP162b1 | Arabidopsis thaliana | ucgauaaaccucugcauccag | SEQ ID NO: 294 |
| AtmiPEP163-1<br>AtmiPEP163-2 | Arabidopsis thaliana | uugaagaggacuuggaacuucgau | SEQ ID NO: 295 |
| AlmiPEP164a1<br>AlmiPEP164a2<br>AlmiPEP164a3 | Arabidopsis lyrata | uggagaagcagggcacgugca | SEQ ID NO: 296 |
| AtmiPEP164a1<br>AtmiPEP164a2<br>AtmiPEP164a3 | Arabidopsis thaliana | uggagaagcagggcacgugca | SEQ ID NO: 297 |

TABLE 4-continued

List of the microRNAs (miRNAs)

| miPEP | Organism | Sequence of the miRNA | SEQ ID |
|---|---|---|---|
| BrmiPEP164a1<br>BrmiPEP164a2<br>BrmiPEP164a3 | Brassica rapa | uggagaagcagggcacgugca | SEQ ID NO: 298 |
| CpmiPEP164a1<br>CpmiPEP164a2 | Carica papaya | uggagaagcagggcacgugca | SEQ ID NO: 299 |
| CrmiPEP164a1<br>CrmiPEP164a2<br>CrmiPEP164a3 | Capsella rubella | uggagaagcagggcacgugca | SEQ ID NO: 300 |
| GrmiPEP164a1<br>GrmiPEP164a2<br>GrmiPEP164a3 | Gossypium raimondii | uggagaagcagggcacgugca | SEQ ID NO: 301 |
| MtmiPEP164a1<br>MtmiPEP164a2 | Aledicago truncatula | uggagaagcagggcacgugca | SEQ ID NO: 302 |
| OsmiPEP164a1<br>OsmiPEP164a2 | Oryza sativa | uggagaagcaggguacgugca | SEQ ID NO: 303 |
| AlmiPEP165a | Arabidopsis lyrata | ucggaccaggcuucaucccccc | SEQ ID NO: 304 |
| AtmiPEP165a | Arabidopsis thaliana | ucggaccaggcuucaucccccc | SEQ ID NO: 305 |
| BcmiPEP165a | Brassica carinata | ucggaccaggcuucaucccccc | SEQ ID NO: 306 |
| BjmiPEP165a | Brassica juncea | ucggaccaggcuucaucccccc | SEQ ID NO: 307 |
| BnmiPEP165a | Brassica napus | ucggaccaggcuucaucccccc | SEQ ID NO: 308 |
| BomiPEP165a | Brassica oleracea | ucggaccaggcuucaucccccc | SEQ ID NO: 309 |
| BrmiPEP165a | Brassica rapa | ucggaccaggcuucaucccccc | SEQ ID NO: 310 |
| AtmiPEP166a | Arabidopsis thaliana | ucggaccaggcuucauuccccc | SEQ ID NO: 311 |
| AtmiPEP166b | Arabidopsis thaliana | ucggaccaggcuucauuccccc | SEQ ID NO: 312 |
| AtmiPEP167a | Arabidopsis thaliana | ugaagcugccagcaugaucua | SEQ ID NO: 313 |
| AtmiPEP167b1<br>AtmiPEP167b2 | Arabidopsis thaliana | ugaagcugccagcaugaucua | SEQ ID NO: 314 |
| AtmiPEP169c1<br>AtmiPEP169c2 | Arabidopsis thaliana | cagccaaggaugacuugccgg | SEQ ID NO: 315 |
| AtmiPEP169l1 | Arabidopsis thaliana | uagccaaggaugacuugccug | SEQ ID NO: 316 |
| AtmiPEP171a1 | Arabidopsis thaliana | ugauugagccgcgccaauauc | SEQ ID NO: 317 |
| AtmiPEP171b | Arabidopsis thaliana | uugagccgugccaauaucacg | SEQ ID NO: 318 |
| MtmiPEP171b1<br>MtmiPEP171b2 | Medicago truncatula | ugauugagccgcgucaauauc | SEQ ID NO: 319 |
| ZmmiPEP171b | Zea mays | ggauugagccgcgucaauauc | SEQ ID NO: 320 |
| AtmiPEP171c1 | Arabidopsis thaliana | uugagccgugccaauaucacg | SEQ ID NO: 321 |
| MtmiPEP171e | Medicago truncatula | agauugagccgcgccaauauc | SEQ ID NO: 322 |
| MtmiPEP171h | Medicago truncatula | cgagccgaaucaauaucacuc | SEQ ID NO: 323 |
| AtmiPEP172a1<br>AtmiPEP172a3 | Arabidopsis thaliana | agaaucuugaugaugcugcau | SEQ ID NO: 324 |
| AtmiPEP172b1 | Arabidopsis thaliana | gcagcaccauuaagauucac | SEQ ID NO: 325 |
| AtmiPEP172c1 | Arabidopsis thaliana | agaaucuugaugaugcugcag | SEQ ID NO: 326 |

TABLE 4-continued

List of the microRNAs (miRNAs)

| miPEP | Organism | Sequence of the miRNA | SEQ ID |
|---|---|---|---|
| AtmiPEP172e1<br>AtmiPEP172e2<br>AtmiPEP172e3 | *Arabidopsis thaliana* | ggaaucuugaugaugcugcau | SEQ ID NO: 327 |
| AcmiPEP319a1<br>AcmiPEP319a2 | *Arabidopsis cebennensis* | uuggacugaagggagcucccu | SEQ ID NO: 328 |
| AhmiPEP319a | *Arabidopsis halleri* | uuggacugaagggagcucccu | SEQ ID NO: 329 |
| AlmiPEP319a | *Arabidopsis lyrata* | uuggacugaagggagcucccu | SEQ ID NO: 330 |
| AtmiPEP319a1<br>AtmiPEP319a2 | *Arabidopsis thaliana* | uuggacugaagggagcucccu | SEQ ID NO: 331 |
| BrmiPEP319a | *Brassica rapa* | uuggacugaagggagcucccu | SEQ ID NO: 332 |
| CpmiPEP319a | *Carica papaya* | uuggacugaagggagcuccuu | SEQ ID NO: 333 |
| CrmiPEP319a | *Capsella rubella* | uuggacugaagggagcucc | SEQ ID NO: 334 |
| EgmiPEP319a | *Eucalyptus grandis* | uuggacugaagggagcucccu | SEQ ID NO: 335 |
| GrmiPEP319a | *Gossypium raimondii* | uuggacugaagggagcucccu | SEQ ID NO: 336 |
| MtmiPEP319a | *Medicago truncatula* | uuggacugaagggagucucccu | SEQ ID NO: 337 |
| OsmiPEP319a | *Oryza sativa* | uuggacugaagggugcucccu | SEQ ID NO: 338 |
| PpmiPEP319a | *Physcomitrella patens* | cuuggacugaagggagcucc | SEQ ID NO: 339 |
| ThmiPEP319a1<br>ThmiPEP319a2 | *Thellungiella halophila* | uggacucaaggaagcucucu | SEQ ID NO: 340 |
| AtmiPEP319b1 | *Arabidopsis thaliana* | uuggacugaagggagcucccu | SEQ ID NO: 341 |
| AtmiPEP394a1 | *Arabidopsis thaliana* | uuggcauucuguccaccucc | SEQ ID NO: 342 |
| AtmiPEP395c1 | *Arabidopsis thaliana* | cugaaguguuuggggggacuc | SEQ ID NO: 343 |
| AtmiPEP395e1 | *Arabidopsis thaliana* | cugaaguguuuggggggaacuc | SEQ ID NO: 344 |
| AtmiPEP397b1 | *Arabidopsis thaliana* | ucauugagugcaucguugaug | SEQ ID NO: 345 |
| AtmiPEP398c1 | *Arabidopsis thaliana* | uguguucucaggucacccug | SEQ ID NO: 346 |
| AtmiPEP399b | *Arabidopsis thaliana* | ugccaaaggagaguugcccug | SEQ ID NO: 347 |
| AtmiPEP399d1 | *Arabidopsis thaliana* | ugccaaaggagauuugccccg | SEQ ID NO: 348 |
| AtmiPEP403 | *Arabidopsis thaliana* | uuagauucacgcacaaacucg | SEQ ID NO: 349 |
| AtmiPEP447a1 | *Arabidopsis thaliana* | uuggggacgagauguuuuguug | SEQ ID NO: 350 |
| AtmiPEP447a2 | *Arabidopsis thaliana* | uuggggacgagauguuugugug | |
| AtmiPEP447b1 | *Arabidopsis thaliana* | uuggggacgagauguuuuguug | SEQ ID NO: 351 |
| AtmiPEP447b2 | *Arabidopsis thaliana* | uuggggacgagauguuugugug | |
| AtmiPEP447c | *Arabidopsis thaliana* | ccccuuacaaugucgaguaaa | SEQ ID NO: 352 |
| DmmiPEP1a<br>DmmiPEP1b | *Drosophila melanogaster* | uggaauguaaagaaguauggag | SEQ ID NO: 353 |
| DmmiPEP8 | *Drosophila melanogaster* | uaauacugucagguaaagauguc | SEQ ID NO: 354 |
| HsmiPEP155 | *Homo sapiens* | uuaaugcuaaucguguauaggggu | SEQ ID NO: 358 |
| AtmiPEP157c | *Arabidopsis thaliana* | uugacagaagauagagagcac | SEQ ID NO: 412 |
| AtmiPEP157d | *Arabidopsis thaliana* | ugacagaagauagagagcac | SEQ ID NO: 413 |
| AtmiPEP160c | *Arabidopsis thaliana* | ugccuggcucccuguaugcca | SEQ ID NO: 414 |

TABLE 4-continued

List of the microRNAs (miRNAs)

| miPEP | Organism | Sequence of the miRNA | SEQ ID |
|---|---|---|---|
| AtmiPEP164b | Arabidopsis thaliana | uggagaagcagggcacgugca | SEQ ID NO: 415 |
| AtmiPEP166c | Arabidopsis thaliana | ucggaccaggcuucauucccc | SEQ ID NO: 416 |
| AtmiPEP166d | Arabidopsis thaliana | ucggaccaggcuucauucccc | SEQ ID NO: 417 |
| AtmiPEP169a | Arabidopsis thaliana | cagccaaggaugacuugccga | SEQ ID NO: 418 |
| AtmiPEP169h | Arabidopsis thaliana | uagccaaggaugacuugccug | SEQ ID NO: 419 |
| AtmiPEP169n | Arabidopsis thaliana | uagccaaggaugacuugccug | SEQ ID NO: 420 |
| AtmiPEP170 | Arabidopsis thaliana | ugauugagccgugucaauauc | SEQ ID NO: 421 |
| AtmiPEP396a | Arabidopsis thaliana | uuccacagcuuucuugaacug | SEQ ID NO: 422 |
| AtmiPEP399c | Arabidopsis thaliana | ugccaaaggagaguugcccug | SEQ ID NO: 423 |

TABLE 5

List of the control Pre-miRNAs

| Pre-miRNA | Organism | Sequence of the Pre-miRNA | SEQ ID |
|---|---|---|---|
| Pre-miR169 | Medicago truncatula | TTAGGGTTTTCAGCTCATGGTAATAAAAATGTCATCTAATGTCTTGCATGT GGGAATGAGGTCATATATGCAGCCAAGGATGACTTGCCGGCGAGCCTCTT TCGATACTTTTATGACATAATTAATCATGTGGATAGCCAAGGTACTAAACT CACTTTGCACTAAAACAAATATTTTTGCTTTAGTGCAAACTTAGTTTAGGC GCTTCGCAACGGCTAGTCAAATGTCCTAGTTCCAATGTGATTGGTTGTCCG GCAAGTCGTCTCTGGCTACGTAAAGGCCTCCTTTTTTCATGCTAGATTTTTG ATGATTTGATATAGCCACACATATTTTGGAA | SEQ ID NO: 359 |
| Pre-miR169a | Medicago truncatula | AAGAGGCAGAGAGAGTAATGCAGCCAAGGATGACTTGCCGACAACATTG GCGAATGTTCATGTGATTTCTGCCTCATTGTGCCGGCAAGTTGTCCTTGGCT ATGTTAGTCTCTCATCTTCT | SEQ ID NO: 360 |
| Pre-miR171a MI 0001753 | Medicago truncatula | TGAATTCCCCTCCGCTTTTTGATGTTGGCTTGTCTCAATCAAATCAAAGTTC TTGAAATTTGAGTTCTTTAGTCTGATTGAGTCGTGCCAATATCATATTAAG CGATAAAAGTC | SEQ ID NO: 361 |
| Pre-miR171h | Medicago truncatula | CCACAAAACTATAACTAGCTAGAAGCTTTAATCGCCTTATTTATTATAATA ATAATAATAAATATGGCTTCAGCTGCAAAAGTATACATGGCGTGATATTG ATCCGGCTCATCTATATCTTCAAGTTCAATCATCCATATTCATATCAATTTC AGACGAGCCGAATCAATATCACTCTTGTTTGCTTCATTGCATATTAATTAT ATACTTCATTTATAAGTTATAGTTTGCCATATATATATTAGATTGATTCTGC AGAAGTAGACAGGAGTGGTGTTGTTTCTGCTCATCTTATTAAATAATGAAT GAATGAATGACATTTGCTTACTTATAAGACGAGCCGAATCAATATCACTCC AGTACACCT | SEQ ID NO: 362 |
| Pre-miR393a | Medicago truncatula | AACTGCAACTTGAGGAGGCATCCAAAGGGATCGCATTGATCCTATAATAT TTCAACTTTAGTCACTTTAATTTTCTCTCATATAATACTTAATTGGGATCAT GCCATCCCTTTGGATTTCTCCTTTAGTAGCTAC | SEQ ID NO: 363 |
| Pre-miR393b | Medicago truncatula | AGGCATCCAAAGGGATCGCATTGATCCCAAATCTAATTAAGTCCCTAGCTA CTTAATTAACAACTTAATTTCCTTAATATCTCATAATATTTGGGATCATGCT ATCCCTTTGGATTCAT | SEQ ID NO: 364 |
| Pre-miR396a | Medicago truncatula | TGCTTTTCCACAGCTTTCTTGAACTTCTTTCGTATCTTAAATCTGTTTTCAA GATTAAAAGTCCTAGAAGCTCAAGAAAGCTGTGGGAGAATA | SEQ ID NO: 365 |
| Pre-miR396b | Medicago truncatula | TATTCTTCCACAGCTTTCTTGAACTGCATCCAAATTGAGTTCCTTTGCATTG CCATGGCCATTGTTTTGCGGTTCAATAAAGCTGTGGGAAGATA | SEQ ID NO: 366 |

TABLE 6

List of the control miRNAs

| miRNA | Organism | Sequence of the miRNA | SEQ ID | |
|---|---|---|---|---|
| miR169 | Medicago truncatula | CAGCCAAGGAUGACUU GCCGG | SEQ ID NO: | 367 |
| miR169a | Medicago truncatula | CAGCCAAGGAUGACUU GCCGA | SEQ ID NO: | 368 |
| miR171a | Medicago truncatula | UGAUUGAGUCGUGCCA AUAUC | SEQ ID NO: | 369 |
| miR171h | Medicago truncatula | GAGCCGAAUCAAUAUC ACUC | SEQ ID NO: | 370 |
| miR393a | Medicago truncatula | UCCAAAGGGAUCGCAU UGAUC | SEQ ID NO: | 371 |
| miR393b | Medicago truncatula | UCCAAAGGGAUCGCAU UGAUC | SEQ ID NO: | 372 |
| miR396a | Medicago truncatula | UUCCACAGCUUUCUUG AACUU | SEQ ID NO: | 373 |
| miR396b | Medicago truncatula | UUCCACAGCUUUCUUG AACUG | SEQ ID NO: | 374 |

TABLE 7

Polymorphism of the DNA sequence of the different regions of pri-miR171b

| | Size | # SNPs | # mutations | % SNP | # haplotypes |
|---|---|---|---|---|---|
| pri-mir171b | 1127 | 91 | 100 | 8.07 | 161 |
| 5' pri-miR171b | 129 | 4 | 4 | 3.1 | 5 |
| miPEP171b | 62 | 2 | 2 | 3.22 | 3 |
| Pre-miR171b | 118 | 1 | 1 | 0.85 | 2 |
| miR171b + miR171b* | 42 | 0 | 0 | 0 | 1 |
| 3' pri-miR171b | 259 | 39 | 42 | 15.06 | 89 |

EXAMPLES

A: Analysis of the miPEPS in Plants

Example 1—Characterization in the Model Plant *Medicago truncatula* a) Identification and Characterization of MtmiPEP171b1 (miPEP171b1 Identified in *Medicago truncatula*)

Figure 1:
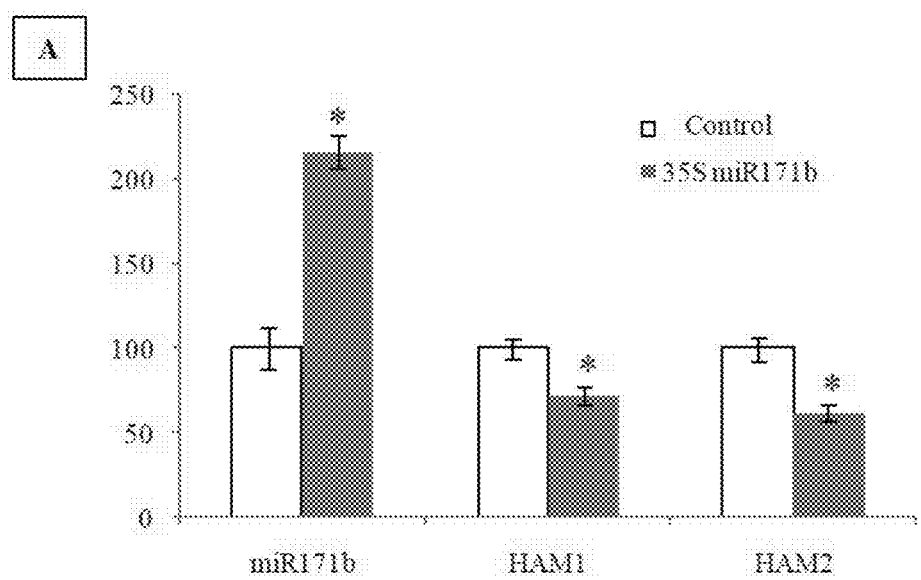
FIG. 1. Effects of overexpression of MtmiR171b (miR171b identified in *Medicago truncatula*) on the expression of the HAM1 and HAM2 genes (A) or on the number of lateral roots (B) in *M. truncatula*.
Figure 1:
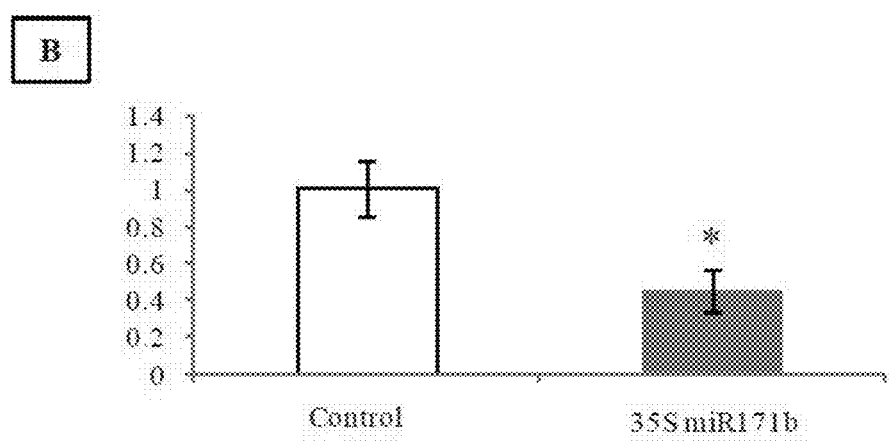

This microRNA is expressed in the meristematic region of the roots. The overexpression of this microRNA in particular leads to a reduction in the expression of the genes HAM1 (Accession No. MtGI9-TC114268) and HAM2 (Accession No. MtG19-TC120850) (FIG. 1A), as well as to a reduction in the number of lateral roots (FIG. 1B).

The sequence of the primary transcript of MtmiR171b was determined using the RACE-PCR technique. Analysis of the sequence of the primary transcript made it possible to identify the presence of several completely unexpected small open reading frames (sORFs). These sORFs were called miORFs for "microRNA ORFs". These miORFs potentially encode short peptides, from about 4 to 100 amino acids. No significant homology relating to these miORFS was found in the databases.

The overexpression of the first miORF, called MtmiORF171b, leads to an increase in the accumulation of MtmiR171b and a reduction in the expression of the HAM1 and HAM2 genes (see FIG. 2A), as well as to a reduction in the number of lateral roots (FIG. 2B), as was already observed in the overexpression of MtmiR171b.

In order to determine whether MtmiORF171b leads to the real production of a peptide and whether the regulatory function observed above is indeed carried by said peptide, a synthetic peptide, the sequence of which is identical to that potentially encoded by MtmiORF171b, was applied on the roots of *Medicago truncatula*. Application of this peptide leads to the phenotype already observed above in the overexpression of MtmiORF171b, i.e. it leads to an increase in the accumulation of MtmiR171b and a reduction in the expression of the HAM1 and HAM2 genes (see FIG. 3A), as well as a reduction in the number of lateral roots (FIG. 3B).

The results of these experiments demonstrate that MtmiORF171b encodes a peptide capable of modulating the accumulation of MtmiR171b, and the expression of the target genes of MtmiR171b: HAM1 and HAM2. Said peptide has been called MtmiPEP171b1 ("miPEP" corresponding to microRNA encoded PEPtide).

Moreover, MtPEP171b1 leads to an increase in the accumulation of MtmiR171b (FIG. 4A) and of pre-MtmiR171b (FIG. 4B).

b) Specificity of miPEP171b1

The expression of different microRNA precursors of *Medicago truncatula* (MtmiR171b SEQ ID NO: 319, MtmiR169 SEQ ID NO: 367, MtmiR169a SEQ ID NO: 368, MtmiR171a SEQ ID NO: 369, MtmiR171h SEQ ID NO: 370, MtmiR393a SEQ ID NO: 371, MtmiR393b SEQ ID NO: 372, MtmiR396a SEQ ID NO: 373 and MtmiR396b SEQ ID NO: 374) was determined and compared between control plants and plants in which MtmiORF171b encoding MtmiPEP171b1 was overexpressed (FIG. 5A), or between control plants and plants grown on culture medium containing MtmiPEP171b1 (FIG. 5B).

The results obtained indicate that MtmiPEP171b1 only leads to an increase in the accumulation of MtmiR171b and not of the other miRNAs, which indicates that a miPEP only has an effect on the microRNA from which it is derived.

c) Localization of miPEP171b1

Moreover, the immunolocalization of miPEP171b1 in the roots of *M. truncatula* reveals the presence of miPEP171b1 in the lateral root initiation sites, showing a co-localization between the microRNA and the corresponding miPEP (FIG. 28).

Example 2—Characterization in the Model Plant of Tobacco a) Conservation of the Mechanism in Tobacco In order to determine whether the mechanism of regulation of the microRNAs is conserved in other plant species, the regulation of MtmiR171b by MtmiPEP171b1 was tested in a different cellular model. For this, MtmiR171b and MtmiPEP171b1 were introduced into tobacco leaves.

The accumulation of MtmiR171b was measured in tobacco leaves transformed in order to express MtmiR171b of *Medicago truncatula* starting from wild-type pri-miRNA capable of producing MtmiPEP171b1, or starting from a mutated version of pri-miRNA incapable of producing MtmiPEP171b1 (in which the start codon ATG of MtmiORF171b has been replaced with ATT) (FIG. 6 and FIG. 20). Absence of translation of MtmiPEP171b1 leads to a marked decrease in the accumulation of MtmiR171b.

The accumulation of pre-MtmiR171b was measured in tobacco leaves transformed in order to express MtmiR171b of *Medicago truncatula* alone (control), or additionally expressing the wild-type MtmiORF171b of *Medicago truncatula* (35SmiPEP171b1 ATG), or a mutated version of MtmiORF171b in which the start codon ATG has been replaced with ATT (35SmiPEP171b1 ATT) (FIG. 7 and FIG. 21). The expression of MtmiORF171b leads to an increase in the accumulation of pre-miR171b, and this accumulation of pre-miR171b depends on the translation of MtmiORF171b to micropeptide.

Moreover, in the tobacco leaves transformed in order to express MtmiR171b of *Medicago truncatula*, untreated or treated by spraying with MtmiPEP171b1 (0.1 µM) for the first time 12 h before sampling and then a second time 30 minutes before sampling, it was observed that MtmiPEP171b1 may be used directly in peptide form by foliar sprayings (FIG. 8).

Moreover, it was observed in tobacco (as in *Medicago truncatula*) that the MtmiPEP171b1 leads to an increase in the accumulation of MtmiR171b (FIG. 9A) and of pre-MtmiR171b (FIG. 9B), but reduces the accumulation of pri-MtmiR171b (FIG. 9C).

Taken together, these results indicate that the mechanism of regulation of the microRNAs and of their target genes under the control of miPEPs is conserved between the species.

b) Intracellular Localization of MtmiPEP171b1

Tobacco leaves were transformed in order to overexpress MtmiPEP171b1 of *Medicago truncatula* fused with a fluorescent protein (GFP) (FIG. 10). The results obtained indicate that the miPEP is localized in small nuclear bodies.

c) Identification of miPEPS from Databases

Genomic databases of plants were searched for the presence of open reading frames within primary transcripts of 70 miRNAs, and 101 miORFs capable of encoding a miPEP were identified.

At present, AtmiPEP165a and AtmiPEP319a2, identified in *Arabidopsis thaliana*, have already been characterized. The experiments conducted in the model plant of tobacco made it possible to demonstrate that the overexpression of AtmiORF165a or of AtmiORF319a leads to an increase in the accumulation of AtmiR165a or of AtmiR319a respectively (FIG. 11).

miR165a regulates transcription factors such as *Revoluta*, *Phavoluta* and *Phabulosa*. miR319 regulates genes of the TCP family.

Example 3—Characterization in the *Arabidopsis thaliana* Model Plant

Example 3A—AtmiPEP165a

Regarding AtmiPEP165a, it has been demonstrated in vivo in *Arabidopsis thaliana* that treatment with AtmiPEP165a leads to a phenotype with greatly accelerated root growth (FIG. 12).

Moreover, treatment of plants with higher and higher concentrations of miPEP165a shows a dose-dependent effect on the accumulation of miR165a and the negative regulation of its target genes (PHAVOLUTA: PHV, PHABOLUSA: PHB and *REVOLUTA*: REV) as a function of the amount of miPEP165A (see FIG. 22).

Example 3B—AtmiPEP164a

Regarding AtmiPEP164a, this was synthesized and was used for investigating an increase in the accumulation of miR164a in roots of *A. thaliana* treated with the synthetic peptide.

Northern blot analyses indicate that treatment of the plant with the peptide miPEP164a leads to an increase in the accumulation of miR164a (FIG. 23).

It has also been demonstrated in vivo in *Arabidopsis thaliana* that treatment of the plant with AtmiPEP164a increases plant growth significantly (FIG. 24).

Example 3C—AtmiPEP165a

Regarding AtmiPEP165a, this was synthesized and was used for investigating an increase in the accumulation of miR165a in roots of *A. thaliana* treated with the synthetic peptide.

Northern blot analyses indicate that treatment of the plant with the peptide miPEP165a leads to an increase in the accumulation of miR165a (FIG. 25).

Example 4C—AtmiPEP319a1

Regarding AtmiPEP319a1, this was also synthesized and was used for investigating an increase in the accumulation of miR319a in roots of *A. thaliana* treated with the synthetic peptide.

Analyses by qRT-PCR show that the overexpression of AtmiPEP319a1 leads to an increase in the accumulation of miR319a (FIG. 26).

It was also demonstrated in vivo in *Arabidopsis thaliana* that treatment of the plant with AtmiPEP319a1 increases plant growth significantly (FIG. 27).

Material and Methods

Biological Material

The surface of seeds of *M. truncatula* was sterilized and they were left to germinate on agar plates for 5 days at 4° C. in the dark. The young shoots were then grown on 12-cm square plates filled with Fahraeus medium without nitrogen and containing 7.5 µM phosphate (Lauressergues et al., *Plant J.*, 72(3): 512-22, 2012). The lateral roots were counted every day. In pots, the plants were watered every other day with modified Long Ashton medium with low phosphorus content (Balzergue et al., *Journal of Experimental Botany*, (62)1049-1060, 2011).

The peptides were synthesized by Eurogentec or Smartox-Biotech. MtmiPEP171b1 was resuspended in a solution of 40% water/50% acetonitrile/10% acetic acid (v/v/v), and the other peptides were resuspended in water.

The leaves were watered by spraying with the peptides using peptide solutions at different concentrations (0.01, 0.1, 1 µM), firstly 12h before sampling and then a second time 30 min before sampling.

Reverse Transcription of the microRNAs

The RNA was extracted using the reagent Tri-Reagent (MRC) according to the manufacturer's instructions, except for precipitation of the RNA, which was carried out with 3 volumes of ethanol. The reverse transcription of the RNA was carried out using the specific stem-loop primer RTprimer171b in combination with hexamers for performing the reverse transcription of RNA of high molecular weight.

In brief, 1 µg of RNA was added to the stem-loop primer MIR171b (0.2 µM), the hexamer (500 ng), the buffer RT (1×), the enzyme SuperScript reverse transcriptase (SSIII) (one unit), the dNTPs (0.2 mM each), DTT (0.8 mM) in a final reaction mixture of 25 µl. In order to carry out the reverse transcription, a reaction of pulsed reverse transcription was performed (40 repetitions of the following cycle: 16° C. for 2 minutes, 42° C. for one minute and 50° C. for one second, followed by a final inactivation of the reverse transcription at 85° C. for 5 minutes).

Analyses by Quantitative RT-PCR (qRT-PCR)

The total RNA was extracted from roots of *M. truncatula* or from tobacco leaves using the extraction kit RNeasy Plant Mini Kit (Qiagen). The reverse transcription was performed using the reverse transcriptase SuperScript II (Invitrogen) starting from 500 ng of total RNA. Three repetitions (n=3) were carried out, each with two technical repetitions. Each experiment was repeated from two to three times. The amplifications by qPCR were carried out using a LightCycler 480 System thermocycler (Roche Diagnostics) by the method described in Lauressergues et al. (*Plant J.*, 72(3): 512-22, 2012).

Statistical Analyses

The mean values of the relative expression of the genes or of the production of lateral roots were analysed using the Student test or the Kruskal-Wallis test. The error bars represent the SEM (Standard Error of the Mean). The asterisks indicate a significant difference ($p<0.05$).

Plasmid Constructs

The DNA fragments of interest were amplified with Pfu polymerase (Promega). The DNA fragments were cloned using the XhoI and NotI enzymes into a pPEX-DsRED plasmid for an overexpression under the control of the constitutive strong promoter 35S, and using the KpnI-NcoI enzymes into a pPEX GUS plasmid for the reporter genes, by the method described in Combier et al. (*Genes & Dev,* 22: 1549-1559, 2008).

For the miPEPs 165a and 319a, the corresponding miORFs were cloned into pBIN19 by the method described in Combier et al. (*Genes & Dev,* 22: 1549-1559, 2008).

Transformation of the Plants

The composite plants having roots transformed with *Agrobacterium rhizogenes* were obtained by the method described in Boisson-Dernier et al. (*Mol Plant-Microbe Interact,* 18: 1269-1276, 2005). The transformed roots were verified and selected by observations of DsRED with a binocular fluorescence magnifier. The control roots correspond to roots transformed with *A. rhizogenes* not containing the pPEX-DsRED vector. Transformation of the tobacco leaves was carried out by the method described in Combier et al. (*Genes & Dev,* 22: 1549-1559, 2008).

Northern Blot

Northern blot analysis was carried out according to the protocol described in Lauressergues et al. *Plant J,* 72(3): 512-22, 2012.

The biological samples were homogenized in a buffer containing 0.1 M of NaCl, 2% of SDS, 50 mM of Tris-HCl (pH 9), 10 mM of EDTA (pH 8) and 20 mM of mercaptoethanol, and the RNA was extracted twice with a phenol/chloroform mixture and was precipitated with ethanol.

The RNA was loaded on PAGE 15% gel and transferred to a nylon membrane (HybondNX, Amersham). RNA was hybridized with a radioactive oligonucleotide probe labelled at its end, in order to detect the RNA U6 or for miR164a.

The hybridizations were carried out at 55° C. The hybridization signals were quantified using a phosphorimager (Fuji) and normalized with the signal of the specific probe of RNA U6.

Histochemical Labelling

Labelling with GUS was carried out by the method described in Combier et al., (*Genes & Dev,* 22: 1549-1559, 2008). The samples were observed with a microscope (axiozoom).

Immunolocalization

Roots or plantlets of tissues of *Medicago* were fixed for 2 hours in 4% formol (v/v) with 50 mM of phosphate buffer (pH 7.2), and then embedded in agarose LMP 5% in water (with a low melting point). Thin sections (100 μm) were obtained and were placed in Pbi (phosphate buffer for immunology) on Teflon-coated slides, blocked in Pbi, 2% Tween and 1% of bovine serum albumin for 2 hours (PbiT-BSA), then labelled overnight (12 h) at 4° C. with the primary antibody diluted in BSA-PbiT. The sections were washed with PBiT and incubated at ambient temperature for 2 h with a secondary antibody diluted in PbiT-BSA. The slides were then washed in Pbi for 30 min and mounted in Citifluor (mounting medium). The primary antibodies and the dilutions were as follows: 1716a (1:500, v/v). The secondary antibody was a goat anti-rabbit IgG antibody coupled to the Alexa Fluor 633 fluorescent probe (Molecular Probes), and was used at a dilution of 1:1000 (v/v).

B: Analysis of the miPEPs in Animals

Example 4—Identification of Candidate miPEPs in *Drosophila*

A first study carried out by RACE-PCR in the model animal *Drosophila melanogaster* shows the existence of miRNAs that are expressed during embryogenesis, miR1 and miR8.

As in the plants, miORFs were identified in each of the two miRNAs studied. For example, miR8, known for its role in the regulation of growth in insects, has a miORF potentially encoding miPEP8.

Regarding DmmiR1 (identified in *Drosophila melanogaster*), it has two DmmiORFs potentially encoding DmmiPEP1a and DmmiPEP1b.

A phylogenetic analysis shows evolutionary conservation of the presence of the miORFs among the dozen *Drosophila* species analysed, i.e. since their divergence more than 60 million years ago (FIG. 13).

Moreover, the miPEPs identified in *Drosophila* have several similarities with the plant miPEPs. If their primary sequence and therefore their size evolve rapidly between species, a reduced size (from 32 to 104 AA) is found, as well as strong conservation for a basic overall charge (pHi from 9.5 to 12) (FIG. 14).

Taken together, these results therefore indicate the existence of regulatory miPEPs, encoded by the primary transcript of the microRNAs, over a broad spectrum of eukaryotic species. These discovered peptides represent an as yet unexplored reservoir of natural molecules that may regulate a variety of fundamental biological functions, both in plants and in animals.

Cells of *Drosophila melanogaster*

S2 cells are cultured in a T75 flask in 12 mL of Schneider's medium (GIBCO), containing 1% of penicillin 100 U/mL and streptavidin 100 mg/mL (Sigma) and 10% of decomplemented foetal calf serum (30 min at 56° C.).

The transient transfections are carried out using the FuGENE® HD transfection kit (Roche), according to the recommendations. Conventionally, 1.5 million S2 cells, previously seeded in 6-well plates (3 ml of medium per well), are transfected with 250 ng of total plasmid DNA. The DNA is brought into contact with the Fugene (3 μl) in 100 μl of OPTIMEM (GIBCO). After 20 minutes, the transfection reagent formed is brought into contact with the cells in the culture medium. The RNA of the cells is extracted 66 h after transfection.

C: Characterization of miPEPs in Humans

Example 5—Characterization of HsmiPEP155

The DNA fragments of interest (HsmiPEP155 and the mutated miPEP) were synthesized or amplified by PCR using specific primers, and then cloned using the enzymes XhoI and NotI into a pUAS plasmid permitting their overexpression by means of the GAL4 transcription factor, the expression of which is controlled by a constitutive strong promoter.

The different constructs were produced either by PCR amplification on genomic DNA of HeLa cells, or by RT-PCR on total RNAs of L428 human cells. The amplified PCR fragments are digested with the HindIII/EcoRI restriction enzymes and then cloned into the vector pcDNA3.1. The DH5a strain of *Escherichia coli* is electroporated and then cultured on a solid medium (2YT+agar+ampicillin). The plasmid DNA from different clones is then prepared and sequenced for verification. The constructs are then prepared using the QIAfilter Plasmid Midi kit (QIAGEN) and stored at −20° C.

The HeLa cells (established tumour line, ATCC CCL-2.2) are cultured in a 6-well plate in complete medium [(DMEM (1×)+Glutamax+4.5 g/L glucose without pyruvate+1× penicillin/streptomycin+1 mM Na-pyruvate+10% calf serum] and placed in an incubator at 37° C. and 5% $CO_2$.

The cells are transfected when they are at 50% confluence. At the start of the experiment, the complete medium containing the antibiotics is replaced with complete medium without antibiotics.

For each well, a mix A [250 µl of Optimem (+Glutamax) (Gibco)+2 µg of DNA] and a mix B [250 µl of Optimem+4 µl of Lipofectamine 2000 (Invitrogen)] is prepared, and left for 5 min at ambient temperature. Then mix B is mixed dropwise into mix A, and left to incubate for 25 min at ambient temperature. The mixture is then deposited dropwise into the well. 4-5 hours later, the medium is changed and replaced with complete medium with antibiotics. 48 hours after transfection, the cells are stopped. The medium is aspirated and discarded; the cells are rinsed with PBS 1X. It is then possible to store the cells at −20° C. or extract the total RNAs directly.

For each well, the RNAs are extracted by depositing 1 ml of Tri-Reagent (Euromedex) on the cells. The Tri-reagent is aspirated and returned several times so that the cells are lysed correctly, and then it is transferred into a 1.5-ml tube. 0.2 ml of water-saturated chloroform is added. It is mixed by vortexing, then left for 2 to 3 minutes at ambient temperature. It is centrifuged for 5 minutes at 15300 rpm and at 4° C. The aqueous phase is precipitated from 0.5 ml of isopropanol after incubation for 10 minutes at ambient temperature and centrifugation for 15 minutes at 15300 rpm and at 4° C. The supernatant is discarded and the pellet is rinsed with 1 ml of 70% ethanol, with centrifugation for 5 minutes at 15300 rpm at 4° C. The supernatant is again discarded and the pellet is dried for a few minutes in the air. For best-possible removal of the genomic DNA potentially remaining, the RNAs are treated with DNase. For this, the pellet is resuspended in 170 µl of ultra-pure water, 20 µl of DNase buffer 10× and 10 µl of RQ1 RNase-free DNase and held at 37° C. for 30 minutes. Then 20 µl of SDS10% and 5 µl of proteinase K (20 mg/ml) are added over 20 minutes at 37° C.

A last phenol extraction is carried out with 225 µl of a phenol/$H_2O$/chloroform mixture, and centrifuged for 5 minutes at 15300 rpm at 4° C.

The aqueous phase is then precipitated from 20 µl of 3M sodium acetate and 600 µl of 100% ethanol for 20 minutes at −80° C. Then it is centrifuged for 15 min at 4° C. at 15300 rpm. The supernatant is discarded. The pellet is rinsed in 1 ml of 70% ethanol, centrifuged for 5 min at 15300 rpm at 4° C., the supernatant is discarded again and the pellet is left to dry for some minutes in the air.

The pellet is then taken up in 15-20 µl of ultra-pure water and the RNAs are assayed.

10-15 µg of total RNAs is then analysed by Northern blot on 15% acrylamide gel [solution of acrylamide/40% bis-acrylamide, ratio 19:1], 7M urea in TBE 1×. Migration is carried out at 400V, in TBE1× as migration buffer, after preheating the gel. The RNAs are then electro-transferred onto a Biodyne Plus 0.45 µm nylon membrane, for 2 hours, at IV and 4° C. in a transfer tank. At the end of transfer, the membrane is irradiated with UV at 0.124 $J/cm^2$. The membrane is then pre-hybridized in a buffer 5×SSPE, 1×Denhardt's, 1% SDS and 150 µg/ml of yeast tRNA, for 1 hour at 50° C. in a hybridization oven. Then the nucleotide probe is added, labelled at 5' with $\gamma$-$^{32}$P-ATP (0.5 to $1.10^6$ cpm/ml of hybridization buffer) and is hybridized overnight at 50° C. The membrane is then washed twice in 0.1×SSPE/0.1% SDS at ambient temperature and exposed in an autoradiography cassette containing a BioMax HE screen (Kodak) and a BioMax MS film (Kodak), in order to detect a microRNA, for 24-48 hours, at −80° C.

The invention claimed is:

1. A process comprising:
 a) identifying an open reading frame (ORF) from 12 to 303 nucleotides in length contained in the 5' or 3' portion of the primary transcript sequence of a microRNA (miRNA);
 b1) exogenously contacting a first plant cell expressing the miRNA with a peptide encoded by the ORF or a nucleotide encoding the peptide; and
 b2) comparing between:
  i) a phenotype in the first plant cell expressing the miRNA in the presence of the peptide encoded by the ORF, the peptide being present in the first plant cell independently of transcription of the primary transcript of the miRNA, and
  ii) the phenotype in a second plant cell of the same type as the first plant cell expressing the miRNA that has not been exogenously contacted with the peptide encoded by the ORF or the nucleotide encoding the peptide,
  wherein a change of the phenotype in the presence of the peptide relative to the phenotype in the absence of the peptide indicates that the ORF encodes a bioactive miPEP that modulates the amount of the miRNA;
 c) synthesizing (i) the miPEP that modulates the amount of the miRNA, or (ii) a nucleic acid sequence encoding the miPEP that modulates the amount of the miRNA and that does not comprise mature miRNA; and
 d) introducing into a third plant cell (i) the miPEP that modulates the amount of the miRNA, or (ii) the nucleic acid sequence encoding the miPEP that modulates the amount of the miRNA and that does not comprise mature miRNA resulting in the increase of the amount of the miRNA that encodes the miPEP in its primary transcript sequence,
 wherein the synthesizing step c) is not performed endogenously in the third plant cell, and wherein the third plant cell expresses the miRNA.

2. The process of claim 1, wherein the nucleic acid sequence encoding the miPEP that modulates the amount of the miRNA and that does not comprise the mature miRNA is operably linked to a heterologous promoter.

3. The process of claim 2, further comprising the step of expressing the miPEP in the third plant cell.

4. The process of claim 3, further comprising the step of isolating the miPEP from the third plant cell.

5. The process of claim 1, wherein the introducing in step d) comprises:
 formulating the miPEP that modulates the amount of the miRNA or the nucleic acid encoding the miPEP that modulates the amount of the miRNA and that does not comprise the mature miRNA for administration to a plant or part thereof; and
 administering the formulation to the plant or part thereof.

6. The process of claim 1, wherein the synthesis in step c) is chemical synthesis or synthesis in a cell that transgenically expresses the miPEP that modulates the amount of the miRNA or the nucleic acid sequence encoding the miPEP that modulates the amount of the miRNA and that does not comprise the mature miRNA.

* * * * *